(12) United States Patent
Anderson et al.

(10) Patent No.: US 12,006,531 B2
(45) Date of Patent: *Jun. 11, 2024

(54) METHODS AND SYSTEMS FOR RAPID DETECTION OF MICROORGANISMS USING INFECTIOUS AGENTS

(71) Applicant: Laboratory Corporation of America Holdings, Burlington, NC (US)

(72) Inventors: Dwight Lyman Anderson, Minneapolis, MN (US); Jose S. Gil, Winnetka, CA (US); Ben Barrett Hopkins, Sherman Oaks, CA (US); Stephen Erickson, White Bear Township, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/674,876

(22) Filed: Nov. 5, 2019

(65) Prior Publication Data
US 2020/0140919 A1 May 7, 2020

Related U.S. Application Data

(63) Continuation of application No. 14/625,481, filed on Feb. 18, 2015, now Pat. No. 10,519,483, which is a (Continued)

(51) Int. Cl.
*C12Q 1/66* (2006.01)
*C12N 15/86* (2006.01)
(Continued)

(52) U.S. Cl.
CPC .............. *C12Q 1/66* (2013.01); *C12N 15/86* (2013.01); *G01N 33/569* (2013.01);
(Continued)

(58) Field of Classification Search
None
See application file for complete search history.

(56) References Cited

U.S. PATENT DOCUMENTS 4,861,709 A 8/1989 Ulitzur et al.
5,221,623 A * 6/1993 Legocki .............. C12Q 1/6897
435/189

(Continued)

FOREIGN PATENT DOCUMENTS

AU 2013222411 2/2019
CN 1231701 10/1999
(Continued)

OTHER PUBLICATIONS

Schofield DA, Molineux IJ, Westwater C. Diagnostic bioluminescent phage for detection of Yersinia pestis. J Clin Microbiol. 2009 (Year: 2009).*

(Continued)

*Primary Examiner* — Michelle S Horning
(74) *Attorney, Agent, or Firm* — Kilpatrick Townsend & Stockton LLP

(57) ABSTRACT

Disclosed herein are methods and systems for rapid detection of microorganisms in a sample, without culturing for enrichment of the microorganism. A modified bacteriophage is also disclosed which comprises a non-native indicator gene in the late gene region. The indicator product is not a fusion protein. The specificity of infectious agents allows a specific microorganism to be targeted, and an indicator signal may be amplified to optimize assay sensitivity.

11 Claims, 18 Drawing Sheets

Specification includes a Sequence Listing.

Related U.S. Application Data continuation-in-part of application No. 13/773,339, filed on Feb. 21, 2013, now Pat. No. 9,482,668.

(60) Provisional application No. 61/940,959, filed on Feb. 18, 2014, provisional application No. 61/601,231, filed on Feb. 21, 2012.

(51) Int. Cl.
  *G01N 33/569* (2006.01)
  *G01N 33/58* (2006.01)

(52) U.S. Cl.
  CPC ..... *G01N 33/56911* (2013.01); *G01N 33/581* (2013.01); *C12N 2795/10121* (2013.01); *C12N 2795/10131* (2013.01); *C12N 2795/10143* (2013.01); *C12N 2795/10221* (2013.01); *C12N 2795/10231* (2013.01); *C12N 2795/10243* (2013.01)

(56) References Cited

U.S. PATENT DOCUMENTS

| | | | |
|---|---|---|---|
| 5,656,424 | A | 8/1997 | Jurgensen et al. |
| 5,824,468 | A | 10/1998 | Scherer et al. |
| 5,837,465 | A | 11/1998 | Squirrell et al. |
| 5,846,774 | A * | 12/1998 | Xia ............ C07K 14/005 435/243 |
| 6,225,066 | B1 | 5/2001 | Jacobs, Jr. et al. |
| 6,300,061 | B1 | 10/2001 | Jacobs, Jr. et al. |
| 6,544,729 | B2 | 4/2003 | Sayler et al. |
| 6,555,312 | B1 | 4/2003 | Nakayama |
| 7,252,996 | B2 | 8/2007 | Boccaccio et al. |
| 8,318,474 | B1 | 11/2012 | Smolke et al. |
| 8,557,970 | B2 | 10/2013 | Encell et al. |
| 8,865,399 | B2 | 10/2014 | Schofield et al. |
| 9,482,668 | B2 | 11/2016 | Anderson et al. |
| 10,519,483 | B2 | 12/2019 | Anderson et al. |
| 10,913,934 | B2 | 2/2021 | Gil et al. |
| 2004/0137430 | A1 | 7/2004 | Anderson et al. |
| 2005/0003346 | A1 | 1/2005 | Voorhees et al. |
| 2005/0202487 | A1 * | 9/2005 | Klepp ............ C12N 1/02 435/6.16 |
| 2007/0010001 | A1 | 1/2007 | Bujanover |
| 2009/0155768 | A1 * | 6/2009 | Scholl ............ C12Q 1/70 435/5 |
| 2009/0246752 | A1 | 10/2009 | Voorhees et al. |
| 2010/0291541 | A1 | 11/2010 | Evoy et al. |
| 2011/0201013 | A1 | 8/2011 | Moore |
| 2011/0281329 | A1 | 11/2011 | Lenherr et al. |
| 2013/0122549 | A1 | 5/2013 | Lu et al. |
| 2013/0216997 | A1 | 8/2013 | Anderson et al. |
| 2015/0218616 | A1 | 8/2015 | Anderson et al. |
| 2017/0121688 | A1 | 5/2017 | Gil et al. |
| 2017/0131275 | A1 | 5/2017 | Anderson et al. |

FOREIGN PATENT DOCUMENTS

| | | |
|---|---|---|
| CN | 104245961 | 12/2014 |
| CN | 104245961 | 5/2017 |
| CN | 107422115 | 12/2017 |
| EP | 0743366 | 11/1996 |
| EP | 2 817 422 | 1/2019 |
| HK | 1205762 | 12/2015 |
| JP | 11337553 | 12/1999 |
| JP | 2002160525 | 6/2002 |
| JP | 2005/524394 | 8/2005 |
| JP | 2006510002 | 3/2006 |
| JP | 2007/523628 | 8/2007 |
| JP | 2010/507371 | 3/2010 |
| JP | 2010088456 | 4/2010 |
| JP | 2015510598 | 4/2015 |
| JP | 2017074074 | 4/2017 |
| JP | 6636967 | 12/2019 |
| WO | 99/45396 | 9/1999 |
| WO | 03/035889 | 5/2003 |
| WO | 2005/001475 | 1/2005 |
| WO | 2007/055737 | 5/2007 |
| WO | 2008/124119 | 10/2008 |
| WO | 2013/126584 | 8/2013 |
| WO | 2015/126966 | 8/2015 |
| WO | 2017/127434 | 7/2017 |

OTHER PUBLICATIONS

Tanji Y, Furukawa C, Na SH, Hijikata T, Miyanaga K, Unno H. Escherichia coli detection by GFP-labeled lysozyme-inactivated T4 bacteriophage. J Biotechnol. Oct. 19, 2004;114(1-2):11-20. (Year: 2004).*

U.S. Appl. No. 13/773,339, Final Office Action, dated Jun. 9, 2015, 18 pages.

U.S. Appl. No. 13/773,339, Non-Final Office Action, dated Oct. 31, 2014, 12 Pages.

U.S. Appl. No. 13/773,339, Non-Final Office Action, dated Mar. 3, 2016, 26 pages.

U.S. Appl. No. 15/263,619, Non-Final Office Action, dated May 13, 2019, 21 pages.

AU Patent Application No. 2013222411, "First Examination Report", dated Nov. 2, 2017, 4 pages.

Bague, J., "Detection of Recombinant Human Erythropoietin and Analogues Through Immunorecognition and N-Glycolyl-Neuraminic Acid Identification", Doctoral Thesis Pompeu, Fabra University, Department of Experimental and Health Sciences, Available Online at: http://www.tesisenred.net/ bitstream/ handle/10803/ 31969/tjm.pdfsequence=1, 2011, 20 pages.

CA Patent Application No. 2,865,308, Office Action, dated Jun. 4, 2019, 3 pages.

CN Patent Application No. 201380019483.3, Office Action, dated Feb. 4, 2016, 11 pages.

CN Patent Application No. 201380019483.3, Office Action, dated Jul. 7, 2015, 14 pages.

CN Patent Application No. 201380019483.3, Office Action, dated Jul. 18, 2016, 9 pages.

CN Patent Application No. 201710263366.1, Office Action, dated Jul. 31, 2019, 10 pages.

Edgar, R. et al., "High-Sensitivity Bacterial Detection Using Biotin-Tagged Phage and Quantum-Dot Nanocomplexes", Proc. Natl. Acad. Sci. USA, 103(13):4841-4845 (2006).

Elena et al., "Expression of codon optimized genes in microbial systems: current industrial applications and perspectives. Art. 21", Frontiers in Microbiology, 5:1-8 (2014).

EP Patent Application No. 13751965.8, Extended European Search Report, dated Sep. 30, 2015, 7 pages.

EP Patent Application No. 13751965.8, Office Action, dated Apr. 11, 2017, 6 pages.

EP Patent Application No. 13751965.8, Office Action, dated Jan. 30, 2018, 6 pages.

EP Patent Application No. 19152164.0, Extended European Search Report, dated Jul. 10, 2019, 6 pages.

Goodridge. L. et al., "Reporter Bacteriophage Assays as a Means to Detect Foodborne Pathogenic Bacteria", Food Research International, 35(9):863-870 (2002).

Hagens et al., "Bacteriophage for Biocontrol of Foodborne Pathogens: Calculations and Considerations", Current Pharmaceutical Biotechnology, vol. 11, No. 1, Feb. 10, 2010, pp. 58-68.

Hagens, S. et al., "Reporter Bacteriophage A511: CelB Transduces a Hyperthermostable Glycosidase from Pyrococcus Furiosus for Rapid and Simple Detection of Viable Listeria Cells", Bacteriophage, 1(3):143-151 (2011).

He, Y. et al., "Monoclonal Antibodies for Detection of the H7 Antigen of *Escherichia coli*", Appl. Environ. Microbiol., 62(9):3325-3332 (1996).

Inouye, S. et al., "Overexpression, Purification and Characterization of the Catalytic Component of Oplophorus Luciferase in the Deep-Sea Shrimp, Oplophorus Gracilirostris", Protein Expr. Purif., 56(2): 261-268 (2007).

(56) References Cited

OTHER PUBLICATIONS

JP Patent Application No. 2014-558827, Office Action, dated Nov. 1, 2016, 9 pages.
JP Patent Application No. 2017-016551, Office Action, dated Dec. 21, 2018, 12 pages.
JP Patent Application No. 2017-16551, Office Action, dated Jan. 19, 2018, 5 pages.
Kodikara, C. et al., "Near on-line Detection of Enteric Bacteria Using Lux Recombinant Bacteriophage", FEMS Microbiol. Lett., 67(3):261-265 (1991).
Kutter et al., "Characterization of a Vil-like Phage 11-20 Specific to *Escherichia coli* 0157:H7", Virology Journal, Biomed Central, 8(1):430 (2011).
Loessner, M. et al., "Construction of Luciferase Reporter Bacteriophage A511: LuxAB for Rapid and Sensitive Detection of Viable Listeria Cells", Appl. Environ. Microbiol., 62(4):1133-1140 (1996).
Loessner, M. et al., "Evaluation of Luciferase Reporter Bacteriophage A511: luxAB for Detection of Listeria Monocytogenes in Contaminated Foods", Appl. Environ. Microbiol., 63(8):2961-2965 (1997).
Lu, T. et al., "Advancing Bacteriophage-Based Microbial Diagnostics With Synthetic Biology", Trends Biotechnol., 31:6:325-327 (2013).
MacDonald et al., "Regulation of a New Bacteriophage T4 Gene, 69, That Spans an Origin of DNA Replication", The EMBO Journal, 3(12):2863-2871 (1984).
Miyanaga et al., "Detection of *Escherichia coli* in the Sewage Influent by Fluorescent Labeled T4 Phage", Biochemical Engineering Journal, 29(1-2):119-124 (2006).
MX Patent Application No. MX/A/2014/010069, Office Action, dated Apr. 25, 2017.
Noguera, P. et al., "Carbon Nanoparticles in Lateral Flow Methods to Detect Genes Encoding Virulence Factors of Shiga Toxin-Producing", Anal. and Bioanal. Chem., 399(2):831-838 (2011).
International Patent Application No. PCT/US13/27155, International Search Report and Written Opinion, dated May 6, 2013, 8 pages.
International Patent Application No. PCT/US2015/016415, International Search Report and Written Opinion, dated Jun. 22, 2015, 12 pages.
International Patent Application No. PCT/US2017/013955, International Preliminary Report on Patentability, dated Aug. 2, 2018, 9 pages.
International Patent Application No. PCT/US2017/013955, International Search Report and Written Opinion, dated May 15, 2017, 16 pages.
International Patent Application No. PCT/US2017/013955, "Invitation to Pay Additional Fees and Partial Search Report", dated Mar. 20, 2017, 7 pages.
Rees et al., "The Use of Phage for Detection, Antibiotic Sensitivity Testing and Enumeration", InTech, In: Understanding Tuberculosis—Global Experiences and Innovative Approaches to the Diagnosis, Feb. 15, 2012, 15 pages.
Rees, C. et al., "The Use of Phage of Diagnostic Systems", Division of Food Sciences, School of Biosciences, University of Nottingham, SuttonBonington Campus Loughborough, Leicestershire LE12 5RD, UK; the Bacteriophages, 2nd edition (2006) Richard Calendar—Oxford University Press, 2006, 15 pages.
Schofield, D. et al., "Phage-Based Platforms for the Clinical Detection of Human Bacterial Pathogens", Bacteriophage, 2(2): 105-283 (2012).
Smietana, M. et al., "Detection of Bacteria Using Bacteriophages as Recognition Elements Immobilized on Long-period Fiber Gratings References and Links", Optics Express, 19(9):7971-7978 (2011).
Tanji et al., "*Escherichia coli* Detection by GFP-Labeled Lysozyme-Inactiva Ted T4 Bacteriophage", J. Biotechnology, 114(1-2):11-20 (2004).

Ulitzur, N. et al., "New Rapid and Simple Methods for Detection of Bacteria and Determination of their Antibiotic Susceptibility by Using Phage Mutants", Appl. Environ. Microbiol., 72(12):7455-7459 (2006).
Wu, L. et al., "Trace Detection of Specific Viable Bacteria Using Tetracysteine-Tagged Bacteriophages", Anal. Chem., 86(1):907-912 (2014).
Bachrach, U. and Friedmann, A., "Practical Procedures for the Purification of Bacterial Viruses", Applied Microbiology, 22(4):706-715 (1971).
Billard, P. and DuBow, M., "Bioluminescence-Based Assays for Detection and Characterization of Bacteria and Chemicals in Clinical Laboratories", Clinical Biochemistry, 31(1):1-14 (1998).
Jacobs, W. JR. et al., "Rapid Assessment of Drug Susceptibilities of *Mycobacterium tuberculosis* by Means of Luciferase Reporter Phages", Science, 260(5109):819-822 (1993).
Zink, R. and Loessner, M., "Classification of Virulent and Temperate Bacteriophages of *Listeria* spp. on the Basis of Morphology and Protein Analysis", Applied and Environmental Microbiology, 58(1):296-302 (1992).
U.S. Appl. No. 13/773,339, Notice of Allowance, dated Sep. 6, 2016, 8 pages.
U.S. Appl. No. 14/625,481, Final Office Action, dated Aug. 27, 2018, 10 pages.
U.S. Appl. No. 14/625,481, Final Office Action, dated Jun. 13, 2019, 11 pages.
U.S. Appl. No. 14/625,481, Non Final Office Action, dated Jan. 4, 2019, 11 pages.
U.S. Appl. No. 14/625,481, Non-Final Office Action, dated Oct. 18, 2016, 10 pages.
U.S. Appl. No. 14/625,481, Non-Final Office Action, dated Jan. 25, 2018, 8 pages.
U.S. Appl. No. 14/625,481, Non-Final Office Action, dated Apr. 26, 2017, 9 Pages.
U.S. Appl. No. 14/625,481, Notice of Allowance, dated Oct. 30, 2019, 6 pages.
U.S. Appl. No. 15/263,619, Final Office Action, dated Nov. 26, 2018, 21 pages.
U.S. Appl. No. 5/263,619, Final Office Action, dated Feb. 12, 2020, 27 pages.
U.S. Appl. No. 15/263,619, Non-Final Office Action, dated Mar. 26, 2018, 19 pages.
U.S. Appl. No. 15/263,619, Non-Final Office Action, dated Sep. 28, 2020, 35 pages.
U.S. Appl. No. 15/409,258, Corrected Notice of Allowability, dated Nov. 13, 2020, 8 pages.
U.S. Appl. No. 15/409,258, Final Office Action, dated Sep. 17, 2019, 11 pages.
U.S. Appl. No. 15/409,258, Final Office Action, dated Mar. 7, 2019, 9 pages.
U.S. Appl. No. 15/409,258, Non-Final Office Action, dated Apr. 20, 2020, 6 pages.
U.S. Appl. No. 15/409,258, Non-Final Office Action, dated Sep. 19, 2018, 8 pages.
U.S. Appl. No. 15/409,258, Notice of Allowance, dated Oct. 5, 2020, 10 pages.
AU 2013222411, Notice of Allowance, dated Oct. 31, 2018, 3 pages.
AU 2013222411, "Second Examination Report", dated Oct. 4, 2018, 5 pages.
CA 2,865,308, Office Action, dated May 1, 2020, 3 pages.
CA 2,865,308, Office Action, dated Mar. 24, 2021, 4 pages.
CA 2,865,308, Office Action, dated May 1, 2018, 4 pages.
CN 201710263366.1, Office Action, dated Oct. 9, 2018, 12 pages.
EP 13751965.8, Notice of Decision to Grant, dated Jan. 7, 2019, 2 pages.
EP 19152164.0, Office Action, dated Oct. 29, 2020, 4 pages.
IN 1908/KOLNP/2014, First Examination Report, dated Sep. 28, 2018, 7 pages.
JP 2017-16551, Notice of Allowance, dated Nov. 20, 2019, 3 pages.
JP 2017-16551, Office Action, dated Sep. 6, 2019, 4 pages.
JP 2019-228941, Office Action, dated Feb. 12, 2021, 9 pages.

(56) References Cited

OTHER PUBLICATIONS

MX/A/2017/014852, Notice of Allowance, dated Feb. 23, 2021, 2 pages.
MX/A/2017/014852, Office Action, dated Aug. 17, 2020, 6 pages.
U.S. Appl. No. 15/263,619, Final Office Action, dated Jun. 28, 2021, 34 pages.
Guerrero-Ferreira, R. et al., "Structure and Transformation of Bacteriophage A511 Baseplate and Tail Upon Infection of *Listeria* Cells," The EMBO Journal 38:e99455 (2019) 20 pages.
Kutter, E. et al., "Characterization of a Vil-like Phage Specific to *Escherichia coli* O157:H7," Virology Journal 8:430 (2011), 14 pages.
BR 1120140205124, Notice of Allowance, dated May 10, 2022, 3 pages.
BR 112018014166-6, Office Action, dated Dec. 6, 2022, 4 pages.
CA 2,865,308, Notice of Allowance, dated May 4, 2022, 1 page.
Close, D. et al., "Comparison of human optimized bacterial luciferase, firefly luciferase, and green fluorescent protein for continuous imaging of cell culture and animal models," J. Biomedical Optics 16(4):047003 (2011), 11 pages.
Cui, B. et al., "Engineering an Enhanced, Thermostable, Monomeric Bacterial Luciferase Gene as a Reporter in Plant Protoplasts," PLoS ONE 9(10):e107885 (2014), 11 pages.
GenBank E12410.1, "Nucleotide sequence of the luxAB gene," 2005, 2 pages.
Hall, M. et al., "Engineered Luciferase Reporter from a Deep Sea Shrimp Utilizing a Novel Imidazopyrazinone Substrate," ACS Chem. Biol. 7:1848-1857 (2012).
Kim, J. et al., "Sensitive Detection of Viable *Escherichia coli* O157:H7 from Foods using a Luciferase-Reporter Phage phiV10lux," International Journal of Food Microbiology, 254:11-17 (2017).
Kutter, E. et al., "Characterization of Vil-like Phage Specific to *Escherichia coli* O157:H7," Virology Journal, 8:430 (2011) 14 pages.
Zhou, Z. et al., "Enhanced expression of a recombinant malaria candidate vaccine in *Escherichia coli* by codon optimization," Protein Expression and Purification, 34(1):87-94 (2004).

* cited by examiner

SEQUENCE LISTING

<160> NUMBER OF SEQ ID NOS: 7

<210> SEQ ID NO 1
<211> LENGTH: 2196
<212> TYPE: DNA
<213> ORGANISM: Homo sapiens

<400> SEQUENCE: 1

```
catatgagtc ttgtgatgta ctggctgatt tctacgacca gttcgctgac cagttgcacg      60
agtctcaatt ggacaaaatg ccagcacttc cggctaaagg taacttgaac ctccgtgaca     120
tcttagagtc ggacttcgcg ttcgcgtaac gccaaatcaa tacgactcac tatagaggga     180
caaactcaag gtcattcgca agagtggcct ttatgattga ccttcttccg gttaatacga     240
ctcactatag gagaacctta aggtttaact ttaagaccct taagtgttaa ttagagattt     300
aaattaaaga attactaaga gaggacttta agtatgcgta acttcgaaaa gatgaccaaa     360
cgttctaacc gtaatgctcg tgacttcgag gcaaccaaag gtcgcaagtt gaataagact     420
```

```
aagcgtgacc gctctcacaa gcgtagctgg gagggtcagt aagtaatacg actcactata    480
gggagaccac aacggtttcc tccctgtagt cttttgtttt aactttaagg aggtcaaatg    540
gaagacgcca aaaacataaa gaaaggcccg gcgccattct atcctctaga ggatggaacc    600
gctggagagc aactgcataa ggctatgaag agatacgccc tggttcctgg aacaattgct    660
tttacagatg cacatatcga ggtgaacatc acgtacgcgg aatacttcga aatgtccgtt    720
cggttggcag aagctatgaa acgatatggg ctgaatacaa atcacagaat cgtcgtatgc    780
agtgaaaact ctcttcaatt ctttatgccg gtgttgggcg cgttatttat cggagttgca    840
gttgcgcccg cgaacgacat ttataatgaa cgtgaattgc tcaacagtat gaacatttcg    900
cagcctaccg tagtgtttgt ttccaaaaag gggttgcaaa aattttgaa cgtgcaaaaa     960
aaattaccaa taatccagaa aattattatc atggattcta aaacggatta ccagggattt    1020
cagtcgatgt acacgttcgt cacatctcat ctacctcccg gttttaatga atacgatttt    1080
gtaccagagt cctttgatcg tgacaaaaca attgcactga taatgaattc ctctggatct    1140
actgggttac ctaagggtgt ggcccttccg catagaactg cctgcgtcag attctcgcat    1200
gccagagatc ctattttggg caatcaaatc attccggata ctgcgatttt aagtgttgtt    1260
ccattccatc acggttttgg aatgtttact acactcggat atttgatatg tggatttcga    1320
gtcgtcttaa tgtatagatt tgaagaagag ctgttttac gatcccttca ggattacaaa      1380
attcaaagtg cgttgctagt accaacccta ttttcattct tcgccaaaag cactctgatt    1440
gacaaatacg atttatctaa tttacacgaa attgcttctg ggggcgcacc tctttcgaaa    1500
gaagtcgggg aagcggttgc aaaacgcttc catcttccag ggatacgaca aggatatggg    1560
ctcactgaga ctacatcagc tattctgatt acacccgagg gggatgataa accgggcgcg    1620
gtcggtaaag ttgttccatt ttttgaagcg aaggttgtgg atctggatac cgggaaaacg    1680
ctgggcgtta atcagagagg cgaattatgt gtcagaggac ctatgattat gtccggttat    1740
gtaaacaatc cggaagcgac caacgccttg attgacaagg atggatggct acattctgga    1800
gacatagctt actgggacga agacgaacac ttcttcatag ttgaccgctt gaagtcttta    1860
attaaataca aaggatatca ggtggccccc gctgaattgg aatcgatatt gttacaacac    1920
cccaacatct tcgacgcggg cgtggcaggt cttcccgacg atgacgccgg tgaacttccc    1980
gccgccgttg ttgttttgga gcacggaaag acgatgacgg aaaaagagat cgtgattac     2040
gtcgccagtc aagtaacaac cgcgaaaaag ttgcgcggag gagttgtgtt tgtggacgaa    2100
gtaccgaaag tcttaccgg aaaactcgac gcaagaaaaa tcagagagat cctcataaag      2160
gccaagaagg gcggaaagtc caaattgtaa ctcgag                                2196
```

<210> SEQ ID NO 2  
<211> LENGTH: 52  
<212> TYPE: DNA  
<213> ORGANISM: Artificial Sequence  
<220> FEATURE:  
<223> OTHER INFORMATION: synthetic primer

<400> SEQUENCE: 2

```
tatctgaatt ctaagtaact gataatacga ctcactatag ggagaccaca ac             52
```

<210> SEQ ID NO 3  
<211> LENGTH: 40  
<212> TYPE: DNA  
<213> ORGANISM: Artificial Sequence  
<220> FEATURE:

<223> OTHER INFORMATION: synthetic primer

<400> SEQUENCE: 3
aatgaaagct tttacaattt ggactttccg cccttcttgg    40

<210> SEQ ID NO 4
<211> LENGTH: 169133
<212> TYPE: DNA
<213> ORGANISM: Unknown
<220> FEATURE:
<223> OTHER INFORMATION: bacteriophage JG04 sequence

<400> SEQUENCE: 4
gtggtaatgc tagttatgac gcgcctggtg gtgccggtta cacttcccaa ttcggcggtg    60
gtaatggtgg cgatgctggg ggtcggggcg gagatggatg gggtaatcac ttatctagat    120
ctggcggtgg tgctcctggc agagcagtat tcggaagttc accgtcatgg ggtgctacag    180
gcacaatcta cggctcctgg atttaaacga taatacctct caattataaa tattgataaa    240
tgggaggtaa tatggcagca ccaaaagtat cattttcgcc tagtgatatt ttatttgggt    300
tgctagaccg catttttcaaa gataacgcct ctggaaatat tcttatttca agagttgctg    360
ttgtagttct tttgttccta atggcactaa tatggtacaa agggaatatt tttatggatt    420
attacgtgag gtcgaaatat gatacttaca cagaagtaat tcaaaaagaa agaaatacac    480
gatttgaatc tgcggcttta gaacaactac aaatagtcca cgtcacatca agggcggatt    540
ttagttcggt gtattctttc agacctaaaa atctaaatta tttcgtcgac cttattgcgt    600
atgaaggtaa gttacctagc acagtaactg aaaaatctat gggaggattt cctgtcgata    660
aaacgacagc agaatattcg gtccatttaa gtggacttca ctttacttct aaaacagatt    720 tgctttctt acctaccaaa tcaaaaactc ctgaactggc gtatatgtat agttgtcctt    780
acttcaattt ggataacata tatgcgggaa ctgtttctat gtattggtat aaggggtcgg    840
atgtattaaa tgaagaacgc ttggctgcaa tatgcaacca agcagcaagg atattagggc    900
gggctaaata attagttgtt agaatacatc gtcaaatggc gataaatatt ttcaaaacct    960
tcattgaatt cactaatcag tgttttcttt tcttcggcag ttaaatttgt aattagtttt    1020
ctgaacgaat tctgatttag ctgccgacca tctttttaa ttccaatctc attcaagaat    1080
ccgatgaaat ttgctcggtc ttcaacaata tcttccctag agaatttaat caaaatagaa    1140
gcaaccgtaa taatttcacg tacaatttca atatctttat tcataacgtt ttattcattc    1200
cattttgttg atatgagtat agtaccatta tcagtgttga ttgtaaacag ctttttctac    1260
acttttaacg taatcagtgt agtcttcctg ttcatacgag tgtaaggcca agaacgtggc    1320
taatagttca ttatagacta aagcctcacg ctcacgttct gcctctacta cgttctgcag    1380
attatggctc atatcattcc ttataactat caatgtagtc ctgtatgtca aagaatgaca    1440
tttcatattc tagggcatta agagcccgtt cttcagtata gtcagaacca agacgatag    1500 tgatttcacc aggcttcatg tgattgaaat caacgctaaa aggaatacga aacatactt    1560 cgtctgccat atctacgata acactacgat acacttctcg gttaacctga taaagctcta    1620
cgagttcttc gcaacgaata acaagttcag tggcaggatt ttctttgatt ttagtaagca    1680
tagtctttac ccttatgttt ttgtttgcgt ttagattgaa gttctgattt cttcttgtcc    1740
ttatggacag aagccttatt gaaatcgtgt tttgctacaa gattgttcat aatgattta    1800 aacctcattt aaacatttat cggtaaaaga aaactttta gccacagaac attcgatgat    1860
gtgttctttc aaatctttag agtcagtata acccatctca gtaataaagt ggcgaattaa    1920

```
agctttattc ttatcattaa cagaattaaa ataatctgct ttagaatcaa ttattctcat      1980
catctaattt ccttaattga tattgcaacg agctaataat ttcttcgttc attttaatat      2040
acatgtcacg caagaaaggt tttaacccat cacgaataat tgctaacgta tcacctttac      2100
ataaattaac caaataagga tgatctaaag cgtcccaacc aggctgatta gcatacatac      2160
catagttttc ttccatcata tgattaagac gtttgatatc ttggatacgt gattcaatag      2220
catctttctg gagttgttta atattcatta ataaaggtcc tctgaataaa gttctttctc      2280
acttccgcca cgttcaatac gtacctgtcc agcatacgtt gcaataatca ttgcttcttc      2340
acgtgtccag taattagagt attggtcgat aaagccttgg tcatcaccac aaacttgttg      2400
cgagactaat tgaggaccaa ctatatcaag tacttcagcc atatctttag agtaatgacg      2460
aactccagga ataaccagag ttccaccgct cttcaattta aacctattag ctgcacatac      2520
tataacacgt tgaactttt ggtcattatt ccaatagcac gtttgccaac agatttcagg       2580
aacttcattc attatatcat cagcagaata atcataaccg taggactgaa attttttctgc     2640 tagactttca ggagtctcac gagacaaggc caaatctaat agctctaaac gttctttaaa      2700
tgatttcatt taaaccattc cttaatacgt tgccaaatag attttttgtgc ttgtttattt     2760 acaccaatcg aacgaataac cggttgtgac tgctggtatt ctttataatc ttctttatag      2820
atttcgtaag ctgcatcaac aaatgaactg atcgcagcca tgtagtttt acgaaggcca       2880 aatggcgcgt cattatttc acgaataacc gtatattggc ctgctttaat ctttacaatt      2940
gtccctaaat aagccccgtg gtaccaaata tcccatcctt cctgagtagg ttctgcacat     3000
ttacgaagtt cgttaataat attcagctta ttcattatgt attcctcaca gtacgttagt      3060
tacaagggta atgatttctt tggacacatt agggaagtca atgtaagtat atttaccacc     3120
gatcttaatc ttaacatcat tttcaagaga agtaaacagc tttgattcag tttctgacat     3180
gttgtatgca aagattctaa gagcgccatc tcgacgaatt tcgatctgac gaatgcctag      3240
aactcgttta gcgaatcgaa cttctaagtt actacggttt tcaccaattt ctttaacttc     3300
aactttatct ttaatattt caaaaacaaa gtttgctaat tcatgcattt caggagtaac      3360
tccacgtgct tttctggtgt tacgtttctg aagaagttct ggagcatttt cttgggcaaa      3420
gaggtctgca gcttttttgga taatatccat tgcttcgccg gttgccacaa gtccatcacc     3480
ggatttttcg actaaaccctt tcttaatcaa tacaccaatg ttagagttaa caactgatgc     3540
gttgtattcc gcttccagag cttcacggac attggcagca gtggtgaagt tgttcttaat     3600
gatataaacc attattgcag cagttttttc attcagagcg ttttcagaag ctttgatgat     3660
gtaagtaact ttagacattt tatttctcca aattagtatt tgttttgata ggtctataat     3720
atcatgtttg aagcaaaagt aaactttatt ttgggctctt tttcaaaagc cctggtaaaa     3780
tttacaaact catttctttta ataaggctaa taagttttgc cttttttagaa cgaagcttttt   3840 ctaaatgata tccgtttgaa ccgcgaacaa ctaaagaatt gatttcaact tctaagaaat     3900
ttaattcttc aacaagtgct ttacgtggag cattcatacc aggtttaact ttaccgaaac     3960
gagtagttgt gttttgggtt aatttcattt tagacatttt atttctccaa tttggttgtt     4020 ttgtttgat aggtctataa tatcatgttt gaagcacatg taaactgttt tgtgagaaaa      4080
aaatgcacaa aagggagccg aagctcccta atcatgtttg tccaaccaat acagccaaat     4140
cactagtgca gctattgcac cgagaaatcc taaggctagg gcactcaaag tgcctccaag     4200
tctttagtgt actctgtcac aacatcagta gacttccaat actcattttc ttctttctta     4260
```

-continued

```
gctttagctt cttctgctag tttacgtgct tcgtcagaag tgatatggaa gatgttaaga      4320
cctaccaatt tatcgatatg ttctttatac atttcgattt gtgctagctc ttcagtcaaa      4380
gctttacgag tcttgccttg aatcacaatt tcgccactga taacttttt  gatgaagtgt      4440 gccttagcaa aagccagttt aaatgctttt tcagattcaa tgattttgtt atcaatacgt      4500
ttctgaacgt aagtcttacg gacttcaaca aaatctttga ttaagtccac tacgttatcg      4560
tagaccgtta atttacccttt tcattaatc actgtgatgt tttgtgaacg acgttcgatg      4620
agactaaaat ctttcatgat tttttcatga cgtagctctt cgtcatctgg aagcgagtac      4680
tctttacgga acttcacctt aaacccaaag ccgtgttcac cacaatcatc ttcccatgag      4740
attagacctt tgtcttccaa cgggtcaaga accttactca catacgtttc acggtcgaat      4800
ttatatggga tttcagttat ctgcatttga gtgcgagatg tgaacttata tgttccgtga      4860
atctcataac gcccatcaac ttcatgcact tcaccgcgga attccgggaa ttcaactttt      4920
ggtttagtga cattttacc  ttgaagagct tgtaatacag cctttttgac cgatttaaaa      4980
ctatgaggca gaatatttgt tgcgtaaccg gttgcaatac cagagacacc gttcaaaaga      5040
actgtcggaa tataggaag  atagaatttt ggtggaacgt gttctttatc ttcatgagct      5100
ggagcatatt cagtatcttt atatacgtta tagaaatttt tgcttacacg agcaaaaata      5160
taacgagatg ctgcagcttt ttggactgtt cgagaaccaa agttgccttg accatctaat      5220
agtggatagt tgttattcca tgtgttagcc atcaatgcac ctgcatcttg tgcagaagat      5280
tcaccatggt gataacctaa atctgcaaca ccgcctgcaa ttgacgcaag tttatgaaat      5340
tttctcttat taccacgagc caaatctaat gcacgatgaa ccacaaaacg ttgaaccggc      5400
ttaaatccat caatcatatt tgggattgca cggttttcaa cggtgtacat cgcatatgct      5460
aaggcttcgt tatcaataat acttttttaaa ttacgagaat tcaattgcat attttcacca      5520
tattaatgaa cgaataacca ttataacatc tgaaatgaaa agcactactt ggattagtcc      5580
aaacatcaca ccgtagtaca gaatcgtaaa caacaacaag agcccgaagg ctcctgctaa      5640
gattttctta atcattactc gccttttaac acgttaagaa gagctaagac cgctaaggta      5700
ccttgtgata cggcctgttg aaataccgtt gtttcgcctg taactaaagt gttaacgaat      5760
aaaaacgacc aacacaacaa tgcaataatc catgatacca ttttaattac ctcacaaata      5820
aattaaaggc ctaacttaat aggcctgtat aaattagtaa ctctgcagaa taaatttgaa      5880
attatcggcc agaagacggt tcatttcagt gagtgtttga tattctgatg tatggttgcg      5940
agtgaatgcc agagccaatt gacctttacc ataaccagta gtcaggggtt tcatgttctt      6000
ggctgaaaca aagattacgt catattcaat attattagtg cccatggtac gggctagttg      6060
cgaacggcct tgacgaatgt gagaaagaat tgcatccaac ccttgtttag aacgttgacg      6120
tcctacaaag aatcgtgctg ctacttgtcg ccagtcagat gaacctttaa caaagaagta      6180
aaaaccttca cgagaacgaa actctttaga aacttcagaa ccgtattcgc cattacgaac      6240
tactgcaaca acttcaccgc caactgccag aaggtcttta cgagttaaat atttggacat      6300
gctaatttcc tcaattgatt aatgttttttg taatccatga gagcattata ctctgctctc      6360
aagagtttgt acaattttat tcggctatat cagaacgttc aaaagctct  tcaacagtta      6420 aacattcagt gtcatcttca ataaagaatc gagtccaaca cgttggggcg atacagttat      6480
gagtttgtcc ggcgtagaa  gctacacgaa taagctgctg accattattc agaacaaatt      6540
tttcaccaat ttcaacatct ttaaaaagct tagccatttt tgtgttcctca tgtttcagta      6600 ggactactat accataatcc taccgtgatg taaacaatta aattacatta aaatatgtta      6660
```

```
aagccagcca tgttccagtg aacgaacatg caatgtaaaa aacagtatca caaattgttt   6720
ttagtacaat aagaagtgca tttttcataa gtacctcaac acaattgaaa atattataca   6780
aatcattggg atactaagca accatattcc tatccacatt ttagagctca tatctcaact   6840
tccgcgagtt ccatatatcc tttgttgata acctctttaa ggtctttaga aagaataaca   6900
ttaaaatggt cgttcatatg cccgttaacc agacgagtta tttcggcttc agatgacata   6960
taaggcacgt ccgagtccca atgagataga cctaattgag tataaatcat cccttcgtca   7020
tctgcagtgt tgtacattga acaaactca ccagtcactt tatgttttgc gtagaaaaat   7080
ttaaatttca tgatgttatc ctcttttaga taggactact atatcatagt cctacttagt   7140
tgtaaacact tttatgaaat taaagatgaa gataccaccc gttgtagttg ctcttgcgga   7200 cgatttctt taggtcttca tggtctccaa cgaactttat agaataagag aagacgtcag   7260
gtgatgtttc tttgacattc aatataataa tacagtcagc gactcgatga ttaaggaagg   7320
gccctatgtt gattccgttg ccacccggat aatcaccact gtatcctgtg gtaacagaaa   7380
tccatttcga atccatctga tgggtcttta cttctacgcg tagaccacag tacttaggat   7440
gagctaaaac gtcccatgca tacgtgtacg ggtcttctac gtcttcatta cctttattaa   7500
catatccgtc tagccaattt gctactacat actctgcaaa gactgcaacc ttacaacgtc   7560
gaacaacgtc ttcttttatt tgtcctggat cttgtttcaa cgagtaccga gcagtatcag   7620
cgatcttaac cttcatttcg ctagtcaaaa actcattcga caggataaat gtcggaagac   7680
tcttcagcct caacagtccc aagttcgtct ttaccataga tacctctaat gtgtagttcg   7740
ccaaaataaa tgcggtcacc ttcttcaaga tattctgcat ctaccggtgg gatttcaata   7800
acaacttcgt cacattctaa ccagccgtag tgtgcatcac ctgggtgttt taccaattta   7860
gcacaataaa cggatttaca cttatgatga ccacgaagat tagcaatttt ggattctgat   7920
acgtcaaatg gatgaatcat aattacccct aaagaaaaaa aaggggaccg aagtccccaa   7980
ttattattct gcaaataatt cagtaacgtc tgaaattact tcataacggc aagtacgcat   8040
cttagcatca ccgtagtcaa ccgggatgga tacaacatcg cgtggatgaa ctttaacttt   8100
cacaacttta tctgagcttg aaccaaagtg gcgaatataa gatttagcac aaacatggag   8160
accgcgagaa caggtttgtg tatcatcatc gttaacacga gtacgaggca ttgaaacaac   8220
tttacctggt gagttatcaa atgtaccgct ataacaatct aaatagtctt tacgaactac   8280
tttccacgca tagaaatacc catcttcagt gatttcaata tcgtttgcaa ccaagaagtc   8340
gaataaacgt tgtacagctt tttcgcttgg gttttctaac aggttttcaa ggaacggcag   8400
atagaattta aagtcttcgc cttttttccat ggaatcaata atacgattaa ccagtcctga   8460
acgaatttct atacttgat aaaataaact accaccttca atagtaacat taccatcaac   8520
aaacttagta atagctttct tgatgttaat aagttcgaca gctttactaa ggtttcctgc   8580
gaccagatta gctttaattt cttcaaaatt tgcatgactt gacggggtcg cattgtatgc   8640
tacgcgtcct tcaataattg aaataaattt agatgacgcg ttccatacga tttcaggacg   8700
atgtccgccg ataataggtt catcattttc tggaacttct tcgattacat aagaggcatc   8760
gtttgcttca gggacaacgc cttctgcttt aaaattctta acaatcttac gaagagtatc   8820
tgttgaaatg tcgaagtaat cggcaatttc tttacgagtc catttgcctg attcaaccag   8880
gccgtaagct tctaactgtt cttcttggga caagcatttg atattgtaca taatgtttcc   8940
ttatttggcc gcttccacgg ccttcatgaa tttaacgatt tgagcgacct gttctttaga   9000
```

```
aagagtacca cgtcgtccca tgtattctga cacaatatga taattggttt cgaattcaat    9060
aaccatttta tcatcattat cgtaagcatt atctttaagc ttatcgaaaa ttttagcaca    9120
caattctaac ttcttattca ggtctgtatt agtagcacct gcgaatcgat tccatcccca    9180
acgattattt actgttgaga gttttgcaaa atctttactg atttctttgt ttttagagct    9240
aaaatactta ctaaggaagt taagctcttc attacgagta atatgattca ataaggctg    9300 tgctctacga cttggtgata catactcatc ataatccact ttatcgatta gcgtaatata    9360
gtcattaatt gatttttcga caagcattc tacttcacca agtttacgaa ctttcttagc    9420
aatctgtgga cgaactacag tgaactcttt aatacctgac aaatcagcaa tacgggtcaa    9480
gaaattggag tcatagttca accaaccttt atctgcgtca agacattcag cgttagaacg    9540
attacgaact atagcataac cttggatttc atctgcttca cttgccggaa taaagaggtc    9600
ttctgatacc caaacatcgt tttcattctt aaagaatcga tgagcacttg gcgatttagg    9660
acgaggctca ttagtccgtt tcctgacttc aatccatggc ttaacgattt gtaaaagctc    9720
tgaagtcttg tacatgttaa tgttgtcgcc atcaaagata actttaaggt gttccagaag    9780
tttcattgca tcttcgtctg tagggtcaac gaatagtacg cttttaccaa aaccacgtgg    9840
aactttaccg ataatttaa cctcgtcttt agacatttca attgaattaa gagctcgcat    9900
taatggaacg cgtcccttaa cgtcgtcaat aacaatttca cgttttaa tgttaatgcc    9960 gatcaggctg ttaattgaaa tggttgatga tgagctacca ctttcacaaa tacgacgaag   10020
acgaggggat tcaacgatat cgtatacgac accaagatta caccactcag gtcccatttt   10080
aaaacgtttg tacagctcag aataagttag ttgttcttta gagtatttca gtgattcaat   10140
attagacccg gcctttttcca tgtatttacg agcggtatag ccaagagaat caatttcgcg   10200
gaacacatga cgtgggtatt tacaatcaat ccatttctta gaatcttcag cgaacaattt   10260
agcatcgatt tctgcaacgc gtttatggat atttgctact gtacgtttat caaatgacaa   10320
tgcttcacga gacggagcta cgtctagttc acccataggg aatttaatat aagctgtagt   10380
gcatcgtgtc atcatccatg tttgttcttt aataacactt ccgattggat atacaatacc   10440
gccataaaca gccatgatat taccacgttc accccatgga gcttccttgg ccaaatatac   10500
atcatcaaat tctgggaagt atttaatatc tttaacacca cgaacttctg caatatcacc   10560
tagaggacgc ataacatatg caatttcgga tgcaaacttt tcaaaatctt ccgggttaac   10620
cggtacaact acttctacac ccgtacggtc atcaggaccc atcttatcta caaaggtcgg   10680
cttaatctgt ggacctgtgt catcttggta gattacgtaa ccacgaactt caccattatg   10740
ataagacgta aggttaaacg tatcagtata tgctaatgga gctttagagc cgagtccgaa   10800
tccaccaatg aaatcgttac tcgatgtttt agttgaagca aaatatgagt tataaattcc   10860
tggctcttcg tcattaccac gaatagtgaa atcactcata ccaggtccaa aatcacgaac   10920
tacaaaacgt gggtctaaac gacctggagc ctgaacaata aacttatcag tgcaaccgtt   10980
aagaatttgt ccatcgatac agtttgtaat taattcacgt acacaagcta attctttgtt   11040
tgtataaagg tcattagaca aaatcttata aactttgcta ttgccttgaa tagtaaatgc   11100
tgtgctttta ccgcctgaac caataatcgt ttctttagcc gtttcaataa tcatatttt   11160 ctctcatcac aagttacgtt taaaaatttc tgctacttca agaagttctt ctttagtagc   11220
tgtgtcggtt tgtatttat atcgaatttc cttaaagcgt tctttaaagg actctgctga   11280
ctcgatatca aaaatctttt ggataagccg gaattcccgg agcactgctt tatcaaaaag   11340
ttccaagtcc acgttatatg ttctcataat attctcttca gtagattcct agggcactat   11400
```

```
tactaaagac tatataatct atcatcttat gtgtaatagt gcctcaggcg attcaggatt    11460
tacgctgtga agattttatc ccacatcgca acaaccgcat ctcggttata cttcttccat    11520
actgcttcag cacgtttaac tcgagcttcg tatgtgtcag tgaattctaa tacagctttt    11580
gtgtaaagcg caactacttc tttcttagga gtagagggat caatttctac acgcacagta    11640
tctgggtcat attcgaatgt cgcgtgcgga taatccttaa aaactaactg aatcacaggg    11700
acacctttag agatggcttc aatagaacta ttctctaccg tacccgtgtc aggacacgta    11760
ttgataagtg ctttagctgt tttaagacgt tccatgattt cactgtgtgg agcatcaata    11820
ataacaggat acttagccgg tggtgcccat ttactaggac aataaccaat accattttcg    11880
cctagtgctt taatcgcttc aagagcaaca tcagtacgac gcattttagt gtcataacgt    11940
tgtgcactaa taatcagatc agtcgccgga agaacttcag gtttctcatt caaacaaata    12000
accggataat cttcagcttc aaacaacgga tttgctcgcc aataatcata atcaattttg    12060
tcagtcagac ctgaagtcat ataacaatat ttgcgttcaa attcacggaa ggctttagta    12120
ggagcataac tcttaccacc gttcttatga atttgaatag tctggtccca aatttgaaca    12180
atgccacgag atacaggttc aaatggtgtt gccataaaat tcttatgaac tttagaaaga    12240
cctgcgtctt taattgcctg aacggttagt ttggtcggtt ccattgtaac aacgaaatcg    12300
tactcattaa tgccggctag ttcaacaatc ttacgagcca tagtataact catacctaga    12360
ctgaatttag tcagatgacc aacaggatga tgattaacct tccaatcacc aaatgtgtca    12420
ttatcaaagc cgatataatc aatatcagca ccgatggaca caagatattt caacacattt    12480
aaatgtactg cttcaagacc accttgtaca cgttctgggt taaatgggac tgcgcgagat    12540
gggataaaca taactttcat aattaagcct tattaaaatt aaaatgaagc tcccgaagga    12600
gcttaggaca tccattcttt acgaagttct gaatcatcac ccatcagcat ttcaaagagt    12660
tctttccaat tttcaggaag tttaactacg tcgtacacag ggttctgaat catttcacga    12720
tactctgact tttcaaggga gcctaatccc ttaatgtatc gaatactatg cttaggcagt    12780
gtatctttaa cttcttcata ctcagctaca gtataaaacc attttgagt tttaccaatt     12840 tgtgcaataa ttacaggcgt tttaacaaag cgaatacgtc cttgttcaaa caattcaggc    12900
caattactaa agaaagcaag caaagcagga taaatacttc caaggccgtc atgatcggca    12960
tcggtcataa ttgcaatatt acgatagttc gtattctctg cttttttcacc aagaataaga   13020 cccgtgatag cacagatatc aaagagctct ttgttcttca tcatatcagc atatgacata    13080
ccccagctat tcatcacctt accacgtaat gggaatccac cgtgtagttc acggtcacga    13140
acatcaatga gatatccaat tgccgaatca ccttctgtta agaacaatgt cgtatctgca    13200
tctttaccac attggttagc tttaatatgc ttatgaacct tagctttagt tgcctttta    13260 gctgctttag tttctgcagc cttttctgct gccaatttac gagctaatgc tgcttcaaca    13320
ataggcataa tcaaggcttc gttttttaaga agtgcctgag caattttctt agcgtctaat    13380
tggatatgat tacgaatatc accatacgtt gacgttaaac gttctttagt ctgagaatca    13440
aaacgcatgt tgctcatgtc tctaataaac atcaacattg tgagacattc tttaacacga    13500
gctttagtga cttcaatacc cttatatttc ttttttaatac ccggcaaaag atgttcgcag    13560
atatcgtcca ttacacattc aacatgatgt ccaccgtttt tagtatggat gttattcaca    13620
taagttaaat gacggaagcc atctggcgat gttgtgaatg ctatagagac tttatcatt    13680 tcttgaatga tgttatcttc gccaaattgt ttagcaaatc gtttaaaatt accatcgacc    13740
```

```
tttttaccat taaatgtgaa cttgatatca ggataaacga ctgccaatgt ttgaagtcgg   13800
tctaaagtaa tatctaaata aatttgagat aaattatgct cttcaaatga agtgaaatca   13860
ggagtgaaga ttactttagt gcctttacct ttagatttct tagaagacca tgatttgttt   13920
tccattccgt ttgaacagtt aacagtgatt tcattttcgc catctgacgt gatgcctgta   13980
aacaacgtag agaagatatt agttaaacta ctcccgacgc cgttcatacc accagtcttg   14040
cgttcagagt catcaccaaa gttaccaccg gcctttggaa tagtccaggc tgctacaggc   14100
ccaggaattt gttcacctgt ttggtcggta actaaacctt gaggaatacc acgtccgtta   14160
tcttccaccg aaacttgatt attttttaatt tgcacatcaa ttttatttgc aaacttaaat   14220
gatgtacgaa tagcttcatc aaccgagttg tcaataatct catcgattaa tttaaccaga   14280 cctgaacat attcaacttg ttgatattta ccaaacaaaa aacgctcgtg ggcttcttta    14340
gcagaagaac cgatatacat accactacgt ttcttaatat gttctacatc tgacaatacc   14400
ttaatttcat ttttaatcat gttgtctcct cgttatgaag gtattctatc atccgaaatc   14460
taaagcaaaa agggccgaag ccccttattta aatttaattt tctgaagtgc atcaattgca   14520
gccaaacgcc cttgttcact tttaactgta atgaccacat cgcctgatac gatcaccgaa   14580
ccatcaacaa attctataga gccttttttg aaatcgacag ctgtatctgg ttcctgaact   14640
tcttcaaaga atttaaattc tgcaccataa agcagaatat caccttgcat actatgaata   14700
gttcggccat aatcgcctac ggcttctaca gcaatcattg aaacgccgta accaatcatc   14760
tcttccacaa taaatctttt ggacaataaa gtagtatgca gattagtatt aagacgttta   14820
ccagtcgtat taagaattct caagaaatta tcttcttgac ctttgataat acgatatttc   14880
ttaccaactt caaaaccttt aaaagccata attaacccctt cttaagtaag tcgtaaaaac   14940
caccgttcac atgtttagga gcagaaaccc gacgagtaga cagacgatga cattcagggc   15000
aaacatcgtt ttctcgttca gaaattcttt taatttttttc atattcatga ccgcaatatt   15060
cagattggca tttatagtcg tataacggca ttattattcc ttaaaatgtg ctttcaacat   15120
ttgatacaaa gaccatgcct ggtcgttatt ttcgatagta attgtcatca ccggaaattc   15180
agacaattcg tcaagttcac cagaatcttg ctcttcggac gcttgatacg gatttccaac   15240
ttcgtcaaag aactctgctt cattcgtaga gagccagata aagttttcat caagaatatc   15300
accgcctgtt gcgtatccaa ccatgccagt agatgtcaca attttagtag gacgaccaag   15360
atggtcaaca tctaatactt taaatggttc catgccaaga cgtcgtgcat aaatcccatt   15420
atcggtgtgg tccttaataa actcttcttg ggcacgttta tctttaaatt ggtaccatga   15480
gttaacgcgg aatttattag ccattagtaa gtttccttcc aataagttgt accgttttca   15540
gtgatttcac ggaagatacc atagatgggc atttcatcgc caagttttttc gtaaacgtaa   15600 accacttcgg tgtagcataa aaattcggtc cagttttttct gtacaacaac taaatcagga   15660
ttaaacagaa catcttcaaa ctcatcgatg tttgaatcag tagttacgtt tttaatgatt   15720
tgacgtttca taatattctc ctcttgtttt gataggtcta tagtatcata gaccatagtt   15780
gttgtacatc attttagcaa aataaaatca acttgttctg ccaatgaacg tctaaacatt   15840
aattgacaac ttccgagtat gaaatcaggt gcttcataga ccgcgatgta gtatccttta   15900
gctttcaaga gttcaacatc cacttggtca tcaaaccatg cataaaccgc gtcaacactt   15960
tcaaatccaa aatagaaccc ttgagcccaa tcttcactca attcaaatgt gtactcaatt   16020
ctatggtatc ttaagatatt ttgttcaagg agtttgtctt catttactgt aggacgatta   16080
gggacattat agttgtcgcc gtgatggtag aagttacctg agagtattcc atgcttatca   16140
```

```
aggaactccc atgtttcttc agagttgtca gtgccagacc aaccgtaagg tgagcgaggt    16200
tctttattcc aagaggtttc ccaaattctg acggctttac cgtcttcgat aacaattcct    16260
ggtaatgatt cacgttgagt acaaaaacta cgttctacgc ggtaaactaa catattattc    16320
tcctctggtt gatatggtta taatatcaaa accagaggag aagtaaacaa ctttatgcga    16380
aagcagctgg gctatatttt ttaatttgga attcaggaac taccatgaac tgaccagcga    16440
aaacgatgtt ataaagctta acaccatctt ctacccaacg gtcgctaata aatccggcga    16500
tttgcttagt tttccatggc gttccatcag ttgccgcagc aatagtgaat tcatggtctt    16560
tttcaacaga aactgatctg catagtcccc atttgaacgc ttttttcttct ggctcaatga    16620 actggcttga gacgtagcca atattaccat tagcatcacg aactttaact tggttacgac    16680
caaaaaccgg atcactcaca gaaagaactt caaccaactt cccggcaact ttagagcgag    16740
aagcaacaga tacatatacg taatcacctg tagagagatt tacaatattc ataataattc    16800
cttaagcttt acgaggagac acatagcgag tgatttcaga ttcttttaaca actcggaagt    16860 cacctaagaa tacgatattg tataactttt caccatcttc aacccattgg tcactaatga    16920
agccgcacat aatatcagtt ttgtttggat aaccatattc gtcgatgaaa tcaaattctt    16980
tatcagtccg gaattcaacg cctttgcaaa gggcccattt gaactgtaca ttatgctctg    17040
tggattcaac tttttctctt gaagcaaaag cactactcac aggcgtttcc aagaactttg    17100
cacgaacata agcaaatttg gttcctgtg tcccaaaact aggaataata cgaactttta    17160
cctcagaatc ttcatctttta acgccttctt taagttgaat acttacaact tcaaccagct    17220
ttcctgcagc tttagaacga gatgcagacg atacacgctt aatttcacca atagtaatca    17280
taatttctct ctctttgttt aagttgaatt cattatactc catccgtcct tggatgtaca    17340
acattaatta aggatattaa ccacagcact acgtggaact acactaaaat cacctgcatg    17400
aacaacgttc agaagttcaa caccgtcttc aatccattgg tcagttaccc atccatttac    17460
tggacctgcg agcgggcgtc gaattgaaac atatttacac agcaaatcag taggctcaat    17520
aggcttaatc agagtaccgt acatacaagc gatatccata tcaatacaga tgtctttaac    17580
gggttctact tcttcaatca acagttcaaa gtctgtgctt ggaagggcgg tagtagaaat    17640
tgtaccatat gaattttttaa tttctaagaa taaccaaggg ccttcagctt gtttgatgaa    17700
gttaacaata gtgaaactat tgccttgagt ggcacctaaa atttcacaaa acttttcgta    17760
agctcgcact gaagcactgt accagttgat ttgttttttcg tctttcagga tgtaagtagc    17820
cgtagtattg atattcataa tgttttttcct gtttggttaa gatagaaaga ttatactcca    17880
accatccttg gttgtaaact gattttatcg ctgttttaca cttatcgggt caggattctc    17940
agggacatct tcaaggccaa gcgcataacg ctgagcatat tttaacatca aaatatcttt    18000
agcacaatca tgaatactat catgggcaac gaatcctttt agcgtaccca tcggtaatgg    18060
acacatactt aatcctcgtg tcaacgagta agcttcgatt gccgtacgaa tatcgcgttg    18120
agcccagaat ttaaccggtt ctaatttatc agtatcaatc tctggttcaa gaacaccttc    18180
atcacgatag agatcacgaa tcaaatcgac caagatcggg aagtcaaagc tcataccacg    18240
gcaccacatt tgcgatttcc attggtcaac tttattagct cgacaataat ctaaaaagat    18300
tttaatgcct tcaagcgtag tgacatcgtc ttcagacgga gccaggtttt tacgtgcttc    18360
tgctgattgt tctttccacc atttcatagt ggatttagcg aaaactcgct tccctttttg    18420
agaagctaaa ttaaattaa ttcgcttacc tcgttgaaca agttcttcaa atgattcaac    18480
```

```
aacttcaggg tcggaattat atgcaataac cgccaggtca ataacagccg cttttgatgt   18540
attgccgaat gtttcaaaat ctataataac atcagtgctc ataattttct ctcaaataaa   18600
atggacgtca aaacgaccac gagttgtgcc gacatacaat agctgtttag ctaattctga   18660
atcggcataa tggatacacg gtgtataaac aaaggccgtg tcaacagaca taccctgagc   18720
cttatggaag gttgatactg gtagtgcctt caccttagtg aacatacgtt tagcatccca   18780
gaattcactc catggagctt taccaccttt attccagaat ttgtatgttt ctgctgtctt   18840
agccaaaaac aaattgaatt tataaagctc ttcttcagaa gaaataaccc ttatatcctc   18900
gcggacgtat tcttcatcat ccccatatgt ttctactgta agattccaat atcgtatcat   18960
atactcgcct gaaacaccac gtgctttaac gaatgtagac gtttctacag catctcgaat   19020
acgaacgaat tgcccgttat tgaaaagcat ttcggtcata tttttgccat ctaacttata   19080
cgtcttggta acggctctt gtagaacaat gacttcatct ttaataaatg gcttttctgt   19140
ttcgagaagt tttcggcgaa taattgaatt taacttgtct actgactat ttgtgaatgc   19200 catcattcga ttttcgaaaa ggtcttcagg agttttaacg acattaaaat agttcatcat   19260
atatgattta aggtctgtat atccatgaac accgtgccca tcaactactt tatcataaat   19320
ccatttgcca ttacgaatat cagtcgcaac atcaataatt ggcgcattgc tacgtttaac   19380
ttctgtaagg ttgcattgca cgaagtcttt gtgagtgaag aaaggactta gatacgcagt   19440
ggattcgcct gggtctacag gtcgaatctg acatcggtca ccaattccaa ttactgtgca   19500
ccatttaggg atactagcta acattatttt aaacagagaa cggtcacaca ttgatgcttc   19560
atcaaataac agtacacgac acaaggctaa gtcgggaacc ttttctgtt caaataacac   19620 gttttcttcg tatgtagttg ggttgatttt aagaatgcta tgaatagtcg atgcttcttg   19680
acctgcaagt ttgcttagaa ccttttttagc agcgtgtgta ggggctgcta aaataatacc   19740
tgattctcca gaagaaataa gggcttcaac gatgaatcta gtaagggttg ttttacctgt   19800
accggcaggc ccattaatag ttacgtgatg tttcttttct ttaatagctt tcataacaac   19860
gttgaaggcg tttttctggc cttcggtcaa atcatcaaat gtcatcgtaa agtccctgca   19920
attggaatac taacaatacg gccagtatct agaattcgtt gatacaatct ttgcgtctcc   19980
gcatctagtt taatgtgttt catttcaagc ttattaaacc agaacttacg cggagtttcg   20040
accattctta gaactcccat tttttaaatct gttttatact gtgttttcaa agtatcgaaa   20100
actttatctg caatatcctt tctaaaaaat actgcaggac gatgttcatc aagtggaact   20160
gggacagtaa atccttccat atctcgataa actattgcat atacataaac cataattaac   20220
ctttaatcag ttggaataat gatgcgctaa gtggtaggcc acgtttcaat tttaatttac   20280
caatgaaacc aatcttttca aaacgttgca gaccttggat aacttatca tatgtatcga   20340 aaagcgattc agcgtcagtt aatttagttt tagttttcca gtcagagcct ttaagaagaa   20400
cgttgagttt agtaagttca tgtccttccg cttgatgtga gccgttaatg cgtgctttca   20460
aagcaacaat tctaagttta gattcgttag ataaaggttg attttttcatc atgttcgcca   20520 tatgcttaac acgattttca cgttttgctc ggattttttaa aatagtacca taaaccttt   20580 tgatttgggc ccatttcttc tcgtcgagat taagttctc tacttacgg gcagaaggat   20640 tagcgatacg tcttgcaatg gcatcacgtt tctcaataag ttcttctaat gttaaatcag   20700
aacgagccgt gttatatttt ttcttaactg ggataacatt accttataatg tagccgatat   20760 tgttatcaaa acgttctaag gataatttct caccttcaac agagttattg aaagattcac   20820
ctgagtaagc gcagaccttt tgatcaagaa tgttttttaag gtaattaaag tctaagttaa   20880
```

```
aatccttaga gcgtctcttc gcagaagctc tggtgtggtc aagacgacga tttattttgt    20940
taattttatt atttgataac ataatatttt cctctgtctt acggacgtta ggtcatttag    21000
ctgataggtc tataatatca tgccctcagg tagtgtacac tctttttttc ataaaatgct    21060
ttaatttttt atgtgttata atggttctga gttccatccg gttattccaa tccagtcagt    21120
aaccgacaat agacagattc cagattgtat aacgtccatc ttgaataata gaatctacac    21180
gcagtatagt ccctataggg agcataaatt cgcattcgtc agatataagt ctagcattag    21240
accgtcttgt tgcttcaggg aaagctccat gaactcaca agatggcgca gccagaatca    21300
tgttaagcat atgttcacgg aagttgaaag caaatggtgc atctttgatg cagaacatat    21360
taaatgttcc ataaaaatta tatgaagcga agttacgtgc tacactgaac actgggatga    21420
agctcattac tctatcaaat ttaataatac taccaatgcc tttatcatcg agtgtggtca    21480
tagttttctt agagattcca cgatacattg tctcgggaac tgaagacgtc caatttctac    21540
gaacaattgc acttaaatct tgttgaatgc tatcaggctt gttttccata cattgccata    21600
gtacactttg ttcaatgtcg ctgaattgct catcgatttt gtactgaagc atatcttgat    21660
aatctgggca ttgagcacga cgaaccattt cttcaatttc acactcgtta tacggcataa    21720
acatttaggt ttctcctgtg gttgataaag gtatagtatc atcatcggaa gagtttgtac    21780
actaaaaatt caacattttc aaatgaatga ttttgtataa ccgagataaa gggtcatatt    21840
ctaagtcttc aatttctaca atctcaaatc tagagatacc tgagaccatg tattcttgtt    21900
cagattcaat catatctagg acgtcaacac gttttcttc cataacatgc ttagggttct    21960
ttccggcgag tacaatgtta accatgtttt ggtagtaatc gaaatgaac ggagcattcc    22020 tgagactaag aatagtgtac gtttgatatt cccaactccc agagaactgt ctggccgtac    22080
caaagtctgt tgtaaacgat gttactcgtc cgggagacca atgacatcca acagaaagaa    22140
gggaaagacg ttctacttct tctggagtta caccacggta gagttctact ggtactgtag    22200
aagtcatatg cttacgaaca agatggtcta attcatagtg gaaatctggg tcttccttat    22260
aatcagtgca agcccagaga atgttttgtt cttgtttagt gaattatca tcaattagtg    22320 ctgcgagata ttcgcgttct tgaagttcag attgacatgt catgatagac ctccatttaa    22380
agataagcct atcataacac gagaggaggg aatgtaaact acttttaag cttccctact    22440 aaaggcccat cagggccagg ttgttctaac atgaataacg atgctttaaa aagcaatgtt    22500 aacccttca ccattcgata ccatgtctca aagtcttttt ccttgatttc tagtaagaat    22560 ttctcttaa atttctcttt catttccaag gactccatgg tggagggtcg tcataataag    22620
aggcaaggtc tttcagggct tcaacaggta aactaaagcc gtgtcgttgt ataatactat    22680
ctagttcatc aacaagttca ctatgatgca ctttaggagc cttgacttca ggctcatcaa    22740
acatactcat aaggtccata ttattcacct aaataaaaac tagcaggttc agagaatgtt    22800
tctagcgcta caccttttgt cttaaaaaat ttccaaatag ctcgttgcaa atggattaaa    22860
tctgctaatg atgtaataaa gtatttttg gcaaaatacg tatggtctcg cttttcaaac    22920
aggtctaaac gcttttcagg attcacataa accgcatttt ctgtggattc atacccaag    22980 tcctttatgc cttcttcaag actaaacgga gaattttag aatgagtaat agctccaact    23040
cgctctacac gaattttgta acctttagga atctgcaatt gcagaattc ttctacgata    23100 tattgcggat tatttagact tttgttaatg agaatagcta tttctagtgg agtcttatct    23160
tctactggta tatgtttaaa tgacttggct tcaagcaaat acattttaaa taacatagca    23220
```

```
tccattataa tttcctcgat ggttcaccca tataaagttt tacaatacgt tcgccttcat    23280
cttcgacgag ctttttcttca tgtttctgga attctttagc catattctct tcaagaacat   23340
ctaaccaatc ttctggaccg acaccatcgt cccagctttt aaaccattta actatcttgt    23400
tcattcgcag ctccatgagc ttgaaccaca atcagaataa cttgacccag aatcaccagg    23460
ccaagacgat acgtatgaat gattataact tgaagagctt gaagcattaa cctgttttgt    23520
ttttggacga ataacttctt ccatcattcc gtcaccaata tattcccaac ttttttcatg    23580
tgtatcagga ataggcatca taccttcgcc tggtttaaca gcaaacaact tcttcagtat    23640
cgtaagcatt aattgttcct cgaacaaaac gaacaccacc atcatcccaa cggatttcgg    23700
cattaaattt gacgtcttca ccatccatca tgaatgagtg tacgactaca tcatcgtaat    23760
atccaagacc gtatttcaac gaaacttctt gagcaatcaa agcacctaat gtgttattag    23820
gtttaatcca acgatttaac atagtgttct cctcttgagt aagtaagaat atcttaacat    23880
agttttttagt ggatgtaaac tctagaaacg aaaaaaggaa tcccgaagga ttccttaaat   23940
tatttaacca cttactggtg tagggtaaa cattgcagcg ttcttagttt tccagtcagc     24000
tgcatcagaa actacagtag aataagctgc ttttctgat ggaaagattt ggtaatgaga     24060
atctgcaatc cgatgttcgt ttgaataaat ctcaaacggc acagaaactt ccatacctt     24120
aacttcttta ccttcaccag caggatgcgt aaaggttttg atgtttacat aaccacccat    24180
aattaactcc tttgttgttt aattacaggt gtatttataa tgaatttctt cgggacaata    24240
aaatatccga atttagctaa tataacaaca ccaccgttaa ttattaccgg agaataatca    24300
tctggagtat taaatttcca gtggagtcta gtattatatc catcagagcc gaatgcttta    24360
ttagccggtc tcccggcttt ttgccatgca taaaaatcaa gtttcatttg caacccaatc    24420
aaccatatgt agatggtctg ataattgact aacatgctga agctgattag acaggagctt    24480
acaaataagc tcactgttat cattttttaaa tagttggtca atacgtttct tatgagcttt    24540
cttaagctga cgtttattta aacgagccat taataacctc ggtcttggcg agcgaagttt    24600
tcagcattct tcaggtaata cagtttaaag atttcttcag ccgaaagacc tagaccttgg    24660
aacatattca gaacgaaatg aagaatatca atcatctcaa atttaatttc aagctggtct    24720
tcaggagaca gttcatcgat acgacgattt cggtattcag catgttgtgc tttccaaggc    24780
ttccatacac tgctggcggc ttttttcacca ttgctcatac caccaagtga agtcagcagt   24840
tcacggaatt catcatcaat ataatctttc tgattacgca gccaatcaac aacatcacca    24900
gcagtggcca attcatcagg atgtttgtta tgttcaggct tgtcattagc cagacgaacc    24960
tgtaaagatt tctgcatatc aagcattacc tgcagtgggt ctttatcttc gtgaatcaga    25020
gcattaaaat aagcttcttc tgctttatca acaccagaaa taagttgtga acattcgtta    25080
aagtgtgcca ttatttttcc tttcaattca gtataagaaa gttaattcta acattaattt    25140
tataaagcgt aataaataat aggtaactaa ggagatatta tgtttaaact tccatcgtta    25200
atcaacgcta ttaaaggcaa taaaagaaa actgctatcg ctgcaatagt tgtaggtggc     25260
attatttcat ggaacttcgg gattgcacca ttgttagttg cccatggtat tatagttcct    25320
tctgttccat tggatactgt agttgatttg gcctttgcta ttatagggct tgtttaaatc    25380
ttcgaataac gagataatct cattttagca tgcaacccac ttgaaatatt ctgtttcata    25440
tattctaaaa tttcttgtgg tgttgcattt tctttcatta ccatatcatt cacatccttt    25500
gatctccatg gagctcggtc ccagaacatg acacgttcgc ctgcatcaac taatcgcttc    25560
atacgagcta tagtatccgg atgcctaggt tcattatcca ttacccatac ccgacgttct    25620
```

```
ttaaatggta ccacatctaa atctatcgag ccgcctgtaa tagcgattgc attgggtatg   25680
aataaactat caatagggcc ttccattacc cagacgtctc cttccttaac acgttcaaca   25740
ccataaattt tgttgcaga ctcaaacgct ttaatagtga tatatttctg aggagcatct    25800
ttgcgaagtg cacgtccttg aaatgactca gccttcccgt cttttattaaa aataggaatc  25860 actaaacgcg gttctggaat ctctttctta tacgtaccag gttgaatctt gttgaccaat   25920
ttaggccatt ctaatgtgaa ccataatctg ttccacgatt ctttaggaat acaccgagac   25980
ttaacatatt tcacaatagg atgctcttca ggcagcttgt ccagacgaga acaagacggc   26040
aaagaattta tagtcttttt ctccggttct ggtttatgtt caggaaccct ttcaatcttt   26100
ggttccattc tagctttttc tttacgaact tccattagat attcacgata aagctcttcg   26160
tcatactctt ttaagtatcc ggaaatcgta ttatgatatt gacagttata gcaatgcaca   26220
ttacctggag taccgccata ataccatccg cgggctttca ttgcatctgt ctgagagtcg   26280
ccacaaactg gacaacgaaa cgttaattta aatgtgcttg aattattgat ttgtctaaaa   26340
cgaggtaggt gagaaaacgc acgataagca aattcattat ctatccattc agccatagta   26400
ttctccagag gccttaaatt aataaggcca tcatatcaca acttattgat atttacttta   26460
attcgctttc ttttcttgga aggaatttgt tctggacctt tatttacgac tgcacctgta   26520
gttgttcctg atgcaatagc ttgagggctg ccacctgaat caccagccac catatcctca   26580
aataaaggga gttcttaaa tatttctttc tgctgttctt ctgtaatgtt atagcgggat    26640
gctacagcac tccaggcaga catcattgag gccattccat taagtcctgg aacagtgctc   26700
atcattcgct tcattgaacg aactgaagca tgaaaaggtg tataagccgc tttctcttca   26760
ggagtagaag gacgtttaag aacacttcca cgttcgtcga ttattttggc ttcgtacgct   26820
ttccattctg taaaaggttt ttgcattagt cgaataaact tatatgcata aactgaatct   26880
attgcagtgt taataatacc cataggtacc tcctgagtat atttaatcaa tcacaaagat   26940
cgctttatca ccgttcgcat ctgtgacttc atatgtagtg tcttcatagt gtggaatatt   27000
ccaaattaca ccatcattag cttttacgct aaatatggcat tggtgttttg aaacaacttc   27060
ataatcttca aaacttgtaa aaacactaat tttagaacca gtgcaaattg cagtagtcat   27120
tttaacctcg attcataaat gcattaaata tttggtcatc aacagaaatt tctaattcga   27180
cttcaattgt ttcagtcttt tcttcaggtg gtaattcgta tccacacact acaattttt   27240 catcgatatc aaaatataca gaagcaatac gattaatgtt actttcagtt aagtctaaat   27300
caacatcaac atctttttga cctacactta aaggataact aatacgagtt attttattat   27360
ctttaacaaa gagtccacca acatactctg tactacgttt gaagtttaca cgtttccgaa   27420
ttgaaagata tgatacatct ttaccgtgag ctcggctcat aggacataat gaataactag   27480
aataagagat gtcaaatcct acgccttcaa catgtgctag agtatcatga gtaaaccaat   27540
tatagtcgta tgctaaatcc attaaattat aatatgtgaa aggcactgga ttaacatcat   27600
atgttgtacc tttaaaatct gcccaggcga cgatttcgtt atctttaaca attacaaaaa   27660
ttataccgat atggtatccg ttattatttt cattcggtgt tatattataa cattgtgcat   27720
taggaaattt accatatttta aatggcgcgt ttttgtgcat ataataaatc atattattca   27780
cctgtgattt cggttacgat atctttgtta tcgaaattag ggtcacaata caaaacatag   27840
ttgtactgca tgataccgcc agacttaagt tgttcaacaa ctttattaac catattaggt   27900
cggtctcgtt tagtgatatt catgatatca gagaagattt gttgttcaac ctcttcttga   27960
```

```
tttgcagtca ttgaccactc acagaggtct ttatcataac ctgctgtaac tggagccggt    28020
gcacatgata ctgcaagtaa gattgctgcc aatgataact tttcatttt aactccttag    28080 ttgatttgat aggactacta tactatagac catctataat gtaaacaagt ttattctttt    28140
tcgcgaataa taattacttg ttgaggctgc tgagcagatt tcttttcggc gacgatagac    28200
caaattaaag ttccaatcca accaatcatc gtccagttaa agagtaaaga tacaaagaag    28260
attgctgttg tgcttttgt gccacgaata agtgcgatta cccaaggcaa catgtaaatg    28320
atgattgaac caatacctgc gattaaaact gctactgaac tagctacgaa taattccatg    28380
ttaatttcct cttgatttgt tatgtttata gtatcttatt ttaactttgg tgtaaaccga    28440
ttaattaaat ttgtttaaac gttcaataca ctggacgtag ttattcgcga tttgtttctg    28500
ggaaggctct ttaccagttg tttcaacata gcgaatgaat gcgatttcag tagcctgtaa    28560
gcaatgttct ttaacgcgtt gttcttttga caatgctaca gtatcagaat cacgataacg    28620
ttgagcatgg gcatcagctt gaatcattcg attacctaca gtaaccgggt cttccacttc    28680
aactttaggt tggttgtact gtttaacatt cgggttataa atcaattggc cgacattatt    28740
agggataaag ccatgagcac cacatccagt taatccaaat accattgcta aagtgattaa    28800
ttttttcatt tcaatttcct ctgtagttga tagaaagata gtaacacagt atgtagtgct    28860
tgtaaacagc tattttaaa attatcgaaa atcagcttca aaaactttct cgtcattaat    28920
aaatgcttta actaatgcat tgttcacttc agcaagttgt accgcaaccc actcgatttc    28980
ttcacgatca cctgataaca tgatatcttt agtgaacatc tcgccgcttt taaaccagcc    29040
aataaaagta actttagtta atttgctcat atttcctcgc aaaatgccca ttcagcgtga    29100
taaactgtag cacctttagt atcattcatt tgaactacat ctaccggaga aattactcga    29160
tagagacgtg gttcacctcc ataagagcgt gctgctcgtc ctgcataaat ctttgctaaa    29220
ccgatatctt cagtaaagaa tacacgatcc aagttttct tacgtccagt ttcagacaga    29280
actcctgttt cttcaggagg acaaagcatg ttttcgatgt tagctgaact acttgaaccg    29340
tgataaaaaa tcttaaattt tgctttacaa tcgatggttt tcattttgtt ctccagtagt    29400
tgataggtct ataataacac aactactgga gaagtaaact taaaaatgta atttagatac    29460
atctgcgttg atttcacttt ggtttgcgtc atatgcaatt aaacgaaccg ctttagatgg    29520
gtcattcaat gcatagaaat gatggaacat tgctcgaacg atatcaccat ttacgagttc    29580
tacctggata ggagaacctt tttcgagttg gaaatgttca taagctttga tggttcgcag    29640
ataatcaagt ttttgatttc cggctccaac gatttgtacg atacgtttgc ccatgttttc    29700
catacgagat acaatagatt taggagcaag aataacgtag gttgccagcg gagaaactac    29760
ttcaacagat gtgttttcgg tgattgcagt aaaaattgct tgagacatat tcataatgtt    29820
ttcctcttgg ttggtgtaag tacatcatat catgcctaga ggaagatgta aaccccgaaa    29880
ggagaccgaa gtctccttt tattaaaatt ttaactcgtt ggctaagcta tctaggtcag    29940
cacgtgttgc tttggcttta cctacgcgtt ccgtacgatt cacctctgcc tgacgcatct    30000
gagcacctgc gttttcattt actgtgttag gtgtgttcat gccttcttgc tcaatctcaa    30060
tccatttctg gttaccttta cgtacaccca tcaggaattt attccactta ttcttatcac    30120
catatcgtga tttgatttgt ttgataagtt gttgttcagc ttgtgcaagt tcttcggttt    30180
caattacagc caacatgaaa tctgctgttg ctggtaaacc tgctgattct gcaatatcac    30240
tcatgttcat gtctgaagca tcccatgctg cacgtcctac ttgagctgca gtccatagaa    30300
ctgtttcaga ttctactgct aatgcacgaa gttcttctgc gatagcttta actaatgtgt    30360
```

```
agctattttc agtgtaaact ctgatacgac aagacccaca aatacctaag taatcaacca    30420
tgattacaga tggcacaaag ttcttcttaa gttttaactc attaagcaat gcacgaaatg    30480
tattagcatt agctccacca gtaggatact gtttaactac taaacgtcct aatgttgttt    30540
ttgaacgcca ttttccatc ttggctttat attcagcata agatacgtta ccatcatcga    30600
tatcatcgag tgatacgtca agcatgtttg catctatacg cttagcacaa acttcttcag    30660
ccatttccat ggaaatataa agaacattat gtcctgtttg aagataatct gcagcaagtg    30720
aacaaaggcc taaagattta ccaacgttaa caccggccat taaaacgttc agtgtacctg    30780
tttctgcgcc acctttggtg attttattaa gaatgtttaa tttgaacggg accttacgtg    30840
ctttatttag ataagaaagc cagcgtgctt catagtcttc catccagtca tgaccaacat    30900
aactatcaaa cgaaattgaa agtgcttgac gcataaatatc aggaatagct cctacgtcag    30960
gcattttctt gttacgttgt tctggaggta gttcagcatt agactgaatc tcaatgattt    31020
tggatgtagc attatacatc gcttttttgct ggacatattt ctcagtttct ttaaccaacc    31080
attcgtggtc ttcaggagta tcagccaatt tttcaattag gtctgaagtt cctttatatt    31140
cggcttcagt taaagaactg ttatctaaag ccacctttaa tgcattgata gatggcattg    31200
cattatattc gttaacgtgg ctctttataa ttttaaagac attttttgcc ggtccacgct    31260
caaaatactc agaatccata taaggccaga ccttagaaaa ataagcctgg tcgtatacga    31320
gatgagacaa ataatttct accacgataa ctccttaaaa gaatttaaat ttttcttgg     31380 ttcgttcatt aaaagcttgt tgtacttgca ttgtaacaca tttttcaaca tgtggtgcaa    31440
gttctgcttt tctgtcctgg tcaagaactg caaagtccat tacgattta ccatcaaccc     31500 agtctagttt tgtaatatag actatatgat gggaaccgtc ttcaagtgta atcagaatct    31560
cttgaatgac attttccatt gctgaacgga taatttttaag agattcatta aacactcgtt    31620
ctttgcgaat gtcttcccct tccgaagaag gggattcatc aacgatttct agatttaaat    31680
catcgagatt attcatcgaa atcttccatt tcgtcaaggt cgttttctat atctgctgca    31740
gacggagcat cagaagcttt aacaggaact ttagttgttg ctttgcaatt aataaggtcg    31800
ttaacagcgt catcaacttc tttaatagaa gagatagcac ctagtttata tttagtttca    31860
attgcatctc ggaaaggttt gtgtttaaac aacggtcccc agaattctac acaatcagta    31920
gctttagcac gccacgattt ctcttcacga atcatttcac ctgtttcttc gtcaaggaat    31980
tcgcgagcat accaaccggc tttaggctta acaacaaatc caatttcagt tgccatttct    32040
aacaagccac tgaatggatc aataccgcca tcaaaattaa ccgtgattgg gaaagtagat    32100
ttctctttaa ctgtacgaga ttttctgct ttcaacgtga agtcataacc ggtcaattct    32160
gtaccttctt taacctgacg tttagagata aagaatacag tgttagcaga gtaaagaata    32220
cctgtaccac cacccataat ctctttagga tatagtccgc cgatttccat tgctgtatgg    32280
ttgattgcaa cacacggaat atctttaata gtcagataag gggtcacaat acggaacaga    32340
gatttaagtg ccttagcacg ggacatatca cctacgactt tctcgttcaa tgcatcttcg    32400
gtttctttct tagatgcagt attaccgatt gaatcgataa agataataac tttatcaccg    32460
cgttcaatag cgtcaagctg attagtcata tcaactttaa gttgttcgac agattgaatc    32520
ggagtatgaa ctacacggtc taaatcaaca cccattgaac gaaaataaga ttctgaagca    32580
ccaaattctg agtcatagaa caaacagatt gcatctttat atttcttcat atacgctgca    32640
accatagtta gtccaaacag cgttttaaag tgtttagaag gtgcagcaaa aatagtcaag    32700
```

```
cctgattgca atcctgcatt cagagcacca cctagtgcaa tattcaacat cggaatacga    32760
gtagggactt catcacgatt attaaacagc ttagacttag tcaagtctgc agtcatttta    32820
gaagtagaag ctttaatcag acgagatttt aaatcagaca ttgtatttt ccataggcat     32880 cattatattt tactcatgtt taaaagataa aacgattata tactaagggt tatacagcat    32940
ttaaaacttt aaacaggctc ttaacgagcc catttgatga tttctgtaat caaaccatta    33000
cgttcgcttg cattaaatcc tataactttg ttagcaccat catgattaag taattgatat    33060
gtttggattt tgttatgaat tgcaaactct tcaaaatgtg aaatgactgt attaaaaccg    33120
aatgaagaca aagtaataag gtcgtcttca aaactttcag tcatttcgtt acgtgttaaa    33180
ataattgtga acacatcatg gttttggcaa agacgaacat agtcctgttc ataaacgtca    33240
agaaccgagt ccgcatcttg tcgaatacgt ccataaaccc agttactaat atatccacgg    33300
tctaacagat aaatcttagt agggtctaaa taattcaaca tcgtttcgaa acagccaact    33360
tcatttcgag acttaacatc gaaacgccca tcaactgttc gtttagggaa atcaatcttt    33420
acatatcttt cactaatttc cattatgtca ttaatgaaag ttgttttacc agcattatcc    33480
ggcccgtcta ctaaaataat tttagccatt ttattcctcg attacgacat cttcgtattt    33540
aggtatatta tacggtgaag aaattaaagc attaaagtag atgaactcac caagacctgg    33600
atggaatact tcttcaggat tttcgaaata ttgaatcttc ggacgtcctt taagaatttg    33660
atagtactca gttttagttg gattaaaaat tcgaatcagc gcttcttcag gatacttatt    33720
tctgtcgaaa ctattatttg gatcagttat ataaagcggt tgacctaatt gaattgcgca    33780
ttcaaccact tgttcaaaac gatagcatgg gtcactaatt cgaaatggat gaaaaatacc    33840
atctagatga ataggagcca aatcacctac aagacgctgc atgatggaag gacgtataac    33900
tttatgcgtt acgataatct tattaccatc tgcacctgcg ttaaccagca cttcttttg     33960 acgttcattc aacacagtag tttgaagtga acgattaaca gacaacatgt cggtttttaa    34020
gaattcatca atataaaaac gtggtttatt agggtctgca gtgatattga aattgaattc    34080
tacatcaaaa gcgccgtcat atccagtgat atctgtgatt agaaaatcac aatcataata    34140
agcaattaat gaatcaacca caaattcatt ttcagaccaa aaatatttac gagtgttata    34200
cgcgttatct ttataccata atggaacaaa cttaaattct gggaaaagac gttcacattc    34260
tttaatatca gatgcattac gtggatatgt aatcacatca cccggattag cacggtgcaa    34320
atgaagttgg aagttgccat ccttaaggat agcatactgt ccagtttcat aagaccgcat    34380
actcaagata ggtacgcgga aaatagccat tagtcaagga atcctttaac ataatcaaaa    34440
tcacgttcaa acacatgggc acttaccatg gtatgagtat aatcaccaac ttctacacca    34500
cattcgttag cgatataatg aagtaatttt ccttggagat aaaaatccaa ctgcataaca    34560
acagcacagt tctgggaacg catatgacag tgggtataaa gcttaccgtc acgaatataa    34620
taagtcactg agtcagtaca tggatattca agcgtttcgt ccgaatcaag caaagcctga    34680
tcagaacttt ctagaatttg aacacaact cttcgggagt taggcttctc tttaagttct      34740
tttagaagag ctggtaattg ggccgcaatg cgaggaccat agaaagtgtt gaagttcgcc    34800
ggcaaaacat ctgattttgg tttagaaata aatttagcga cattaggata tgccttaaac    34860
gcttcttctg cgttggtacc accagaaatc ataaacttcc agaagtcttc ggcatattca    34920
taagagatgc ggttaatacg tgggtcggtc atttttgaatg atgatggagt gtcaacaact    34980
actgtcatag acccaatttc attacaacgt ccaatacgag aatcagttac gaattccggg    35040
ttttctaaaa tttcacgatt gactgcttta aatgcggttt gaaaatctgc ggctttgata    35100
```

```
tatttcattg tgttatgttt tcccatgttt acctcaatac aatttattat atactcaatt    35160
cgtaaagctt atttgaattt cttggcaatg ttgatataac gtaaagcttc agaatctata    35220
cttccaagaa cactatgaag gaatgcatca gtgtagtatt ccaattgaac aggttcttta    35280
atcactttag ccgctttggt ttcaaacagg cccataaggg cctttttaag aatttgttcg    35340
atagtgttca gtttcatagt caaaatctct tcgttaagtt tataattaaa acttttcta    35400 gaaatcattc cgggtacctc aaagcgtcat cagagttagt tatatcaata atagatatgg    35460
agttttctgc taacccgttt ttagataatt gacgtttata ataccttta caatatgtac    35520 acgttgaccc acagatttca ttagcacaat caaaatctgg atgtctgaac caccttttt    35580 ctaaaaagcc atctaacaaa gaggtttcaa tatttactgt atgtgaaaac tcagtctcat    35640
tttcaagagt gaaaatagtc tctaaaggct tccacagttc taacaaatta ccttcaaact    35700
tttcagaagc gtatgcttca agaactttca aaatgtagtc tgtgctacct gtacgtcctg    35760
aaactttgaa ttgagtgata ccaatatcat tataaagttt caaatcttga ggacgaacaa    35820
aacgagttct cagccagtta aatgggtctg tatcacgagc tttaatacag tgctgcattg    35880
gatatccatt taaggattta gcatcatcag cggtaacatc agtactatgg aaaatatagc    35940
aagagtcacg atagctacaa tgtgttgtat accctttacc agcattagaa cagaactcat    36000
ttacaagaac ttcaaatatt atattgttct tattgcaaaa ctctgctgca cgcttcagga    36060
aagaaactga acggttctta tgaattccgc aacagacctt tttgatgtta tattggtcgt    36120
gcaagtattt gatttgagtt acagcatcga catgtagaat tgttgaaact tcaatctcaa    36180
tgtctttatt gacttcacga acaatttcca taacaacagg gttagcgata gtaatacgcc    36240
atacgcctat tgaccaaaga tactgaacat aatcctgaat agctttcttc ttccactcga    36300
ctagttctct ttttgaacca ggatttatcg tgttgagtgt atagttaaag caaataccta    36360
attcgttaca acgtttaacg taatcttcta acatcttttt gtcaacgtca ggaagcctaa    36420
aatcaggtct ggctgctaca aaagccattt ctcttgtaga gccgtatact tcgtttatca    36480
agctattagg ataagtttta ttgagctcta cgatttttatc aagaagagct aaatcaaaat    36540
tcgttccgat ttttaaaagta ttcatttttt gcatctcgcg ttaattgatg cgatggtttt    36600
tgcaggtctt acttaaatta ttatagattc ggtttatatg atttaaatgt ttcgaattcg    36660
cctttattca taagagcttt gaattcgtca ggacgcatag ctttgtcgtc gataatccaa    36720
tcatatactg gttatgtgt tagcaaatta tggtacttca agccaatgtt tgccaagttc    36780
tgaatcagac ttgggagaat gtcaattgct atacgaccag gacctactga cttcatacca    36840
cgagcagtgt aaagcgttat ggtatgccct gcatcataca gggcattaat ggcagacacc    36900
atttcgacgt ctggtttgaa gttcacgtaa tcacgattgt tattccactc tgttatacaa    36960
tcatcgacat caaaacaaag attaagcatg ttttctacac ggtgcattag attcgttccc    37020
attgatgagt gatatcgcca ccgattggac gataggaaac accagtttct ttatcagtta    37080
gtacccattt accaggattt tttgtaatca gagtagccgt tacaggttct gctacgtcat    37140
aactaataga gccgtcttga agtacacggc ccatgttatg taattgctta gtcagaagtt    37200 ccatacctt ataatatgcg gcaaccgctt taagtggatt attcttgaaa taaccaccta    37260
atgcaatcca gataattgct actgccaaat gatgatactc gttaaacgaa ctcatctttc    37320
catatttgta aactaatgga ttgatgttaa tagtcacatt acaagttgtt tcatcaatag    37380
taaactgacc ccaggtcgga ttagcattga attcatcata acctgaaaca gcataaagca    37440
```

```
ctttagcttc atcatacaat tttggcccgt aaatcttggt ttcaccaaaa tatccacgag    37500
ggtcgataaa cttgacttcg ccgttatcgg taatcatagt attactgaag ttcgggtcac    37560
catgaataac agagtactgt ccctgagaac ggttatgata acgaataaga tgttctaaag    37620
cttgtttcaa cattggcttc agacgtccaa tcttagtgta gttcacatgt gtgatttac     37680 caaatgaatc aatcaatggt tgaatacttt cacaacgatc aataactttc gtatagaatt    37740
ctttagtgaa atcacggcga acagtttcag gacttacaaa ataagtgtct gtgctgaatt    37800
tcagtgcatc taaaattgca tcaacaattt gtggacgagc aagactcgat ttggatttaa    37860
tatattcaaa tgccggctta cctttaatgc gttccatttc aaagttattt tcattaacag    37920
aaactaactg aggaactgaa tctgatttca ctttaagata ccatgaaatc tcatctttct    37980
gaagagctcg gccctgttcg gttaatgcga atttagttac agtttcttca ccaatttcaa    38040
ctgcattaaa actacgatta agttcacgaa cttcatgagc tttttcaagt ttaggcatat    38100
cacctaaatc aattagattc ataagctctg atttattgaa tgcgctgccg taaaggaatt    38160
ctacgaaatc acgtcctttg cagtattcat gaatttcctc atcagtagaa cccatataga    38220
attcccagtc tttgaactga taaattccta caacattacc acctgttgaa cctacgttag    38280
tgatattttc accgtcgaaa ttatatcgac attcgtcacc cttaacatag attgcgttaa    38340
cattccaaga ccatgaacca aaatcaggaa taatatcaca ccagttaaca attacattat    38400
ggccatctaa atctttgtgt aatttagcaa gagcataagc agaaccatac gcttcatcaa    38460
ctgtacgaat agtcacattg aacccttctt gctcacaata agctcgaaca gtttcagcaa    38520
attttgaatg aactactaca ataatttcgt ctgcgccaag gtcagaataa attgtataca    38580
aattgctcag aatagtgtct tgtttatagt taacaagcac cttaggaata tggtgagtaa    38640
ttggatataa acgagttgct aatccagcac caagaataac agcttttttc atgttgaagt    38700
cctcattggt aagtaggtgt attgtacact attctagtta aagcattcat actttgcctg    38760
tagaccaatc ataatccatc caattacaag tgttggaatc attaccggag ccgttaagct    38820
ccagtagata gtcatgacaa gcatcaatag taaaagtcct attgttattg ctttcattgc    38880
tcgcctcgta acatggcacc tagtgcaccg cctggatgga acttaaggaa atcattagag    38940
gtaaatccac gttcagatga aaggttgata gcgaacgtat cgataagcgc taacaacaat    39000
gtagtagaca tcgtcggagc taaagagttc tcgtcaactt ctaccgcgat accggtacag    39060
aacgtataat caaaaagagc ttcgtattct tgtggaatgt cagggttaca atgtaacaga    39120
atctgtttaa cctgaggacg aatcatacga agatgtttag caacacctat catttcttca    39180
gtcttaccgg aacgactgat gtgaactaat acatcattag gtgcaataaa tcctgcgtca    39240
ccatgagaat aatgcccagt gttcaaatac atgctaggaa tacctagtga agcaaatgtc    39300
tcagaagctt tagttgcaat attagcattc ttaccaacac ctgtaataat tactcggctt    39360
tcataattac tcagtccagg gcgtcgaaga gtttctagaa tagcattata acgagcaggg    39420
ttttgactaa ttactttggc catagcggcc aaagaagaag cttgttttat gattgcgtca    39480
atagcgatag taataggagt agttttcata tttctctcat ttaattagtt tactgtccat    39540
gacattatat caaaaatcga acatatcgaa cagagatgct ttcttctcgt aatcgagttt    39600
cgctgctgat gtgaatcctt caagtggttt aataaatgtc ttctcaagga gaacagtgta    39660
gtccatccaa tgaagtacgt cgtctttaat taaatctgtg atttcagtac cagaaggcca    39720
tgcgatacat ttatcaccga atgggttcc atcacgtaaa ggcagaacgt atacctttc     39780 gccttctaca acttgtggag catcaatatt acctttgata gctctgttat atgtcagaat    39840
```

```
tccacgaata tggaacgggc atttgggacc agggaatcca ccaacgtcat atttagcaat   39900
gttattcgca gaagataccg acgcgatgct aatataattc aattgacgga attcttttc    39960
aaactcttta aaatattctt gtaatgattc ttccttct tgaagcatac gacgaataca     40020
ttctttaaga gctttctgta ctgctttagg ggtcgaagat ttctgagtct ctagacccat   40080
gattttgagt ttaggctcag cgtaacgagt accttccata tcccacacgt ttaatgcata   40140
acgtttctta ccagtccaga atccaccaat acctttagaa ccgagcggag gaccagcgat   40200
agcttctcgg tccatgaaca ttaagtgttg tttattgttc atgtattcgc acatttcacg   40260
gaaacctcta tcaatagcag gttccatacg ttcacgagcg aacttatcta agaagtctac   40320
ccaatggttg gtatcacgga atttagattc accaacctta tcgataattt tatcagcaga   40380
tacgtaaata gagtctgtat caccataaag aacgaaagct tcaccttccg taccacaaac   40440
ttcgttcaga tattcattaa ctttacgttc aatccactgt aaagccattt gcccaaatgt   40500
tgtgattgca gtagcattac gcaaatcata ataacgaac catacgttac caagtgcacc    40560
ataaagcgag ttgatgagca atttacggtt aatctgtgca gtcatacctg caacttcagt   40620
acgttgagct ctaaacaaca tttcgttaag agatttagca gacaactttt taatcttttc   40680
tttaatctca tcgctgaagt cgaaacgata atcaacatct aatggttcgt caacagaaag   40740
attaggatta tgtaaggctt ctttaattat ttcaccatta cgttgagctg caagcatgta   40800
accttatgt tctttacgtt gattaaagac cttagtgatt tcagttggaa ctacaccgtc    40860
acggtcttta taatcatca tgccgttagg agagcaactg tacacatctg aaggacgttc    40920
agcgattgcg ttaatataat catgcaatgg agctacttta aacgttcctg ctattgtttc   40980
tgggctaata ttcacttggc gaataatact tggatacaga gatgtaaggt cgaaactcat   41040
tacatatttg tatcgatttg gaataggttc cttaacaaaa gcgccaggat aaggttgaac   41100
cgggtgagaa cgaccttgtg gaatcacctt gttctgctct ttaaggctat taaaaataat   41160
agcatcccat gtttaattg ggctaaacac agattgaatc tgtatcttag cataataacc    41220
catgtccaag ctcaagttaa tgaactggcg tttagcatca attgcaata cacgatatac     41280
gtcgataatg ttataagaaa tatatcgttg gtgattgctt tcacgaagct tagaaatagg   41340
gccgtcatat ttcagtttac cgacattcaa ttcaaattct gaatgtaat ccagagaata    41400
cgacggttga ttggtaaaag agaatttttt gtaaggtca atgtaatcaa gaacagagat    41460
accgaacaat gtaatgattt cacgagaacc atacatgttt tcgataactt taacacgagt   41520
tttacgatgt ggcgacaacc gtttcgcagt agattcgcca aaaatattct tgattcggtt   41580
atacacatat ggaatatcaa atgactcaac gttccatcca gtcaaaatga caggagtttt   41640
ctgttgccag aagttgagat attccatcaa caattctttt tcgttatcga acggcatata   41700
aatgatttta tcgataattt cagatggaac ttcatcacca ccttgttctt gaagcttagc   41760
cgcaatttcg atagaccatt cttctacatt gccatatgga gaattcaata gatcaaatac   41820
gtagaacctg tcgtcaattg agtcataatg ggtgatagca tcaatcggat gttttgcttg   41880
tgacggctca gggaacccat ccggggatgt tacttcgatg tcgaagttag ccacacgaat   41940
ttttgtatgg tcgtatttga tttcatagtt ataagtgtca gacaaatacg ccaatttgaa   42000
atcgtccatg ccaagtgctt caagtccgat atcttccatg cgtttaatcc attgggaggc   42060
atcacgcata ttagcgaaca acttacgagt acaaggttta ccgtagatat cgaaatattt   42120
agtagcctga ctttctggac aatgagcaaa cagtgatggt ttatattcta cttcacgagt   42180
```

```
acgttcacgg ccattagaat cgatgtaacg ttcaaaaatt gaatcaccaa tctgttcaac    42240
cgttaagtaa aattctttca tttaatttcc tttagacgag ttattgtctt ttgtttgttg    42300
atgaacttat tatactccaa atgggaccga agtcccattg ctttaattac caattgtata    42360
ttttgctttc aaagtccagt catctttctg tttaaaagag ataacacgga agttattagt    42420
caggccaaac agatcttcac gagcagagtc ttcaataaca atcaatcccc agtcttcaag    42480
caactgagca atcgaatcac gtcgctgata gtcttcacca tcaatatcaa cctgacgtcc    42540
gtccatacgc aacatttctt taaagtggac aatatagtac ttaccttgct tttggaggat    42600
atgacaagac tggtaaagga ctttatcttt gttattagcg atgcccatac gggtcaaagt    42660
ctctttgact ttaagaaaat cttcagggtt cttcaattta atttcaatca ttttttaccat    42720 tccaatgcta atttttttaaa ttgttttttgt tcttttacgt ttttagtaac ttctttgaga    42780
aattcatcag tgaccatggc cttcagttct ttaaggacta ttggcaactt gttatttttt    42840
tcaaggagcc gcttatactc ggtagcatcg ttcatgttga ttgtgtaatg tttcatcaac    42900
agtttgataa ctagtaactc tgaagtgtct tcgactagtt tagcccattt agagaatcga    42960
cgaccacgtg gaattgccgc catcatatag ttgaagtgcg cttcatcact taattcagaa    43020
ccgactaagt tcatcatgta aacggctggc atacattctg ggaactggga taatgagttc    43080
tcaaccataa attttgagta gtcgacctga gcaattgaca tagatttctt ttcattaata    43140
gcattaatga ttttaaagaa ttcattctca ggttttttctt taaacatatc agcacatttt    43200
tgaatcgcat cagcgtcatt agacttccat gcaatttggt gctcgttaag ctggacgtca    43260
tcatcgaata agttcatatt atttccaagt cagttcacag gtcagttgaa gaagcatata    43320
cataacatgt aattcaatat tacttgctag tccatgaaac ttattatttt cgcctgcaat    43380
ttcgtaaagc gaaataatac ttttaccagg tgcaacttgg tcataacatt ctgaaactaa    43440
tttatcgatg aaccatgaat aatctgcagc atattttgga gctaatgcac gaagctgttt    43500
gatatctttg ttcttcattg cttcgataac atcagagact gtgccacggt cattagttac    43560
gatagacaga atacctgcat caagaacacc tttagacgag tactggtcta attggccaat    43620
tgtacgacga aagtctggga agttcttttt aaccagagct gcaacaactt tcatatcagc    43680
gatttcgata ttttcgttct tacagatttc aaccatacga tgaatcattt tcttcatcat    43740 cgagattttta tcttcttcag tcggacgacc gaattcgata actctacaac gactacgtaa    43800
tggttcaata attccatcaa tattgttagc agtgataata atagagcagt tactagagaa    43860
ttcttccata aacgtacgaa ggtgacgttg tgattcggca aggccactac ggtcaaattc    43920
atcgataaca ataactttag gcttgccttc cattgagact gaacgagcga atgcagttaa    43980
cgggccacgc acaaaatcaa tcttacaatc agaaccgttg acgaacatca tttcggcatt    44040
gatatcatta cataatgctt tgctacggt tgttttacct gtaccaggag aaggagagtg    44100
caaaataata tgaggaagtt ttccttttaga tactaaagac ttgaatgttt catggtcata    44160
cgcaggcaga atacattcgt caatggaaga aggacgatat ttctgttcta gaatgtgttc    44220
tttggaattg atagtaatca tgtaattttc ctcattatca ttaatctgga ggatttctcc    44280
tccataatcg tactacatta aacgtaaagc tttgacttag aagtcgtgag tagaatcggc    44340
ttccattgca ataacataac ttacttgaga gctttcaaac ttggctgcaa ctttatcacc    44400
agctccccac aacattactt tatagttacc tggctggatt ttcatattag ccatattgat    44460
tacgaagtta aagttgttag aaccatcata atcggtaaga gtcaaagaat acttaggacg    44520
agttagtcca gaatcttcaa ctttattgta accattgata acaattttac catctttatt    44580
```

```
tgtaatagca attgtatcaa tctggagacc acgtgaaact cgaagcaatt gttgaaggtc    44640
ttcagcttta atttcagtaa tcacagaagc caccgggaat tgaattggct tattaggaaa    44700
aacaatggtg ctcttgtcgg cagcaggcca ataaaccgtg gaacgtgtat ctgcaatttt    44760
aatattgcca tcagtgtgca ttgaaatttc agcatcgtca gacactagac tcaaaatgct    44820
taagaagcta ttcaaatcat aaagtgctac gtcaaaatca atttcatcag agatatttgc    44880
ttccgcataa gtggtgccat taactgcacg ggtcataata aatttacctt gactcagcag    44940
aataccagag ttaatagagg caaagttttt cagaatagcg atagtatctt tagacagttt    45000 catttattt cctttcaaga caattcaaag tttataacaa atttattatg cagcaaccat     45060
ctgcttttta atagcttcag gcagtgattc aatatattct ggaattttag aagcaacaat    45120
ttcgccagct gcaattaatt gttcgtcggc atcaacacag tagaaatctt ccagacgctc    45180
agaaccatct ttatcaagaa cgattttttcc acctgcttca atagaatctt tatagtgctt   45240
acgcatcaga tgaatccaca tatcagatac atcgttatca ataaaaccat aaatcataaa    45300
acgagtttct tgtggcaaag attgaagctt tttagcactt gcgtcatcac aatgcaggac    45360
ccatgcttta cgaacacgat tatggttatg tgggttagag tcagtacgga tagaagtaac    45420
tttcagatca gcagcagtga aacctttagc agtagtaaac atattatttc tctcttattc    45480
gtagaagtca gtaactgtcc atgcggaatt gcgattagac attattttat tatactcatc    45540
tttaaaagca gatttgagca tttgttcagt aacaatatgt tcttcacctg aaaacgtatt    45600
ggtcaaaaca tatttttta tttcaggaac aacgagaaga tgttgtccgg ttgaatactc     45660
catgttgttc tccatttaat ttgatgtggt cattataacc acatcgtgtt aaagcgttta    45720
tgaaacagtc atcacagtaa atcgtccaac tttactcatc tgaagatgtt gtccataacg    45780
ttgagggtca tggtctcgat gagagataat gaacacatta gtattttgta aacttccaag    45840
aatggtatct atagccttaa cagcttcaga atcaactgcc ccatcaaaaa cttcgtcaag    45900
aataagagtg ttgattttaa caccagaaac ttttttcagca atatctcgcc atgtaaacaa    45960
caatgcgata tctatacgtg ccttttcacc ttgactaaat gaagcataac taaaatcttc    46020
acgaccacgt gattttatag attcattgaa ttcttcgtca atagaaaaca cgtaatcggc    46080
ttccatgatt ttaagataat ggttaatctg cttgttgaac agaggcacat attttttaat    46140
gatagcacct ttaataccag aatcttttaa catatctgtg ataataccac gatggtattt    46200
ttcaagaacg atatccgatt tgtttaat gattttatca agttcttttt gaagcaaagc      46260
tatctcatcg gcatggttga taaattccgc tgaggcttgt tctattgcag ctttaacttt    46320
cttagcttta tcaatagtgg caatcattgc ttgtttcttg gtacgaatat cagatgcaag    46380
gtcctgttta gtcttaacat tagctcgata ttcgtccact aggacactca gattatctct    46440
gtggcaggta agttgctcga atgagtgatt acattcatga agcttatcgg taatcttaga    46500
gacaataggg tcaccctggt gcaactgtga tgcacaagta ggacatgtac cgccatcatg    46560
atacatctta ataactttgt tatatgagtc aattttagat ttaatcaaga atgcttcttg    46620
tcctatcttg ttgaatgcct cagtagggtc ttcgtcaaga acgatattaa gtagacgctc    46680
gttagcttct tcaattctg cttttaatga ccgagcttct ttggctaggt cgtcatacat      46740
attctgtaga cgcgctacat tatcgccaga taatttcttt tgacgttcga tattctcatt    46800
ataaatctta atttgttgga taataccatc tttcttggca tcaagaactt gcccctggga    46860
attaagttct cgaacttgag acttattgat tttatccatt tcagcgagtg ttccaacttc    46920
```

```
taataagtct tcaacaagct ttctgcgagc agggggtgcta agagccatga aagggggtata   46980
ccctgccgtc ccaagcacaa cgatctgttt aaaagacgcg tatgacattc cgatgctacg   47040
ttcaaattct tcttggaagt cgcgactgct ggcagattca tcaagacgaa caccgtcaac   47100
ggagatttcg aaaatattgg cttttggcc tcgtttaatg aagtatttt tatcatcgaa     47160
ttccatccaa agctcaacta agagctcttt cttgttcgtg ctattaatga tttgtccttt   47220
cttaacatca cgaaatggtt taccgaaaag tccgaaagta atggcttcta acatcgtaga   47280
tttaccacca ccattttac cagtgattaa tgtcttttgg actttatcta attggatatc    47340
aataggattc ccacctaccg acatgatgtt ttgataacga acacgattta atttaaatga   47400
tttcatatgt attctcttcg aatgaagtcc tctacatatt ttaacatgtc atctctatca   47460
gcaaaatatt catctagttc tgcatacata acaacacctg gtgcgtactc acaggtaaca   47520
tacattgttc caaagaaacg aggagttgtc tcctcgtaat tctcagtcca ttcaacgata   47580
ccaatataac cgtcaccaat actaaattca tgacgatgga tttcatagtc agtcttcgtc   47640
attatacgca tcctcgatac atgcttcagc cattttaaga atagagccag gagtatcgtt   47700
gtccattata ttaaagctaa attcaatagc ccagtcggta cagacatgaa cggctttaac   47760
ttcattgcct tcaacgcgta atggctcaat ccaatacttg atagtgttct cgaatccatc   47820
atcatcttta acgtctattt caacttcaag cccaagccca gcattgttaa attcatctaa   47880
agtcattgtg ttgcctcaat ataaagttcg ttggaatatt tgaccagcgc ttctctgtct   47940
tcgtctgaga tatctggaat cgcgtcaata tattctttaa tgatatcttg aagtgattta   48000
atctcgattt cctggtcgtc atcagattca acactgttat caactttaga aaccatacga   48060
agagagtgaa ctacttttc aagttcagat tcaaatttag tcaactctga atcaatttct    48120
gatactataa cacgtacggc tagattagta taatcagaat aattgatttt gcctttaaac   48180
ggataagtga ttcgtcgatg ccatgtcgtt tcattaggaa taaattccat acgttcaaca   48240
tcagtgtcaa atacccagaa tccacgtggg tcgttctcgt cacctgcagt aagggtccat   48300
ggtgtcccaa tatatttgac gttagcagct tcagagattg tgtggaagtg gccggaccag   48360
acttgtttat aggtctttaa gaaatacaggt tcaagcccat gagacttcat tcctttatag   48420
aaataaaagc cattcagttc ccagtgccca acacaatacg cagcagaaga agtcttgata   48480
tgctctaaga tttcacctgt atttcttca cacatccatg gaacgatatc aatcagacat    48540
ccatcaaaat ctacagtagt tggatgttcg taaatagtaa agttttcaaa ttgagttaac   48600
aattcagaaa cagtgttagg tgttattgta ttcttaaacg ccatgtcgtg atttcctatc   48660
gtgacatgaa cgtgaatgcc tgctttagaa atcatatcaa cgatttcacg attgaattcc   48720
attgtacgat gtgtaattgc tttacggacg tcaaaccaat caccgtattg aatccaagtt   48780
ttaatcccgt gtttcttaga gtattcaatt gcttgacgaa taccatcacg ttgaatatct   48840
tgaacccatg ggtcgtcttg tttgactccg atatggaagt cgcctaagtg caaaattttc   48900
atattatttc ctcattagtt aattcattct atcatccgtt tgtaaagcaa aaaaggaact   48960
ccgaagagtt cctatccaca tagtacaccg tacagaggct catttggact tttaaatcga   49020
atgggcttgt acgtaatagt tccttcggct ttagctttat cataagactc tttaaaacgt   49080
ctcattcttt ctgctttgcc tttacggatt ttatcgaaat tttcagaagt cgggatgttc   49140
atcatgcata agcacctctc ggaaaatgcc taaatcgatt tctctcatcg tttccaccat   49200
ttcttaactt gaaatgaatc aacccacacg agttgttttg ggtctgcctt tacaataggc   49260
ggacaaattt ctgtaataga accatcgtga tattccttt cagaaatttt aacacaaaga    49320
```

```
ggaccaccca atttaacggt gaaccctgcg ttcagcttca gacgtttaaa ctttgtttga   49380
actagcgcca ttaatgatgt cctcaatagc ctgacgagta gtaacccact ggattttaat   49440
taacttgtca ttatatggtt gtcgtagaat atcccgagat ttcttaatag cgtattcgta   49500
agcttcgaag ttgttttgaa ttgctgcttc ttgagcatgt gcataaagac ggtttagttc   49560
aaaacgattc tttttaagaa tcttttcgga ttttttacgt gcttcagctt cattttttctt  49620 ttggatttct tgtagcattt tagctactgc atcttctgct tctttatttt caataatctc   49680
ggtagtcata ttatctcatt aaattaaaat aaaaacgtcc gtcctcttca atacagaact   49740
cgtactcaac tggagtccca tttatcgaaa atgcacgtc atgtgggttc aaagggtcga    49800
tgtcaaaatt aattttaaat tctcgaccca acagttttac caaataaggg attgcttcgt   49860
caaaaggttc ttctaagtag ttagagatat caattgtcat cctcatataa aaatccaaa    49920 ctaggcgaat cgctaacaac ttccttcttt tcagcccag gagctttata agcggattct    49980
tcataatgcg tcattttatc gtagatgtct tgaataaacg tttcatctac caacgctacc   50040
atatcatcgt catgactgtc gtagacatta tgaacgaagt aactatattt ctttgcaact   50100
tccttacgtt ctttttgat acgttggaca aaagcattaa acaagctcg agttatgtat     50160 gcatgtgggt tattgtactt agtttcgtcg aaattatgaa gtcccttaat agaggcttca   50220
atcccatctg caatcatctc ctgcttccaa gactgggtat atcctgaaaa gttgaaacgt   50280
ttggacaggc cttcggcgat aagcataatt gctaaaccga tggtatcatt ctgacgaata   50340
attttgtttg ggtctttatt atttaagagc tcctttttcc actcgattat agcagcgaga   50400
agctctttat tattcacata gttattttta ggttttttgtt cagtcataag tacctcttgg  50460
ctcaattcat aggtctatta tatcataata tttagagacc tatcttaaag cacgagatac   50520
tatcggagca acaataagc ctggaatact ttttccatta aacgtttgaa ctcatagata    50580
tcgatataaa gctcggttaa tccagctcca taaagaaaat ctaaaaagtt ctcatgtgtt   50640
tcgttatagt cgccttcgtt taattgagat acatgagttt cccaaaaacc aacacctta    50700 acgaatggaa aatacgtgac tttcatgtat tcatcaacat aaaattcgcc cagcttttct   50760
tcagttatgc tgattcgagt taatttcatt ctagttcctt tgctgcttca agagcaacat   50820
ccagcgaatc aaattggtca acgaaatcaa tattcaacgc atcgtcaacc gtagcatata   50880
accaccattg tttgaattcg tattctagaa taaatccagg cccttcaatc tgaggaagac   50940
ctagactatt tgtaccaact tcgtaaccag ctagacgcag gtcattaatc aaagtttctg   51000
ttaatacgct cattttgccg ccttaacaat tttcaggtca acgaattttt tcttacgttg   51060 attttcata cgacggatag tcttttcaga gatttcatgt ttctgataag ctttagattc     51120
aacaccaaat gcagcaacgt caaattcaga aagaatatat tgcactagaa tttcacgaat   51180
agaattacgt ccaattttct ggtcgtgttt ttgcatgatt tcataaagac ggaattccca   51240
tgcgtcaaga acttgaggag taacaatatt gccggattcc agaagagcaa caactttatc   51300
gaaagcgaaa gaattaacta cgttttgat tttagtagac atattatttt cctcggttat     51360
tttattatcc gatgagagaa ttatactcat ctctcaagag tttgtatatt atttttaagc   51420
atgaaaagta agtaatttgt atcacgtgga gtaatatcaa cacccatatc aaagatgcct   51480
ttatagattg ggtatttgtt ttcggttgta tcgaagctga aactatttcc atcacaacta   51540
acagtaatag catctgttaa aatgtcatac tcaatcctaa caattgaatc cccaattta    51600 acgtcgaggt gttttttgaa tttgataaaa tctaattctt gggccatgat attttcctca   51660
```

| | |
|---|---|
| ttttaagacg ataggaagat aataacatgt cttcctatcg ttgtacatta ttaaccgaac | 51720 |
| tttttagcgc ctttccagcc ttcgtacata gctgcacaag tcaatagtac agcgtgctgg | 51780 |
| cattctttgt atttgtaaat ccagaaccag cgtaagaagt cttcatcctc aacgccgttg | 51840 |
| agtttcatat tggcaaagaa ttcggcacgt tcttcacgaa gcttttgcga taacatagat | 51900 |
| tcaggattca ttttgtattc cacgcccat tttcatcgat gaacttaatc cagtcattta | 51960 |
| cagaccattt agttgtatca ccctttggat taacatttaa agtatataat ccttgcttaa | 52020 |
| aaagcattcg tttaatattc ataatttcct caactgtaac gataacattc gttagcttta | 52080 |
| cgtttggctt cagtatgaga agtattataa tcatactctt ctttactgta aacatctttt | 52140 |
| ttcaacttac gaacctcttt gcggagttgt cgattcattt cattcttgac ttcagaatca | 52200 |
| acacctttca tacgtttcca tttatctgag cggaagatgt tttcaaccat gtctttgtgg | 52260 |
| ctaacaccgt caggagcttt acgcttacca aaatagtcgt aatcgcgaac tttcaaatct | 52320 |
| ttacgacgat atgttttacc cataagtacc tcagaggttg attgatacaa tgcgtttgat | 52380 |
| aaaattcact tcacttactg aaaggtcttt aagaccgatt gattctaaac gctgagtaag | 52440 |
| cgtcaacatt gggatatagt cccattgagt tttagacgtt tgataagtac gaacgccatt | 52500 |
| agcaatttca acatgcaaat ctgaaatggt aacgaatacc ggtcgctcat cattaacttt | 52560 |
| aagggttaga acaactttct ttgaatctaa actaatcata gtttaatttc cttcgcgatt | 52620 |
| gaacagaaga taccacggtc acaaagcatt tcaccaattt ctggatattt gattgaacga | 52680 |
| taccaaacat ccaggcttga aattctggtt atccgtactg cattaccatt gacagaataa | 52740 |
| tactggtcaa ccttaattc tttatcttca attgtcattt tgttttcctc tatagcagat | 52800 |
| ggtttaatct taacatatct atcgaggatg taaactgttt tatgaaaata tttttgattt | 52860 |
| gagaggggca caaggagata gtgaagtgaa gattccaatg gattatatta gaaatgagat | 52920 |
| aaagaagacc aggcggcacc tggtcaatct tctatgatat cagagtcgta tcctaatgaa | 52980 |
| atcaaggact ttttaaactc tgcaatattc ttttgtttct tatcatttaa aaatatgaca | 53040 |
| ggataacgaa tattaagtga agtgaatcct gcacgtttag caagagatac gattaaagga | 53100 |
| cggtcatatt caatcttacc attattagtg aggactttat aaaatgtata aggagcattg | 53160 |
| agctccttta aaagttttgt aacagtataa catcctggac aacgtcctac ttcttcaggg | 53220 |
| atgccgtaga tttcaatctt attctttaag ttcgagtttt gttccacgag aaataattcc | 53280 |
| ttgataagcc caataaggag gattaacaga atcctcaccc gagttttctt caggaaaata | 53340 |
| aacctggata acaaatccag atgcatcaaa ggtaaaataa accgtaggca gttcacctaa | 53400 |
| caattcggca cgagcattaa tttcttcgag atctcgttca cgtccagccc aaaaactagg | 53460 |
| atttagacta cattcgtaaa aataatagtc attaccgaac atatcaaacc ccttccaact | 53520 |
| ctctaccacg taccgctcaa aactaatcat aattaagcct tttatcaag aacagaattc | 53580 |
| agtttgttag taattttgtc cagacgctca ttgaactcac tagaagataa gcccttttct | 53640 |
| ggagaaatta aactaatcac gaaaaataca ccagtaaaag gaataagaaa aatagctcca | 53700 |
| actgccataa acaaaaagaa cgttacagtt gtaagaaaat cagctaaacc tttacgaaat | 53760 |
| ttatacatat ttacccttaa ttaattaacc aagcgttgat aagcaaacca tattgcgaat | 53820 |
| aaaattctgg accaaaatga aaaatcatat catttatagt atccataatg tagttcaatt | 53880 |
| taatcatgtt tccacacccc atcggtattt gaccaaagtc gctgattatc tgatcctcgc | 53940 |
| cacagctttt tggtcggaag attttttctca tacttcccat caataataac atcaacatat | 54000 |
| ttaagcattt ctagctgttt aatatcttca aacttatatc ctgtccacaa ccaaatgctt | 54060 |

```
ttattaggat aaagattttt aatagtttga actacagagt gaataacatc tcggttgtca   54120
ggatagagag ggtcacctcc ggttatagtc aatccttcta tataatcatt attcaaacat   54180
tcaattaatt gttctagtgt ttcaccagtg aatggaacac catttctagc attccatgtt   54240
gatttattat aacacccttc gcatttatgc aaacaccctg taacgaaaag aacgaccct a   54300 caaccagggc cattaacaaa atcgcaagga taaatctat cataattcat tggtgtttaa    54360
ccctatgcat gatttcttta tttttaccga gattaaatcc gcgttcgttc ggatttccca   54420
aatagccgca tgttcttctt atggtgttca tcttttta gg atcagtttct ccacaaactg   54480
aacaaacaaa tccgttttca gtaggagtca tttcatgagt acttccacat gtaaaacatt   54540
tatctactgg catattaaca ccaaaataat ctaaatgttg tgcagcataa tcccagacag   54600
cctcaagtcc ctttaaattg tttttcatat ctggaagttc aacataagaa atgtgaccac   54660
ctgtcgcaat gaaatgatat ggcgcttcac gagaaatctt ttcaaacgga gtaatatttt   54720
cttctactga acatggaaaa ctattagtgt accagccttt atcagtgaca tcttttacac   54780
ttccatattt ttctgtatca agtttacaga agcgatagca aaggttttca gcaggagtag   54840
aatacaagct aaaagcaaaa ccggttcttt cggtccactg cttaagacga gcattcattt   54900
tagttaaaat ttcttgtcca atatcacgac cgacaagaat attcaattcg tgaataccga   54960
tgtatcctaa agacactgaa cttctaccgt ttttaaataa ctcaattata tcatcgtcgg   55020
gtttaagacg aaccccgaat gcaccttctt ggtaaagaat aggagcaaca gtcgctttaa   55080
ctccttttaa ggaactaatt ctacacatca aagcttcaaa gcacagatcc attcgttcat   55140
tgaataattc aacaaatttc tgttcattga actgtgttcc aatataagaa tctaatgcga   55200
tacgaggaag attcagtgtt acaacaccga gattattacg tccatcaaga atttcattac   55260
cagtcgaatc tttccatacg ctcaagaaac tacggcagcc cattggagaa actggaactg   55320
aagaaccggt aatagcttta ttattcttaa cagaaataat gtcaggatac attcttttgc   55380
ttgcacactc tagagcgagt tgcttaatat catagttcgg atcgtcttta taagattaa    55440 cgccttcttc aacaaacata acaagcttag ggaaaatagg agttattcca tcacgaccaa   55500
gtcctttaat gcggttttta agaattgctt tctgaatcat tcgttcagtc caatcggttc   55560
ccgtaccaaa tgtaattgtt acaaaaggcg tttgtccgtt tgaactaaag agagtattta   55620
cttcatattc ataagcttgg aatgcgtcat agacatcttt ttctgttttg gattgagcat   55680
aattcagaat gtctggtatt tgccattttt ctgcatcttc aacatgttta gcgtatgtac   55740
gtttaacata aggagaaaga actttatcga cattcgcaaa tgtagttccg ccatactgat   55800
gtgaagcaac ttgtgcagta atttgtgcca taattgcagt agcaacacca atcgatttag   55860
gcgtttcaat ttgagcattg cccaatttaa atccgttctc aagcatcccc tttaaatcga   55920
ctaaacagca attggtaaac ggaagagcag gagaataatc aatatcatgc atgtggataa   55980
ttccactttc atgcgcattc ataataaaag acgggaccat attttggca atgtgcttag    56040 acacaatacc agccataagg tcccgttgag ttggaaaaac acgagaatct ttattagcat   56100
tctcgttcaa aagatcttta ttagttttat aaattaatcc ttcaatttct ttttcaattt   56160
tcattttaaa ctctttctaa gctgcttttt gaatgaagct attaattgtg ttttagtatc   56220
agattcatta tattcaaatc ctctttgaag catctcagtc atcatttcct ctttacctag   56280
tcttgagaac tctttagttt tgtctggaac aaaattagga tggatattat tatcagaata   56340
atcttgtttc aaataagcaa gaagagcttc aagccattcg aggtagtcga catcacgacc   56400
```

```
tttaagacca gaacggttga acttatgctt catttggcct tctgctgcgt tgcacagatt    56460
acagagtaat ccacgaactc taccggcttt tggcccgttt aactcgtggt cgtggtcaag    56520
atggttacct tgaacatcag ggtctaattc acggtggcaa ataggacact taccgttctg    56580
tgcatcataa aatttttgtt tttcttcttt atattttgcg cctgataata acatgataaa    56640
cccttacctt aaatagataa gggtatttat aatttagtaa atgttataaa agttacgatg    56700
agaacgttta gctttgcgaa gctgacgttt agtaggacga actgtaaatg gttgtccaga    56760
gaaaaaattc ggatcggttt taataagcaa ataccaatca cgcttgccat tttttaataa    56820
acggtacaat aatttaactt gcataataat ctcttcccat ttccatatcg attaattcat    56880
ttattgaagg ttcatcataa catggttctt cgtcgttgta aactgtttcg acgtctggct    56940
cgacagtctc ccatcgagca gaataccacg gtttaacccc ggagtttatt gagctcttca    57000
taatcaatcc aggattctag ccctgacggc aggtcacatt caatgttcca cagaagctct    57060
tcaatggctt gcaggcgatt atattcttca acggtaatgg taaccattgg tgcaaccggt    57120
tctgcctttt taaccatcat atcgttcatc aggacgtaaa ggtcatcacg aacgacagtg    57180
tcgttccaac cccatgattt ggcttcgtaa gctaatgatg aagggagcac atttaaaact    57240
tcaataatag ttggagcatc aggaccaagt tcattggcac aaacttcgta tacatcttgg    57300
aaatctttaa gatttaatga atatgtcatt taaaatattc tcgcagttta ttgttctacc    57360
caggcacagg aaacttcgaa atcaggacca ccgtattccc agtgatattc accaacagga    57420
atccagtcac cgtgctcgtt ttcttcatag tcctcagcct caaggccaac gaatcgccat    57480
tggacaccga tgattcgatt acccattaat atatgaaatt caccccatgg attatcgata    57540
gcatattgga tatcgttctt agcacgagaa cacatttctt gatataacaa agcttctaat    57600
tcgccctgat cataagggcc cgggaaagtt aaatcaatac tcatttaaaa tattctcgta    57660
gttggtcaaa tccaccaata tgacttccat caggagcaaa tacttgaggc atagtcaatc    57720
caacttgtga ttcacgtcca agcttaacaa gaagctcagc aattttctca tcatcaaaaa    57780
cacctttttc tggcataaca ttaatgaatt cgaatggctg tttcttaaca gtcagcaatc    57840
gtttcgcatt atcacaataa atgcatttat gaatagtaga gtcatacccg tacactttaa    57900
acattatttt tcctttcatc gattaaatat gcaatgccaa atacaataca tgtaataaaa    57960
cctgtgatac agatagaaac caacaacact gtaccaaaga accaaatcaa gttatcttta    58020
gtagtttgtt tgatatccat ctcacgaatt tctatagcta tcgtatcacc tttattcaga    58080
agcgtataaa acgacggtga tacacgcctg tcaaaaactc gtccttgctc atctttatag    58140
actgcaataa attctaattt agaatatttt cctgtagatt ggcctgagat taattccact    58200
acctccacag gaattacttt agtttccatg taagtattct gactgttcca aatgaatgga    58260
ataacggcaa aaactaaagc tgcgataaaa caacgaaggc tatatctcat tataatattc    58320
tctcaaattt gtggaagcat ttacggcatt tcaatttcaa gttatcagtg gtccagttaa    58380
ccagttggac ttgatagtt ccacattccg ggcatggatg ttttgctgct gatttggcag    58440
cattttcacg tcgttcaacc attttcatta tttcgttcca tgctggagga acgaactctt    58500
cttcaccgtg gattttatct cgctgaacaa attcaatctt tgaactatcg tcaataaact    58560
taaccaagcc atgattagtg ctcatatcaa tatcctctaa aagacgtagt ttcattataa    58620
cacctcaatg gcatttcgta aaccgtccgc tttcgcattc agagctttta acgatttagt    58680
ctgttcttta atctgggctt cgacttcttt cagacgagat ttgagatatt cacgttcttc    58740
gctcaagttg tcaacttttt ctactttagg ttctttaata gtcttaagtt tatactcgtt    58800
```

```
agggttcttc agcttaattc gggtgcgaga actgtataac attgaaccgt tatcttcgga  58860
ttcgtcgaac gtttcaacaa catccatagt ctctaacaat gtaataagtt tataagacaa  58920
tgaacgaacg gttttgttat gcttattaat ttcttcagct ttcatggtac cgagattacg  58980
tgagtagtaa taaggaacct ggatatcaat tgataatgat gcgttaccat taccggtcgg  59040
tttgaatact gcagtaaccc aatctttaac atgaacttta tttgtacgac catcaccgcc  59100
cgtgaataat ttacgagaat gtttaaaaag catattcact tggttattga attcacaagc  59160
aaatttatca gcgaatttag tttcaggaat ggtagagaac caatcagcta aatgagtctt  59220
tttaacatca ttaacaatag tgaattcaac caaatcagtt ttagatgtca cagatttaat  59280
aaagctcggt ttcataaagt ttttaatgtt atcgcgagct acagtagaag ataataaacg  59340
agaacgttta aaccattgaa gcagtgtccc taatgaatga gaatacgcat tctgagtatc  59400
tttacagata tgattttctt ggcctgtgta tgtaccaaaa tcgcgaagaa taccacttac  59460
tacatctcgg tgtggaacat caaatcctag tgcaccaaca gcgcgctggg catgaacgtt  59520
agcgataaga ccggcaaagt attcaacgta atgtgaacgt gtcataatat tttcctctcg  59580
ttaagataga tttattatac tccaaccatc cttggttgta aactgattta tgattttaac  59640
gcattcattg cgttaaaaag tttagagtac tgcaactgga gattcgttac aacactttga  59700
gcatcacgaa gcttagcttg tgctttgtca agttcaacgg acagtggtc tacagtagcc  59760
ttgatttggt tgtaatgata atcttcggcc ggaagaaggt cattagaaac atttagtttt  59820
actgccgaca gtttgcacac atttggcaaa cctttaaaca taccggggttg tgtcggagaa  59880
tatgcgctta gaacctctgc attaccgact ggtgttgctg tgatattgcc ttcgaacgtt  59940
gcattttcct ttttaagatt ttgatagtat tcagagtctt tgtgccacca tggcgcagga  60000
acctttttac caatagatac acgagcctgg atagcgatat ggcccttatt cttgataggg  60060
tcgataatat taagctcacg agaataaatt gctttaatct ggtagatatt atcacctaaa  60120
acttctaacg cttggtggaa tacacgagca acgttatcgt tcttaggttt atacgtgaga  60180
gtgaactcgt tctcactgat aaccatgatt tccaacttat cgtaagtata tttcaaatgt  60240
ttcatgttaa ttgcttgagg acgaatacga gaagcaatgg ccatcagatt gttaaggtta  60300
ttccggaact gcttagcgaa atattgtcct tcaccgccaa tacaaaaatt acgaagtttc  60360
tgtttggcta ataaacggct gaactcacca ttttttaatga actctttaac gggcgtgtta  60420
gtaacacatt caaattgagt aaacatacga gaagtaatcc cataatacga acagatttcc  60480
tcaatctctt caggagtctt tacaggcata cggataggat taggtcctgg agtatatgcg  60540
ttcgaggtaa attctttgat aagttctcta cgtgtaatag ccatttttata ttcctcatgt  60600
tgaaaattt attatactcc aaccatcctt ggttgtacat cattccttaa gaagtttac  60660
tacttgaata agattagctc gttctgtttt atttttaccg tttaagcctg ctaatcgtga  60720
gatttcatcg tcagtttgtt gaatagttac attaagttca ttaatcaaag cttcaaagta  60780
tttgatttgc tcagcatgtt ttgattcaaa tttctgaacc ggaataacgt cttggttcag  60840
ttcatcaata aggtctttaa gagcatcttc ttggttgata tcatattcaa cttctttttat  60900
ttcttcaacg agctcgtctt tatatctaac gtcttttagt cctggagctg gtcctgaaat  60960
ctcttcttta agagtacaaa catacccaat acggtatcca atgccgtctc gcttgatatc  61020
aacttcgtcg ataaatccac aatgtttaag accagagccg attatgtcaa atatccttg  61080
acgtcgtcct tcaaacgtta cacgaactac taagacagtt ttaccaccaa ccttttgaag  61140
```

```
ctcacattta taaaagtctg ttgaacctga ataacgtgga tgagttttaa agttcatctg    61200
acgatctagg cccatttgta aacgtgctgt tacggccata aaacgtgttt ggttctcgtt    61260
aagatgagca acaatccatt tcaaaggcat tttacactgt tcatgaccga acaaatcagt    61320
acgtcctaga ttacgcagga tattgttaga gttaatcatc gacagaacgt taagtttatt    61380
cagcgcgctg aagattccat cagccattga ttttccataa cctttacacg ctttaataag    61440
tgctcgcggc agattagtat agatttcaga cggcatatga aaatcaaatt tactagtcag    61500
taattgatga acttggatag caatttgctc ataattaagt gctctgcgat cgttatggtc    61560
tttaaaccac actttaatct gtgaagcaca taaaccgtta atttcatgtt ttaccgcatc    61620
agatgtaatg ctcataacta tttcctcaga ttgaattgga actcaaaacc attataaccc    61680
gtccttgggt aaagcgttta tgcgtgaacc gtctttaaac gttcttcaaa tttccgaaga    61740
gtactaatac gttctgcttt ctgttttgta tagtttgcaa tacgttctga agtgagagcg    61800
tatcgttcgt ttactgtttc tttcatgaag tcagggattt cacgagaagc tttaatttca    61860
tcaaacttgt cgagtactgc ctggtcttca gcgattaaat tttcatacat ctcgatatct    61920
ttcttgataa actcgatatc ttcctgagtt actttggata aacgagatgc tttatccttt    61980
ttgtactgct cgttagtttc acgagaccag aataatgtac gttttttgtt agtgtttttg    62040
tagacttcca caattccaac tgaatcgatg ataacaatcc aattccagcg agatttgaaa    62100
atctgacctc catccacggt aatctcgtta ccataagcaa cgtcattaaa gaacttgctc    62160
tgtgcttcag atttaaattt accgtcgtta taatttacca ggttgaaaat atctttagcg    62220
ttcatgtttt acctccagta gttgataggt ctataataac ataaccatag accttgtaaa    62280
caactaaaag aaactttttt cggtattttt tccactgaac caaacagact tcgggatttt    62340
ttgtaatttt tcagatttaa gtttctcttc ctgttctttc ttatatacac tcttgtcgta    62400
ctggagcatc tctatggcat tcttttgcaa atgatctaag gtaattaagg ctttagtttt    62460
tcctttcaag gaagagtcct ggcgaacttc ctcgctatat ttcatcgtag aactaaccat    62520
acgatgtgca tagagttcga ctgcggcttt aatttttgc ataaaatcca taacatatcc    62580
tctttgattt gtacatcatt attttttaaat atttctatgc cctcagtagg ttcctggtgt    62640
ccttctttga ggtaagccat atgattattc atctttatgg cttttgttac ctcagaactt    62700
cctataagct tatttcagta aagtaacttc cgagatttct tcccaaccat ctttatcagt    62760
tgaaataaaa tctgctacat aaagagccgt acgtaatgat acattgcgaa gacgagatac    62820
gttagccttc atccaggaca atgctttata cgtttctgca tccgtcagac cacgtttctg    62880
catcatgtca gtagataata ttacatcttc aactcgaacc ataatctctt cattagagtg    62940
tactccaagg tcgagataca ctgaacgaga tactaaagct tgaaggtgtg gagcaagttt    63000
cgaaccccgt tctaactctt tatcgatatc aacgtttgta atgaaaacga tagtaccttc    63060
aaactcaaat tctttatcaa taccctttatc ctcgagataa gatgacgcag tgctccaaca    63120
aactttgcgt ttatctccgg tatctaatgc tgctttaaga aggttcagga tgtccatatc    63180
tgagaatacg tcaacgtcat cgattaagag aacgctgtct tcatcacggt tgagccaaag    63240
ttgttcgtaa aggccaatac tggagatttt accattaatg ctttttgtatt tgatgaaacc    63300 attatcatta gcattattaa gtgctttatc cagagaatac gtcttaccaa taccagctgc    63360
acctgaaata atgagtgaac gaattttgcc atcaataatg ccattcgtca tcatgttcat    63420
tactttaaag cgtttgttga tacgagtttt catatcttca gtgctttcaa caactgcaac    63480
tggtgacgtc tcaactcctt ccattacgat gtctgatttg aagacccata ctccacgttc    63540
```

```
agaaccatca atcataacga aaatttacc gtcacctaag tgggaacatt caggattaag    63600
ctttgccggg aaccatgtct tgtggcaac ataagaacca gagatttcgt tattacgata    63660 gataccttt ttgatttgaa cgttgaacat tttattctcc aaatttactc atttcgtttc    63720
gataggtcta taataacatg tttaaagcaa aagtaaacaa ttatttgcga cgagattttt    63780
tggtaagagg ttgaaagaac actgctttac cggcaggagt caaagtgact cgtaatgcat    63840
taccgattcc caaggatgct ttaaccagac ctttagattt cagttcaccg aatgcttgac    63900
gttggtctgc attacgagtg ttaaccataa gacctttatc accagcttca cgaatcattt    63960
ctaacatttt ggttttcatt ttgttttctc ctcttgtttt gataggtcct ataataacat    64020
atcctaaaag catgtacact acttttaaa aatatttga ccccctaaag ggcccgaagg      64080
cccttatcat ttatagtatg aattgtggtt ttctaagtag acttgctcaa ggaagtcatc    64140
ccagaaactc atatctactt tttgctgcat accgttctta gcggcttgtt ctgcggcatg    64200
ttcaacttgg tcaacgatat cttctaagaa ttcctgtacg gttttaaacg tatgtttacc    64260
aagcttaaca tcgagaataa atggagcatc ctgaagcggg taaaccaggt cgccggtttt    64320
gtaaatttct aagagctgaa gtccaccacg gcatgcatga ctcaatgctt tccaatcaat    64380
accttcgtta gcttctgcct tacgagcacg ttcaccatag ttctcttcca gtttaaccag    64440
gatggcattg aactctttat tggttaacgt gtcttggaat ttacggtcta acagattata    64500
gaatgtttgc ttacctgttt tctcgttttc ggtttcaatc cacgaagcaa attcacctat    64560
aggcagaaca ttcttcatat gtgataaacg aattactgca ccgttgacaa agtattgtcc    64620
ccattcatta gaacgtttaa gggcttggcg gagaacagcc agacgagaac ccttgacgcc    64680
atatttagaa gcttgcttac ggacataccc taaataagat ttcatgttag tggtatagaa    64740
acgagatctg ttatcttgaa tatacttcca tacatcaggc aaatcagatt taactactag    64800
actcggtgga gtgtgaagca tatctaatgc gacggtttca ccatctgcag ctagtttaaa    64860
gaaatatttg agactataca actcatggtc tacgtcgtct tttgtgttct tagaagatgt    64920
gttattcgtg ttcttgctca tatgttcttt aacgttaccg gtcaaaatat cacgagcatg    64980
agggacataa atttctttaa aatcaacgtc agattcagga gtagacgttc cataaaggtg    65040
gctaccaaag taagccttaa caatcgtttt cattatttag ccttatattc aagagtagga    65100
cagacttttt ctttacgagc tttaaggtat tcacctatta atgatttctt acgttcaata    65160
ggctcaagtc catttttaat tcgttcttgg ttttgcgcaa tgagctcaat ttctttataa    65220
tacttccgct ctctatataa gtcgattagc cacggtatgc ctaatactaa aactatagaa    65280
ataccaacac ataatgcaat gaataaaaca cctacaccaa ttgaggccgg aaccaatgac    65340
cataaactac taaagacaaa gaatttagtt aaaatttcat ggccaacgat tgtggccgct    65400
gctaaaatcg caaatccaat aatcgaaaca aacaataccg ggagaaacgt tttccaaaaa    65460
taagcacaca acgttttcgg acgattccat gtactattaa acgcggcata aattttaaag    65520
tgccaagagt tttcattgat aatcataata attccttatt tcaaagttgg gataatagaa    65580
tcgagataag ctttaagagc aactgcttca tctttgtcta atgtaacgat atgttgacga    65640
aggtcatcaa tttggcgaat aactacaaca tcgccatctt cataagaagg attaacgcct    65700
aggaccgttg tatagtcagg gcggtcctga tttgtaataa aagcattacg gcatttagcc    65760
cattgaagtt tggccttttt ggctgtttca gattccatta attctttcac cttagtgacg    65820
aatgttttcc aattattaat agaaaggcat tcatcttctg tttcgatatt aaccccgcta    65880
```

```
taaagaccgt gataaaaacg aacttgaagg tcttcatcga tgttaattac agatgcatgg   65940
ccgggcggat tgagtttcaa aatcttgtcc agttccatag gaagaatagt aacagaatca   66000
tcttcttgtg tcagaacata cacataacca cgttttttcga tacataaatc accaaacaac   66060
tcggttgttt caattacaat tttcatatta ttcaccaatt aaagtttcaa caaaattcac   66120
caaatcattc agacaagcat caacctgttt ttcataaaag tcttcgttat catttactgc   66180
atgataagct acatcattca aatctgaatc ggcttcacgt aaatcacgga taaggtccat   66240
caatttatta gcttgttcac gggtcatttt accatactcg tttcaataag attcactatg   66300
ccgtttacca tgttataagt aaacatcgga taattgtatt gtactacaac ataagcgata   66360
agcaaaagtt tcattttgtt ctccgttcgt tttggtagga ctactataac ataatcctac   66420
caagatgtaa actaccgatt gtgttttaaa tgctgataaa gttcttcaac ttgtttaggg   66480
tccaaaacaa ttaggtcatt tcttggcga agataaatcc atcccttatc accagggcca   66540
tttttacaaa acatcaccac catatcatca tcttcagcgc tttcaggtaa aagttcaagt   66600
acaccgtctt cagattttcc agtataatcg taaagcataa tatcctcaca taatctcgtt   66660
aacatacgtt tgcaattctg tgtgggcgtc agccatcttt ttcattgcct tattgatatc   66720
aatatcgcca tcttcgcacc catgggcatt ctcccaatca gatacggcat tagcgtactc   66780
ttcaatcaaa aacattaact tagaaatttt tctttacgt gacataacgt tctcctctag   66840
taagtaaaga ctactataac acaacctgcg gagaagtaaa ctgatagata caaaaaagcc   66900
ccaaccataa ggaaggggct agtaaattag atagatgtag gctctaattt tattttcatg   66960
aactcagcaa attgtctggc agtttttatg ccttgttcct ggcattcaaa tgcatcatca   67020
caggggctat ttttgtaatg ctttgccata tacttataaa attttttcaga attctcaaca   67080
ttttgaattt cgaacaaagt atatacgttt ttaatccctg attccataaa gttatcaaag   67140
tatgggtcaa catatgcagt gccaacaata ggagtcgttg ctgcaaaaaa ccccagcatc   67200
gccacaatgg ctatcgctct taaggccata taggcctcct gttaattttg gccagtattt   67260
attttttcgcc tttggacggc cttaacatct gcgaggtatt tttccagctt tcgcttgcgt   67320
gtataatcag cttagaacc agtttgacga atatcctcgt ttaaatgaga atagaatgt   67380
cctaattctc ttcggatttc gtccaattgg gttacagtaa gattacgaag ttgtctttcg   67440
tttaattgct gcatatatat acctcttggt tagatattag tatttataac aaccctgtca   67500
aatcgttcca atgcttccgg cataatgaca cgtatctatc ggtatcacca atttcaattt   67560
gtccaccatc tgtaattgga agtccatctt ccgtgactct agctaccatt gtggcttttt   67620
taccgcaatg acagacacct ttaagttcaa caagcttatc ggcaatagcc attaatgctt   67680
gagaaccttc aaatagatta cctttaaaat ctgttcgtag tccgtatgcc attaccggca   67740
cattgtatac gtcaacaata cgactaagtt gatacacctt ttcagtagtt aagaactgag   67800
cttcgtcaac aaatacacag tgaatatcct tttgtgctgc agcccattta taaaattcaa   67860
agatatccat gtcttttgta attatattgg catcctgacg aataccaata cgggagacta   67920
tttcaccttt tgaatcgcga gtatcaatag ccggtttaag aactaataca cccatgccac   67980
gttcttata gttatgtgcg gcagtaagta atgaagcaga cttaccagcg ttcatagcgg   68040
cataggtaaa aattaaacta gccataagag tcccttatag tgaattcacg tagtcaatga   68100
gttcttgttc tttcctgtca aatgattcca tcaatgcttg atattcttcg tctgttaaag   68160
gagcatattc atagtacgca ttagtggctg cttgctcatc caataggtca tggataagtt   68220
cgaacagttt agttttctct tctttagtca atttcattta ggttcacctt ctttaacgaa   68280
```

```
atctgggtaa gggtaaaatc ctgagtaaaa cccttcacct ttatgattgc tacaacctttt    68340 gttcgaacag taacaccaat aatcaaaatc acaagccatt tcgtcattgc ataaagcaaa    68400
aactacaggc cattcgcatt tttcgcattt agcacctgta agaatttttg tttgactcat    68460
aaccatttga cctgcatgca atattcttcg acatgctttt tacgaccttt cttatcaata    68520
aaggtatatt ccataaagcg tccatgataa cgacgttcaa catcgtgagg ggtgttaata    68580
ggacacttag tctgacgaat ttcttcccat tcacgaataa taactgcttt attctttggg    68640
tcatacgggt gaggataatg cacattcata acaatggttc ccaatcaaca atcacaatttt    68700 ctagtttagt ggaatacgta tctaaaatct cttcgatgac atcccagttt ccaccaccaa    68760
tacctgcacc aattcttggc atataaatta caggctttgt tatcttattt tttccgaatt    68820
catttaattc tattatacaa ttcattaaag cagagtactc aaaattaggt cccggctcaa    68880
actgtgtata aagattaaag caataagctt tattggtctt aaaatatttt tcataaaccg    68940
aataagtccc gagtttagac tcgtctccga attcggtttg aagtttatcg gcttctaaaa    69000
tttttggata agcctttgcc aattgacctg ctacaccggc acccattgta tgaaaacaat    69060
tgcacccatg agcaatatta ttacctttag aaaacagggc gacaatatcg cccttgatat    69120 agttttttaat cacttgctac aagtcctcta gtataagagt caactagacg gtccaccata    69180
gaattgcatg ctgccttatc tttaggttcc gccaccgagc attctaatat ttgccatttt    69240
ttatagtatc ttttaattaa ggtagacgcc ttgaacctac tagacgcccc atctttttct    69300
ccgtctttat acgcatataa caattttttgt gaaaaatcta ctttcacactc ttgactttta    69360 ccacaataat cagacgccgt tctgtttgta tactccgtta catcagtata tgtagtatta    69420
gcaagagcgt taaatgaaac caagccaact attaaagcta acattttggt cattctttta    69480
tttccagtag tttatttgat ttaaggtaat tagccttttc taggacttca gaagcatatt    69540
tacttccagc acttgtcttc caccccgcat tatatgagga tatagctttt cttatatccc    69600
cgttatgtat atttaaccaa taagaaaatt cgatataagc ccatctggcc gaattagacc    69660
gcttagatag catttctta atttgggcat cagacatatt ataaccaagc tggttaattc    69720
ttgccctcat tgttggtaga tagttttgga acattccata cgcatggtga cctttcttat    69780
ctttaagatt aataccggca gatgattctt gccatagtat tgcggccatt atgtatccaa    69840
gtcctttctt atgcatatttt tcatgcgttt taaattttcc gtccttagaa aactgttccc    69900
caaactgata agcataattc aagttatcga gttggacatt actaaaagta tgctcggagc    69960
tatgtgctga taacgaaaga gcaaatagac cagcgagtag tgcttttctc atgtttacct    70020 ctagattta atcactgctt tagaagcttt tcctggtagt cgttactgt taataatagc    70080 cattctacat tgaagagtct tcattttgaa tgttggattt tcgcgacaga ctgtaagtcc    70140
taaccaaaga tttccatcag ttatttctaa acggcctggg cgatattcga caccttcgac    70200
aaaatcttca tcaacatctg gacgtgccgg cattgataaa aattctgcaa cttcttttaac    70260 atgattttt actttatgaa ataattcaaa aacgtaattc tcatctattt ctctctggat    70320
ggcacgatct aagagatgtt gagaatactt gatatgaaag cctggtagtc caagagactt    70380
tgcagcatct tttataccgg catttatttt gcggaactcc gttcaaaga ttcgacggag    70440 tttattacgg cggataaaaa cttccgaatt gatagtcatt ttgatttctc ctctagttga    70500
caggtctata gtaacacaac tagaggagaa gtaaactact ctttgaaagg aattaacttt    70560
ttaactgctt tagatacttc gtcacgaacc tgatggaagt tcttgagctg ttcaaggcgt    70620
```

```
tgttcgtaat acgcaatctc atcttcttca agacaatcgt cagcgtcttc tttcagatat    70680
gccttgtact cattaaagag ggcccatagg cggttctcaa agtcatcaag gctttgaatt    70740
ttcttgtgct tcggaacaag gccaaaagga ttgctttcag ttatgcgtct agatgcttca    70800
taatgagttc caaagcctga taggatttga gccattagta ttttctcca ggtcgaaata     70860 ctgcacgaca ggcccacatg ctggcttctt ttagatgttg cttagcatac ttaagagcct    70920
gtactgcatc catatcttct ttggtttgtt gctctgtttc attttctttc aagatatatg    70980
cttcttcaat cagagcatca aacaacaatc caagacggac ttctgcatct ttaatagcgt    71040
tcactttacc gattttatcg tcggtatgtg gcttgtagcc tttaatatct tcaatcgaca    71100
taaggaattt cctcatcggt ggcaaggtca tattcgacca attggatagg ctcattaata    71160
ccatatccac gtacagtgat atcagttgcc ggatagtttc cagtaatatc acccattcta    71220
aatgcttcaa tgaatgattg ctcgcctgag caactaaacc aggcggcaaa acattttaaa    71280
acatcttcag acccttctat aatcaattta gccattatag actctcagta aaggtacgag    71340
cgataacgtc acgctgctgt tccggagtca gagagttaaa gcgaactgca taaccggata    71400
cacggatggt cagctgcgga tattttccg gatgcttaac tgcatcttcc agagtttcac     71460
gacgcagaac attaacgttc aggtgttgac caccttcaat tttaacttta ggttgatgtt    71520
caatttcaat ttcacgggca ttcaaaccgt agaaaatttc cgggtctaca atagcgtctt    71580
ctttaaaagt cttagaggca ataatccggg cttgagtacc gtcttcaaaa taaatagtgc    71640
ctttgtgtgt gccttcaaga atttgatatg ctttcatata acctcaatta gaaaataaat    71700
ttatccaagt ttttctta atcaaaaatg ggtcggaatt aaacgccatt aaactttgag      71760
tgattaatcc cttaaatggc ccatcaataa attccatttt gaaatgcgga atactagtca    71820
taaaccgtgc attaggagca gtacaaagaa cctgctgccc tgcgaacggg cctttagtca    71880
aacgatatcg tttaggttta aaatggtaaa tctcataatt ttctacaaga gccctttat    71940 tgcatactgg gctgttataa caatattcaa aaacttcaat agtggtcatc attgcattcc    72000
aatcacaaaa aattgaggac gagcattacc gccgatgcaa tatttgcttt tgcaacagtg    72060
ttggactgtt ttaatatgga cattgtaaat cttatccata tcaggagctt taataggctc    72120
gtcaattatg tacagaatac gagaaagcgt taatccacgg aatttagaac cttcattgcc    72180
aataaaacta cggacagaat cggtaaataa acggaatcga atatcatcgc tagaataacg    72240
agaaaattct tttttaatgt tgccagcaga aattttagca taggctgaag tattagaaag    72300
aacaataact gttccaccgt catacagcca attaacagca aaattagtta ctgcagtcga    72360
tttacctgat tgtctgccgc cgtctaaacg aagtgtacag tactgcttga gtacgtcttc    72420
aaatggtggg gcataaccgt tcttacaaat ttcttctact ctagcatcag aatggtgtgt    72480
aaaagcattc atcagggata gataaggacc agttaaaaat gttctcattt agtttctctt    72540
ttaggttggg ccattccgtg gcgcatgaat tgtccatttc tgtatttacc cctctaagta    72600
attatgaata tactatcaca attctaggag aaagtaaact gttatttacc tttaattact    72660
ttagctgctt cgatagccgc ttgctgaagg tcatccatag acataccgaa tttagaagca    72720
aagttatcaa ttttctttc gacagcattc aaaggcttgg cctgtttacc ttcattagcg     72780
ccaggaagag cgagaatacg ctctttgtca atataaaggc ttacaagttt cttacggtct    72840
ttatcggaca aatcatgaaa tgaatgggcc ttttattta gcggcttc taatttacct       72900 gcactcactc gcgcttcagt aataaattct tgatatgttt tcatttttg tttccttgtt     72960 gttttgatag agtaattata ccatattaat acttaagcgt aaacaattta agcttaccg     73020
```

| | |
|---|---|
| ccagaaataa ttccgaagtt gttaaaatcg tatccaatat cgtcaacatc tactttagga | 73080 |
| tttactacaa cataagcaat ttcactacgt tttgcatagg tgttgatttc tttaccatcg | 73140 |
| ccacctaaga aagaataccc attacgtttt aatgagccaa agtcttcggc atcaccaatg | 73200 |
| aaagctttaa ctttaaattt aggacctttg gcatctgctt caatgataaa ttcttgatac | 73260 |
| attttcattt ttccttagta aattgattta ccatagtatt tgtaccaagt aggacgttga | 73320 |
| gcaattttt catctaagcg tgcttgactt atcgcaacgg acgcttcgga cgggacataa | 73380 |
| ttattacgaa attcggcagg gatgtcggaa atatcctgga ctgtcgtgtc cttgattttg | 73440 |
| aaaccacgtt tcaagcattc agcgattagc tcgatttgtc gtaaacgtaa aaattcaagt | 73500 |
| ttgtcgtaaa agaatgttac gtgacctgtg cctaagataa atgttggaga gattttaaaa | 73560 |
| tcctttacac gttaccgtt ttggacatgt ttacggactg cactaaatac gcgtggtaat | 73620 |
| tcacgatact cagccataag atgttgatcg gtcagttcag aaacaagtgt taaattgata | 73680 |
| cgagtcataa tttcctccaa gtagttgatg aatgtatagt atcaaaaccc ttggaggaag | 73740 |
| taaacactat ttttctgaag cgcctgaaat atatttttca agacgttgtt tcatcagcga | 73800 |
| gccgttctta gcgatttctt ccggtttatc gcacatacgt aacaaggctt caagcttagc | 73860 |
| gatatcgctg gtacgttcaa atttgcgagt atctatctta ctagcaagtt cagaaatacg | 73920 |
| tgctaataga ctttcggctt caaccaaagc tgcacctagc ttagttgcaa atgtgtcagt | 73980 |
| agcttcgtta agaatagatt ctgataaaaa ttcactatat gttttcatat atacgctttc | 74040 |
| caagttcctg ttttaaatgt tgagattacg cgtttcgcgc gattaggtgt ctgacgatac | 74100 |
| catttagatt gggcgagatt tactgccgct tcatcccaac gtttctgttg aagcatacga | 74160 |
| agagaattag taaaaccagc aacgcctgct acacccattt ggaagaccat attgaccaat | 74220 |
| gcacatcgac gaaccgcgtc taaagaatca tataccggtt taagtttagc attacccaag | 74280 |
| attccgcgaa cggctttatc gacgtcttca ttaaatagct tttcagcctc atcaagggta | 74340 |
| attgtaccgt tgcatttacg accgatcatt ctgtcaagtt cagctttagc tacggctaaa | 74400 |
| gacgggttct tgttactaa atggcctatg ccaatcgtcc aaaagccttc agtgtctttg | 74460 |
| tataaagtca gtctaagacc ttcgtcatta cgaagcatt caaatatatt cataatacct | 74520 |
| cccacgttta taggaggtat ttattactta taggatggta gtgagcacct tatataatga | 74580 |
| tttgcccatt acatattccc attgagaagg tttaattaaa gcgaatgcat caaattcagg | 74640 |
| aatctgtcgt ccgtccggga atgtatgata tgaattacaa acactgtttc tgaattgctc | 74700 |
| gtgctctaca gggatggtat ataggaacag atgaatattc ttattgtctg agtaatgatg | 74760 |
| ttcacctagg tctttcagga aggcagggtc atattgtgta aacccagttt cttcttcgca | 74820 |
| ttcacgaata gcggcttcga taggagattc gccaggttcg acacggcctt taggaatatc | 74880 |
| ccaccgatga gctaatgcac ctttaggacg agaaccagtt acacgaccca tgaataattc | 74940 |
| tttatctttt gtcatgaaga taataccggc tgatagttct ttcacttat ttttcttact | 75000 |
| catcatctcg gtcccatgat ttggccatta attcggacat aaattcttca atacgcgttt | 75060 |
| ctttagatgg acttcacta ttagagaccg caagtttgta atctgcaata ggactgaaca | 75120 |
| aatcaaggtc catattaaga tcgtctttga ttttttcttc tgacacatct ttatcatatg | 75180 |
| tgtacagata actatcacat gattctgatt taatgtaaat tgctatactc atctcaaatt | 75240 |
| cctgcattcg gtaataaaac gttcaacttc attattcttg gcctttatct tgtctttacg | 75300 |
| ttcctgtaaa ctacttttaa caagattaat aatgatgcct atagtacctc caccaataat | 75360 |

```
accaccaata atacttacga tagtagatgc taataagata gcgataatat ctggtatggc    75420
aaaggcactt actttagtac taaaaaacca taccgacggt acaaatataa tccatcctgt    75480
tatccattga cacttattga aaaactttc  aagatcagct tgagttgttc gtattacttc    75540
atcgataggt tgatatccat taatgtatct gttcacgata atacctgctg gctggtcgat    75600
tttaaattct tgacaaatac gtttcactaa gtaggatgga catcctgtcc aatctactga    75660
atagtatgaa ataccttcat tgccgtcgtc aatattagac caatatgttt tgttaatcat    75720
taccagcctt ccatagggaa ttccagataa acttgggcat tgacacgaat ttcattggta    75780 atcttttaa  ctcggtctgt attacgagat acacgtccga accaacgcca tccattacta    75840
attgcacgag aaccagtgtg ccatgtttgc caatcaaact gaagaagagt acggtctgga    75900
gcttcccatt tctctagttc acctttttca attttttcga ggacttcttt gtgccattgg    75960
cgatagataa gttcgccatc aggaatctga ctgaactctg cagttcctgt tgcaaaatga    76020
gtaggacaca cgtcagcgtt aacaagacca agaatatgtt cagaatggta acgagggtta    76080
tcatagtcag gttgtcctgc agtaataaag tgttggccga ctggaatatc agggcgagga    76140
acatcgtcat ggtgatatcc aggaatagca ggataccaac caggcatcag catatgaacc    76200
cgagaatcaa atacaacatg ttgattagtc caatcaattg ggagattggc aataaagcta    76260
cgagtaatag gaccgccgtt atcccaagca aaactcaaat cacagttaaa gaacattggt    76320 tcattttga  tttggtcatt ttgtacgtta tgagcaaaac cacctactgc acgagcttga    76380
ctattaaaca ctttagaact attcatatta ttttcctcga cattctttaa tgaaattttc    76440
tagattggta gattcaatag cttttttacg agcttctgcg tgttcttctt cagacaattt    76500
acatttataa ttaacccaga cgttatggtc aaaactagtc gtggcatata ataacaaagc    76560
cccgacgaat aataaaaatg gtgataagaa tacaaaacca ggaacaccat ccatatcgta    76620 agcctttttgt aatactgcaa cagaaagagc tacgtaaaaa agtgatacaa atatagttaa    76680
aagaccaatt cggttggttt cgcctaattt cataatattc tcctcatgtt ttaataggac    76740
tactataaca tagtcctata attgtgtaaa cagttttgcg aaattatttg aaaggtttta    76800
ccatatggaa atttttgttta aaacgtttta cataatcgtc atgtcctaag ctttggtaca    76860
tacttacaac tttgctgtag ttttcccaag cgtattcacg gaaccagcct gacgtgattg    76920
aagtacagac tttttctaat gccatcataa aactatcacg tggatggatt tcaaagttat    76980
taggaatctg agaacgttct aacgctagta cacatgattc ttcgtatacg ccggctaatt    77040
tgaccatttc tggtaatgat tcgaacttct cgcgtgaggt catgacttca gaaccatctt    77100
tcatataaaa tgtatacgct ggacggtctg ttagtgcaat ggcttcgtga atagtatcat    77160
ggtcatacgt atagatgtca tctttaaaga atgcgctttt agaagtgtca agaactgggt    77220
gagcatagtt caaggtttct ttctggcgtt tcagcataat ttcagtaagt tcatcgttca    77280
gtgtaacacc tttaccacga agatactgaa tatggttcat agtctttaaa aagaatggat    77340
tatttttctt gaaacgatga gacatcttaa ttgcaagaca catctcagga gttgcccagt    77400
aaaacccgtt caaacggtct ttagtcaaat ttttcttggc gtattttaaa aggtcataag    77460
aagacgtgaa atcttcagga gtgagttcac cgactaattc acggacatta gtgattgccg    77520
gaacaatata tgcttcaaaa tgagtttcgc gtccattatg gaagcatttg aaaacttgga    77580
catcagggtt atcttggtga acatatacac ccatcatttg atttttgaat acattccaag    77640
aaccttggtc cgcaataaag tcccagtcac tattttgat agcgctagaa tcaataagac    77700
cgtgatagtg aagtgcacga gaaccaataa ctaacatcat aatattttcc tcgaatttag    77760
```

| | |
|---|---|
| attacttaaa tttcgcgaca tgcgatatta tattcatccc agaggtcgtc atgtgaagcc | 77820 |
| tctactaatg gaacgattgt gccgtttatg tcttcattat aagggcaaat tgtacagtgc | 77880 |
| gcatcttcga atcggatgcc tttgtgttca gattttttat aacgcatatc gaatatcttt | 77940 |
| gcaaactttt cacgagtaat agttttagca actacttcgg ttcctatact ttcgtaataa | 78000 |
| accattgttg tctccattta atttgatagg actactataa catagcccta tcttgttgta | 78060 |
| aactgtttta gcaagaataa ctagatgata cccagccttg aacagtaata ctattatttg | 78120 |
| ataacgagat tgcgtcctgg agattcagac ctgcattatc ttcaatccac aatgtaactt | 78180 |
| cttcacgctc ttcggttgca atctggaaca ggttttctag agcagctacg gccgtacgta | 78240 |
| cagcacaatc taattcacga gacatatgat ttccttaaca agtgtgagaa gatgcaaccc | 78300 |
| aaccaccatc ttcaaggctc aagttgtagt cgtattggta aacgtcggcc cattcagcat | 78360 |
| aaccgttttt tgtacaacgt tcaagatcgg ctttaagatg tcctggtgaa tgataggttc | 78420 |
| cacccatgcc ataagctgga tacaagttga atgttgtgtt ttgtttatta gcaatttctt | 78480 |
| tggcagcctc aatagctgca tagattttttg ctacagcttc agccagttcg gtttgttctt | 78540 |
| tagacataat gattccttag cacaacgcag aagacgaaac ccaagcacct tcagtaataa | 78600 |
| cgtaaccatt accttcacgc ttaacatcgc caccattatt ttcaatttca tctttcatcc | 78660 |
| actgggatac gatttcaccc ttaggataat aagtacgacc gctaccataa tcacctacag | 78720 |
| aaaatgatac tgcatattgg tctgcgatct ttgttgcttc ttcttcgatg cgttcagctt | 78780 |
| gattcagaag tttataaatt gcatctgaag cggatttggc atcattaaac tctggtactt | 78840 |
| taatttcaat aatcttactc attttctaca ttccttaata aagttttcga ttgtttcatt | 78900 |
| ttcactttag ctaggagttc attataacta atcatttgag aagcgtaaac agcataaatt | 78960 |
| cagttaaggc ttttgcatct tatttcctta acgaattcca tagcttcttc atattcatac | 79020 |
| tttttaacag cttcatcata ctgagcttgg gcttttgcgc actgaacttt ccattctctt | 79080 |
| aatcgggctc tgtgatgacg tccttggtac caatatccca tccagttaat aggcattaat | 79140 |
| aaaaacggta caataagtgg tgcgacgaac attaatgaaa atgctgcatc agacgatata | 79200 |
| acttcactag aatctaaaac ggctcctata atcataaaga ttaaaaatgc taaagctaaa | 79260 |
| atagggccaa atagtacttc atttgggatt aatttacgct tgtattcata cgcccagggc | 79320 |
| ttacttggca tgtataggt tggctttgac atattctcta cattccataa taattgctc | 79380 |
| aaggattaaa ttgttagtga aattaggact aacaaccata gtttcataaa gcgcatcaat | 79440 |
| agcacttaaa gcatcaactc tcttaagcaa aggcttgcct tcatacatag tttcagaatc | 79500 |
| gacgattaac gtaaagtagt atttttttatt atcgactaga acttctgtat cgatataaaa | 79560 |
| catattgagc ctcagaagct tatctctaaa accataataa tcttcagagc gttcgctgat | 79620 |
| atattcccat tcagtgttta aacaacaaac agaccacgta ggagcaacga atcagtgaa | 79680 |
| tctaatatca tggtctgcaa ctagtttagc aatagctccg atatcatgaa tcataatacc | 79740 |
| tggggctaat aaagattttc tgctatggct agccgttttc tcggtggtct cataagaaga | 79800 |
| cgaccagtac catttacgtc cggttgcaac atatcgtaat gaatcaacta agacgtagg | 79860 |
| tggatttacc ttatctcgga actcttcgaa cattgagtca atatcattat tttggtttcg | 79920 |
| catgttaact cctttattat ccaaaaggag gaccggagtc ctccgtatta ttttattttca | 79980 |
| aagagttaat atattcttgt acatcagcag aagtggtttc gacgccggct ggagtgccat | 80040 |
| tgaacgtttc aacacgagtc agagtgtctt cgatatcaac cttagtcagt gcagcaattt | 80100 |

```
caatcacatc atcagccgta gagataccaa gggcattggc tgctcgagtt tcacgaatgt   80160
attcgagttt gattgccaga ttctgacgag catcatcaag ttcaacaacc ttacgagcaa   80220
tttcaattcg catagcggca taaccgtcag cttttgtatt aagttgttcg gcagttcgac   80280
gatacagaag accaagctta gcatgcatgg taacatcttg tccttcagcc aggagcttac   80340
gaatttcacg ttccttagaa gcggcttgct tgttcttttc attaacaagt tcgcgaatac   80400
gttttttcttc attaatagat ttaacagaag ccgttttag ttctttgatt tgggtaatca    80460
acttatctgc agctgcgtta tactgttctt cgacagtcag attttagcc atagcagtac      80520
ccagtttagt gcggatgaat tcaacaagtt tcttcagtgt gttcatatta ttaccttca      80580
attggtggtt tattatccaa tgagagcatt atactctgct ctcaagagtt tgtaaattat    80640
ttttaatca aattgacata aaacttggcg tcttccgggt gcatgccttc gcagtattct      80700
tcaaccatga acttcttaac agcttcataa ggaccactca gattaagctc agttgtccaa   80760
aacttggaat cttgggctga atcgatacga acttcagggt gtcggttgcg aataacttct     80820
tcggtgtatt cataatcaac gacatcaata ctaactttag ccattttgtt tctcctctgt     80880
agttgataag tcctatagta tcaccatcat tggtgtttgt acatcattat ttttaatttt   80940
tccaacttaa caacttgtag tgtccttcat tcatacgcgg tttatcccaa gaaatactaa   81000
tatatgattc gccatcaata gaagtcgccg ggttttctc taccgtaaga ccttcactt      81060
ccagccattc aatagtattt gcgcataaat ctgaagaaca cctcatcgga aactggcaag  81120
attttcacc tttagatgca gcgttataca tctttctaa aatacgcttt tgcacgtttt      81180
taaaatggt ttcagcagat tcttcagatt ttttattcag atcagtataa agactcataa    81240
tattctcctc attaataggg ctcataatat ctcaatcata agcccatgta cgcatttatt   81300
tcatattatc gaaatattct tcagcgattt cgacattatc atggtaaact ttagaagaca   81360
gtttaacata accttctgcc gcgaacatat taatcacaac ctttacagta taccattgtc   81420
cgtcttcatt acccattact gcgtaagttt caaacatcgg atggtcaggt ccaataactt   81480
taatatcatt caccgtacgt ccgaaatctt ctggaacgca tttcataaag aagttgaaca   81540
gttcaccgta attatccatt tcattctcca aggtttttct gtatcggtag ttgatagttt   81600
tatagtacca cggaagaaca gggatgtaaa cagttttgt gaaaaaaaa ttttaaaaa       81660
gttttgtgga attctagggc agggagggga aatcaaagga tatgataata tattataaag 81720
ggcagaaact aaatgatgcc tagagaggtc gggaaaggcc tagataccaa aaagccctat  81780
catttagata gggctttaaa attatttacc tagtttagtt attatagctt cggcagcagc     81840
ttttagctta gatgcagtgt taatacgatt tttaatttca gtatacgcat cgccaagaac  81900
atcaaggcta tcagaataaa cacttacact attgcgttcg ctatttgaaa tagaaccttt   81960
agttttacga tcaaaatcag tgtacacgtc ttgaagatca cgggctgcct tctttgcatc  82020
atccaatgca tcaagagctt tattcaaagc attgacgtat tttttagtg tcaaacatat    82080
tcttagaaat tttaacaggt gcacgttcag gagtagctaa ggcggattta ggaacctgtg  82140
tgccagatgc cagtttctta gaaattttga aaaatgcttt attgaaacta tttcttgac   82200
tcatcgtaaa agaactagta tcgatgttat acatttcaat agcttagct ttccacttaa    82260
gaaaatcgcc acggtctttt ggatccaagt ggaagaatac tttagtaaga tctgcttcag 82320
atggtaatt tgctgcttcg gttaaaaatt cggcgtaggt tttcatttaa aatccttgaa    82380
ataatttatc ggttggttat taattattta ttacttggt attatcagta acagcattct    82440
ctgagagatt caaactaaaa agccccaacc ttttggctag ggctaagaat gttatttgat  82500
```

```
ttgtttagca gaccaaatgc ggtctttaat aagttttggg atatcttcaa catactcaag    82560
gctatgagcg tgaggattat ctttgaagct atgtgctcgt gccagtttct ggccttcagt    82620
tttgattacc aaaagttctt taagaattgc ttcatactta gaaataattc ctttggcgat    82680 attttttct  tgagctgctt tagggcccgc ttttggtgct ggtgctttac ctgtagcttt    82740
ctggaacaat tcacctgatg cagctaggct tttaaaaact cggctaacag tattagcatt    82800
agtaaaacct tcggctttaa aatctctaat aaaacggaaa cgttcttcat cagaggcgtc    82860
tttgtaagaa tatttacctg cttgaattgc tgcaatcgca gcggcttta  catctgaact    82920 agattgttca gtcaaaaatt ctgcatatga tttcatgtta cttttcctaa gttaattaac    82980
ttatctattt attattatgc aaaaaagccc caacctttcg gaaggggcta agccttgcgg    83040
taaccttgtc ggggttccac ctgctaaggc aagtgtttgt acgaaacgcc gggattcgaa    83100
cccggttatt aagcagttga cgctactcaa tatttttaaa aggccatatc tcgaccatat    83160
ccgaacgttc cgtcaaaaac gctactcggc ttacggcaaa gatatttcct cgaatcgata    83220
attctgtgcg ccgtttctgc tgtgatgtaa ggggatatta acgaatcata aagatttatt    83280
aagaccagtc cttactcagg gaacatcagt ccgacgactt accggtagcg acccggcttc    83340
ttattttggc atatcatcaa tttgctctcg acgccgacgc catagattaa tcgcttcatt    83400
aacacattca gcgtttggta tatgacggca ataatataat gattcacgtt tctgaaaccg    83460
atgttgcaat gggatttcgt ttaaaaggtc tttacgatca aagtattcaa aactagttaa    83520
ccctgaacgg ttttaatga  acttccaatg tccgaattca ttttgaacat agatgtaatc    83580
ggcatgctga tacagcgaat taatcaatcg atgagaaata actgtatcat attcgttaaa    83640
ataaaacgtt aaatcatgaa ctaccagata aatattgcct ttcatatttt cctcacttaa    83700
agttggtcga gacagaagga ttctaacctt caacctacgg attagaagtc cgttgctcca    83760
tacaattgag ctatgcctcg aatatatggc ccagaccaga ttcgaactgg taacctttcc    83820
cttatgaggg gactgctgct aaccattgag ctacagggcc taaataactt tctattatga    83880
aaggcacttt agagcacctt tggtaataga gggtatgaat taataataac acataattct    83940
taaagcaaat caatcatttt aacggttggc aaaacgattt cttcttcaat ataagcaaat    84000
tcgacacgtt caactacacg caagaaatcg taatcatagt attcagaagc atagccaaga    84060
atatcaataa gtccttgaga tatctcatcg cctttcacaa agaacaggtc gaatacgcgg    84120
gcttcgtctt cttcagattt atcaccaagg tctacttcga tgccaaagac cttttttaata   84180 aattccggtt ggagttggtc tgagaacagt ccttcaacca gatattcgta gataataagc    84240
gagcaacgac cgaatggtgt attaccgcaa taacgttcgg ctttggtgct agaatgacgg    84300
ctcttaaatt tcttcaagag atatttaaac tgttggagct catgctcttc cacttcaaac    84360
aatgttttgg ttttatagtt gtcaccatca ctttcatagg tagtgacatc aattacgtag    84420
cccttaggaa ttgtactgcc taatcgaata ttcatttaat caccgtacca tattaatgta    84480
attatattca atgcaacgta atttcaaagg attcttgaaa atatcatatt caagagggcc    84540 ttttctgtt  tcaataaaga aatcaaagtt aactgtgtta aatttatcat cttcacagag    84600
taatttaacc tgtgaagacg aacggtcaat gtaaacctttt tcaacttcaa aatatgttaa    84660
aatgccataa tcatcgatca atgctttagc tgcacgttga tcgctttcgt atccattctc    84720
gacagatttt actttagcat aaagaatcat gagtgttcca ccacttcaaa agtatgtgca    84780
tttacaatct ggtaccagtc aaaatttttct tcagcatttt tgtagatttc acgaagagct    84840
```

```
tcaacagttt ttcctgtagc aacaagatca tcaataccac caagaggata acagtcataa    84900
ccagcaaaca gaaggaaatt aatagtttct gtaggttctg gatgcagtgt accattgtca    84960
tcgactactt caaagaacat ataaccaggc gatttagatt taatccaagc ccatgcttga    85020
gccgctgaat caaatggttt gcgtatcaaa cgacaatcag ggtctttaga aggatttgct    85080
tcaaaatccg catatacacg atatttcatt ttactcacct tttgcaattt tatccataac    85140
gatagcgatt aagccgatta gaaatgctac taccaatgag atagaatttt ctgttgttgt    85200
cagtagtcca caaatgaatc ctacaaacat cgaaaaacta aaagccattg aagcaattac    85260
tacagcaaca ttacgaatca gttcagcgcg tttcatttta ttctcctcag tagttgatag    85320
ggtaatagta tcaccaccct atctaaaagt aaacggtttt ataaactatt ttattccgcg    85380
tgatgcaatc gtattctgcc gtttaacacc agtttgttta aagtcatgac tgtcgatttg    85440
atcggtgcga gcaactccga atgatgattt aatcttagct ttagatcctt tagttataga    85500
aataaacatc tcggaagacc ctttcttaaa gtctgatgca gatacttcaa caccgttctt    85560
agcaagtgac ctcagaattg catccgcgta ctcatcatca agactcgctt gagtattaat    85620
aacaaatgtc tttggtgcag ccgcttcatt gataaattct ttataggttt tcattttatt    85680
ttcctaatta attttgatag gactactata acatagtcct attagcatgt aaactactta    85740
cagaagggtt tttgcaataa ttttaagctg agctacagaa atatgcttag ctttaaacag    85800
tgcagtctct tcagccggag agataacaat agtagcgcca tctttcttag cagaccatcc    85860
atcccctaag taaacagtac cttttacttc ttcgccgtca accagactaa tcatcggttt    85920
accctcacgt cctttatttg ctttaataac ttcggaagta agggttgctt cagtcagagt    85980
agaaacgtta gcatcaggtg atataaattc tttataggtt ttcattttat ttccttgagg    86040
tcgtttattt gataggatga tagtaacacg ccatcatcct tatgtaaact gttttgtgaa    86100
attattttag atcttcggcc caatctagtt ttaagggttc tttgtattca cggtcgagaa    86160
taaccggaat agctacatca ccactgaatg atagttggcc aacgttatat gataacgtta    86220
tatgtggagt gtagtcgtcg aaatcatgag tagcacctaa agctcgtgcg tactgatgac    86280
gacatctaag atattcggaa tcaagaacta aaaccagtac agcaccgtcg tcagtttttcc    86340 atacctcaag gtgtcctgat tcggcaacag aataactacc actagatgta gtatatggta    86400
tgtttacacg tgaataacaa attgttgaat gaagcttttc acgtggtact ggattaggaa    86460 ttcttaatttt gcgctggagg tcttccagcg catcaagtgt taattctgaa aacttagctg    86520
cgacgtagag gccttgtgaa aagtcctcaa atttcattat tcttcttctg tggtttcagc    86580
tttaacaagt tcacgtactg cttctaccag gtcttccagt ttaacagatt cacttgtaat    86640
accgaccagt tgagcaatct gagctagggt attctgaaga agtttagaat cgtcagaaat    86700
acgagcggcg gcatcttggg tatcaagaat acgagatttc agaattacga tttcagactg    86760 cagttttttca atagtttcat tggacatttt attaccttaa gatttttttca attttagaat    86820 aaagctcttc taacgagccg tcgtttgtaa taactaagtc gccttcttca ataggcaacc    86880
cagcttctgt aatatgttta tcagtggatt ccgtaccaga gcgaaccaca tgaataactg    86940
tagcacccat cgctctagca gtttccattt catggacttg gcgcgtatcg gtcacaacgt    87000
agtaatcgaa atcacttcca atataatcca tatagtttaa tgcaaaaagc ttaacccaat    87060
acatacggtc aaataaatta acgacaacat ccgtaccgag ggcttgcata agacggcgga    87120
tcgaccatgt gtcgttgata ttattttatag cttcacgcag ggcttcatat ggtttaatat    87180
ctagatatga atatccacct tctaacgatg ataatacttt aacattatta attggtaaat    87240
```

```
attgactttg taaataaatt agcgcttctt ccaataattc aataacatcc aacttattga   87300
gatttaatgg tgtttcacgg tcgtatccaa tgccttcaaa gtattcgtat ttcaactctg   87360
tgaatacatc aggattttca gcatgtctac gtccccaggc tattgctaga gcgtctttaa   87420
ttggatatgc taattggtat tttacggatt taaagtttga attgatgtaa tcagcagtag   87480
tgtctttacc actacgtttg atgccactta aaaagattag ctccataggt tttcctcata   87540
taatttataa gtgattataa catacggagc tagaagcgat taacgcaagg aagggtgtct   87600
agaaatggat ttagattcgg ctgcttgacg aggctgttga gatacaatga cttcgccgtc   87660
tttttctatc gtcatatacg cgtagtgaat agttgctacg cacgtaacgg caggatcaga   87720
atcttcagtg taactaaatt caatttcgct caaatcagaa atccatggtt tatagaaatt   87780
tgccgtcaaa acgacttcag tcttattgtt gtttaaaatg tgcaaagtaa caaactcagg   87840
accatcggca tgggctgtat tatgaccggt tatatagtta ttagtgctga gcatccattt   87900
atacatgttc atccaggacg tcatgtcttc gtcaactata aatcgtacaa taaaagggtc   87960
atattcaaat gtggtgcctg cacgcattgc acgacctagc cccattgtgc ctgtcacagt   88020
ttcaacaaca ggaattctca cacctggcag tggagccgtt tgggcattga gcacaaaacc   88080
tgaagttcgt gtactatccg ggatatccac aacaaagttt gttatatttg tttggttaaa   88140
aatctgtctc gctggacgag tcataagcac ctcaaaaacg ctttaataaa aatgcagtat   88200
aatggtttta ggtctcttcc attaatctgg ttcaacagaa tatcagaaga acggaagaga   88260
atagaattaa gatttccaaa cagtattcgc agagaaacgt tttcctttgg acataaattg   88320
ctgagtaggt aacatgatta tgttagccca gtctttagga gcgatttctg ttattgttcc   88380
tctaatgtgg cctggcaggt atgctttaat cattttgtcg gcaccttgaa atcctttcac   88440
cttgctccag tctatcttca actttgtgtt attagtaata gtagttgtgc tagcatattg   88500
cttcagcaat tcttcaagaa actgttgacg tgctttaggt gggatatagt gcaagtttaa   88560
cccgtacatc aaattatgtt tacctaatcc taaataaata atcaaaggat atcggtccca   88620
gtatggcaga gtatctttat gtttagcatc atacacgtaa gtataaattt tgcctggcgt   88680
aggcttgact actttatgac cttttacact tttcttaatt gtttcaacaa accacttaga   88740
tgatttgttg tttactgctg cgccttcatt tctaatcttt tctcgtattg aactgcgaaa   88800
cgagtttatc atcagaagtt gacgttcttg cttattgagt ttattttag gtttagattc   88860 aagcgtttca attttctgtg cagtcttaat agatgatgca tatctagaca ttgcagatgt   88920
aaacgacgag tattttattc cttttgattc tgcaaatgct tttgcagtga ttcctttctc   88980
tttagctttc ttgtattcta atcctatctc aatccatttt ctttcattca tagactgagc   89040
aatcttaggg gcttgtacgc cttcagatat aatttggaat atgctcataa ttaccccttg   89100
tatccgagtt tcctaagtcc gtcttcggtt agaactcgaa attttatatt tctcttttct   89160
gcgacagcag aagcagcttt ccatttgtcg cagttcacag accaggtgta tatttcgttc   89220
atataacgtt tctttgctgc ggtcgtaaga tttacaggct taataggcgg ttgagtttct   89280
ttctttggtt ttatttctac aaagaactct tgacctgatg catctttcat ccatatgtcc   89340
atatagtatc gacgtttctt accttcagca ttacaaaaat atggaattac ggctgtttca   89400
ctaccccatg caataatttc cggattttta tccaaccatt cgaaaagaa ttttcccag   89460 tttgaacgat acgttatttt ggtatggtct ccacggtatt tttttaaatt ttttgggacc   89520
catttaccag agtaggccat gttgtcctcc ttataaatag tattattatt tataccaatt   89580
```

```
tcatattgga aggagactat cttgttattt acattcttcg acccaatagg atatagtgct   89640
aaaaccatta ataagaacgc acctactatt cctatgacag acatatttcg taactataaa   89700
gagtacttta aacgtgttgc gaccaactat agattacaaa cttattatat taaaggttct   89760
ccacgccctg aagaactagc aaacataatt tatggcaacc ctcaattata ctgggtcctt   89820
ttgatgtgta atgacaatta cgacccgtat tatggttgga ttacatctca ggaagcggcg   89880
tatcaggcat ctattcagaa gtatgcaaat gctggcggag accaaattct ttaccatatt   89940
aacgagaacc gtgagaaatt ttacaattta gtttcatatc cagacgagcc tttagtgtgg   90000
tatgataaag gtgatgaagc tcgtaagtat ccgcaatata aaggacccttt agctgcagta   90060
gatacttatg aagcagctgt actagataac gaaaaacttc gtaaaataaa aattgttgca   90120
aaggaagata taaactcgtt tatcactgat ttgattcgtg agatggagat tgcataatgg   90180
aaatgattag tagtagcctt aattggttcg ttggtgttgt tgaagacaga atggacccat   90240
tgaaacaagg gcgtgttcga gttcgagtcg taggacttca tccagcgcag agagcacaag   90300
gtgacgtaca aggtattcct accgaaaaac ttccatggaa gactgttatt caacctatta   90360
cgtctgcatc aatgtcaggt attggtggtt ctgttacagg tcctgttgaa ggaactcgag   90420
tatatggtca tttcttagac aaatggaaaa caaacgtat tgtactcggt acatatggtg   90480
gaattgtacg cgaaaagcct aatagactcg aaggtttttc cgaccctaca ggtcaatatc   90540
cacgacgttt agtaatgat acgaacgtat taaaccaagg tggtgaagct ggttattatt   90600
cgaattctaa cgtaattcaa gacaacaact tggactatgg tataaacccg gatgatacag   90660
atttagcaaa tattccagaa gataatgacc ctaattttac aataacagaa atgttacgtc   90720
gtgatgaagg tcttcgtgat aaagtgtatt gggaccatct agggtatcct acagtaggta   90780
ttggacacct tatcgtaatg gaaaagaccc gagacatgac tcgaattaat aaattgttat   90840
ctgatcaagt agggcgtgaa gtaacaggaa atcccgggac tattacatta gaagaagcaa   90900
cagcgttatt tgagaaagac cttgctaaga tgcagaaaga cattcgttct aattctaaag   90960
taggtcctgt ttatgctaaa atgaacaggt ctcgtcaaat ggcattagaa acatgtgct    91020
tccaaatggg cgttggtggc gtagcaaaat tcaatactat gcttaaagcg atggccgcag   91080
gtgattggaa aactgcatac aaatctgggc gtgattcatt atggttccaa cagactaaag   91140
gacgtgcttc acgcgtaaca acaattattt taactggtaa catggaatca tatggcgttc   91200
ctgttaaaac accaccttca ccaggagtcg gtgccgattt agttactaga ataccgatc    91260
cagaagaccc ggccggtcct cctgttccat tagattcgcg tatcctttt aaagaacctg    91320
aatcaagtta tcgtggtgaa tacccatatg ttcatgctat ggaaacagaa agcggtcata   91380
tccaagagtt tgacgacact ccaggtaacg aacgttatcg cttagttcat ccaacagggt   91440
catatgagga agtttctccg tctggtcgtc gcactcgtaa aactgtagaa gaccttttttg   91500
acatcactaa tggtgatggg aatttcctgg tttctggtga taaacttgtt aacgttggtg   91560
ctaacgaaat atattataac atggcggacc gcctccatca aatagatggc agcgacacaa   91620
tcttttattcg tggcaaccaa gttaaaactg ttgaaggcga tggaactctt tacgttaagg   91680
gcaatatcaa aatagtcgtt gacgggaatg cagatattct tgttaaaggc gatgctaaaa   91740
ctcaagttga agggaatcat gactatactg tcaatggtaa tgttaaatgg actgtcaatg   91800
gtaatgttga tatgactgtt gctggtgatt ggtcggagac aatgactaca atgagctcaa   91860
tagcttcagg acaatatact gttgacggat ctcgtattga tattgggtaa tatatggcac   91920
aaatacttcc tttaaatacc gacttaggag aagacatgga agggggtctt attgacgtcc    91980
```

```
tttttactcc gcagttagaa actaccgaaa ctttggtgtc aataaatata atagattatg    92040
aaccaacaca aggcattaca gttgacggta atcacttata tggaacatat gaaagcgtat    92100
ttagcttttc ttcagatgca ttgaaatatc gattaaacga tgattttaaa actgcatctt    92160
catgggaaga tttaccacaa gaccaaagca ctcaactata tttgtggaga gctcctcaga    92220
atcttcgtaa agtgtttagt tatacggttg aaatgattta taactaccaa gaagaaagtt    92280
catcaggcgg cacaagaagt gactctggta cagaacctcc accggctcca gtacaaaaaa    92340
ctcttactaa ggtttataca aaaactatag taggaaattg gagcaaatgg gctcaacaat    92400
tacgaaacta tgtttatgcg aggccataaa aatgtctgga ttaagttacg accagtgcgt    92460
tacaacaggt catgaagcat ggcctcctac agtaattaat gcttctcaat ctaaagtatt    92520
caccggcggt attcctgttc ttgtagcagg agaccaaata acacctcata cagaaattaa    92580
aaaaccgtac gagactcatg gtggtgttac tgaacctcgt acatctaaag tatatgtcac    92640
cggtaaaaag gccgttcaaa tggctgaccc aatttcatgc ggggacactg tttctcaggc    92700
ctcgtcaaaa gtctttataa aataggaatt aaaatggcaa acactcctgt aaattatcag    92760
ttagtcagaa cagcgaatgc tattcccgaa attttttatcg ggggcacatt tgccgaaatt    92820
aaaacaaata taatcgaatg gctcaatgga cagaacgaat ttcttgatta tgattttgaa    92880
ggttcacgtt taaacgtatt gtgtgacctt ttagcatata atactcttta tatccaacag    92940
ttcagtaata gtgcagtgta tgaaagcttt atgcgtactg ctaacttgcg cagttccgtt    93000
gtacaagcgg ctcaggataa tggatatctg cctgcatcta aatcggcagc acaaacagaa    93060
attatgctca catgtacgga tgcgttaaat agaaactata tcactattcc gcgtggtact    93120
cgtttcctgg cgtatgctaa aggtacttct gttaacccgt ataactttgt ttccaccgaa    93180
gacgtcattg tagttaaaga caaaaataat caatatttcc cacgtcttag gttagctcag    93240
ggacgtattg ttcgtactga attaacattt gataaattaa aacctatcat tattcgtgat    93300
aagaacattg accgtaattt ggttaaattg tatgttgacg gagcagaatg gattaactgg    93360
actcgcaaat cgatggttca tgctggttct acttcaacca tttattatat gcgagaaact    93420
gttgacggga acactgaatt ttattttggt gaaggtgaaa tctctattaa cacgtcgaaa    93480
ggtgctttaa catctaacta cattggcggc cttaaacctg tccagggttc taaaatagta    93540
attgaatata tttctactaa tggtgctgaa gcaaatggtg cagtaggatt ctcttatgct    93600
gatacattag ctaatatcac agttattgga attaatgaaa acccaagtaa taaccctgac    93660
ttcgttggtg cggatggcgg tggcgaccct gaagatattg aacgtatccg tgaattaggt    93720
acaattaaac gtgaaactca acaacgatgt gtgactgcga ccgattacga cacattcgtc    93780
tctgaacgat ttggttctat tattcaagcg gttcagacat ttacggattc atctaagcct    93840
gggtacgcat ttattgctgc taaacctaag tctgggttat atttgacttc cgtccaacga    93900
gacgatatta aaaattatct taatgagtat aacttaggga cgataactcc tgttgttatt    93960
tctcctgatt atttgtttat taaatgaat attcgcgtta cgtatgcatt gaacaaatta    94020
caggaatctg aacaatggtt agaaggccaa attattaata aaatcgaccg gtattatatt    94080
gaagacgtgg aaattttta ctcgtcattc gcaaaatcta aatgctaac gtatgtcgat    94140 gacgcagata tttctatcat tggttcgtct gcgactattc aaatggttcg cgaggtacag    94200
aacttctaca aaacacctga aacaggtatt aaatacaata accagattaa agatagaaca    94260
ttagaatcta acgtgttttc atttgatagt ttacgcgttg accctgaaac ggaagctact    94320
```

```
attaaatacg acgttcgcat tgtaggttca gatagaaatg accgtggcat tggacaagtt    94380
atcattggcc cgtttgcaga tggcgacgtt atagaaaatg cttatattca accatatact    94440
ggtgacgatt ttaataaact tcatgttacg gacggaagaa acaaatatta ctctataggt    94500
gaagtaaatt atccggctga ttcaatttat tggaatatag ctaaaattga tttaacttct    94560
gataggtttg aagttcaaac tattgaactc tattcagacc cagctgatga tgttatcttt    94620
actaaagacg ggtcattaat tgtatttgaa aatgacttac gtccacaata tttaaccata    94680
gatttggagc ctatttcaca atgacagtaa aagcgccagc agtcacgagt ctcagattat    94740
ctaaattgtc cgcaaaccaa gttcaaattc gctgggatga ggttggcgct aatttctact    94800
attttgtgga aatagctgag accaaaacag ctaacgggga agcaattccc cgtaatagct    94860
atagatggac taatttagga tataccgctg ataacaattt cttttgagtct ggtttaaatt    94920 cattaacaac atatatgatg cgtgtggcta cagcagcgga gggatttgag cagtctgatt    94980
ggagatacac cgaagagttt gaaacatttg aaataaacgc ttacacattc caacatatga    95040
ttgaaatgca attagctaac gagtttattt ctgaaaaatt tacaaaaaat aatacaaact    95100
acgttgattt taataatgac acgatcatgg cagcactgat gagcgagtcg ttccaattca    95160
gtcctgcata caccgatgtg tcatcgatta gaaattttat aattggtgaa aatcagtatc    95220
atgaaatcca ggggcatatc caggatgtat gtaaagatat aaatcgagta tatctaatgg    95280
aatctgaagg aattctttac ctttttgaaa gattccaacc tattgtaaaa gtgtctaatg    95340
ataaaggcca aacatggaaa gcggttaaat tgcttaatga ccgtgtagga tatccacttt    95400
cacgaaccgt atattaccaa tcagactata cgacgtattt gctcggctat gataagattt    95460
tttacgggcg taaatcatct gatattcgtt ggtctgctga tgatgttcgt ttcagttcac    95520
aagatgtaac atttgctaaa atcggggacc aattaaattt aggttttgat gtagagattt    95580
tcggtacata cgcgtcatta ccaggaaacg tatcacgtat tgcagaagct attacttgta    95640
atgatgacta tgtttatatt gcggccagag ataaagttcg cttcgttaaa accagtaacg    95700
ctcctattga ttcagatcca ttatctccga cctattccga acggttgttt gaacctgaga    95760
cgtttacaat aacaggcaac cctaaagcag tttgttataa aatggattct gttggtggaa    95820
gaatattcgc tcttattatt ggtgaagttg aaaacgttaa tgacgaccca agaacaaagc    95880
ctattttgga ttccgttgat aaaggtgtat acgttttaga ccatgacgct ggaacattta    95940
aaaggatatt tggtaatacc gaagaagaac gccgtcgtat agaaccggct ttcaccaata    96000
tgtctactga tggtgttgag ctttatatct cttctagtaa ttttaaattt ttagaatctg    96060
atattgttga cgacccagaa acgcaatcta agtacggact tttgggagca gttaagtatg    96120
aatatcctag agaatggctc gcagataaac attaccatat gatgattttc gcatcaaacg    96180
aagaaagtaa ttgggaaact ttttcaccaa ctcctatgca gtattatgcg gaacctttct    96240
ttagttattc tagaaaatca ggcacacgtt cttggattaa taactctgat agagcggtag    96300
tgatttattc tgatttgctt tacacaaagg tagtggaaag ctaccctagc acttcacctg    96360
atcgtaaagt tcacgaatac tggaatgatg gcgattgtaa gattgttatg ccgaatatag    96420
aattcactgg atttaaaaaa tacgcatctg gtatgttgtt ttataaatca tcaggtgaaa    96480
taatttcata ttacgatttt agttatcgtg ttagagataa cgtttctata atttggaagc    96540
ccactaacgt atttttgacc gcctcattac aaaaccaaga aaaagaaact tcttgggttc    96600
ctgttgaaga gacaggtcta gctgacccgg atttacgccc attactcact acaatgatgc    96660
cggagtctta tctgttggat aatacaaact ttgaagcatt ttgtgaagcg tatattcaat    96720
```

```
atctttctga tggatacggg acccattata ataacttatt gaatttgatc aaaaataaat    96780
acccacgaga agaacacgca tgggaatatc tttggtctga aatttataaa cggaacattt    96840
atttgaatgc tgagaaacgt gatttagttt ctaggttctt tgagtccaga agttatgatt    96900
tttattctac taaaggaact gaagcgtcgt ataagttttt gtttaaagtt ctttataacg    96960
aagacgttga agtggaaatt gagtcatctg ctggaacgga gtacgatatc ataattcaat    97020
ctgattctat aagtgaagat ttggttggac aaactatata caccgctaca ggtagatgta    97080
atgttacata tttagaaaga agctattcta aaggtaaatt acaatggact gtgactattc    97140
ataaccttt aggtaggctt ttagtcggtc aagaagtaaa agccgaaaga ctagcagatt    97200
ttgaaggtga aatagttcgc ggtattaaag gtaaagaact tgcccaaaac actatcgatt    97260
attttaatcg tggtagagct tattacgtca tgaaaataaa gtcaaatctt ccatcctctc    97320
gttggaaatc tgacgtacta cgttttgtac atccggtagg atttggattt attgcaataa    97380
ccttattaac aatgtttatt aatacaggat taacgcttaa acatgttgaa actattatta    97440
ataaatataa aaattataag tgggattccg gactgcctac ggaatatgca gaccgcgtcg    97500
ctcgtttaga ccctcaaggt aatgtagaat tcaatcctgt tacaggtgaa gtaatttatg    97560
atgctggtcc ttatgccggt atcgaatacc ctttacctgc aaattataac gaagaaaatg    97620
ataactctat tttccaagga caattaccgt ccgaacgacg caagccaatg agcccattat    97680
ttgatgcatc aggtacaacg ttctctagat ttagagagct tgttaatgaa agattgttag    97740
ataacgtggg aaatcctaga gacccgatta atccaccaca ggttaaatta gatgaatgat    97800
tcaagtgttg tctatcgttc gatagttact tcaaaattta gaactgaaaa aatgttgaat    97860
ttctacaatt caataggtga tggtgataat aaaaacacca tctttataac gtttggtcgg    97920
tctgaaccat gggctgctaa tgaaaatgag gtgggcttcg ccccaccgta tccaacagac    97980
tcggttttag gtgtaacaga tatgtggact aacatgatgg gtttagttaa agttatccca    98040
tctatgttag actcggttat tcctagacgt gactggggag atattcgtta tccggaccct    98100
tatacgttca aaataaatga tatagtcgta tgtaatacag ccccatataa cgccactgaa    98160
gtcggagctg gatggttagt ataccgttgc gtagatgttc ctgatgttgg gatgtgttct    98220
attgagtctc tcgacaacaa agaagaatgt cttaaattag gcggtaaatg gactccatct    98280
gttaggtctt taacccctcc tgaaggccgt ggagacgctg aagggattat cgaagttggt    98340
gatggatata tatgggagta tctttatgag attccacccg atgtgtctat aaaccgatgt    98400
actaatgaat atatagtcgt tccatggccg gaagaagtta agaagaccc tgctcgttgg    98460
ggatatgaaa acaatctaac ctggcaacaa gatgattttg gccttgtgta tagagttaaa    98520
gcaaacataa ttcgttttaa agcctatta gactcagttt attteectaa tgcagcactg    98580
cctggtaata aaggatttag acaaatttct attatcacaa acccgttgga agctaaactc    98640
cgtcctaatg accctaatat aaaagctgaa aaggattatt atgacccag agatttacag    98700
cgtcattcgg gtgaaatgat ttatatggaa aaccgtccac ctattattat ggcaatggac    98760
caaaccgaag agatcaatat tttgtttatg ttctaattta gggagacttc ggtctcccttt    98820
tcgtgtataa atagtataaa ctattaagga ttagccacat gtatattcaa actccaaaac    98880
aattgattga cgttggcgaa attggtaacg cttctacagg cgatatcctt tttgacggcg    98940
gtgttaaaat aaacaatgat ataaatgcta tttacaatgc gtttggcgac caacgaaaaa    99000
tggcaactgc taatgggaca ggaccaaatg gacaaataat ccatgctact ggatactacc    99060
```

```
aaaaaggagg tcctactgat tatttcaccc ctgttccagt aggaagtaga cacgacatag   99120
atgcttccac cggtggtgtt attgttactg ttgctagagg tgaactcggt gattccgtgg   99180
aatttataaa ttcaaacggg tcaatttcgg taaacaaccc attaagtatc caagcattag   99240
attctattaa aggtgttgca ggtaatttag ttataaccac acctatact aaagttactc    99300
ttcgttgtat ttcttctggt acaggcggct caatatggga ttattctaca gaaagtatgt   99360
ttagtcatac cgaaattcct gtagacggga catggaatat tatttcagac tatgtcaata   99420
ttcctctatt ttataaaact gaatataatg ctgctaaact tttggttaca tgccaatctg   99480
ccaatggcag aaaaattaaa tcatgcgaaa taaatattct aatagataca attaattcaa   99540
gagttatttc aaccgaatac gcagtgatgc gcgttggtaa tgataacgaa gaagatgaaa   99600
ttgcgaatat tagttttcg ataattaaca attttgccac tatgcacagtt tcttcacata   99660
taaatggtct tcgagtggca gctaaagtta tttcaactca gaaaattagg gtcgctcaat   99720
aatgaaacaa aatattaaaa ttgggaacgt cgttgatgac ggacaaggcg attaccttcg   99780
tcgtggtggt gcaaaaatta atgaaaactt tgatgagttg tattatgaat taggcgatgg   99840
cgaagttcca tattccgctg gtgcctggaa aacataccat tcttcagatg gacttaatt   99900
agctgctgaa tggggtaaat catacgcaat tgatacttca acagggcgtg tttctataaa   99960
tttacctaaa ggaacagtgg aagattataa taaagtaatt agagcccgtg atgtattcgc  100020
cacgtggaat attaaccctg taacattaat tgctgccagc ggtgatacta ttaaaggttc  100080
ttccagccca gtagaaatca atgtgcagtt ttcagactta gaattagttt actgttctcc  100140
tgggcgctgg gaatacgtta aaaataaaca aatagacaaa attactagtt ctgatattag  100200
tagtgtagct cgtaaagaat ttttagtcga agttcaaggt caaactgatt ttcttgatgt  100260
atttgggtct gtttcttata atgtgaataa tatccgtgta aaacatcgtg gtaacgaatt  100320
atactacggt gatgcgttca gtgacaatag cgactttggt tctccaggag ctaatcccgg  100380
agaaatcgtt gcattagatg gtaaaaacat ccgtttaaga caaccatgta atattggcga  100440
caccgtacaa attgaaacct tttggatgg gattacacaa ttacgcagtt cttattctcg   100500
ccgccaaata cgtattttag attcaaaatt aacaacccgt ccttccttag aaggaagtgt  100560
atatgtcgct gatttgtcaa ctttgaaatc tattccttt tccgcatttg gagttaatcc   100620
ttcagaaccg gtcaataccaa attctttaga agttcgtttt aacggtattc ttcaagaatt  100680
agctggtact gttggtttac ctatgttcag atgtgaagga gctgacgcag aaacttctac  100740
tgagtgttca gctttaggtg ggacttgggt tacatctaac acagattatt ctattgaata  100800
tgatgataac gatgcaacta tcgcacgtgc tttagtcttt gaccgtaagt ttgaagacca  100860
agacattatt gatattacat ggtttaataa cgatttaggc actttattaa gtatcgatga  100920
cattttagat acaactgatg aaaggtatgt cgcacaaggt gcaaccgtaa atgtgacagg  100980
cgatgtggct ttgaccgatt tcaataatat cggatggcct aatgtagaac ctgttccgac  101040
atatagcagg gaattctcgt ctattgcaaa tattttaaac actatttacc ctgtcggtac  101100
tatttacgaa aatgcggtga accctaataa cccagccaca tatttaggat ttggctcttg  101160
gaaattatgg ggacaaggaa aagtattagt tggatggaac gacgatatta gcgatcctaa  101220
ttttgcatta aataataacg accttgattc tagcgggaat cctacacata ccgccggtgg  101280
aacagtcgga acaacgtcta acacactaac taattctgat ttacctccta ctcaaactga  101340
cgagaaagtt cttatttccg atgagaacgg tacaattatt attggtggtt gtcaatacga  101400
ccctgatgca gaaggtccta tatacaccaa ataccgtgaa ggccacgcca caacgaatag  101460
```

```
tacacacgta ccgcctcaag ctgtaaataa tattcaaccg tcaattaccg tataccgttg   101520
ggtaaggatt gcataatgac catacttagt actaaagcgg gagtaatatc ccgcgaagca   101580 gatttttag  gatttagaaa aaatcctact caaattgata ttttaaacaa ccaaggcgta   101640
ggttctgtaa ctatttctca attggcaaaa ggattctatg atgataacgt agaatctgca   101700
ataaacgatg ttcataatat tgctagagca gatgtaggaa cagttacaat taacacctca   101760
ggtgtatctc ctgaaggaac ttcacaggta gattattggt cctttagtgg aagtgtaact   101820
gaccctagtt tgcccgatgg aagccctgtt attgtaaaag tttatggact tcctgttaat   101880
gctactgtag gtatgaccgc cgacgaattt gttgtacaat tacgtactac tctccggaat   101940
gcgatttccg accaattggc tattgcagag tataaagatg acccaactgt tgggactaaa   102000
ttacaaataa catatttaga taaccaaaga cacgtactcc caacgtattc ctcttatggt   102060
atcacggttt ctcaagaaat agtgtctcag gctaagtccg ggtacggcac ttggaattta   102120
ctaggtgcgc aaaccattac tcttgacaac catatttcac ctacaacctt ttattatttt   102180
gtgagaaccg catgagtaac aatacatatc aacacgtttc gaacgaatct gtatatgttg   102240
aatttgaccc ggtagggtca aattttgata gttcaataac caatgtccag gcagccttag   102300
cctcaattag cgcgtatggt gttaaaggtg ttccggacgc aagtgaagca gaaaaaggtg   102360
taattcaatt agcgacagaa caagaagttc ttgatggatt taatagtact aaagccgtta   102420
cacccgccac attaaatgca agacttcagt atccgaacgc gtcagaaaca caatacggtg   102480
taactaaata tgcaacacaa gaggaagcca ttgccggcac tttagacact gtttctatta   102540
ctccgcttaa attagaccaa actattgata acacgttctc tactcgttat tccaccgaaa   102600
caactaatgg tgttattaaa attgcaactc aaaccgctgc acttgccggg tctgatgata   102660
ccacggcaat gacaccgctt aaaactcagc aattagcaat aaaattaatt tctcaaatag   102720
ctcctaataa cgacccggct tcagaatcta ttaccggtgt tgtgcgttta gctacggtgg   102780
ctcaaacacg tcaaggaact cttcgcgaag gatatgcaat ttccccatac acctttatga   102840
attctgttgc aacacaagaa tataaaggtg ttatacgtct aggaacacaa gcggaaatta   102900
atagtaattt aggagatgtt gctgtaacag gtgaaacgct aaatggtaga ggagctaccg   102960
gttctatgcg tggagtcgta aaattaacga cgcaggccgg tgttgcaccc gaaggcgata   103020
gctctggagc attagcatgg aacgcggatg taattaatac acgcgtgggg caaactatta   103080
atggttcttt aaatttagac catctcacag caaatggaat ttggtcacgt ggcggaatgt   103140
ggaaaaacgg tgaccagccg gttgcaacag agcgatatgc atctgaacgt gttcctgttg   103200
gaacaattca aatgttcgca ggtgatagcg ctcctccagg ttgggtttta tgtcatggcg   103260
ggaccgtttc tggagaccaa tttccggact atcgaaatgt ggttgaacg  agatttggcg   103320 gtgattggaa taatcctgga attccagata tgcgcggcct ttttgttaga ggagctggta   103380
caggtagcca tattttaaat aatcgcggac aagacggcta tggaaaggat agattaggtg   103440
taggatgtga cggcatgcat gttggcggtg tccaagcgca gcaaatgtca tatcataaac   103500
acgctggtgg atggggcgaa tatcaacgtc acgaggcacc attcggagca tccgtatatc   103560
aaggttattt gggtactaga aaatactctg attgggataa tgcgtcatat ttcacaaatg   103620
acggcttcga attaggtggt caccgtgacg caacaggcac tcttaaccgt gaaggactta   103680
tcggatatga gacccgtcca tggaatatat ctttaaatta tattattaaa gtccattact   103740
aagggtaaaa aatgatcgaa ttaaaaagtc taccatacgt tgatggccct cctgatgagg   103800
```

```
gtcaaaaacg tttaaactgg attaaaaatt cagaagaaat aactggcgct gatacgttat 103860
acggttctga aggagtaatg aaccgtccaa taacagaagt tcaacgaaat gtagaaacaa 103920
ttaacgataa cgttaagact atcgcagaat ctttagatac cgctaatgcc gatattgtca 103980
caattaaaag tatcttggat gtttctggtg acgtagatgc tttagcacaa attggacata 104040
acactgatga tattgaagta ttaaaacaca ctgtaaattc acacagtgtt gatattttaa 104100
acactgaaga aaaactagat gatactattg ctaatatcgg agtagttaat ccagaaacag 104160
attcagtgta tcgtactgtg cgtaacgacc ttctttggat taaaaccgaa ttagggcaat 104220
atactggaca agatattaat ggtgtcccga ccgaaggtaa tgaaagcacc gggatgaaac 104280
gacgtattat tactaacagc tcagtgttgg ttgaccaagg cgttcgttta accgagttag 104340
aaaataaatt tgccgattct gatgttgggg ctctgacaac cgaagttgaa acctccgtc 104400 aagaaatagg tcctagacca tcgttaacag taccggttta cactcgttta tccgtattg 104460 attcatccat ttctatccaa actagagata ttgcggcatt aaaagatttt gttggatatc 104520
ctaattcaac cgctattaaa actcaagtcg aggccaatcg tctttctata tcaacaataa 104580
attcagacat taactcgcct ggcggtatta agccacgttt gacaacgtta gaaactacta 104640
taggctctcc agatttacca actactcttc agggtaagat caaattaaat accgattcca 104700
tttcaggtat taacacagtt ttaggtgttg attcttctag tggtttacgt tttaatgtag 104760
catggcttaa tcaggtggtt ggcgttgatt caaatggtgg acaacctgaa ccggctggtt 104820
cacttttata taggactcgt attcttgaaa ctggtgttac cgacctaggc aataacattc 104880
aaaacgttca aactgaattg ggaactaatt cgtctggtat taaaggacaa gtaactagtt 104940
taaataaact tataagcggc accaacccaa acggtcaaac catagaagaa cgtggtatat 105000
tgccaacagt taaaaaccac gacacgacaa ttacggattt aactacgcgt gttaccactt 105060
tagaaacaga ccttgctgca gcagaagcag aaattcaagc ccttaaagag gctggatata 105120
tcaaagatgc tccttcagac ggtaaattct atgttcgtaa agatggtgct tgggttgaac 105180
ttcctacagc ttaatgaaaa gggccttcgg gccctaaagg atttatatgt caggttataa 105240
tgcacaaaac cctaaagaat taaaggatgt aatattacgt cgtttaggcg ctcctattgt 105300
aaatgttgaa ttaactacag accaaattta tgattgtatt tccagagcat tagaacttta 105360
tggcgaatac cattttgacg ggttgaataa aggtttccat gtattttttg ttgatgacga 105420
agaaaaatac cgtcacggcg tatttgatat gcgtggttct aatgtatttg ctgtaacaag 105480
aattataaga acaaacgttg gctctattac ttcaatggat ggtaatgcaa cttatccttg 105540
gttcactgat ttccttttag gaatggcagg tgtttctggt ggtatgggta gtaattgtgg 105600
taaattctac ggtccgaacg cttttggtgc cgacctcggg tattattctc aattagtatc 105660
ttatatgggt atgcttcaag atatgattgc tcctcttcca gattttggt ttaactctgc 105720 aaacgagcaa ttaaaagtaa tgggtaactt tagacagaaa gatgtcatta tcgttgaatc 105780
gtatgttcgc tcttatatcg agacccataa gatggtagga aatacagtag ggtacggtca 105840
ggtcggtcct cgtgattcat ggtctatttc tgaacgttat gataatccag accataattt 105900
agtcggacgt cgagttggtg aagatcctgc aaccaaacaa ggcgcatata caaccgttg 105960 ggttaaagat tatgcaactg cattagctaa agagcttaat ggacaaattc ttgctaaaca 106020
tcaaggtatg atgttaccag gcggtgtcac tgttgatggt gttcgattaa ttgaagaagc 106080 tcgtgtgagag aaagaagctt tacgagaaga gttatattta ctagaccctc ctgcaggtat 106140
tttggtaggt taatatggca acttatgata aaaatctttt cgccaagcta gaaaatcgtg 106200
```

```
gtgggtattc tcagacaaat gagaccgaga ttttaaacaa atacgtgaac ttcaacaaat    106260
acgaaaatag tcaaaccota gccgatgttc tagtggcaga aagcatacag atgcgcggta    106320
ttgaatgttt ttatgttcca cgtgaatatg ttgccgtgga ccttatcttt ggtgaggacc    106380
ttaaaaataa atttactaaa gcatggaaat ttgctgcgta tctgaactct tttgaaggtt    106440
atgaaggagc gaaatcgttc ttcagcaact tcggaatgca agttcaagat gaagttacat    106500
tatctattaa cccaggtctt ttcaaacacc aggtcaataa tcaggagcct aaggaaggtg    106560
atttaatata cttcccaatg gacaacagtt tgtttgagat taactgggtt gaaccatacg    106620
acccgttcta tcaagtaggt aaaaatgcga ttcgtaaaat tactgcaggc aagtttattt    106680
actctggtga agaaatcaat ccggtgcttc agaaaaatga aggtatcaat atacctgaat    106740
ttagtgactt ggaacttaat cctgttagaa atcttgacgg tatccatgac attaatatcg    106800
atgaatattc tgaagttgag caaatcaatt cagaggcaag tgaatacgtt gaaccatatg    106860
tagtagttaa caaccgtggt agacaaaatt caccatttga cgatgggttt atgaattaat    106920
aaataaataa gataaagcaa acaccggtcg aaaggccggt taggagaaat gatgtttggc    106980 tattttaca actcgtcgtt caggcgtatat atcacaatga tgggcgattt gttttcaaat    107040
atccaagtta accgtcaatt gtctacaggc aataaattaa ttagagttcc tattacgtat    107100
gcatctaaag agcactttat gatgaaactt aataaatgga cctctataaa ctcacaagaa    107160
gatgtggcta agtcgaaac tattctacca cgtataaatc tccaaatggt agatttcgtt    107220
tataacccga cttttaaaac gaatatattg aataactctc ttttgagtaa atcgactaag    107280
gatattgtag accaatacaa cccatcacca attaaaatga tttttgaact gagcatcttt    107340
actcgttacg aagatgatat gttccaaatc gttgagcaaa ttattccata ttttcagccg    107400
cattttaata cgactatgat tgagcaatat gggcaggata ttccatttga aagggatatt    107460
aaagtcgtat ggatggcagc agcaatggat gaacaaatag acggtgataa tttatctcgt    107520
cgacgtttag agtggtcatt aacatttgaa gtaaacggat ggatgtatcc tccggtaggc    107580
gcagctgaag gccttattaa aacgactat cttgattttc atgctaatga acgagacctt    107640
caaacagccg ccagtgtttt tgaatcagtt gatacagaaa ttaaaccgag agacgttgaa    107700
gcacaagatt ggaacggtga agttgaacaa acttatactc atgatattcc aatcccgact    107760
ccaccaaccc ctcctggtcc tagaaaacaa taagaggtaa atatgaagg tctagatatt    107820 aataagcttt tagatatctc tgacctccct ggaatatctg gggaggaagt agaggtatat    107880
gctcctttac aattggtgga agttcagagt aatcctcaaa accgcacccc ggatttgaa    107940 gatgactata gcgttgttcg taagaatatg cacttccaac aacaaatgtt aatggacgct    108000
gccaagattt ttcttgagac ggctaaaaac gccgattctc ctcgtcacat ggaagtattt    108060
gcaactctta tggggcaaat gactacgacg aacaaagaaa tactgaagct tcataaagat    108120
atgaaagaaa tcacatctga acaagttggc actaaaaagtg ctgctccatc tagccagatg    108180
aatatccaaa atgctacagt gttcatgggc tctccaacag aattaatgga agaagtagga    108240
gatgcttacg aggctcaaga agctcgtgag aaggtgatta atggaacagc cagttaacgc    108300
attgaatgat aatcacccat tgaatgaagg tgacaaagtt gttattctac cgcctcattt    108360
agctgaacgt aaagaagaag atggtatcta ttggattaaa tccccaatggg atggtaaatg    108420 gtacccggaa aaatttagtg attatctacg tataaacaaa atagttaaaa ttcctaataa    108480
ctcagataag cctgaattat ttcaaacata caaagataag aataataaac gtacacggta    108540
```

```
tatgggttta ccaaacctta aaagagcaaa tataaaaact caatggacct atgaaatggt 108600
cgctgagtgg aaaaaatgcc gtgatgacat tgtatatttt gctgagacat attgtgctat 108660
tacccatatc gactacggta caattaaagt acaacttcgt gactatcaac gtgatatgct 108720
taaaataatg tcttctaagc gtatgactgt ttgtaacttg tcacgccagc taggcaaaac 108780
gactgtagta gctattttc ttgcccattt tgtttgcttt aacaaagata aagcagtagg 108840
tattcttgca cataaaggct caatgtcagc ggaagtatta gaccgtacaa aacaagcaat 108900
cgaattactc cctgattttt tacaaccagg tattgttgaa tggaacaaag gatctattca 108960
gttagataac ggttcctcaa ttggcgctta tgcttcatca ccagatgcgg ttcgcggtaa 109020
ctcattcgcc atgatttata ttgacgagtg tgcatttatc ccaaacttca tcgattcgtg 109080
gcttgctatt caacctgtta tttcttcagg gcgtcgatca aaaattatta ttacaaccac 109140
gccaaatgga ttaaatcact tttatgatat ttggactgca gcggttgaag gtaaatcagg 109200 cttgaacct tatactgcaa tttggaactc ggttaaagaa cgtttataca acgatgaaga 109260
tatttttgat gatggatggc agtggtctaa acagactatt tcagcctctt cattaacaca 109320
gttccgtcag gaacacacgg cggctttcga agggacatca ggcacactta tttccggtat 109380
gaaattagct atattagatt atattgaagt tacacctgat agccatggat ttcaccagtt 109440
caaaaagcct gaggaaggtc ataaatatat tgcgacgtta gactgttctg aaggacgtgg 109500
acaggattat catgcaatgc atattattga tgttacgaca gataaatggg aacaagttgg 109560
tgttctacac tctaatacta tttcacacct tatactccct gatattgtgt ttaaatatct 109620 aatgaatat aacgaatgtc caatttatat tgaattgaac tcaacaggtg tttctgtcgc 109680
taaatcgctt tatatggacc ttgaatatga aaacgttatt tgcgattcaa tgaatgattt 109740
aggcatgaag caaagccgta gaactaagcc tgtaggttgc tctacattaa aggatcttat 109800
tgaaaaagac aaactcaaaa taaaccatag ggctactatt caagaattca gaacgtttag 109860
tgaaaagggt gtatcttggg ctgctgaaga aggttaccac gacgacttag tgatgggtct 109920
tgttattttc ggatggttgt caacgcagca gaaatttgca gactatgcgg ataaagatga 109980
catgcgcctt gcatcagaag tattctcaag agaattacag gatatgaatg acgactacgc 110040
cccggttata tttgttgatt gtgcaagtaa ttcggcagaa tataatccat cagcacatgg 110100
cctgtcaatg gtataaataa aataaagcaa attaagagga attaaaatgg cacttctctc 110160
tccgggcgtt gagctcaaag aaactaccgt acagagtact gtagttaata actccactgg 110220
taccgctgcc ctggctggaa aattccaatg gggacctgca ttccagatta acaaatcac 110280 cgatgaagtt gcgttggttg atatgtttgg tactcctaac acagacaccg cagattattt 110340
catgtctgct atgaacttcc ttcaatatgg taatgacctt cgtgttgtac gcgctgttga 110400
tcgtgatact gctaagaact catctcctgt ggcaggaaac attaatttta ctatttcttc 110460
ggctggcaca aactacagag tcggtgataa agttgtagtt aaatattcta cagatgttat 110520
cgaaccagac ggtgaagtta cttcagttga ttctgacggt aaaattttga atatctttat 110580
tccttcaggt aaaattatcg ctaaagcgaa agaaatcggc gaatatcctg aattaggttc 110640
aaactggact gccgaaatgt ctgggtcttc ttctggtctg tctgcagtaa ttactattga 110700
ttcagttgta atggattctg gtattctgtt gactgaagtt gaaacttcag aagaagctat 110760
tacttctcta actttccaag aatctattaa aaaatatggt gtcccgggtg tagttgctct 110820
ttatccaggt gaacttggag accagctcga aattgaaatc gtatctaaag cagactatga 110880
caaaggtgct tcagcccagt taaaaattta tcctgatggt ggcactcgtt attctactgc 110940
```

```
taaagcaatc tttgggtacg gtccacagac tgatgaccaa tatgcaatta tcgttcgtcg 111000
caacgacgcg gtagtccaga gcgtagttct ttctactaaa cgtggtgaac gagatattta 111060
tggtagcaat atcttcattg atgatttctt tgctaaaggc gcaagcaatt atattttcgc 111120
tacggcacaa ggttggccaa aaggtttctc tggcgtaatc aaactgaatg gtggcttatc 111180
atctaatgaa acggttgaag ccggtgattt aatggaagct tgggatttgt tgctgaccg  111240 tgaatcggtt aatgcacagt tgtttattgc tggttcttgt gctggtgaat ctttagaagt 111300
tgcttctaca gttcagaaac acgttgtagc aattggtgat tctcgtcaag attgcttggt 111360
tctttgctcg cctccacgtg cagctgtagt tggtattcct gttaatcgtg cagttgataa 111420
tctggttgat tggcgtacag cgtcgggaac ttacactgat aataacttta atataagttc 111480
tacttatgct gctattgatg gtaactataa atatcaatat gacaaatata acgatgtgaa 111540
tcgttgggtt ccattagctg ctgatatcgc cggtctttgt gctcgaacag acaatatttc 111600
tcagccttgg atgtctccag ccggttataa ccgtggacaa attcttaacg ttattaagct 111660
tgcaattgaa actcgtcaag cacaacgaga tcgtttgtat caggaagcta ttaaccctgt 111720
tactggtacc ggtggtgatg gatatgttct gtatggtgat aaaactgcca cttctgttcc 111780
ttcgccattt gaccgtatta acgtacgtcg tttgtttaac atggttaaaa cgaacattgg 111840
ttcggcatcc aaatatcgcc tgtttgaatt gaacaacgca ttcacccgtt cttctttccg 111900
tacagagact tctcaatatc tacagggtat taaagctctt ggtggtgtat ataactttaa 111960
agttgtttgt gatactacca ataacacccc agcagttatc gaccgtaatg aatttgtagc 112020
tactttctac ttacaacctg cccgctcgat aaattatatt acgttgaact tgtagcaac  112080 agcaactggt gctgatttcg acgaactgat tggtgctgta ggtggctaat aagacgcctg 112140
atgggctatt tcggtagccc atataaatat actatatcgt ttaaaaatta attctatggg 112200
catccggtta atcctaagcc catattacta cagaggctaa tatgtttgta gatgacgtaa 112260
ctcgtgcctt cgaatctggt gatttcgctc gccctaacct gttcgaagta gaaatctctt 112320
atcttgggca aaactttagc ttccagtgtc gtgctactgc tcttcctgct gcgatcgttg 112380
aaaaggttcc tgtttcttat atgaaccgta aaattaacgt ggccggtgac cgtacattcg 112440
atgattggac tattacagta atgaacgacg atgctcatag tattcgtcag aaattcgttg 112500
attggcaagg tattgcagca ggacaaggta atgaaattac cggtggtaaa cctgctgaat 112560
ataaaaagac tgctatcgtt cgtcaatttg ctcgtgatgc taaaactgtc actaaagaag 112620
ttgaaattgt tggcttgtgg cctactaacg ttggtgaagt atctcttgac tgggattcga 112680
ataacgagat tgaaacgttc gaagtaactc ttgctcttga ttggtgggaa taatctggtt 112740
ggggagaaat cccagcttc  ccgtgatgac ggagaagtcc atataaatat aactataatt 112800
cccattcgga gaatacaatg aaatttaata tcttaagttt gtttgctcca tgggcaaaaa 112860
tggacgaacg tgattacaaa gaccaagaaa agaaaatttt agaatcgatc accacaccaa 112920
aattagacga cggcgcgaaa gaatacgaag tatctgaaaa tgaagcacag caaacatata 112980
atgctatgtt tcagagaatg ttcggtagtc aagaaccagg gctcaaatca acccgtgaat 113040
taatcgatac gtatcgaaat ttgatgacga actatgaagt ggataatgcc gtctctgaaa 113100
tagtttccga tgctatcgta tatgaagatg atacagaagt cgtttctata aatttagaca 113160
acacaaaatt tagtccaaat atcaaatcaa tgatgttgga tgaatttaac gaagtgttaa 113220
atcatttatc tttccaacgt aaaggttcag atcatttag  acgttggtat gtggattctc 113280
```

```
gaattttctt ccataaaatt attgaccota aacgccctaa agaaggtatt aaagagcttc 113340
gtcgtttaga cccacgtcaa gttcaatatg tccgtgaagt tattacaacc actgaagctg 113400
gtgttaaaat agtcaagggt tataaagaat atttcattta tgacacatca cacgaatctt 113460
atgcttgtga tggtcgcata tatgaagctg gcacaaaaat aaaaatccct aaagccgcga 113520
ttgtttatgc ccattctggt ttagttgatt gttgtggtaa aaatatcatt ggttatttgc 113580
atcgggctat taagccggcg aaccaattaa aacttcttga agatgctgtt gtaatttatc 113640
gtattactcg tgctcccgat cgtcgtgtat ggtacgttga tacaggtaat atgccttcaa 113700
gaaaagcagc agaacatatg caacatgtta tgaacacgat gaaaaaccgt attgcatatg 113760
atgctaccac aggcaagatt aaaaaccagc agcatattat gtcgatgacc gaagattatt 113820
ggttacaacg acgtgatggt aaagcagtaa cagaagttga tacattaccg ggtgcagata 113880
atactggaaa tatggaagat gtacgttggt tccgtaatgc gctttatatg gctttacgta 113940
ttcctattac ccgtattcca agcgaccaag gtggtataca gtttgatgct ggtacttcta 114000
ttacacgaga tgaattgaca tttggtaaat ttattcgtga gctgcaacat aaatttgaag 114060
agatattcct agacccgctt aaaactaatt taattcttaa aggaattatt acagaagatg 114120
agtggaatga tgaaataaat aatattaaga taaaatttca tcgggatagt tatttctcgg 114180
aattaaagga tgctgagatt ctggagcgtc gcattaatat gcttcagatg gccgaaccat 114240
ttattggtaa atatatttct cacagaacag ctatgaaaga tattcttcag atgtctgacg 114300
aggaaattga caagaggct aagcaaattg aagaagagtc gaaagaggct cgtttccaag 114360
accccgacca gaacaagag gatttttaat ggacgattta attcaagcta ttaaatcaaa 114420
cgacctcgtt gctactcgaa agttttttga aagtgcaatg gcagaaaaaa cggttcgttt 114480
gattgaagca cgcaaagcag aaatcgcttc tcaattttttg attgaaggcg aagaacctga 114540
agaagaagaa aagaaagcta agcttcgga agacgacgct gatgaaggcg atgacgaaga 114600
cgaagatgat gaggacgatg aataatgtat cttatccctg aatcttatga attggtactc 114660
gaaaatgtcg aagcacttat tcctgaagca cagggccgaa tcgatgcatt gtcttctgct 114720
ctcgatattg acgatataaa tactattatc gagaacatgc ttgaaactga acggattta 114780
gctgttgcaa tggcttccat tattaatgaa gagcagttaa atgagtttat cgttaaacat 114840
gtttcttctc gcggtgaagt caccccgcact aaagaccgta aaactcgtga acgtaacgcg 114900
ttccaaacaa ccggtctttc taaagcaaaa cgtagacaaa tcgctcgtaa ggtcgttaaa 114960
gctaaaaaag ctaaccottc aggccaagtt aaaggcatgc gtaagcgtaa aaaagctctt 115020
aaacgtcgta aagcattagg attaagctaa tgaataaacc cgagttactt attgaaactt 115080
ggggtcaacc cggtgagatt attgatggcg ttccaatgtt ggaatctcat gatggaaaag 115140
attctggctt aaaaccaggg ctttatatag aaggtatttt tcttcaggca gaggttgtta 115200
accgaaataa acgtttatat cctaaacgtg ttttggaaaa agccgtaagc gactatatta 115260
aagaacaagt cgcaaccaaa caagcccttg agaattaaa tcatccacct cgtgcaaatg 115320
ttgaccctat gcaagccgct atcattattg aagatatgtg gtggaaagga acgatgtat 115380
atggacgcgc tagaattatt gaaggcgacc atggtcccgg cgataaatta gctgctaata 115440
tacgagctgg ttggattcca ggtgtttcct ctcgtggtct tggttcttta accgacacca 115500
ataaagggta ccgtatcgtg aacgaaggat ttaaattaac cgtcggtgta gatgccgtat 115560
ggggaccttc tgctccagat gcttgggtta ctcctaaaca aatatcagaa tcagaaaatt 115620
cggtggaaat caccaaaaac agtgctgatg aagcatttaa agctctcgca gagagtttaa 115680
```

```
aagcattata aataataatg taatctaaac cacaggacac taaaatgatc aaagaacaac   115740
ttttgaaaga agctcagaat atcgagactt cagttgctct taatagtgtt ttcgaatcag   115800
tagaactgtc tccggacgtt aaagctaatt tcagcactgt attcgaagcc accgttaagc   115860
aggaagcagt caaactagct gaatctcata tcaaagctat cgccgaaaaa gccgaagaag   115920
aagttgaaaa ggctaaagaa gatgctgaag agaaagctga taaaaaattg gctgaacaag   115980
cttctaaatt cctggaccat cttgcaaaag aatggctcgc agaaaaccaa atcgcagttg   116040
ataaaggcat taaagctgat ttgttcgaat ccatgcttgg tggtctgaaa gaactgtttg   116100
ttgaacataa cgttgttgtt ccagaagaat ctgtagatgt tgtagcagaa atggaagaag   116160
agctggccga acataaagaa gaaaccgctc gtttgttcga agaagttacc aaacgtgatg   116220
catatatcaa ttacgttcag cgtgaaaccg ctattaatga aagcgtaaaa gacctgactg   116280
aatctcagaa agaaaaagtt attggcctgg ttgaaggtat ggattattct gacgcatttg   116340
gtactaagtt aactgctatt gtagaaatgg ttaaaggttc tactaaagaa gaagccgcta   116400
ttaccgaaag tataaataca gttgacaatg acgctgccgg tcttaatttt gttgccgaag   116460
cagttgacac taccacaact caggtagaac agaattctaa tgtaagttta tatgcgaaag   116520
tcgcatctcg tttctaattt aaaggttaac acaaatgact actatcaaaa ctaaagctca   116580
gctcgtagac aaatggaaag aactgctgga aggtgaaggc ctgccggaaa tcgctaatag   116640
caagcaggct attatcgcta aaatcttcga aaaccaggaa aaagatttcg aagtatcccc   116700
tgaatataaa gacgagaaaa tcgctcaggc atttggttct ttcttgaccg aagctgaaat   116760
tggtggtgac catggttata atgctcagaa catcgcagca ggtcaaacct ctggtgcagt   116820
aacccagatt gggccggccg ttatgggtat ggttcgtcgt gctattccta atctgatcgc   116880
ttttgatatt tgtggtgttc agcctatgaa cagcccgacc ggtcaggtat tgctctccg   116940 tgcagtatat ggtaaagacc ctatcgctgc tggcgctaaa gaagctttcc atccgatgta   117000
tgccccagac gcgatgttct ctggtcaggg tgctgctaag aaattcccag ctctggctgc   117060
tgacactact accgttgtag gtgatgtcta tactcacttc ttccaagaaa ctggtactgt   117120
atatctgcaa gcttctgctg tcgtaacact tgattctggt gcaactgatg cagctaaatt   117180
agatgcagaa gttaagaaac aaatggaagc tggtgcactg gtagaaatcg ctgaaggtat   117240
ggctacttct atcgctgaac tccaggaagg tttcaacggt tctaccgata acccatggaa   117300
tgaaatgggc ttccgtatcg ataaacaagt tatcgaagct aaatctcgcc agctgaaagc   117360
tgcttactct atcgaattag cacaagacct ccgtgcagta cacggtatgg atgctgatgc   117420
tgaactgagc ggtattctgg ctacagaaat tatgctagaa atcaaccgtg aagttgttga   117480
ttggattaac tactcagcac aggtcggtaa atctggtatg accctgactc ctggttctaa   117540
agctggtgta tttgacttcc aggacccgat tgatatccgt ggtgctcgtt gggccggtga   117600
aagctttaaa tctctgttgt tccagattga taaagaagca gttgaaattg ctcgtcaaac   117660
cggtcgtggt gaaggtaact tcattatcgc ttcccgtaac gtagttaacg tactggcttc   117720
agttgatact ggtatttctt acgctgcaca gggtctggct tccggttta ataccgacac   117780 tactaagtct gtatttgccg gtgtacttgg tggtaaatac cgcgtataca tcgaccagta   117840
tgctaaacag gattacttca ccgttggtta caaaggcgct aacgaaatgg atgcaggtat   117900
ctactatgct ccttacgttg cacttacccc actgcgtggt tccgatccta gaacttcca   117960 gccggtaatg ggctttaaaa ctcgttacgg tatcggtgtt aacccgtttg ctgaaagttc   118020
```

```
cctgcaggct ccaggtgctc gcatccagtc cggtatgccg tctatcctga acagccttgg 118080
taagaacgct tacttccgcc gtgtatatgt aaaaggcatc taatcttaat tgattaaatc 118140
ttattttggg agacttcggt ctcccatttt tggttttatt tctgtgcaat ttcgatgtaa 118200
gttttcaaaa tattttgcca attaggcata ccttcttgga catatgccgg agaaccgtct 118260
ttgttttga atgatgcaag tttatcagtg gcccaataac ctttagctcg agcttcagaa 118320
taaactttca tccatacttt gttgaaggca ttaccattaa cttttgcacc atattttct 118380
actaacttaa ctgcttcagc ttccagaact tttaaagtat ctcgtaagaa acgtgcttta 118440
gtcattttgt ttactcctct gtagttgata agtctatagt atcacatacc aaatacgttg 118500
taaacaatct ttataaataa tctatatcac ataaggaaaa aatgcaatga gtaaaatcca 118560
aaaattattg cgtgaatcta caacgtctac tagcaactca atcggtcgcc caaatctcgt 118620
tgctttgact cgcgctacga ctaaattaat atattctgac attgtagcaa cacaaagaac 118680
taatcaacct gttgctgctt tttatggtat taaatatctt aacccagaca acgaattaac 118740
gtttaaaact ggtgctactt atgcaggtga agctggatat gtagaccgag aaaaaattac 118800
cgagctcaca gaagaatcaa aagtcacact aaataaaggc gattttttca aatataataa 118860
tatcgtctat aaagtgctag aagatacacc atttgcagat attcaagaaa gtgatctaga 118920
attagctctt cagattgcgg tcgttcattt aaaggtacgg ttattttcag atgcagctgt 118980
gacaagcaaa tttgaaagct ctggtagcga aatttctgat gcaagattcc agattaataa 119040
atggcaaact tcagtcaaat ctcgtaaact taaaaccggc ctcacggttg aattagcgca 119100
agatttagaa gcgaatggat ttgatgcccc taacttctta gaagatttgc ttgctactga 119160
aatggctgat gaaattaata aagatattct tcagtcttta attactgtat cgaaacgtta 119220
taaagttact ggaattactg acactggatt tattgacttg agctatgcgt ctgctccgga 119280
agcaggtcgt tcgttatatc gaatggtgtg tgaaatggta tcgcacattc aaaaagagtc 119340
aacttatact gcaacgtttt gcgtagcttc agctcgtgca gctgctattc ttgctgcttc 119400
cggttggtta aaacataaac cagaagatga taagtatctt tcacaaaatg cttacgggtt 119460
cttagctaat ggtttaccgc tttattgcga tactaacagt ccattagatt atgtgatcgt 119520
tggcgtagta gaaaatatcg gtgaaaaaga aattgttgga tcaatttcct atgctccgta 119580
tacagaaggt ctcgacttag atgacccgga acatgtggt gcatttaaag ttgtagttga 119640
tccggaaagc ttgcaaccgt ctatcggttt attagttaga tacgctttat cagcaaatcc 119700
ttacacagta gcaaaagacg aaaaagaagc gagaataatt gatggcgggg acatggataa 119760
aatggcagga cgttcagact tgtctgtttt acttggtgtt aaattgccta aaattattat 119820
agatgaataa aaaaaaagg gaccgtaagg tccctttttt cgttatgata ctaattcaat 119880
ccatgcagga cgcaatacat cttgcaccat tcggactaat tctttcttaa caagattcgg 119940
attatcagat gatgttaata caataccttc acgagaagtt tcttccagaa tatcttgaac 120000
agtcaatccc atcactttgc caaaatcttt cggagttact gtcccaatct tagaaatcac 120060
attgttaaca cgatttaatg taacataaca agctagaaca tcaagtaagt ttttgtcaat 120120
ttcggttaat ggaacctgag ttttaatagg cttatcagac ttttttcttt cactgaattt 120180
agagttcttg cacttaatcg ctacacgagt accgtttggc agccatttag ggaaacaagg 120240
cttcagaaca taaccttctg cagtattatc accaataaca ttagcatcaa atacgcaatt 120300
atttgcttcg acaaggtctt ccgatgccgt agcgttataa gcggctaaga cggaatcaag 120360
gtcgtttgga atcgtgataa gagcatcaaa tgttccacgt ccaagcattg gtgccatttt 120420
```

```
aaaaccaaac gtattacaga aatcttgcat ttcgtaatca ctcatgtaat aagtatcacc    120480
gctttcagtg tttatgatga tatcgaatac atagaaatct tttccaccat agtcaacacc    120540
tttctgaatt ccaccaccag cgaattcacc aaagacttga tatgtcaccg gcactgaagt    120600
tgaaatactg cccatgactt cctgaacggc tttaatagct ttatcatact tcttgagtac    120660
gatttcgtaa ccataaaaat cttctgctgg aagaataggg cctgtgcgct tggcgcatgt    120720
gacgttgtca cgttcaataa ttaaactaaa gttggtcccg tggattttct cacgtgctac    120780
ccaaacacca gtagtcaaac cattagtgta gagttttca ataaacttag agttgtagtg    120840
gttttcaaga ctgctgtatt tcttaaacat aaatcaccat tataaataat aatatcaaaa    120900
taattagcag agactctatc tccgacccga tgtttaattt gaatggatag aacctagatt    120960
cattatacca tcaaaaaatg taaagcatat tagaacttga tttctatcca atgcccgtca    121020
cgttggtcat gattaatttt gtactgaaag ccgttatcac gaagccattg accgacttgc    121080
tcggtgatag ttaaatcatt ctttgatgga tagtacgtga attgtgtctg gcctttgtca    121140
gcggctttct ctgccatcac agagaagtta gtaataaaat cactcaacaa attagcttta    121200
atggccagag cccttctct taattcctgt gcaaaactca tttcttcacc ttttattaa    121260 tcaaacgttt acggtataca acttttctt ttgctttaaa ctttgaccga gctgtctcgg    121320
cttagtccca tagtaatcca acttctttag gttgtaaacc aatttttga gcaatttcta    121380 cgaatgaaaa tcccgcctca tgtaatgtat aaacttcaac ttcagctctc ataatcaatc    121440
ccgtattatt tggtttgtgc cattatatac atcaatctca agttgtgttt tgtatgcttt    121500
aaaaacgaag aaagggggccg aagcccctta cgattatgga tatgtataga tgataccagt    121560
ttccaaagca gttttatgga tgatgtatcc attacgtgat tcttgaacat caacttctgg    121620
atagtctttc atcatcttct gaagcgtata acgatgcaag taatacttac taccaggatc    121680
gtcaattttc caatctttac cttcttcagt cattttttgg atttcatcca taacccacaa    121740
accgcaccag atgtaagctg aagtacgatg tggaagagga tgaacataag gtagttcacc    121800
ttctggctca attggagtct gttcagcaat aacaacttca gcggttgaac taattgtctt    121860
tgaagtataa ttatctttag ttaatactgc ttcaacttta attgtatgag tacccgccga    121920
ggaggtatca atactgtaag tattagtaga attactttct gctacgttgt ctttcttcca    121980
agaatacaca atattagtat cacctggagc accagtaaca gatgctgtta aagttgcagt    122040
tccaccaaca gtagtattaa ctgatggcgg agataaagaa atggtggcac tattaaatga    122100
cgcattatta gttactactg ttgcttctgc tgaaatttct tttgtaacat aatttgttgc    122160
agaaacagat acagtgcatt taagagtttt acttccgacc tcggttggag tgaatttata    122220
cgtagcagaa gttgcatccg gaatattact gtcatccatt gaccactgga atgatgtagt    122280
agcacctgaa ggtgcaccag agacatttgc agttaaagta ataggaacac caaagaccgt    122340
agtcggagac tcaggcgtaa tttttagtgt tgaagaatta gcctttttat ttacagtcaa    122400
agaaaccgct gatgattcta ctgtttttatc aacgtaatca gttgcagtca ctgtgacgga    122460
gcaagttata gacttagttc cttcggatgt tggcgtatat tcaaaggttg attgcttttg    122520
accatcaaca gcaatcccgt caactttcca tgtataagca atagcagcac cactaggttg    122580
attgcttaca ttagcagtga atgttgttgc tgttccaatt tctactgccg ccggagaagc    122640
cggagtaaca gcgacggtag aattattttc tttcttatta acagtgatag ttgttgacgc    122700
ttcagctatt tccggatctc ctgcggaaag tgtattagtt gcaaccactt taatttttt    122760
```

```
ttgttcctgc cggagaagca agagtataat ccattgtagc agccgtagac tcctgtgcta    122820
tatcatctac agtccagacg tatgtaatag taccatctgg agtttcacct gcaggtgtag    122880
cagtgaatgt ttgtgaacct ccaataaccc ctgtaggagt taaaggagat aacgtgacag    122940
tgaatgtcat aagttatcct tattttaatg ttatgaaaga agaattacga gtttcacgaa    123000
ttagaactga tccatcgcga ttaatataat aaattaagct aaataatgtt tggtgagcag    123060
aagcgtgcac aaaactagtt gggcgagatt tccaatctgg ggtttcggct atccattgat    123120
aaatccacca aggaacagta acatatcctg ggcctttgcc taatttaatg agtgtaggac    123180
taaaattttc aggcagaaca aattttactt ctttatttac ctctgtctca ggctctttt    123240 cagattcaac aacctgagta attgcttctt cgaatttatc atggtcgaat tctttttctt    123300
gttcgacaac ttctaatact tcaacttgtt ctgttggaga atcaaacaac agaatagctt    123360
cttctttaac ttcttcgttg gtgaaattaa caccgtccac atcatctgcg gcagtaatta    123420
aatcggtgat agataatcca tcagtttcag gtaatggttc atcagccagt gcgttaagag    123480
cttcttcgat atcaataaca atattatcga acgattttgt tttcttaaca ctaatgccaa    123540
attgttccgc atattcaaac agtttagctt tggcttcctt tttatcagaa agagcacgta    123600
actcttcaat atagtcttta tcgatcatgg tatttcctca ttataaatat aactatattt    123660
attacatggt aatttgacat gactgacatt aaagtacatt tttatgattt tagtcacgtt    123720
cgcattgaat gcgacgaaag tacgtttac gaacttcgtg acttttttag ctttgaagcc    123780
gacgggtata aatttaaccc aaaatatcgc tatgggcaat gggatggtag aattcgactt    123840
ttagattaca atcgtttgtt accatatggt cttgtaggac aaataaaaaa gttctgtaac    123900
aatatgagtt attctatatg gattgaccct aaaatctttg agactgaaga ccttaccagg    123960
gaagattttg acgcgtggct ttctaaacaa gaaatttatt caggcaacgc caaaatcgaa    124020
ccacattggt atcaaaaaga tgcagtatat gaaggtctag ttaatcgtcg tagaatttta    124080
aaccttccga catcagcagg taaatcacta atccaagcac ttttagctcg gtattatta    124140 gagaactatg aaggtaaaat tctcattatc gtccctacaa cagcattgac aacccaaatg    124200
gctaatgatt ttgttgatta tcgcttgttt agtcattcga tgattaagaa aattggcggt    124260
ggtgctgata agccgacaa atctaaaaac gacgctccaa ttattgttgg cacatggcaa    124320
acggtagtta agcagcctaa agaatggttc tctcagttcg gtatgatgat gaacgatgaa    124380
tgccacttag caacaggcaa aagtatttct tcaatcatct caggattaaa taattgcatg    124440
tttaaattcg gtttatctgg ctcattaaga gacggaaaag ccaatgtaat gcagtacgta    124500
ggtatgttcg gcgaaatctt ccgtcctgtt agcacgtcta aattaatgga agacggacag    124560
gtaactgagc ttaagattaa tagtattttc cttcgttatc cagacgaatt cgccaccaaa    124620
ttaaaaggta aaacatacca agaagaagtt aaaattatta ccggactaaa acgtcgtaca    124680
aagtggattg ctcaactttc agtcaaattg gctaagaaag acgagaatgc ctttgtaatg    124740
tttaaacacg ttacacacgg taaagaaata tttgaagcta ttaaagagct tggatacgaa    124800
aaagtttatt acgtatcagg tgaagttgat actgaaacac gtaacgcact taaagtcatg    124860
gcagaaaatg gtaaaggcat tattattgtc gcatcatatg gagtattctc taccggtatt    124920
tcagtcaaga atcttcatca tgttattttt gcccatggtg ttaaatcaaa aattatcgta    124980
cttcaaaccg taggtcgcgt gcttcgtaag catggttcta aagctgttgc tacagttgg    125040 gatctcatcg atgacgcagg tgtaaaacct aaatcattaa atactaaaaa gaagtatact    125100
catcttaatt acttgttaaa acacggtatt gatcgtatcc aacgttacgc tgatgagaaa    125160
```

```
tttaactatg taatgaaaac aattaattta taagggcttc ggcccttagg agataaaaat  125220
ggtacttgaa tttaaacaat ttttatacga agcatctatt gacgaattca tgggtaaaat  125280
tgctagttgt catacccta g aagggcttga agaattggaa gcttattata agaaacgtat  125340
aaaagaaacg gaattaaaag atacagatga tatttctgtc agggatgcct tagcaggtaa  125400
gcgtgccgaa cttgaaggcg acgatgagga tgtggaagaa gacttctaat taaaaaaaag  125460
gcccgacctt tttggaaggg ccaaaaacca taggcaaaaa aggtaacact atagtaaaag  125520
ttgggtttcg ttcaattgct cttctgaact ttctgaaacc ggcaattgtt gtacataatt  125580
ataacaagga ccaggatgtg ctggaccttt gtctgtttca acaaccaatg cagaatcgat  125640
tggagtttta cagacaacac aaatcttatc tgacatgatt gcctcctaag ttgaaattac  125700
atatctattt ataccactcg catgcacata tcgatcccca tatcttttgt ataaaaatac  125760
tcgtcgatat acccagcaaa cttccctta atataagga cgtcttcacc acaagggtgg  125820
tctgccagga tacgaatatc ctgacgtcgt agacgatact tttccattaa gaatttaatt  125880
tctgtttcaa attcttcatc attattaaag gcatcttcaa ttgaataacg cattattgcc  125940
ccgcttcaaa ttctcgcata tcctggatat gtttaagtgc aaaactacga gacttaactg  126000
cgtcaagtgc accactacag aactcaagta aaattcccca gtattgtaaa gtagtctcta  126060
ttttaagcac atctttatct gcggccagga cagttttcat ttcagatttc tcatatcggt  126120
ccatactgaa ttcatcacca tcacctcgtc ccgagtagta gtctaatctt gcttttagag  126180
cagttttctt ctgagtctct atacgcaaca tttctttacg aataaatgag tgtttacgca  126240
gccatttgct gtataactta acattattcg ccgtctcata ttgcaacttt gtcatatcaa  126300
tagctaagtc tgcgtctaac tcttcctgta aatcttccag cttcataata ttctctcttt  126360
taactaataa tctcccggct gtatcggaag gacctaaaac cattatacat aggttgcctt  126420
gaagcattac actctattgc ttgacgctaa ctgaagtttg atttgttcga tatcatcagg  126480
gttatctacg actgaaaatc taatctctac tataactgta tagtcatcat atactggcgt  126540
tacacttaca gaaagtttgt cgatgcgtgg ctcatagtta cgaacagctg cctggatatt  126600
acgctcaata gtatcggctg taagtggtgt catgttctcg aaaagttcat caaccaaatc  126660
gcatccaaat tcagggtcga aggggcgtga gccttttcta gttgtcacta tgccaagaag  126720 actatttta atagaacgaa gtcctacaga acgagcaacg tccttgttcc aatccatacg  126780
catttctggg tcgatatctg aataaagttt attgatatta gacattatag taactcaaag  126840
aattctttga ggcctcgtat tgtgtgaacg tgtgacgccc cgcatttggg acatttaata  126900
ggggttgcca gataaattga tggcgacacc aaaagatttt taatattgat catgtcatct  126960
tctgttataa ggccataaag gtcgtttatt tctgcttcag ttaaatcttc aacagggatg  127020
gactctccat tgacaaaaac agcctcaata catgaagcaa tcattaacgc gatatttta  127080 tcatcaaata atttaggttg acggaactta attttaatac cactgaacga ataccaggga  127140
tcggcctgtt catctaattg agtgtgcaat aaattcatat agacttgaaa tgaatgccca  127200
caggaacaat tccaggtgtg ttcttgattc acttcaccta tgaatgtgc ccacagattt  127260 accaacaata actcggcttc ttgtttagtc aagtttttag cgttagagca attagtgata  127320
atattgttca ctgctgattc aatagtaccg gtagcccgag cacctataag tcctaaatat  127380
tcttttaaag taaaggctct acaattcact tctttatcgc ctaaacgtac ggtaaacgta  127440
tatttgtaca tgttaactcc tttattgtgt atttataaat aatagaaaag gagtaattat  127500
```

```
ggctaatata attcgttgta aattaccgga tggtgttcat cgtttcaagc cgttcaccgt   127560
ggcggattat agagactttt tactagttag aaatgatatc gaacatcgtt cgccacaaga   127620
acaaaaagaa ataattgctg atctgattga tgattatttt ggcgagtacc ctaaaacatg   127680
gcaaccattt atattcctgc aagtttttgc aggctctata ggcaaaacaa aagttccagt   127740
tattttcact tgccctaaat gctctaaaga aaaaactgca ccatttgaga tatatcaaaa   127800
agaactagtc gaacctgaac ttgatgttgc tggtataaaa atacgttttt ctttccctga   127860
aaagttttat gacaacaaag cattaatgat aagtgaaaac ataaagaaa tatattataa    127920 tgatgaatgg tacccatgga atgatttgac tgaagagaac caaatccaag taatagaagc   127980
aatagacatt gactcgctcg agaaggttat tgcttctatg aaccctatta atttgaccct   128040
tagattaggt tgttgtgaac gacatgttaa aacatatact gatatcttag aggtttttaa   128100
attgttagtt aaccctgatg agatttttac attctatcag ataaaccatt cactagtaaa   128160
gagtcaatac acattggatt ctattatgca aatgattcct gttgaacgtg gtattgcttt   128220
aacattagta gaaaaggacc ataaaaaatg acagtattcc aacgtccagg atatcctaac   128280
ttaagcgtta aattatacca agattattcg gcttggcaag aaaatagata cgttgaactc   128340
gcagcaacaa taacaacttt aaccatgcga gattcgctat atggaagaaa tgaagggatt   128400
cttcaatttt atgacactaa aaacatccac actaaatgg acggtagaca gatagtccaa    128460
atctctgttt caaattcaaa cacacctctc caagttagaa ctcgaattta tggatgtaga   128520
cattattctg tgtctgtgga ctcaaaaggt gacaatatta ttgcaattga gcttggaaca   128580
atacattcta tagagaacct taaatttggg cgtccattct tcccagacgc aggcgaatct   128640
atacgtgaaa tgttaggtgt catatacaaa gaccgtacgt taattactcc gccaataaac   128700
actattaatg cttatgttcc tgatattcct tggacaagca catttgatga ttatttggca   128760
tatgtcagag aattaggact tgctacagcg agtgataagt tcgtattcgt atggcaagat   128820
attttaggcg taaacatgat tgactacgat actcttattg gtcaagaagg cattaagatg   128880
attgtaggtg agccaaatac tgtaggtcag tatattcaag agcttgagta ccattagta    128940 tgggattta cctggatgac taaagccaac caatttacaa gagaccctat taaaacgcc    129000 acgatattcg cccattcatt tttagataca tctattccgg ttattgttac aggtgatggt   129060
gataatgcta ttcttgtgtc aagatccggc ggatattccg aaatgaccta tcgtaatgga   129120
tttgaagaag caagtcgtct tcagacaatg gctcaatacg acggttatgc taaatgcact   129180
actacaggta atttttaacat aacgcctgct actaaaatta tatttgttga ccaaaagaac   129240
caattcaaat ccgaatttta cgtggatgaa gttattcatg agttatcaaa taacaactca   129300
caaactcatc tgtacatgtt taccaactca atggtgttag aacctgttaa cccagttaag   129360
gttaaaaatg aacttaaatc tgattctacc tctaaagaaa ataattctac cacagtctaa   129420 taaaaggta atgattccca aattagggct caaacattat aatctttta aggatgttaa    129480 aggtcctgat gaaaacatga aaatcttagc tgattctatt tgtaaaaata tgagtcctgc   129540
tgattttgat tttgcatgtc tacatatatt ggaatttaat aacaaactta agtctgaagt   129600
tgaaaaagac ggattcacat ataaactaga tgacgtctat gtatgccaac gaacagaatt   129660
ccaattccaa ggcaatactt tttatttag acctccaggc aaatttgaac aattcgctac   129720
aatcagtgaa atgttatcaa attgcttaat aaaagttaat gacgaagaga agaaatttc    129780 tttccttgag atgcctgctt ttgtaatcaa atgggcagaa gaccttttcga caactattgc   129840 tattccaggc cctaatggtc ctattaaggg tatagcagaa attattggat tgcttgaatg   129900
```

```
aaacctgaag aaatgaaatc catgcgtaga aataaggtca ttgccgataa taaaccacaa 129960
aaagtagctg caacagcagc taccgattca ttagaagcat tgaatgatat ttcatcaaaa 130020
ctagacgatg tccaagccgc gtctgaactc acatcgcaaa gtgtagaaga taaaggcaat 130080
ggaattattg aatcaattgg agacttaaag aattcgacag ataacactgc tgaaggcaca 130140
gagcttatcg cagaagttat tgaaaaacaa actgaagtca ctaaaagtat aaacgaagtt 130200
tctagtgcaa taagctctaa gttagaccga ttagctacat tattagagca aaaattacaa 130260
acatctaccg ctattcaaaa tacaggaggc acctctcttg aagtaattga aacgcgata 130320 cctgttaaag tggttgagaa cgaaacttct gatgagttgt ttaaagcatt acctacacct 130380
gaaaagatta ataataagcc agacgaagat ttcttcccgg tcccggttca agaaagtgct 130440
aattctactt ccgattctaa aggcggtatt agctttaaat tgagcgataa aattgcaatg 130500
ctcactaaaa cagttcaaac cgggtttaat aaatcaatat caatttcaga cagaattgct 130560
ggaatgcttt tcaaatacac tataacggct gctattgaag cagcaaaaat ggccgcactt 130620
attcttggta ttgttatcgg tattgattta ttgatagtcc atttcaaata ttggacagac 130680
aagttcactt ctgcctggga tttatttgat gaaaacttta ctaaattctc cgatgaagct 130740
aaagagtggg gtaaattctt aagcgatata ttcacttcta ttgactcgat aaaacaattg 130800
tgggaagctg gagactgggg tggtttaacc gttgctattg tcaaaggtgt aggaacagca 130860
ttaatgaact taggtgaact aattcaatta ggaatggcta aactctccgc gtctatattg 130920
cgtgctatag gttttggcga taccgcggac gaaatagaag gacgtgcttt ggaaggattc 130980
caagaaacta ctgggaacaa attaaagaaa gaagaccaag agaaagtcgc taaatatcaa 131040
atgaagcgtg acgatgggga attaggaacc gtttctaaag gtcttgatat gttacaacgt 131100
ggcaaaacat tcgttactaa ctgggttcgt ggtaatgaca ataagaaga gtttagtaca 131160 agcgatgagc gtgctgcgga atcagcaaaa ttaaaagagt tacctgaaga ggagcgtaaa 131220
gaggcgtata taaaagctaa tgaaactcgt gcggcactag ttagatttga ggattatatc 131280
gataaaatcg atatgactaa tccggaaaat gctaaaaacg tcgagaagtc ttatgctgat 131340
ttaagtaaac ttattaaaga ccctgaactt aataaaactc ctgttgttaa aaaggaaata 131400
gatgctagat ttgaaaagct aaataataaa atggctgaag ccaaaaaggc tcagacaaca 131460
gttaagcctg aatcttcgac taaatctcca gaagcaaaac aagttcagtc aatagagaaa 131520
ggacgtgctt ctgaatctaa acaacagcaa ccggtagcgg cgattagtaa cacaaataat 131580
gtcgtcaaaa agaataccgt agtccagaat atgaccccctg taacaagtac aacggctcct 131640
ggaattttcc atgccaccgg tgttaattaa ggattattat gattagtgta aagaaatag 131700 tagtagatgc aaaggattta aataaagcaa tcccagtctc agaaagtgct gggcaaagca 131760
ctaaaaccga acaactact aaaacttatg ttgctcaatt tcctacagga agagcagccg 131820
gaaatgactc cacaggagac ttccaggtaa cagaccttta taagaacgga ttattattta 131880
ccgcgtacaa tatgtctgca cgcgattcag gatccctcag gaatttacgt ccggcatacg 131940
ccgggacttc atctaatggt atcatatcag atttaactga taacgtgaaa gatgcagtga 132000
ctaaattctc aaatggattg cttcctgcca gagctaataa gtctactata aataaactc 132060 ctgttgctaa tatacttttg ccacgttcca aatctgatgt tgatacaact tcgcatcgtt 132120
ttaatgatat cggtgatagc cttattacta aaggtggagg tactgctaca ggtgttttaa 132180
gtaacattgc ttctactgca gtctttggtg cattagattc tattactcaa gggcttatgg 132240
```

```
ctgataataa cgaacagatt tatacgactt ctcgtagtat gtatggcggt gctgagaacc   132300
gtactaaagt ctttacatgg gatttaactc cacgttcaac tgaagaccTt atggctatta   132360
taaacattta ccaatatttt aactatttct catatggcga gaccggtaaa tcacaatacg   132420
cccaagagat taaaagttat ttagacgaat ggtaccgttc aacgtttatt gagcctatga   132480
caccagacga tgctgtaaaa aataagacgt tatttgaaaa gattactgca tcattaacaa   132540
atgtattagt tgtaagcaac cctacgattt ggatggttaa aaactttgga cacacatcta   132600
aatttgacgg gttaactgat gtatttggcc catgtcaaat tcaaagcgta cgttttgata   132660
aaactccaaa tggacaattt aatggtctcg ccgttgctcc taacttacca tcaacatttä   132720 cgttagagat aacaatgcga gaaattatta cattaaaccg ttcttcactt tatgcgggga   132780
ctttctaatg tactctttag aagaatttaa taaccaagct ataaatgcag atttccaacg   132840
aaacaatatg tttagttgtg tatttgctac tacaccgtcg accaaatcgt cttcactaat   132900
ttcgtcaatt ggtagttttg cttataataa cttaggGttg gattccgatt ggctaggatt   132960
gactcaaggt gatatcaatc agggcgtaac aaccctgatt acagcaggaa cacaaaaatt   133020
aattcgaaaa tcaggtgtaa gtaaatatct gattggagca atgagtcaac gtacggtaca   133080
aagcttgtta ggtgagttca cagtaggagc ttatctgata gacttcttca atatggcata   133140
taataataca ggtttaatga tttattctgt aaaaatgcct gagaaccgat tatcttatga   133200
aacagatttc aactataact caccgaacat ccgaattacc ggtcgtgaaa tggacccgtt   133260
agtaataagc tttagaatgg attccgaagc atctaacttt agagcaatgc aagactgggt   133320 aaaactctgtc caagaccctg taacaggtct tcgtgcttta ccacaagacg tcgaagcaga   133380
tattcaggtt aatttacatg cacgaaatgg tttaccacat accgccgtca tgttcactgg   133440
atgtattcct gttagtgtct cttctcctga gttaacgtat gatggtgata atcagataac   133500
agtttttgac gtaacatttg cttatcgcgt tatgcaatca ggtgctgtaa atagacaggc   133560
cgctttagaa tggctggaat caggactTat tagtagtgtt tcaggaatgt ttgggaataa   133620
tcaaaatgat tctgggctag gaagtgcagt atcaagactt tctagattag gtgggactgc   133680
tggaggtgtg tctaatataa acacaatgac aggtatggtg aattctacat caagagtttt   133740
aggtctataa gaaaaaggga gacaacgtct cccctttaggg gtttatttac ggaatgaaag   133800
aaatgctggt gctcggaatg gagtatcatc tttagagtat ttaactaata cgaccattgg   133860
tacctctgtt tctaaatgac ctgtcagtac accgataaaa atttgatcag tgtgttcagg   133920
gtcacgaaag ttttaagag gttccatagc aatatggaat gcacctggga atactcgatt   133980
caattcgtca atcacagctt cgttaaaaac atcatccgct gggatagcat cttcaactac   134040
tagttcttga ccattaaagc gaagcataga tttcataacg ttttcctcat gttgttgata   134100
ggatgatagt atcacacatc catgtgcttg taaactatcc ttgaacaaat ttaaacggaa   134160
ccgattctaa atccattaaa gatgctaaca gtttcaatcc tttaggagca ctagttttt    134220 ctacaaatga ggagaacgat accggctcat ccgattcgat ttcaccagtc atagcaacca   134280
cctcgcctgt ttccatgaga acatcaccat cgtaaatgac agcttcatcc aactggtctg   134340
aggacatgac ttcagcttga ataaatttaa ggttggattc taaacctgca ccagtgtcag   134400
atgacgcatc tgtaatttta tttatctgca agagaatgcc tctaggcaaa ataatttctt   134460
gctcattagg gtgattactc aactgtcctg gataaatcac gttaacttta tgggcgccgt   134520
caatagccca tccaacgtta acacggattt gttctggtgc atgcatagct gttcttactt   134580
gactaggaga aatagtaaca ccttcgtcat tatttgtcaat gttaagctct ttgcgaactt   134640
```

```
cttcaggagc aagtccaagg gcaacgttct ctttaaaccc gccgaaaata ataggagcta    134700
gtgaagtaga aacatagttt ctgaagtaga ataccttatt tttaaccatt gcttcgtaaa    134760
taggcattct gatagactga gctctataca acgttagtcc ttcaggtaaa cggtctccat    134820
ttaaaaacgc cgaatcaaga ccatcaatag cgcgtttaac ttcatcttca tctgcaacat    134880
cataaaaatc cggtttataa cgtcctaaca acatattatt gatatcagta tatgcagaag    134940
aggcatattc acgaatagct cgttttttcgg caatagagta ttgtttaggg tcccgattca    135000
ttgttatatt aaaggtgcct ctggccgatt ctcgtgcata agtatacatc acattagaca    135060
agaacgctga tttacgttgt ttccaagttt tttcagatac ttcagctaaa acgtcatcag    135120
ccagttggaa attatctcgt ctaaaatctt caaaccattc gtctctaata gagtctgcaa    135180
tttcgtttgc agcttcaaca aaagcagcta atgctttaac agatgttgtt ttttcggttt    135240
taattttctt agcaaacttt tctaaagtcg gcttaataac actaccataa gaaacttcat    135300
cagcaaatct aaaggattca tcaatacgat tataaatctt attttcgata tcagcaacta    135360
aagtgccttt tgctgtagac gatgcttggg ctagtacgat ttcatatgct tcaggaagta    135420
attcagctgt agctgggcca ctaacttctt tagcagaatt ttcgtatttc tggaatagct    135480
caccttcttg gcggtcagct tctaaagatt gacttgcggc aatagcgcga cgagaaattt    135540
tagtacgagc aataacaggc ttatctttac gtttttcttc tacagcagca atagaaccag    135600
cgatagccgt ttcttggtg accttttcgc cagtcttttt actcacataa acttcaccaa    135660
catcagaatc tactttcgtg tacaactctg tgttaatgtt agggatgcct ttaatatctt    135720
caatgttggc attttacga accatcatca catatgtgtg tttacctgtg aattgataca    135780
ttgcagacaa tactttaaaa cgaccaccag ttttagtaga aactaaacga gcaagaagag    135840
tttgaagttg ttgtccacgt cctttcaatt tcttggtagg gaatcggaac aaaactgcat    135900
ccatacgaag agctttaacc tgttcataca ctgtattgaa aatggtgttg attgcatcaa    135960
taggagcagg accaagacca ttttttcaatt cagcgagatt acccttttca gaaagactca    136020
taataacgac atgagcgtat ttgtcgccaa gtttaacttg ttttacagca tcgccttcgg    136080
aaaggtaaga gaataaacga actacgatgt ttgtatcgat atcaccaatt ttccagactt    136140
gtggaacttt agcttaggg ttcaaattga cgacaggaag actgccttca gattcaaaca    136200
cttcatttaa ttgttcagac atagtgtttt cctttagta ataatttata tttatgccaa    136260
aaagagcccg aaggctctta atccacaatc ggaagcaaag tacgataaac ttcaaaatta    136320
gggccttttt cgtacttatc aaaattgtcc ataaaaatat tataggaatc gttattagga    136380
aaatctaata caatttggga acaagaggtg gaaacatcac caccatcttt attagcgaca    136440
actactgttt ctaaataagc tttcattata aacctgtctg gaccacggt ccaaatacgt    136500 cttcaaatga atccgcttct gttttatcaa aacggaaccc tttaataatt ggaaggaaaa    136560
tacctacagt accttcacgg cctttagaat gaacccaacc attacattcg caatcagcaa    136620
tacgtccaat caatttacct tcacgagctt cagccattaa tcgttcacgg tctaaatcat    136680
gacgctcatc taaggaata agaatcttta caccatcaac tgttttatga gttgtatctt    136740
taaaccctga accacaatcg gttgtaatac gacgacaacg tgatacgagt tcgacaccac    136800
ctaatttgtt agggtcttta gagtgttcat agtatcctac aacttctaaa gcgatatcaa    136860
taacttcttt aaatttaatt aggttcttag agcgtttgtt ttcccaatat gaatcacggt    136920
ttttaaggat aataccttca agaccttggt caacatattt tttataaacc actttagctt    136980
```

```
cgtcaagatt acgaactaac tgattttcaa ttggctcaat tcgattaaag ccttcagcca   137040
tattttcaag agcagcaaaa cgaacatcgt atttctgacc tttaattttg ccatcagaat   137100
agacttcatc taaaggaaca tagtcccagg cttgaagaac catacattcc gcttctttag   137160
gagaaatagt cccttgaaga gatttatttg ctaaaccgtt tgaagtgcta cggtctgcaa   137220
cttgtacttc ttcggattct tcattatcgc caaataagaa cgacaggtca tttcctgagc   137280
tcacagcctt tttaatatca aatgaatgat aaactaattc gccgtcgatt aaaaccccat   137340
tagggtgtct ttcacgggct tctttagtca tttccattag ttcatccgct aatagagtaa   137400
gaccatggta ttcgttacca gcacgagaaa agaattgaac accatcatca cgaacttcag   137460
cgaaacaacg agcaccatct gcttttaatt gggcgaatgc cggccattta atatttttag   137520
taatcaattt ctcatcatat gcagatgcta acatctgtgg ttgcaattga ataagtccag   137580
gccacacctt attcgcgata gacactgaag cacctacttc aaggtcgcgc atcattacac   137640
gacgaaggac ttctacatca tcaggtttac cgtcagcgat ataacccatg agctctttaa   137700
ttgcagcatt accagtgagt ttacgagtgg ctaatgtgaa ctcaataaaa tccaacatgt   137760
catctaattc aagaagacca tacgcttgag acctttcacc tggcccaggc catttcttaa   137820
tataatactg gataccacgt gcatacgtta aacgatacac acgttcaagt aatttgttgt   137880
ccttattttt cttaaggatt tcctgttttg ttttagtaga accgatcgca gctatttggt   137940
ttaaaatatc taaaatcatt tgatatcctc gattttggtt acggttctat tataagccac   138000
ttcatctaga agcgatttca gcgttttctg ataagtggta atccatttac cgagtccttc   138060
aacataatat tctgaaatgt agatgaaccc ttgttcaaca cactctttaa atatttctgc   138120
gtcttttact gaacgaaaca ccggccagtc tcgaaagaac atgttaacat ggccgtagtc   138180
acgtgtggtg tttttgccat ctgtaatatc atgaactaca acataatta gcccttaaca   138240 atttatagac caagtccatt tagacgaatc taaaggaaag ttttgaatcg tccaccatgg   138300
ctgcatatcg gttggtcctg gggttcgcca ggtatatgga gtacgtgttg tcgaggggcc   138360
accaatttga ttaggccatg cacctggact tgttgcacca gattctttaa gcaaatcggc   138420
caatcgtttt aaaaggtctt cacgatctga atttgaatta tgctctggcg gaaccaatcg   138480
agattcaata tcatcccacg tgtgtacacg ttgtgcagtg cgaggaatat catcacgttc   138540
accacgagcc aaccaataaa tcggtacatt aagaatttct gccgcatggt cacagtgatg   138600
agctaaatcg tcaacgtaac aaatcacgtt atatttgtt ttagctagtt cgaataattg   138660
ttcctttgaa gaatcatgac cacacatcat tacttcagag aaagcgcctg ggaacaaagc   138720
attcaaatta aattgtctat tcaatcgagc atcaattgaa tcacctagcg ccgtcacggc   138780
tacaaaatta tagtcttctt ttagtttatt gataactcga agagcatctg aataaggcgc   138840
taagtaacga ataaaatcag agctattata ttttctatt aattgtttac caaggttatc   138900
gtcggtattg aatagtttac caggagaaat aaatttttcg tcctgaatca tttttaaaat   138960
atgttctaat ggaagattat atttttgggc aaaataagga agtccggatt gccaacttaa   139020
acatacacca tcaatatcag tcaaaatagt aggcttcata aagagtctct taataggttt   139080
aacacatcaa taaattcagc ttcagttagt attgtatcat cttttgttag gtggctagcc   139140
atgctgtgct tcaaaatttt tcctttagag gcttgtaagg catcacgaaa ccccttattt   139200
tggatcgcgg cttcaaaata tgcatttgtg tataattctt tccacgcttc ggagtatctt   139260
gaaaacggaa ctcctaacca gaagagagtt ccacggtcct gagctcttgc ataagacctt   139320
ccagcttgct gtgcagccaa tccagacaac ccaaatatac gtctttgttg ttcaacattt   139380
```

```
ttcaccttac atccttggag aaatccttca agacctccga attgaatacc atccataaca  139440
aaaggccatt gagcaaagtt acttaatgca catgacggcc acttgaaatt acttcttatt  139500
tctaattcag acatctttaa cacttataat ttcaacatca gcccaatggc cgtaactagg  139560
cagacggtct tcaatagata aaccaccgtc attttttaagc attttaattg tcttgataaa  139620
tggttcatcc tgtggatgaa taggcgagca gtcagttaca cgataagtaa cttcgatcat  139680
ttctgtacca aacaatttct ggattagttt attcaacatg tttcaaccct ttaataggag  139740
ataactcttt acccatacgt atgtcagaag tcccatcaac ccattgaaca gcatacgctt  139800
cattgataat tacggcggcg gttttaaatt catggagaac tttaaaaatc atcccaggga  139860
ttccaacacc ttttaattgg actgtttgtg ctattaaaaa tttcatattt ttccacttgc  139920
taaagaaatc attatactct aatccgtcct tggatgtaaa ctacttaacg aaattaattt  139980
ccaccggatg aacaacaggt tgagcagtga tatattgagt aattgctttc atgactagag  140040
cttcagaacc aggatttttc tcaacgaatt cacgtgcttg gttatgagct tcgagttcac  140100
tcaataatcc ggaacgttgg catccacggt cttgagtacc ctgttcagat aaaaagacga  140160
cgatgtattt ttcatcgtca tacggtttag acggttgagc aaatgttcct ttacttccaa  140220
aaggagagtt atgacgccac atcacgccgt gaggagtttc aaccttcgta tattcgtgcg  140280
ggccattttt cttaatttct tgatgtggaa cttcatagac cttagggtta ggacattcaa  140340
taaaatgctc atctaaatcg gtcgagaata ttaaagtaaa acaattactg aatttaccaa  140400
cacctgcctg ataaatttta ccttcagaag ttctaatttc acaaaccgag ccagcatcag  140460
taacttctaa aacttcaaaa ggctcgataa ggtcatatga gaacatgttt ttaaggcgtg  140520
gagtaatatc cccattttta aaattcattt tataaaaagt attaacttta aacataattt  140580
cctcactggg agcttcggct cccaattaat ttagatatca aattcattaa gaactacatc  140640
aaagattgct tcgagatgtt caggtttagc tcggttactc aggatatgac gaatccaggt  140700
tttaaccaga agtttacgat taacaccatt ccagcaagga tgagtaccta atcgcgctg  140760 acggaaatca tcatcttaat gcaattttaa aatttgaacc ttccatcgtg attgaaaccg  140820
tgatgccatt ttcaaatcgc atataaacat aattaggagt catgcactgt tcgatttcac  140880
aaactgtacc gttttcgtgt ttccataagc aaataacttc agaagaacca gcgataccgt  140940
tagaaacata tttacgttcg aagttgatgt agttcatttt attctccaga tgtttaagtt  141000
gtttgttggt acaggtatat aataacatat cctgtaccaa agtaaactgt tttatgcaac  141060
tttaatccaa ttgtctaaat ttaaaacacc tttggctttc attttttttcg atcaggttat  141120 ctgctgtaat gcgtccattt tgataccatg taacatcttc agagtaacca gtttcttcgt  141180
caacatatgt ttctgagcga attttaccgg taataatagt ttttaattcg tatgtgtcac  141240
ctgtgaaaaa gtttgctaac acaattttcc aagagaaatc atttgaagga ccttcagggg  141300
tcatacaact tacgaactca aattgctctt tgtataacat ccactggaat tctttaattt  141360
cgatagcttt ataaccgtcg tggtctttac atttgatgta tgagtttaga ttgattttca  141420
ttttattctc cagtttgttt tattgattag gtggtacaag tctatagtaa cacatcctac  141480
aggagagtaa acatcttttt aaactttttc tgccctaaac gcacaaaagg gagaccgaag  141540
tctccctaaa attacgcaac aacctttcca aaacgagaag catcatctcg aagaactgca  141600
cgtgctctgc gcatgatctt ctcaactgtt tgattaatac gagagttcga cccacgcttg  141660
tatccagcgc gtttagaggt accatcaact ttcttttcaa ctgctttctt tgctttagct  141720
```

```
tgttttgcca ttataaattc tctttaaatg aaaatgcagg acttattgac attgcctgcg    141780
caagccctca tgggaacata ggttttggat atttaacgac aggataacca taaaccgtc    141840 atcataccaa ccacgactta gacagataac cttttttctga cgcgtgatag tacaaaatac   141900
attcaagagg tacaccgtaa aactgccggg gtcttaaaac tataatgatt cgcaaatcat   141960
taatcagaca attcgacggc tcctcgattt aacttacttc agggtaataa caaaatgacg   142020
tactgcttta cgagctgctg aagccaaagg cttagcatat ttcagttcat cttttgcttc   142080
cagttcagca gccagagtag cctgagcagg attcagatgt ttgaaatatc gcaggatttc   142140
cagtgcttcg gcttcaacat caattgaagc gccgtagttt tcgtgaccgt tattccatgc   142200
gttgcgttgc agatcaagag cgtgttgtag ttgtttaatc attttaaatt ctcaattcga   142260
gataatattt agtagccacg ttcgtctgaa tttcaccttc tttcgacaag tctctcagtt   142320
gtaggctacc gcttagaaga gtgttctctt catatagtta tttatatcac ttataaagac   142380
acggaatagc tttatagtgg catgttacga atttctgttt aatttcttta ggttgtttaa   142440
gtcccaaagc cacaaatgga tgtggaacat ttcgaatttg tccaactggt agtggagtca   142500
aatcaccgac ttcaacaaaa ccttcaggaa catcaggacc tacagaatga actcacacata  142560 gttcaggaac ttcaccttga acacgtttac caatcacaag tcctgattcg gtaacttctt   142620
catcacctgc ttgagcgggt tcagaaacca gaatgacata ttcaccaaca gcacgaattg   142680
ggagttgtac ttcagacatc ttatttcctt gttgtttgac gatagattaa taataccata   142740
ctattcgtaa agcatattac ataagaagca aacgttcgac cggagtacca tcaaccgaaa   142800
ttactttatc aaggcggaaa gaacgccact gacctaactt ggtatcgaat gctcgaactg   142860
attcacgagg ttcataacga acttctgttg ccggattgtt attttcatat ttgacttcaa   142920
gttcatcgcg cgaagcaaac atagtgcgta catcaccgtt agccttttca aatcaacac    142980 aatgaacgcc tacagacaga atagttttaa tacgttcacg aagaaccata gtttcttgtt   143040
cagttaaaat catattattc accacaaaag tttcggattt gttcccaatt cagagaacga   143100
agattattac gagagtactg aattacttca ataccagctt gttttagaat gtctgcccaa   143160
ttttcaggag atctgtcgta taattctgcg tatacgacct ttttaatacc tgactgcgta   143220
atagctttag tacaatcagg acatggagaa agcgtcgtat ataacgtagc accttcaata   143280
gaattacctt tacgagcggc aaacaaaatt gcattcaatt ctgcatgaat ttcattatta   143340
gcagaccatg cactatgagc agctcgatgt tctttggcta aaacaaaatt atctacccgt   143400
ccaaatgctg tagtgccttc tttatgtcca gcaacgatga ctgggattgg tttattcttc   143460
aaccaaccat tttcagatgc atgttcgcaa cagttaacgc cacctgcagg tgaaccgtta   143520
tatccagtag agataatgcg tccatctttt tcaatgacgg caccaacttt ccatgaacaa   143580
cattttgatt cttgagaaat cagatatgca atctgaaggt atgtgctagc tttcattatt   143640
gaaccttatt aatataagtt aacagctctt tagtttgttc ccaactgatg cacgcatcgg   143700
taacggaaac gccataggac atattatcag aaattttttg atttccttca tgtaggaacg   143760
attctatcat aattcctttg accaaatcat tagctgctaa attttacca ataccaattt     143820 gattgctata atgcccatca gcgtttgcat ggctacagtc aaccattaca taatgattca    143880
gacctactgc ccttgctttg ttagaagctt cttgaatatc agaagaatga tagttcgggc   143940
cgttggtccc gccacgcaat acgatatgcg tattctgatt accttcagct tcaacaatgc   144000
ctacagtacc atcgacgtcc ataccctatat accgatgagg ccaggcggca ctatacatcg   144060
cgtctgtagc tactttaata gaaccattgg ttgcgttctt gaagcctacg cacatcggta   144120
```

```
gacctgaagc aatttcacga tgtgtctgac tttcagtcgt acgagcgcca atagcaaccc    144180
atgagaaaat accagaaaga tacttaatcg tgaatgggtc taatacttca gttgctaatg    144240
gaagtcccat acgtagaagt ttacgacaca atgttcgtgc aactataaga ccgtggttca    144300
tatcaaaact tccgtcaaga tatggatcat ttacaagacc tttccaacct acggtagttc    144360
gaggcttttc aaaataaacg cgcatcacta acagaacatt aggaagacga gtttgaagtt    144420
cagccagacg tttgccgtat tcaaccgcag caatagggtc atgaattgaa caaggaccta    144480
caacaataag tttgcgtggg tcttcaccgt tcataatcga attaacttgt tcgcgatgag    144540
aagccacttg tgatgcgtaa gcttccgaca aaggaataat ctcagccagt tcttttggag    144600
aaataagttt tccgacgaca ggtaacataa caatccttag gagatataaa cagattctga    144660
ttcaacaata cctttaaccg gattagacag gctaagttgg tagtgctcag atttatgacc    144720
attctcgata gtaatgagat agctctcatt atagtgttcc atatactcga gttgcttcaa    144780
caagaccatc actgcctaat ttaagattag taatttggtc accatcttta ggattaacga    144840
ttatgagaaa agaacgtgga gattcttgaa taactcgtaa tgttgcatcc tggaaacgtt    144900
cagacacttt attgatgagt gcttgagcaa attcttttac tttaatctga aattcgtgta    144960
ctgtaattgg attttcactt agcatttcaa tttcctcatt tgttggtaga gttatagtat    145020
cacaactcca ccatgttgta aacttaaatt gcaaaacatt taatttcttg tgaatcgaaa    145080
tcaacttcac actgaattac tagttcagca tcaagaccaa acacaacaat cacatgagcc    145140
gagctgggca acaatgtaac agacacagaa tccacttggt caggcaccag agtattcaaa    145200
acgtagagta gttcagagtg gaccttaagc tcggtagcag tatccagctt atcaaagaaa    145260
tgatttgcga taatctgact aaaaacgacc tttacaattt cagaatattt agggaacata    145320
attacctcag tgtatagtat ttactttaac tcgaacaaca aattgctcgg tcggttcgcc    145380
tacaggaaca aactctacat gatattcgcc tttgtaacga gtattcaggt cgttacgaat    145440
ttcggtaagc ttgttgatta atgtagaact catattaagt ccaactagtt tacgaagcat    145500
tttgtatgct tcatcttcga tttcatgatg tttatcgtac atagttttca tttaaccatt    145560
caattgcctg gtcgacgtta tcaaatatac caccgtccaa acgttcttca tgctcatagt    145620
ccagcacatc aataccgaac tgtccattta ctaaaggcca ggctacaaac aaatattctt    145680
tatgctgttc gatggcctca atcacttcat ataatcgttt cattaaaaat caccatggtt    145740
aacttgccaa cactctaaac caatacgacg ccacatttcc acaacctggt tacggtcatc    145800
aacggccaat ttcacatcat aatacggagc aatacaattc caaagagtt cttccttaac     145860 aacatcgtcc ttacgagtgt caccttgatt acgttgaatg tgcatttccc atggaataga    145920
aaccgtgtcc atccattttt tagttgcttc gtaataacac attgaatctt ctttagttcc    145980
agattcacga ccacttacag taataattgt atacccggcc tgatgaagca tcttaacata    146040
ttcgacaacc ataggggttcg gggcatctgt ggatagttta tccaactcat aaggtccacg    146100
agctacatgt agagctaaag tcccgtcaag gtcgaagata accgctttag gtttacccgg    146160
agttccttta taaaccggaa gtcctttgta ttcacgcata cgagaataca tcgaacgtag    146220
aacatcaata ggaacggcct tgtgccacg tttggcatta cgtttaacca attcagtcca     146280
tggaacatcg aacacttgat atacaacttc atgaccccac tccttagcgt attcttccca    146340
gacaagacga cgttcaggat ttaagttggt gtcagaaata ataacaccct tagttccgtc    146400
ttaacagaga atcatatgtg ccgcgtcgtg ttgcatataa gttacgatac tttctttctt    146460
```

```
ctttgtgtat ttgtactcgt cgcgttcttc gtggcccatg acggattgac gataatcgtc   146520
gcggttgata ttaaagaacc caggattctt agcaataaat tcacgagccc aagtgctttt   146580
accagaccca ggacaaccta cagtcaaaat aatctttttc acagttttac tacctcttca   146640
gcaaattcaa attgtccacc aagaatttta gcaatttcac gtcctagttc agcacctttc   146700
ttgcaatctt gcatagtcca agactcacca ttctgtgatt tacgaagagc ccgtgtattg   146760
atatctgcta caagcgtatg gattaactta tcaattttgg cttggtccat tatttttattc  146820
ctaagaaaat ttcaagaata cgaatgttat gctcgcgccg gtctttatta atttcagcaa   146880
cgtttttatt aattgacgta cttctaacgt ttgaagaaat aaatttaatc atatgacttt   146940
tgagttgttg caaatccaac ccttttttctt tagcagcttt acgaagagct ttacctgctt  147000
catctagtgc ctttgctgca tctttgtcat aattgccaag tgacattcca cgacagatat   147060
caatatactc atcagaccgt ttgatgtaat tctctagtaa tgttttcatt tagatttcct   147120
caattatcca taggagcatt ataatctgct cctgagagtt tgtaaactat tttactaaag   147180
attcaatata ctcgtgaaga gctttagtcg ctactgccca cttattctga tattcatttt   147240
tcagattagc acgagactga actaacaatc ggtcattagt cggaggcaaa gattctaatc   147300
gttgaatctg gcgcccataa atcatagccg ccatttcaga ttcatagata agcccttaa    147360
tgtattcatg ctgttcttta gtcattggca tttttcctct tttaaactac tacgataata   147420
acataacata gtcttctggt catgtacata tcttttttacg tcgtttaacc agatacgaaa  147480
ttcttgagag tcttcaaatg gcattccaac ccatggatta ccatcaataa cctttacttg   147540
ccatttctga ttatattcaa caatagattc aggccatggc ggatgtaaag tttcttttagg  147600
gcttaagggc acatcctggg cacatccagc caaaatgcca atagataata caactgcagt   147660
taatttaatc attctgagag cttcctgagg tcttctgcaa aggaatcgaa ggacctgttg   147720
atttgttttt cgaccaatcc tggcttactt gccaccacgt tcttcttctt cgaatcctga   147780
cggagctttt cattttcagc cttaagttgg tcaactaaaa cacggttctt ataagtcatt   147840
tcttcgattg actgatattg aactttgaag tcgtctaata ctttagcatt gttttttagca  147900
gcctctttaa cagaagctaa ttcagtattc aacgaatcaa ctttgttgtt taagacaact   147960
attgttaccg tagaaactag agcaaaagct gctactatag cataaatcgg atttacttta   148020
agcatgtttg aataatctca atgatttcgt ctcgggataa tccattgata agaactgttt   148080
taggcccatc agtttggatt ttgtaggtct caaacattac acacaactct tctgctgtat   148140
gatatggact tgagattccg aggcggttga atttgtcggt aagagggtcg caaataatgt   148200
agaattttat acctgcgata tgtacgtttg gttgactaat attaatgaac acattagcgt   148260
catatttagt caaattgttt tgaagaaatt ctaccatagc attaactgct tccggcattg   148320
cttcacgttt ctcttcggtg taacgtgttg aatattcctt ttgctttaac ttcttttttag  148380
catttttcgc tagagtagta cgaaggtctg taagataacc gactgcacgg cctttcttaa   148440
agactcggat tccatctgta gaatcaccaa atgctgccac aaccatatcg ttagtaatca   148500
attgcatatt cataattttc tcctcgtgtt gttgataaaa gccatagtaa caccatcctt   148560
ggtgtttgta aaccattaat atccttcagg gatgaaattt ttatgatttt taataaagac  148620
tgattctaga gcagtcataa tttgctctttt tgaaccacct tggtaaagat tcataatgat  148680
gccaaataac caaggtgtct gtgcacccctt acaaacagcc tgagcttcta tagcatacgt  148740
tttacgatct tttcctttgt gcttatcata tgtatctaga cagatataaa atgagcggtc   148800
taagaaatcg agatatgctt tttcgaagag ctcgaccttt ttaaatgaaa actcatcatc   148860
```

```
tgcatacatc gctttaaggt catctgaagc accgttcact atagcaagaa acaacttttc   148920
tgggctagag attgagtctc gagtcgtatg aagagcaaca taccaatcag tcttcaattt   148980
gaaatgagac ccgtctttca ttacggccac atacccttca atatttgtag aagacttaac   149040
atctgatgtc cagtcacctt ctggtacttc aaatcggtct acaagatatt tacgaaaaac   149100
agggtctaga taaatgtcat catactcgat gtattcacct gtgttgttat cgcgaatatt   149160
caaaagaatc aaacgttttt cagggtatgt taaaacaatt ttatttgttg gagcaacgta   149220
ttcgaagtta gcagtgaacc cgtcattaca aagttctaat aaacgatcag ccaagttttt   149280
atggtcgatg tctaacaaaa tactcgtggc cgatacagcc tggtcggatt tgattgaccc   149340
tttagatttg aaacgaacag tcccaccatc aagatatgtc gagactaacg aaccgtcttc   149400
tttagtcatc agatatttta catcatcaag gttaattgac aatgtaaacg ggttctcatt   149460
tagattaaag aattttttcca ttggacgaga agcaatacgt ataggagttt caccatccat   149520
ttcgaacata ataccacgac actctaacgc gtcaggcaat aaccaatctg aatatgaagc   149580
aaagttatat gagaaaatac gatactttttt accgattgga cttacatcat ccgagtagaa   149640
aaatttacgg tcggatgacg atttacacag agataacaga ttataataaa gcttttccat   149700
tttgtatcct cagttagttt ttttttaaatt gtaccacaat ccttgtggta tgtaaactac   149760
tttttcttat gttggatatt ccaaggcggg ttgaactttt tgataaaaag tggttcttca   149820
aggtccattg ttgcgatggt cattgaacca agttcgttgg tgactgaaag gtcaaaacat   149880
tggcgggccc agaattcaac cttttttgcct tgcattaagg catccaaaat cataagtgat   149940
tttcttgaat ctgaagtctg gtcttttcga tttatggctg ttcgataata gttaatgcgt   150000
ttctttaaat tcttggtttt accaatatac acaagttcgt catctatagc aatagcgtat   150060
atgacatttt tcttattagg ggcatcaatg gtttttaattg ttgcatcttc taatagctcc   150120
aattctatat atttaataaa ggaatattcg gcggcaatat ctttcataat aaagtgggac   150180
cgaagtcccg tccttagaaa tattttttgt atgaatttat tacattttgg tctacatcat   150240
tatcaatttg tgcgacaaga taagaactga tttcaacttc ctgaggagct gcttgaacta   150300
aatcagagtt cagatattca cgaatccaag gatacggatg cttggtcgga gcatcagtga   150360
ttgggcatgg caaccacac tgtttcatac gagacacggt caagtaatca acaaaagcac   150420
acatactctg cgtattgata cctggacatg taccatcttt aaaaaggtgt gcagcccatt   150480
ccttctcttg actatttact tccataaaaa tgtcaactgc ttcttgttca cattctttag   150540
caatttgaac ccactcatca ccgtcagtac cagattgaag ttgacggata atgtactgag   150600 taccccttgag atggagttgt tcgtcacgag caatgaactt cataatcttt gcattgcctt   150660
ccataatttc catatttta tggaagttga agtacatgc aaatgatacg taaaaacgaa   150720
tagcttctaa ggcgttgata acatgcaaac agagataaag agacttcatt aggtcatgtt   150780
tacattcttc catgtgcata agactatttg aatatgcatc taaatcatat tcattttcgg   150840
aaaaacactt aaaaatttct ttagcatttt cccattcacg ggttttaatc agaacgtcat   150900
cataataacg tccaatggat tcagcgcgtt tcataatagc ttcatctaat acaattttcat   150960 caaatacctt cgatggatcg gtataaagat ttcgcataat atgagtatac gaacgagagt   151020
gaatagtttc actgaatgtc catgttgcga cccatgtatc taatgaaggg tcagaaatca   151080
gtgccataag taccgcagat ggggccctgc cttggataga atctaataat gattgatact   151140
taagattgtt tgtaaagatg tcctgttgga actgaggaag cttattgaac tgcgcagagt   151200
```

```
ccaacatcaa gtttacctct tctgggcgcc agaaaaacga caattgtttt tcaataagtt    151260
cttcgaaaac tttatgacgc tgaatatcat accgtgcgag gccaagacca gaaccaaaga    151320
acatcggttc attcaaaaca tcgacttgtt gtgtgttaaa aactgtactc attatatttt    151380
ctcacttagt tattaactca tccatgagta aattataatc aaaagtctta aagcttacaa    151440
gcagagcaat cttcagcttt aggtgtttct aattcatagt catctgtacc tgacccatca    151500
cgagtgttat gatagtagag gttttttccg ccaaagtacc agaagtaaag cagatcgtca    151560
agcattactg acattggcac tttacctttc tcaaatactg cagggtcata gtaagtatta    151620
gcagaagcag attggcacac ccatttcaac atgatagcaa cttgggtcaa ataaggttta    151680
ttacctttct tagcaagttt ccacgcatag tcataaagac ccatgttgtg ttcaatatta    151740
ggaactactt gacggaaatt accttcttta gattctttaa tacttactgg gccacgaggt    151800
ggttcaatac cgtttgtgct atttgagacc tggctgcttg attcgcatgg catgagtgca    151860
gacaacgttg agttacgaat tccgtgttct ttgagttcag ctcgaagttc ttcccagtcg    151920
cagacgtagt tcggggctgc gatttggtca atctttttat tgtaccagtc gataggtaat    151980
tcgcctcgag accatttagt gtctgaataa tactcgcaag gtcctttttc tttggcgagt    152040
ttgattgaag ctttgataag gctatattgc aatctctcaa acaattcatg agtcaaatcg    152100
ttagcgtctt catatgaagc aaagttagaa gctaaccatg cagcatagtt cgtcacacca    152160
acaccgagat ttcgacgctt tttggctttt aaagcttctg gaaccggata gtcttgatag    152220
tctaacaggt tatcaagtgc acgtacttgt acttcagcaa gttcattaat tttatcttgg    152280
tcttgccaat caaatttatc taatacaaaa gcagataacg tgcataaacc aatttcagca    152340
tcagggccat tcacatcatt agttggaata gcgatttcac aacataagtt actctgacga    152400
attggagctt tttcacgaat aaatggagtg tagttattcg tgttatcaac aaactgtgga    152460
taaattcgag cagtaccaga acgttcagtc atgaacaatt caaagagttc tagtgctttg    152520
attcttttct ttctgattgt tgggtctttt tcagctttct cataaagctc acggaattta    152580
tcttgatctt caaagaacga gtaatatagt tcgcctgaca tttcgtgagg gctaaataaa    152640
gtaatataat catttttgcc aaggcgttcc atcatgaggt cattaatctg aattccatag    152700
tccatatgtc gaatacggtt ttcatccacg cctttgttat ttttcagaac taataggttc    152760
tctacttcta agtgccacat cggataatac gctgtagcag caccaccacg aataccacct    152820
tgagaacaag attttactgc agtttggaaa tgtttccaga atggaataac acccgtatgt    152880
cgaacttcac ccataccgat cttagaacct tctgcacgaa gcataccaac gttgataccg    152940
ataccagctc gtttagaaat atattcaata attgatgctg aagttttgtt aatagatttt    153000
aacgaatcac cagcttcaat aactacacaa ctagagaact ggcgagttgg agtacgagca    153060
cctgccataa ttggagtagg caacgaaact tgatgagtag aaacggcatc ataaaaacga    153120
ataatatgtt tcaaacggtc atgagtttcg tcttgatgta aggccatacc aatggccatg    153180
atagcaaact gtggagtttc ataaatcttc ccagttgttt tatctttaac caggtatttt    153240
tctttaagct gcatggcacc agcataagtc agatcaaaat ctcgctcatg tttaatccga    153300
gaatcaagat aaatgatttc ttctgcagaa tatctagaca caactcagg atcatatttg    153360 ccttcattaa cacaatacga gatatggtcg ataaaagcag gaggttcaaa ctgaccatac    153420
acatctttac gaagtgcaaa cattaatcct ttagcggcaa catattgata atcaggttct    153480
tcgacagaaa tcgagttagc tgcaacttta atacaaatct tctggatatc tttggtgctc    153540
atcccatcaa ccagatgagt cttaatttct tcatacaatt cgtatgggtc gatttgtgtt    153600
```

```
ccttcacact gccaagttaa gacttgaata attttctgtg catcaaaatt ttgggatacc   153660
ccactgctct tagttacttg catatattcc tcagtatagg ttgatagaca ttactccaaa   153720
cgggatagta ttatcccgtt aatttattat acacttttaa actgaagcgt taattattct   153780
tagcaataat ttctttgtat tctttaggtg tcaagactgt gatattgaaa taaaccaacg   153840
gttctttttc cataccgtaa ccaccacaaa attcacgata ttcataaatt cgttcgtgtg   153900
aatgacaaat gaatcgttca cctttaactg tgatttcact atttggtgaa gggatatcca   153960
gttcggtagg attttcatt tcaaaaattg tggtgccata tgaattaata aaacgtaaaa   154020
tcatttatac cgccatttta gctttgatag ttggatgaga ttcgtaattt ttaagaatga   154080
aatcactcgg attcatatgc tctgttaccc aatgaagctg taatgtcgtg ctccaatcag   154140
agaatccttc aggccaatca attttaagtt cacacagttc tttaggctca cgacgaagaa   154200
cttctttgca ctgctctaca tggttgctgt agatatgcgt attgccgcct gagaatacta   154260
aatcacccgg gataagatta cacatcttag ccacaatatg cgtcaaggca gcgtacgagg   154320
caatgttgaa cggcaggccc aagaaaacat ctacactgcg ttgataccat tgtaaatcaa   154380
gatgaccatt acgcacatta aattgataga acatatgaca aggaggaaga gccatttggt   154440
caatttcggc agggttccag gcagaaacaa tttgacgacg atcagttggt aattttttaa   154500
tacggtcgat tgtttcaact aattggtcca ccaccacgaa atcacgccat tgtttaccat   154560
atataggacc aagttcacca ctatgataac caaggtcttt tgcctgattt tcgtaattat   154620
cgtcccaaat agttttacct tcaattagac taccatgagt acgaagacgt aattcattaa   154680
cattagtaga accggacatg aaccacagta actcggcaat acaagctttc catgctaatt   154740
tcttagttgt tactgcaggg aatcctttag tcaggtccca acgtaattta gttccgaaca   154800
gggcaattgt tcctgtgcct gtacggtcgt ctgtttcgta gccattttct aggatatcat   154860
taatcaggta ttggtattgt ttcatttata tacgctctca gtaatttcgg tgagttcatc   154920
gattctgtag taatgagatt ctaccataga acgttgaagc ataatatctt ggatgaaatc   154980
tttatcaagt tgaacatcgg aattaacacg acatttctta atgattttag tcatcacaat   155040
ttcatcggca taaggcagtg cttgttttaa taaggcagga ccgccgataa cagatacatc   155100
aacatgttca gtagaaagtt taaacggtac gtctgttgaa gggctgaaca agttaatttc   155160
actaccagtc accagggtaa taaattctgc ttgggtgata tagaaccgtg caagttcatc   155220
agttttagtc ctaggcagtt ttctggccat atcagcgaca accacatgag tacgatctgg   155280
tagtagacga ggtaatgatg caaaagtctt agcaccccata accattacag tgttttagt   155340 gcgagcaaca aagttactca tatcttgttt gatatgcttc catggtagtc catcacctaa   155400
tccaaaagca tattccagtt tatcatcgac tgtttagat ggtgcgcatg cgaatactaa   155460
tttaagcatt tttatttcct cagatttttc ttaacaactt tccaatcagc tttgaacgat   155520
tcaacgtcag agtggcaaat ccagaatcct gcactttcac catcttcgta gagtggacat   155580
ccatcacatt cttcgttcca acccatttca cgtaaagctt cttcagcttg ttcaaggagt   155640
tcagcgtctt taccaacgat gttgaagtac catttacctc taacttcaga atctttgatg   155700
ctctggcgtt gcaatctcat tttattctcc ttcacttttg atttgatagg gctactataa   155760
catagcccta tcttgttgta cactactttt taaaagtttt ttgcaaaagt tcgatgattt   155820
cgtcgacgtt ggtttcatct acgatacaat ggattttttgt tacacctaaa gttataccct   155880
cgttagtagg ttgaggcttt actaaatcta cctcagtaaa gtatttgaac tcgtcaggat   155940
```

```
aaatctcaaa atatgtttca atttcaccac cggcagaaca tacagtacca tcttccatag   156000
ttacacttac tacgtttgac gtatcgctat cataatcagg ttccattccg tttacaacaa   156060
aactaggtcc gtggagttca atcaatttta acatcttagc gttattgtgt ggtgcttctt   156120
gaacaaagtc atctttaaat aaagggttga tgatataaga ttttccgatt tccattttga   156180
tttcctcatg ttgttgatag gtctatagta acacatctag ggaagaagta aacaactttt   156240
tcggcaattt acagatactc aaaagggaga ccgaagtctc ccgatttatt atagaccagc   156300
taacaggtca tcgaggtcgc catcatcaga ggatgaggta gagctcatga agtcatcttc   156360 agttttgca gaactaaagg cttccatgtc tttatcaaaa tcgtcaaggt cagaagcaac    156420
tttatctgca acagaagctg ctgcggctgc tgcaccacca agagcggcag taccaagaac   156480
cttagcgaaa gattcattta attttcaaa ggatttgaac tggtctttag ccgtcaaagt    156540
agtaaggtct accatctggt catatagttc tttctggaat gcttcgtcat taatacgagg   156600
aatttcagat tgacccaaga atttagattc gtcgtagttg ctaaaccag aaacctgctt    156660 agctttcaga acgaagttgg caccttcaaa cgggcaagta acatcaactg gagtttcacc   156720
catttcggta tcaacagcaa tcattgcatt gattttgtcc caaatctttt taccgaaacg   156780
atatttaaat actttacctt cgttatctgg agcttgaggg tctttaacaa ccagaatatt   156840
agcccaataa gaagttttac gtttcagttg agaatattca gttttgttgg tattgtacag   156900 gtcatttta ctaatgtact gacatacagg acaagagtcg taatcaccat gtgtagaaga    156960
gcaattttca atataccatt taccatttt cttgaaaccg tggttaacaa gaattgcaaa    157020
tggtagtgcg tcatcagttt ttgctggcag gaaacgaatt accgcttgac cattacctga   157080
tgcatctagc ttcagcttcc attcgccttt atcttctgaa gagaaacctt tgttaccgtt   157140
cagtttagcc atttgagcag cgaggtcagc agtagattta cgtttaaaca ttatatttac   157200
ctttatttag attatttaat ttatttacag ttggttgcta cgacacttat acctcgtagc   157260
tggtatgatt tatttataaa gtaattttaa cacacaagaa ataaagctta atacttacat   157320
gatttgattg tttctatgaa caatttctta gcagcatttc catcgatttg aagtatttt    157380 cgatatgcct ttaatttggt agaataattt tgccagacta aattgtcggt gagttcgtcg   157440
tgcttatcta taatattcaa gaatgaatcc aacaacaaga aggtttcaaa tgaaattata   157500
ttgctttgta gcaatttaaa tatgtagctc gactgaactt tattattata atcaaatatc   157560
tcttgaagcg cactaacttc cactttctta ctgaaatagt agatgttacg tacatcttca   157620
gcaaacgtct ccttggcttg tttgagacgt ccaatatatt ccctatagaa aactaatgca   157680
tcagcgtctg atatctcacc aatccacgca tcttggttag caactaagtt actgatgaat   157740
atcaaggtga gttcctttaa cttatatttc tctgctagtt tctcaaagaa atatttatct   157800
cggcgttttt gatacgcatt atccgaaaca cgcatgcacc agtatatttt gattacgtca   157860
taccgaccat taaaatgttg tttgcacatc aagtatagtt tgtataccga ttttccgtta   157920
atataacgtt ctccatcagg aggcatgcgt attttaatca taataagaaa tctaacgtat   157980
tagttttttc accacgagca actgatgggc gaagcatatt ttcgtcaatt gcttcgcttg   158040
taattttttc aacaattcct gtaggaataa atttagcaaa ttgtgtttct ggaatagaat   158100
tttcttctaa gaaagcagtt gttgcttcta ataagacat accaaattgt tcaaccatag    158160
attcgataat gaatccgttt tcttggcggt caagcaattt agcgatatca tctttatcat   158220
gttttactgc taattcttgt tcagataaac cggcctcatc aaccggttta atatcactta   158280
gtgaaaactg tgtcataaag ctcgactacc tcttcgtttt cagcttcaaa ttggtcacga   158340
```

```
gcatctttat gataaagagc taacaaacga ttaaacattt ttccatcgac accaagctct 158400
tctttagcac gagtacgaat gtctttaatc agttcattat aaccagaaat tttaagtttg 158460
ttatcggaag cttccttgac tagtttagcc agttcttcac catgcacatc ttgattaaat 158520
tcaactgctt ctttcttagc catgtttacc tcagaattca ttaattacac ttgttaattt 158580
agaaagaccc gattttacaa agtatgaata aatcttgcct ttaggttgtt gtttatatga 158640
gttataatac tctataatgg ttgaagcaat attatcaggg atataatcaa aatcaatgag 158700
aaccaaattt tcttggtacc gtttatattc ttctgcactt aataatactt cagcttgaga 158760
acggtcatta gcaattgctt caataatcgt tgttttcata ctcggagttc gttcgccttc 158820
aactcgagta aaccagaaat caccacgaac tcgaacagac gcaacaccgt ctttacggtc 158880
gcctttaaga attttagtca tgcaatcaat ttcggcagaa ccattcttaa ttttaaccca 158940
ttttttctgc ggcggcgacc actgtttaac gttagggtat ttgtgtaatt gtgtaaagtc 159000
accatctgat gcaacaatac acaccttatg accggctaat gacaaatatt tagttaatac 159060
accgatatgg tcatctgctt cgtatttgtc aatatccatt acaacgtatg gcatatattt 159120
cttaatctca tcaacgactt tatggagtgc agtaaaatat ccttcccaat cccactttga 159180
agcttcacga tcggttttac gattttcctt ataatagtaa gcaaagtcac gacgccaata 159240
tccagaagta gcgttatcca tgcacaatac aaattttgta taaccttgct tacgaacat 159300 cactacgttt ttacgaattg aattcaagac tacatgacga accatcggaa cagtaatttt 159360
atcaccatct tcaaagttgt ttaatgcagc tgccaatgca atgttactaa agtctgcaag 159420
cgcaatacct tctttgtaat cttcatccaa catcatttct aaatccatat gaacctcttg 159480
ttcagttagt caacttagac catagtaaca tactagttcg aaagcgtaaa tagtctttta 159540
ctcatttata aatagtaaaa tagaacacat aatgataaga ggactaccat ggttgacatc 159600
aaacgtaagt tcagggccga agatggtctt gacgcaggcg gtgataagat agttaacgtt 159660
gcgcttgctg accgcacagt tggcaccgat ggcgtgaacg ttgacttttt ggtgcaagaa 159720
aacaccgtac agaattatga cgatacgcgc gcgtatacaa aagatttat tgttctttat 159780 gataatcgtt tttatcaagc tttaaacgat attccagctc cggcaggccc tttctctttg 159840
gctaaatgga aggcaactcg tacagatgca gaatggacta cagttcaagg cggagatttc 159900
caattatcag taggtaactc tattgcggtt gatacttcag ctggcactga tattaatttc 159960
actttgcctc aaaatccttt aaatggcgat acagttattt tgtctgatat tggcggtaga 160020
gtaggctatg taaaagttca aattactgca gaggctcaaa gtattgtaaa ctttagagga 160080
caacaggttc gttcagtttt aatgacgcac ccaaaatcta aaatggtctt cattttagc 160140 aaccgcctat ggcaaatgta tgtttctgat tacgaacgta atgcagtcac agtaactcct 160200
gctaagccat atcaggcgca acctaacgat tttatcattc gacgttttac atcagccgct 160260
cctattaata ttacattgcc tcgcaatgct aataatggcg atattattaa tttagttgat 160320
ttagacaaat taaacccgtt atatcacaca attgtcaaaa cttacgatga tacaacttct 160380
atacgagaag ccggtgttca tgtagcagaa ggacgtaata ctgcggaagc attctttgtt 160440
tatgattctg ctaatagctt atggcgtgtt tgggaaggtg accagaaatc tcgtttacgt 160500
atagttcgta atgatactga tttacgccct aatgaagaag ttcttgtttt tggaactaat 160560
aatgatacaa tctcgacggt aaatcttact ttgcctacag atattttgtc tggtgatact 160620
gttaaaatat cgttgaatta tatgcgtaaa gggcaaactg taaaaattaa agctgctgaa 160680
```

```
ggcgatacaa ttgctagcag tatttcttta ttacagttcc caaaacgttc agagtatcca    160740
cctgatgcac aatgggtttc tgttagtgag ctggaattta atggcgatac ttcgtatgta    160800
cctgtacttg agttagctta tatagaagat tattcatctg aaacaaaata ttgggtagtt    160860
caacaaaaca ctgtaaccgt agaacgagtc gatgcatcga gcaatacaac tcgagctcgt    160920
ttaggtgtta ttgctcttgc ttctcaagcg caagcaaatg tcgatttaga aaatgctcct    160980
ggtaaagaac ttgctattac tccggaaaca ttagcaaatc gtacagcaac tgaaactcgt    161040
cgtggtattg ctcgtattgc aacaactgca caagttaacc agaataccga ttttgcattc    161100
caagacgact tgattatttc tcctaagaaa ttgaacgaac gtacagcaac tgaaacccgt    161160
agaggtgttg ctgaagttgc aactcaggat gaaactaatg ctggcataga tgataccact    161220
attattactc ctaagaaatt ggatgcccgt caaggttctg aagttttatc tggtattgta    161280
aaatacacat ctacgactgg tactacagcg gctactgttc gtggtaatgc tgggactaac    161340
gtttataaca aagccgtaga taatttaact atttctccaa aggctcttga ccagtataaa    161400 gctacccta ctcaacaggg cgcagtaatt cttgctattg aaagtgaagt tatcgctggt    161460
gaatcacaaa ccggttgggc taatgctgta gtgacccctg aaacactaca taagaaaact    161520
tctactgatg gacgtattgg tttaattgaa attgctacgc aagcagaaac taacactgga    161580
actgattata ctagagcagt aacgcctaag acgttaaatg ataggaaagc tacggaagga    161640
ttatccggca tagccgaaat tgctacgcaa gttgaatttg atactggaac tgacgatact    161700
cgtatctcgt ctccactgaa aattaaaact cattttgatt cttctgaccg taccagtgtt    161760
aattctgatt ccggacttat tgaagaagga accttgtgga accattatac tcttgatatt    161820
tctaaagcaa atgaaacaca acgcggtaca cttcgcgtag cgacccaggc agaatctaat    161880
gcaggaactt tagatgatgt tcttattact cctaaaaagc ttttagggac taagtccact    161940
gaaacgtctg aaggcgtaat taaggttgct actcaggctg aaactgtaac aggaacttct    162000
gctaatactg ctgtatcacc taagaattta aaatggattg ttcaatcaga accatcatgg    162060
actgctacta cggcaattcg tggattcgtt aaaacttcat ctggttctat tacatttgtt    162120
ggtaatgata cagttggttc aacacaatct ttagaatcat atgagaaaaa tagctatgcg    162180
gtatcaccat atgaattaaa ccgtgtactt gctaactact taccgttgaa agctaaagca    162240
gctgatagta atttgttaga tggtctagat tctcttcagt tcatccgtag agacatcgac    162300
cagacggtta atggttcttt aagtcttact aaacagacca acctgagtgc tccttagta    162360 tctacaagca ctgcttcttt tggttccgaa gcatctgtta ctcgtagatt aactcttaat    162420
gattctagcg gttctgaaat aatttttcact aaaggaaccc aatctcttag taataaagag    162480
aatttcgttg ttagagcatg gggtaatagc gctacagatg gtgcccgtga tacagtattt    162540
gaagcgggtg acgaaaccgg ataccatttc tattctcagc gcgctgctga ataagagta    162600 tcatttaata ttaatggaac actttattca acaggtattg tttctacaaa tggattaaat    162660
gttacaggtg tttctacctt tacagggcct attagtgcta caggcgaaat tgtttctagt    162720
tctcctattg cattcagagc tattaatggt aactatggtg ttatgcttta taatgctggt    162780
aacagttctt atattgcatt aactaactca ggtgaccaga ccgggacgtt taataactta    162840
cgcccgatca cgattaacaa cgccacaggc ttagttcgtc ttgacaatgg tgttcaaatc    162900
acgagtggtg caacaataac taccggtggg ttaactgtaa atagcagaat tatttctaac    162960
ggcgttaaaa cagccactgt ttataccgat aaaccaacag cttctactgt aggttttttgg   163020 tctattgaca ttaacgattc tgctgtatat agccaattcc ctggatactg gacgcgtgat    163080
```

```
aacaaaggta accgtgacca agaaattaaa tatcctggta ctttgactca attcggcaat   163140
agcttagatt cgctttatca ggattggatt tgttatccta caggtgcaaa tggtggtagt   163200
attcgttata ctcgtacctg gcagaaaaat aaagatgctt ggacttcatt tgcaatggta   163260
tttgatagtg gcaacccacc ttcacctagc gatgtcggtg ctatcccatc tgataatgct   163320
gttattggaa accttactat tcgagacttc ttacaattag gaaatgtgag aattgttcca   163380
gacccggtta acaaaacagt taaatttata tgggttgaat aagaggttat atggaaaaat   163440
ttatggcaag gtttggacat ggatacgtcc aaacgccgtt tttatcggaa agcaattcag   163500
ttagatttaa gctaagtata gcgggttcat gcccgctttc aacaactaat ccgtatattt   163560
tgttccaaaa cgagccttta gggttgcagt cttttggtat tggactaaat gttagggtga   163620
taaatccgga aaatggaact atagttgata gtaaattata caattttgcg cctacaaata   163680
atgcaacttc agctgcattt atttcgtttg ttaatacata cgcagataat ttcatttttcg   163740 catttatttc taataacaaa tttaatttgc caccggaaat aattgaatgg tttaaagctg   163800
ctgggagttc agttataccg tcaattgaag ttgctagtct tgttgatatt tcatattcag   163860
cgttttatgt ttcaggtaaa aatactattg cattagaaca cataaaatac agtaataaga   163920
aaacaatttc tgattacgca actccattag atattgtata tgactctatt gctgatatag   163980
gtgctaccgg ctatcctaga cgtacatatg aagctctaga aacgttttta tctcctgttg   164040
gaggaactaa caatgaaata aaaaggatgc ctacgtcatc ccttgttact cctatcgcaa   164100
actatggatt aaagcctaca gattttcttt atttgaaatt tcaattaatg gctgatgaag   164160
aattattaga ggaaggaacc acaagacttt caattcgttt ctttaagtct ccatctagct   164220
ctcctatatc atctaaagat ataaactttg atggaactgc cggggagtgg aagctatatg   164280
aagaatacgt tgaaatacca gctgaagctg atggctttac agtatattgt taccgtacgg   164340
cctcagtcgg tcaaggtgga ctaagaaatg ttattttcac tgaagtatca tgtaacggaa   164400
gtatagcaaa acccgctgag tttggtataa atggtattcg tgttaattat attgatgaat   164460
cgttaaccgg taatgatata atggacttgc ctactcagtt atctaacgac acaggtaagg   164520
tatttgggca ggaatttaaa gagtacacag aataaaggag acttcggtct ccttttcgcg   164580
tataaatact ttaatattaa taaggagaca cgaaatggcc gatttaaaag ccggaagtac   164640
agttggtggt tccgtcatat ggcatcaagg caatttttcct ttaatgccag ctggcgatga   164700
catcctatat aaaacatttta aattatacac cgaatataac aagccaaaag cggctgataa   164760
cgatttcgta tctaaagcaa atggtgggac atatctcaaa aaggtaatct ttaacgaagg   164820
tattgcagtc aaaacagcag atgaccaaac gaatggtatt ttttctggtg gtggtgacgc   164880
cgcgacattc gaccaaacaa acatggatat tgtttcgtgg tatggtattg ggtttaaatc   164940
atctcaaggt acaggtgaaa gaactgttgt aattgatact cgcaccggta atataagttc   165000
taaaggcgtt attgaagcat ctcaattcag agccacaacg ttagcacctt taaataatta   165060
cgaccttact cgcaaagatt atgttgatag tcaaataaat acagttaatg ctaatgcaaa   165120
cagtcgtgta ctccgttcag gagatacgat gaccggcgcg ctgaccgccc caaactttt   165180 ctcacagaat cctgcatctc aaccctcgca tgttccacga tttgaccaaa ttgttattaa   165240
ggattctgtt caagatttcg gctattatta agaggactta tggctacttt aaaacaaata   165300
caatttaaaa gaagcaaaac tgcaggagca cgtcctgccg cttcagtatt agccgaaggt   165360
gaattggcta taaacttaaa agaccgtgta ctttttacta aagatgacca aggaaatatt   165420
```

```
attgatctgg gttttgctaa aggcggtagt attgacggga atgttattca tacaggtaat   165480
tataaccaaa ccggcgatta tactttaaat ggcaccttca ctcagacagg taattttaat   165540
ttaactggta ttgctcgagt aactcgtgat attattgccg ctgggcagat tatgactgaa   165600
ggcggtgaac ttattacaaa aagttcaggt acagcacatg ttcgtttttt cgatggcaat   165660
agccgcgaac gtggaatcat ttatgccccg gctaatgatg gattaactac acaagtactt   165720
aatatcaggg ttcaagacta cgccgctggt agcgaaagca tttatgcatt ttcaggcaat   165780
ggacaattta tttcacctga agtatcggca cggaaatcta tgtcaactcc tcagattttg   165840
actgacaaag tcattacaga cgggaagaag gccggtgatt atgacatcta ttcattagca   165900
aataataatt ctaacacaga taaaaataat ttacgtgtcg tacgtaccga cccggcggcc   165960
gcaatgctcc atgaaatttg tgaaaataac ggcatcagtt ggtattctgg ttcaaccccct   166020
actgattaca tgttgtcatt ttcttattcc ggtgggcttc aagcaggcca ttcaattgca   166080
gtaggtatgg aatcaagtcc tatgacatat tcagccttag gtaaaggttc tattgctatt   166140
ggcgataatg acaccgggtt aaaatggcac caggatggat atttccatac agtaaacaat   166200
ggaacaagaa ctttcatcta cggccctgca gaaacacaaa gccttagaaa atggttatg   166260
ggttattctc cagatgggct tcttatgaca acgccaccga cagaaaacta tgctttggct   166320
actgttgtta cttaccatga taataacgca tacggtgacg tcaaactct tttaggatat   166380
tatcaaggcg gtaactatca tcattatttt cgcggtaagg gtactacaaa cattaatact   166440
cacggcggtt tgttagttac tccaggtaat attgatgtta ttggcggttc tgttaatata   166500
gatggtagaa ataattcttc tacactaatg tttagaggca acacaacagg atacagctcg   166560
gttgataata tggatattaa agtttggggt aatacgtttg ttgatccaag cggaggtatc   166620
cgtaaaaaca ttatggaaat ttctgatgca actagctgga tgagctatat tcaaagactt   166680
actactggcg aagtagaaat gaacgttaat ggttcatttg aatcatctgg tgttactgct   166740
ggagatagag gagttcacac aacaggtgaa atttcatctg gagcagtgaa tgctcttcgt   166800
atttggaacg cagattatgg agccattttt agacgttcag aaggaagtct tcatattatt   166860
ccaactgctt atggcgaagg caaagatggc gatattggtc cacttcgccc atttagtatg   166920
gctttagata ctggtaaagt tactattcca gatttacaat caagttacaa tacgttcgct   166980
gctaacggtt atattaaatt tgttggtcat ggagcgggtg ccggcggtta tgacattcaa   167040
tatgctcaag cggctcctat tttccaggaa attgatgatg atgctgtaag caaatattat   167100
cctattgtta aacagaagtt tttaaacggt aaatctgttt ggtctttagg taccgaaatt   167160
gaatcaggta cattcgttat tcatcatctg aaagaagatg gttcacaagg ccatacatca   167220
agatttaata tggatggtac agttaatttc cctgataatg ttctggtcgg tggtggtgaa   167280
gctgctattg ctcgtaatgg taatatttttc tcggatattt ggaaaacgtt tacttctgca   167340
ggcgacgtaa ctaatattcg cgatgcaata gctactcgtg ttgccaaaga aggtgatacg   167400
atgaccggca ctctttggat taataaagat gctgctggaa tagttcttaa tcctcctttg   167460
gccagtgatt catcattat tcgttccgat acggccgggg tcaataattg gtatattggt   167520
aaaggcggtg ccgacaatgg tctaggtttt tacagttatg ttacaccagg cggtgtatat   167580
ataacaaata acggagaaat atcactttct cctcaaggcc aaggaacatt taatttaat   167640
agagaccgcc tccatataaa cggtacacaa tggaccgcac accagggagg tggttgggga   167700
aatcaatgga atcaagaagc accggtattt gtagattttg gtaatgttgg taatgatagt   167760
tattatccta ttattaaagg aaaatccggt attactaatg aaggatacat atctggtgta   167820
```

```
gattttggta tgcgacgcat tactaataca tgggcacaag gtattattcg tgtaggtaat  167880
caggaaaacg gttacgaccc acaagctgta tatgaattcc atcataacgg cacttttat  167940 gctccaagct tacttaagag cagtagagta tcagctggtg gtggtgaccc tgcatggggc  168000
gggccgtgta ttgtacttgg agataacgat accggtttgc tttgggaaaa cgatggtatt  168060
ttcaacgcat atgcaaacgg ccaaggtgtg tttagtttta gacctggttt agctcagaca  168120
ttcggtgatg ttaacttcca ctgtaatgca ggtatgtatg ttcgtgataa cattgatgtt  168180
aacgacgttt atattcgttc tgatattcgt tgtaagtcgg aaattaagct tattaagaac  168240
gctcaagaga atctaaaact attgggcggt tatacttatc tgcttaaaaa ctctgttaca  168300
gacgaagtta aaccgtccgc aggtttaatt gctcaggaag ttcaagaagt attacctgaa  168360
cttgtttctg aagataaaga gaccggactg cttcgtttga actataacgg tattgttggt  168420
ttaaatacag ctgcaataaa cgagcataca gatgaaatca aggaattgaa atctgaaatt  168480
gccgaattga agcattaat taaatcattg ataaaataat aaaagggcct tcgggccctg  168540
gaggtttata tggcagtagt aggaatccct ggttggattg ggacttcagc cgttgctgaa  168600
acggggcaaa gatggatgac ggctgcttca agggaacttc gtttaggaaa ccccttcatgg  168660 atgtcccaat tcgcgggccg ttcaagagaa ataattcaca cacttggagc agaccataac  168720
tttaatggtc aatggttccg agatagatgt tttgaggcgg gtagtgcgcc tatagtgttt  168780
aatatcaccg gaaatttagt atcatatagt aaagatgttc cattattctt tatgtatggc  168840
gatacaccaa atgaatatgt tactttgaat attcatggtg gagttcatat gtggggacga  168900
ggtggtaacg gtactgtaaa cggaaaccca ggcacaaatg gcggcgatgt aatccaaaat  168960
gatatcggcg gaagacttcg tatttggaac tatggcgtta ttgcatcagg cggtggcggt  169020
ggcggtgcag tgtcattaca gaatagctgg gcgccaaatg ttacagcagg tggcggcggt  169080
ggtagaccat ttggcatcgg cggtggcggc gttaattggc cgggtggtaa tgc  169133

<210> SEQ ID NO 5
<211> LENGTH: 5213
<212> TYPE: DNA
<213> ORGANISM: Artificial Sequence
<220> FEATURE:
<223> OTHER INFORMATION: synthetic pUC57.HR.Fluc plasmid sequence

<400> SEQUENCE: 5
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtaagct tagattgata agaagcagt  420 tgaaattgct cgtcaaaccg gtcgtggtga aggtaacttc attatcgctt cccgtaacgt  480
agttaacgta ctggcttcag ttgatactgg tatttcttac gctgcacagg gtctggcttc  540
cggttttaat accgacacta ctaagtctgt atttgccggt gtacttggtg gtaaataccg  600
cgtatacatc gaccagtatg ctaaacagga ttacttcacc gttggttaca aaggcgctaa  660
cgaaatggat gcaggtatct actatgctcc ttacgttgca cttaccccac tgcgtggttc  720
```

```
cgatcctaag aacttccagc cggtaatggg ctttaaaact cgttacggta tcggtgttaa    780
cccgtttgct gaaagttccc tgcaggctcc aggtgctcgc atccagtccg gtatgccgtc    840
tatcctgaac agccttggta agaacgctta cttccgccgt gtatatgtaa aaggcatcta    900
aacgcgttat aaataaatac tagtagataa ggaggatttc aatggaagaa cgccaagaac    960
atcaaaaaag gcccggcacc gttctatccg ctggaagacg gcaccgcagg cgaacagtta   1020
cacaaagcca tgaagcgcta cgccctggtt ccgggtacaa tcgcctttac cgacgcccac   1080
attgaggtga acatcaccta tgccgagtat tttgagatga gcgttcgtct ggccgaagcc   1140
atgaaacgct atggcctgaa caccaaccat cgcattgtgg tttgcagcga aaacagcctg   1200
cagttcttta tgccggtgct gggtgccctg ttcatcggtg tggccgttgc ccctgccaat   1260
gacatctata cgaacgcga actgctgaac agcatgaata tcagccagcc taccgtggtt   1320
ttcgttagca aaaaggtttt acaaaagatt ctgaatgttc agaagaagct gccgattatc   1380
caaaaaatta tcattatgga tagcaagaca gattatcaag ctttcagag catgtacacc    1440
ttcgttacca gtcacctgcc gccgggcttc aacgagtatg atttcgtgcc ggagagcttc   1500
gaccgtgata agaccatcgc cctgatcatg aacagcagtg gtagtaccgg cctgccgaaa   1560
ggtgtggccc tgcctcatcg caccgcatgt gtgcgcttta ccacgcccg cgacccgatc    1620
tttggcaatc agatcatccc ggacaccgcc atcttaagcg ttgtgccgtt ccaccacggt   1680
tttggcatgt ttaccaccct gggctatctg atctgcggct ccgcgtggt gctgatgtat    1740
cgcttcgaag aggagttatt cctgcgcagc ctgcaggact ataagattca gagcgccctg   1800
ctggttccga cactgttcag ctttttcgcc aagagcaccc tgatcgacaa atacgatctg   1860
agcaacctgc acgaaattgc aagcggcggc gcaccgctga gcaaggaagt tggtgaagcc   1920
gtggcaaaac gcttccacct gcctggcatc cgtcaaggct acggtctgac agaaaccacc   1980
agcgccatcc tgatcacccc ggaaggcgat gataaaccgg gtgccgtggg caaggtggtt   2040
ccgttttttcg aggccaaggt tgttgacctg gacaccggta aaaccctggg tgttaaccag   2100
cgtggtgaac tgtgtgttcg tggcccgatg atcatgagcg gctacgtgaa taacccggag   2160
gccaccaatg cactgatcga taaagacggc tggctgcata cggcgatat cgcatactgg    2220
gatgaggacg agcactttt tattgttgat cgcctgaaaa gtctgatcaa atacaaaggc    2280
taccaggttg ccccggccga actggagagc atcctgctgc agcatccgaa cattttcgac   2340
gcggggggttg cggggctgcc tgatgatgat gcaggtgagc tgcctgccgc cgttgtggtg   2400
ctggagcacg gtaagaccat gacagagaag gagattgtgg attacgtggc aagccaggtg   2460
accaccgcga agaagctgcg cggtggcgtt gtgttcgttg acgaagtgcc gaagggcctg   2520
accggtaaac tggacgcccg caagattcgc gagattctga ttaaggcaaa aaagggtggc   2580
aaaagcaaat tataagccgg cttatttctg tgcaattctg atgtaagttt tcaaaatatt   2640
ttgccaatta ggcatacctt cttggacata tgccggagaa ccgtctttgt ttttgaatga   2700
tgcaagttta tcagtggccc aataacccttt agctcgagct tcagaataaa ctttcatcca   2760
tactttgttg aaggcattac cattaacttt tgcaccatat ttttctacta acttaactgc   2820
ttcagcttcc agaacttta aagtatctcg taagaaacgt gctttagtca ttttgttttac   2880
tcctctgtag ttgataagtc tatagtatca cataccaaat acgttgtaaa caatctttat   2940
aaataatcta tcacataa ggaaaaaatg caagtcgacg gcgtaatcat ggtcatagct     3000
gtttcctgtg tgaaattgtt atccgctcac aattccacac aacatacgag ccggaagcat   3060
aaagtgtaaa gcctggggtg cctaatgagt gagctaactc acattaattg cgttgcgctc   3120
```

```
actgcccgct ttccagtcgg gaaacctgtc gtgccagctg cattaatgaa tcggccaacg      3180
cgcggggaga ggcggtttgc gtattgggcg ctcttccgct tcctcgctca ctgactcgct      3240
gcgctcggtc gttcggctgc ggcgagcggt atcagctcac tcaaaggcgg taatacggtt      3300
atccacagaa tcaggggata acgcaggaaa gaacatgtga gcaaaaggcc agcaaaaggc      3360
caggaaccgt aaaaaggccg cgttgctggc gtttttccat aggctccgcc ccctgacga      3420 gcatcacaaa aatcgacgct caagtcagag gtggcgaaac ccgacaggac tataaagata      3480
ccaggcgttt ccccctggaa gctccctcgt gcgctctcct gttccgaccc tgccgcttac      3540
cggatacctg tccgcctttc tcccttcggg aagcgtggcg ctttctcata gctcacgctg      3600
taggtatctc agttcggtgt aggtcgttcg ctccaagctg ggctgtgtgc acgaaccccc      3660
cgttcagccc gaccgctgcg ccttatccgg taactatcgt cttgagtcca acccggtaag      3720
acacgactta tcgccactgg cagcagccac tggtaacagg attagcagag cgaggtatgt      3780
aggcggtgct acagagttct tgaagtggtg gcctaactac ggctacacta agaacagt       3840 atttggtatc tgcgctctgc tgaagccagt taccttcgga aaagagttg gtagctcttg      3900 atccggcaaa caaaccaccg ctggtagcgg tggttttttt gtttgcaagc agcagattac      3960
gcgcagaaaa aaaggatctc aagaagatcc tttgatcttt tctacggggt ctgacgctca      4020
gtggaacgaa aactcacgtt aagggatttt ggtcatgaga ttatcaaaaa ggatcttcac      4080
ctagatcctt ttaaattaaa aatgaagttt taaatcaatc taaagtatat atgagtaaac      4140
ttggtctgac agttaccaat gcttaatcag tgaggcacct atctcagcga tctgtctatt      4200
tcgttcatcc atagttgcct gactccccgt cgtgtagata actacgatac gggagggctt      4260
accatctggc cccagtgctg caatgatacc gcgagaccca cgctcaccgg ctccagattt      4320
atcagcaata accagccagc cggaagggc cgagcgcaga agtggtcctg caactttatc      4380
cgcctccatc cagtctatta attgttgccg ggaagctaga gtaagtagtt cgccagttaa      4440
tagtttgcgc aacgttgttg ccattgctac aggcatcgtg gtgtcacgct cgtcgtttgg      4500
tatggcttca ttcagctccg gttcccaacg atcaaggcga gttacatgat cccccatgtt      4560
gtgcaaaaaa gcggttagct ccttcggtcc tccgatcgtt gtcagaagta agttggccgc      4620
agtgttatca ctcatggtta tggcagcact gcataattct cttactgtca tgccatccgt      4680
aagatgcttt tctgtgactg gtgagtactc aaccaagtca ttctgagaat agtgtatgcg      4740
gcgaccgagt tgctcttgcc cggcgtcaat acgggataat accgcgccac atagcagaac      4800
tttaaaagtg ctcatcattg gaaaacgttc ttcggggcga aaactctcaa ggatcttacc      4860
gctgttgaga tccagttcga tgtaacccac tcgtgcaccc aactgatctt cagcatcttt      4920
tactttcacc agcgtttctg ggtgagcaaa aacaggaagg caaaatgccg caaaaaaggg      4980
aataagggcg acacggaaat gttgaatact catactcttc ctttttcaat attattgaag      5040
catttatcag ggttattgtc tcatgagcgg atacatattt gaatgtattt agaaaaataa      5100
acaaataggg gttccgcgca catttccccg aaaagtgcca cctgacgtct aagaaaccat      5160
tattatcatg acattaacct ataaaaatag gcgtatcacg aggccctttc gtc            5213
```

<210> SEQ ID NO 6  
<211> LENGTH: 4162  
<212> TYPE: DNA  
<213> ORGANISM: Artificial Sequence  
<220> FEATURE:  
<223> OTHER INFORMATION: synthetic pUC57.HR.NanoLuc plasmid sequence

<400> SEQUENCE: 6

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtaagct tagattgata agaagcagt     420
tgaaattgct cgtcaaaccg gtcgtggtga aggtaacttc attatcgctt cccgtaacgt     480
agttaacgta ctggcttcag ttgatactgg tatttcttac gctgcacagg gtctggcttc     540
cggttttaat accgacacta ctaagtctgt atttgccggt gtacttggtg gtaaataccg     600
cgtatacatc gaccagtatg ctaaacagga ttacttcacc gttggttaca aaggcgctaa     660
cgaaatggat gcaggtatct actatgctcc ttacgttgca cttaccccac tgcgtggttc     720
cgatcctaag aacttccagc cggtaatggg ctttaaaact cgttacggta tcggtgttaa     780
cccgtttgct gaaagttccc tgcaggctcc aggtgctcgc atccagtccg gtatgccgtc     840
tatcctgaac agccttggta agaacgctta cttccgccgt gtatatgtaa aaggcatcta     900
aacgcgttat aaataaatac tagtagataa ggaggatttc gaatgaatag ctttagcacc     960
agcgcctttg gcctgttgc ctttagcctg gcctgctgc tggttctgcc ggcagcattt     1020
ccggccccgg tgttcaccct ggaagatttt gtgggcgatt ggcgccagac cgccggttat     1080
aacctggatc aggtgctgga acagggtggt gtgagcagcc tgtttcagaa tctgggcgtg     1140
agcgtgaccc cgattcagcg cattgtgctg agcggcgaga acggcctgaa aattgatatt     1200
catgttatta ttccgtatga gggtctgagc ggcgatcaga tgggccagat tgaaaaaatc     1260
tttaaggtgg tgtatccggt ggacgaccat catttcaagg tgatcctgca ttacggcaca     1320
ctggtgattg acggcgttac cccgaacatg atcgactatt cggccgccc gtatgaaggt     1380
atcgccgtgt tcgacggcaa gaaaattacc gtgaccggta ccctgtggaa cggcaacaag     1440
atcattgacg agcgcctgat taacccggat ggtagcctgc tgtttcgcgt gaccattaat     1500
ggcgtgaccg gctggcgtct gtgtgaacgc atcctggcct aattaattaa ttatttctgt     1560
gcaatttcga tgtaagtttt caaaatattt tgccaattag gcataccttc ttggacatat     1620
gccggagaac cgtctttgtt tttgaatgat gcaagtttat cagtggccca ataacccttta     1680
gctcgagctt cagaataaac tttcatccat actttgttga aggcattacc attaactttt     1740
gcaccatatt tttctactaa cttaactgct tcagcttcca gaacttttaa agtatctcgt     1800
aagaaacgtg ctttagtcat tttgtttact cctctgtagt tgataagtct atagtatcac     1860
ataccaaata cgttgtaaac aatctttata aataatctat atcacataag gaaaaaatgc     1920
aagtcgacgg cgtaatcatg gtcatagctg tttcctgtgt gaaattgtta tccgctcaca     1980
attccacaca acatacgagc cggaagcata agtgtaaag cctggggtgc ctaatgagtg     2040
agctaactca cattaattgc gttgcgctca ctgcccgctt tccagtcggg aaacctgtcg     2100
tgccagctgc attaatgaat cggccaacgc gcggggagag gcggtttgcg tattgggcgc     2160
tcttccgctt cctcgctcac tgactcgctg cgctcggtcg ttcggctgcg gcgagcggta     2220
tcagctcact caaaggcggt aatacggtta tccacagaat caggggataa cgcaggaaag     2280
aacatgtgag caaaaggcca gcaaaaggcc aggaaccgta aaaaggccgc gttgctggcg     2340
```

```
tttttccata ggctccgccc ccctgacgag catcacaaaa atcgacgctc aagtcagagg    2400
tggcgaaacc cgacaggact ataaagatac caggcgtttc ccctggaag ctccctcgtg     2460 cgctctcctg ttccgaccct gccgcttacc ggatacctgt ccgcctttct cccttcggga    2520
agcgtggcgc tttctcatag ctcacgctgt aggtatctca gttcggtgta ggtcgttcgc    2580
tccaagctgg gctgtgtgca cgaaccccc gttcagcccg accgctgcgc cttatccggt     2640
aactatcgtc ttgagtccaa cccggtaaga cacgacttat cgccactggc agcagccact    2700
ggtaacagga ttagcagagc gaggtatgta ggcggtgcta cagagttctt gaagtggtgg    2760
cctaactacg gctacactag aagaacagta tttggtatct gcgctctgct gaagccagtt    2820
accttcggaa aaagagttgg tagctcttga tccggcaaac aaaccaccgc tggtagcggt    2880
ggtttttttg tttgcaagca gcagattacg cgcagaaaaa aaggatctca agaagatcct    2940
ttgatctttt ctacggggtc tgacgctcag tggaacgaaa actcacgtta agggattttg    3000
gtcatgagat tatcaaaaag gatcttcacc tagatccttt taaattaaaa atgaagtttt    3060
aaatcaatct aaagtatata tgagtaaact tggtctgaca gttaccaatg cttaatcagt    3120
gaggcaccta tctcagcgat ctgtctattt cgttcatcca tagttgcctg actccccgtc    3180
gtgtagataa ctacgatacg ggagggctta ccatctggcc ccagtgctgc aatgataccg    3240
cgagacccac gctcaccggc tccagattta tcagcaataa accagccagc cggaagggcc    3300
gagcgcagaa gtggtcctgc aactttatcc gcctccatcc agtctattaa ttgttgccgg    3360
gaagctagag taagtagttc gccagttaat agtttgcgca acgttgttgc cattgctaca    3420
ggcatcgtgg tgtcacgctc gtcgtttggt atggcttcat tcagctccgg ttcccaacga    3480
tcaaggcgag ttacatgatc ccccatgttg tgcaaaaaag cggttagctc cttcggtcct    3540
ccgatcgttg tcagaagtaa gttggccgca gtgttatcac tcatggttat ggcagcactg    3600
cataattctc ttactgtcat gccatccgta agatgctttt ctgtgactgg tgagtactca    3660
accaagtcat tctgagaata gtgtatgcgg cgaccgagtt gctcttgccc ggcgtcaata    3720
cgggataata ccgcgccaca tagcagaact ttaaaagtgc tcatcattgg aaaacgttct    3780
tcggggcgaa aactctcaag gatcttaccg ctgttgagat ccagttcgat gtaacccact    3840
cgtgcaccca actgatcttc agcatctttt actttcacca gcgtttctgg gtgagcaaaa    3900
acaggaaggc aaaatgccgc aaaaaaggga ataagggcga cacggaaatg ttgaatactc    3960
atactcttcc tttttcaata ttattgaagc atttatcagg gttattgtct catgagcgga    4020
tacatatttg aatgtattta gaaaaataaa caaatagggg ttccgcgcac atttccccga    4080
aaagtgccac ctgacgtcta agaaaccatt attatcatga cattaaccta taaaaatagg    4140
cgtatcacga ggccctttcg tc                                             4162
```

<210> SEQ ID NO 7
<211> LENGTH: 5163
<212> TYPE: DNA
<213> ORGANISM: Artificial Sequence
<220> FEATURE:
<223> OTHER INFORMATION: synthetic pUC19.HR.OpLuc.KanR plasmid sequence

<400> SEQUENCE: 7

```
gacgaaaggg cctcgtgata cgcctatttt tataggttaa tgtcatgata ataatggttt     60
cttagacgtc aggtggcact tttcggggaa atgtgcgcgg aacccctatt tgtttatttt    120
tctaaataca ttcaaatatg tatccgctca tgagacaata accctgataa atgcttcaat    180
```

```
aatattgaaa aaggaagagt atgagtattc aacatttccg tgtcgccctt attccctttt    240
ttgcggcatt ttgccttcct gttttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga caccacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200 cagacccegt agaaaagatc aaaggatctt cttgagatcc ttttttttctg cgcgtaatct   1260 gctgcttgca acaaaaaaa ccaccgctac cagcggtggt ttgtttgccg gatcaagagc   1320
taccaactct ttttccgaag gtaactggct tcagcagagc gcagatacca atactgtcc   1380 ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acgggggggtt   1560 cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800 gggggcggag cctatggaaa aacgccagca acgcggcctt tttacggttc ctggccttt    1860 gctggccttt tgctcacatg ttctttcctg cgttatcccc tgattctgtg ataaccgta    1920 ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt agattgataa agaagcagtt gaaattgctc gtcaaaccgg   2280
tcgtggtgaa ggtaacttca ttatcgcttc ccgtaacgta gttaacgtac tggcttcagt   2340
tgatactggt atttcttacg ctgcacaggg tctggcttcc ggttttaata ccgacactac   2400
taagtctgta tttgccggtg tacttggtgg taaataccgc gtatacatcg accagtatgc   2460
taaacaggat tacttcaccg ttggttacaa aggcgctaac gaaatggatg caggtatcta   2520
ctatgctcct tacgttgcac ttaccccact gcgtggttcc gatcctaaga acttccagcc   2580
```

```
ggtaatgggc tttaaaactc gttacggtat cggtgttaac ccgtttgctg aaagttccct    2640
gcaggctcca ggtgctcgca tccagtccgg tatgccgtct atcctgaaca gccttggtaa    2700
gaacgcttac ttccgccgtg tatatgtaaa aggcatctaa ggcgcgccta taaataaata    2760
ctagtagata aggaggattt cgaatgttta cactggcaga ctttgttggt gactggcagc    2820
aaacagccgg atataaccag gaccaggtgc ttgaacaggg tggccttteg agtttgtttc    2880 aggcgttagg tgtgtcggtg acccctattc agaaagtggt gctgagcgga gaaaacggcc    2940
tgaaggccga tattcatgtt attatcccgt acgaggggtt atccggcttc cagatgggtc    3000
tgattgaaat gatcttcaaa gtggtttatc cggttgacga tcatcatttt aagattatcc    3060
tgcactatgg caccctggtg attgatggcg tgaccccgaa tatgattgat tatttcggcc    3120
gtccgtaccc aggcattgca gtatttgacg gtaaacaaat caccgtcacc ggtaccctgt    3180
ggaatggtaa taaaatttat gatgaacgtt tgatcaaccc ggatggcagt ctgttatttc    3240
gcgtgaccat taacggagta accggttggc gtctctgtga aaacatttta gcttaagcga    3300
tcgcataact tcgtatagca tacattatac gaagttattt gacaggctct gtattacgtt    3360
tctataaata aggaagagta tgagccatat tcaacgggaa acgtcttgct ctaggccgcg    3420
attaaattcc aacatggatg ctgatttata tgggtataaa tgggctcgcg ataatgtcgg    3480
gcaatcaggt gcgacaatct atcgattgta tgggaagccc gatgcgccag agttgtttct    3540
gaaacatggc aaaggtagcg ttgccaatga tgttacagat gagatggtca gactaaactg    3600
gctgacggaa tttatgcctc ttccgaccat caagcatttt atccgtactc ctgatgatgc    3660
atggttactc accactgcga tccctgggaa aacagcattc caggtattag aagaatatcc    3720
tgattcaggt gaaaatattg ttgatgcgct ggcagtgttc ctgcgccggt tgcattcgat    3780
tcctgtttgt aattgtcctt ttaacagcga tcgcgtattt cgtctcgctc aggcgcaatc    3840
acgaatgaat aacggtttgg ttgatgcgag tgattttgat gacgagcgta atggctggcc    3900
tgttgaacaa gtctggaaag aaatgcataa acttttgcca ttctcaccgg attcagtcgt    3960
cactcatggt gatttctcac ttgataaacct tattttgac gagggggaaat taataggttg    4020 tattgatgtt ggacgagtcg gaatcgcaga ccgataccag gatcttgcca tcctatggaa    4080
ctgcctcggt gagttttctc cttcattaca gaaacggctt tttcaaaaat atggtattga    4140
taatcctgat atgaataaat tgcagtttca tttgatgctc gatgagtttt tctaaataac    4200
ttcgtatagc atacattata cgaagttatt tatttctgtg caatttcgat gtaagttttc    4260
aaaatatttt gccaattagg cataccttct tggacatatg ccggagaacc gtctttgttt    4320
ttgaatgatg caagtttatc agtggcccaa taacctttag ctcgagcttc agaataaact    4380
ttcatccata ctttgttgaa ggcattacca ttaacttttg caccatattt ttctactaac    4440
ttaactgctt cagcttccag aactttaaa gtatctcgta agaaacgtgc tttagtcatt    4500
ttgtttactc ctctgtagtt gataagtcta tagtatcaca taccaaatac gttgtaaaca    4560
atctttataa ataatctata tcacataagg aaaaaatgca atgagtaaaa tccaaaaatt    4620
attgcgtgaa tctacaacgt ctactagcaa ctcaatcggt cgcccaaatc tcgttgcttt    4680
gactcgcgct acgactaaat taatatattc tgacattgta gcaacacaag tcgactctag    4740
aggatccccg ggtaccgagc tcgaattcac tggccgtcgt tttacaacgt cgtgactggg    4800
aaaaccctgg cgttacccaa cttaatcgcc ttgcagcaca tccccctttc gccagctggc    4860
gtaatagcga agaggcccgc accgatcgcc cttcccaaca gttgcgcagc ctgaatggcg    4920
```

```
-continued aatggcgcct gatgcggtat tttctcctta cgcatctgtg cggtatttca caccgcatat    4980
ggtgcactct cagtacaatc tgctctgatg ccgcatagtt aagccagccc cgacacccgc    5040
caacacccgc tgacgcgccc tgacgggctt gtctgctccc ggcatccgct tacagacaag    5100
ctgtgaccgt ctccgggagc tgcatgtgtc agaggtttc accgtcatca ccgaaacgcg    5160
cga                                                                  5163
```

METHODS AND SYSTEMS FOR RAPID DETECTION OF MICROORGANISMS USING INFECTIOUS AGENTS

RELATED APPLICATIONS

The present application is a Continuation application of U.S. patent application Ser. No. 14/625,481, filed Feb. 18, 2015, which is a Continuation-in-Part application of U.S. patent application Ser. No. 13/773,339, filed Feb. 21, 2013, entitled "Methods and Systems for Detection of Microorganisms," which claims priority under 35 USC 119(e) to U.S. Provisional Patent Application No. 61/601,231, filed Feb. 21, 2012. The present application also claims priority under 35 USC 119(e) to U.S. Provisional Patent Application No. 61/940,959, filed Feb. 18, 2014. The disclosures of U.S. Provisional Patent Application Nos. 61/601,231 and 61/940,959 and U.S. patent application Ser. Nos. 13/773,339 and 14/625,481 are incorporated by reference in their entireties herein.

FIELD OF THE INVENTION

This invention relates to methods and systems for the detection of microorganisms using infectious agents.

BACKGROUND

There is a strong interest in improving speed and sensitivity for detection of bacteria, viruses, and other microorganisms in biological, food, water, and clinical samples. Microbial pathogens can cause substantial morbidity among humans and domestic animals, as well as immense economic loss. Also, detection of microorganisms is a high priority for the Food and Drug Administration (FDA) and Centers for Disease Control (CDC) given outbreaks of life-threatening or fatal illness caused by ingestion of food contaminated with certain microorganisms, e.g., *Escherichia coli* or *Salmonella* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, these methods have drawbacks. For example, techniques involving direct immunoassays or gene probes generally require an enrichment step in order to obtain adequate sensitivity. Polymerase chain reaction (PCR) tests also include an amplification step and therefore are capable of both very high sensitivity and selectivity; however, the sample size that can be economically subjected to PCR testing is limited. With dilute bacterial suspensions, most small subsamples will be free of cells and therefore purification and/or enrichment steps are still required.

The time required for traditional biological enrichment is dictated by the growth rate of the target bacterial population of the sample, by the effect of the sample matrix, and by the required sensitivity. For instance, a magnetic-capture PCR system for verotoxigenic *E. coli* can require about 5, 7 and 10 hours of culturing for enrichment to detect 1000, 100, and 1 colony forming unit per milliliter (CFU/mL), respectively, in a model system, and 15 hours of culturing for enrichment to detect 1 CFU per gram (g) in ground beef. In practice, most high sensitivity methods employ an overnight incubation and take about 24 hours overall. Due to the time required for cultivation, these methods can take up to three days, depending upon the organism to be identified and the source of the sample. This lag time is generally unsuitable as the contaminated food, water (or other product) may have already made its way into livestock or humans. In addition, increases in antibiotic-resistant bacteria and biodefense considerations make rapid identification of bacterial pathogens in water, food and clinical samples critical priorities worldwide.

Therefore, there is a need for more rapid, simple and sensitive detection and identification of microorganisms, such as bacteria, viruses, and other potentially pathogenic microorganisms.

SUMMARY

Embodiments of the invention comprise compositions, methods, systems and kits for the detection of microorganisms. The invention may be embodied in a variety of ways.

In some aspects, the invention comprises a recombinant bacteriophage comprising an indicator gene inserted into a late gene region of the bacteriophage.

In some embodiments, the invention comprises a method for detecting a microorganism of interest in a sample comprising the steps of incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product, and detecting the indicator protein product, wherein positive detection of the indicator protein product indicates that the microorganism of interest is present in the sample.

In other embodiments, the invention comprises a system for rapid detection of a microorganism of interest in a sample, comprising a component for incubating the sample with an infectious agent specific for the microorganism of interest, wherein the infectious agent comprises an indicator moiety, and a component for detecting the indicator moiety.

In still other embodiments, the invention comprises non-transient computer readable media for use with methods or systems according to the invention.

BRIEF DESCRIPTION OF THE FIGURES

The present invention may be better understood by referring to the following non-limiting figures.

DETAILED DESCRIPTION OF THE INVENTION

Figure 1:
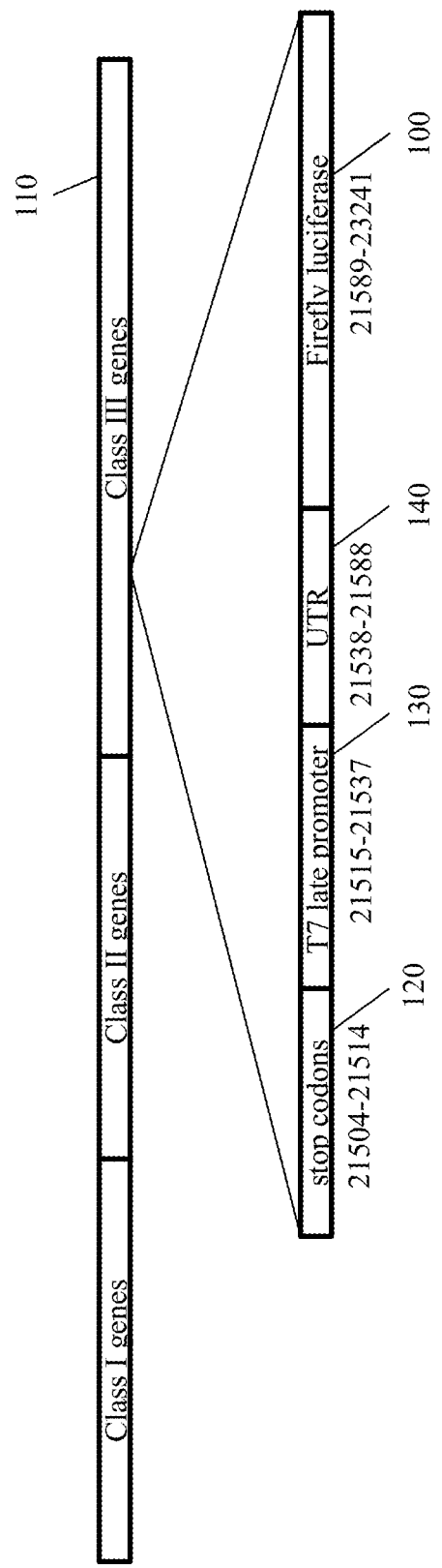
FIG. 1 depicts an indicator phage construct according to an embodiment of the invention illustrating insertion of a genetic construct comprising Firefly luciferase gene and a T7 late promoter inserted into the late (class III) region of a bacteriophage. Also depicted is a sequence comprising stop codons in all three reading frames to prevent read-through and an untranslated region (UTR).

Disclosed herein are compositions, methods and systems that demonstrate surprising sensitivity for detection of a microorganism of interest in test samples (e.g., biological, food, water, and clinical samples). Detection can be achieved in a shorter timeframe than was previously thought possible using genetically modified infectious agents in assays performed without any culturing for enrichment, or in some embodiments with minimal incubation times during which microorganisms could potentially multiply. Also surprising is the success of using high multiplicity of infection (MOI), or high concentrations of plaque forming units (PFU), for incubation with a test sample. Such high phage concentrations (PFU/mL) were previously purported to be detrimental to microorganism detection assays, as they were purported to cause "lysis from without."

The compositions, methods, systems and kits of the invention may comprise infectious agents for use in detection of such microorganisms. In certain embodiments, the invention may comprise a composition comprising a recombinant bacteriophage having an indicator gene inserted into a late gene region of the bacteriophage. In certain embodiments, expression of the indicator gene during bacteriophage replication following infection of a host bacterium results in a soluble indicator protein product. In certain embodiments, the indicator gene may be inserted into a late gene (i.e., class III) region of the bacteriophage. The bacteriophage may be derived from T7, T4, JG04, or another natural bacteriophage.

In some aspects, the invention comprises a method for detecting a microorganism of interest. The method may use an infectious agent for detection of the microorganism of interest. For example, in certain embodiments, the microorganism of interest is a bacterium and the infectious agent is a bacteriophage. Thus, in certain embodiments, the method may comprise detection of a microorganism of interest in a sample by incubating the sample with a recombinant bacteriophage that infects the microorganism of interest. In certain embodiments, the recombinant bacteriophage comprises an indicator gene. The indicator gene may, in certain embodiments, be inserted into a late gene region of the bacteriophage such that expression of the indicator gene during bacteriophage replication following infection of host bacteria results in a soluble indicator protein product. The method may comprise detecting the indicator protein product, wherein positive detection of the indicator protein product indicates that the microorganism of interest is present in the sample.

In certain embodiments, the invention may comprise a system. The system may contain at least some of the compositions of the invention. Also, the system may comprise at least some of the components for performing the method. In certain embodiments, the system is formulated as a kit. Thus, in certain embodiments, the invention may comprise a system for rapid detection of a microorganism of interest in a sample, comprising: a component for incubating the sample with an infectious agent specific for the microorganism of interest, wherein the infectious agent comprises an indicator moiety; and a component for detecting the indicator moiety. In yet other embodiments, the invention comprises software for use with the methods or systems.

Thus, some embodiments of the present invention solve a need by using infectious agent-based methods for amplifying a detectable signal indicating the presence of bacteria. In certain embodiments as little as a single bacterium is detected. The principles applied herein can be applied to the detection of a variety of microorganisms. Because of numerous binding sites for an infectious agent on the surface of a microorganism, the capacity to produce one hundred or more agent progeny during infection, and the potential for high level expression of an encoded indicator moiety, the infectious agent or an indicator moiety can be more readily detectable than the microorganism itself. In this way, embodiments of the present invention can achieve tremendous signal amplification from even a single infected cell.

Aspects of the present invention utilize the high specificity of binding agents that can bind to particular microorganisms, such as the binding component of infectious agents, as a means to detect and/or quantify the specific microorganism in a sample. In some embodiments, the present invention utilizes the high specificity of infectious agents such as bacteriophage.

In some embodiments, detection is achieved through an indicator moiety associated with the binding agent specific for the microorganism of interest. For example, an infectious agent may comprise an indicator moiety. In some embodiments the indicator may be encoded by the infectious agent, such as a bacteriophage, and the bacteriophage is designated an indicator phage.

Some embodiments of the invention disclosed and described herein utilize the discovery that a single microorganism is capable of binding specific recognition agents, such as phage. Following infection and replication of the phage, progeny phage may be detected via an indicator moiety expressed during phage replication. This principle allows amplification of indicator signal from one or a few cells based on specific recognition of microorganism surface receptors. For example, by exposing even a single cell of a microorganism to a plurality of phage, thereafter allowing amplification of the phage and high-level expression of an encoded indicator gene product during replication, the indicator signal is amplified such that the single microorganism is detectable.

Embodiments of the methods and systems of the invention can be applied to detection and quantification of a variety of microorganisms (e.g., bacteria, fungi, yeast) in a variety of circumstances, including but not limited to detection of pathogens from food, water, clinical and commercial samples. The methods of the present invention provide high detection sensitivity and specificity rapidly and without the need for traditional biological enrichment (e.g., culturing for enrichment), which is a surprising aspect as all available methods require culturing. In some embodiments detection is possible within 1-2 replication cycles of the bacteriophage or virus, which goes against conventional wisdom, as it doesn't take advantage of the phage's natural ability to amplify itself and the luciferase signal.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate or lateral flow strip).

The term "antibody" includes monoclonal antibodies, polyclonal antibodies, synthetic antibodies and chimeric antibodies, e.g., generated by combinatorial mutagenesis and phage display. The term "antibody" also includes mimetics or peptidomimetics of antibodies. Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like. Fragments of antibodies may serve in place of antibodies in some embodiments. "Surface-specific antibodies" as used herein bind to molecules exposed on the outer surface of a specific microorganism.

As used herein, the term "free antibodies" refers to antibodies which are in solution and may move freely through a liquid; i.e., they are not initially bound to a solid support or otherwise constrained.

As used herein, "affinity-purified" or "affinity-purification" refers to a series of steps used to prepare and treat antibodies such that they exhibit optimal specificity and sensitivity, including minimal cross-reactivity with undesired epitopes. For example, removal of undesired lipids and proteins from antiserum may first be achieved by salt precipitation steps. Further positive selection (also called "affinity-purification") and/or negative selection (also called "reverse-purification") may be achieved by passing the remaining antibodies over a support (e.g., agarose columns) comprising surface antigens designed to retain antibodies with particular epitope affinities. In some examples, where the starting antiserum is polyclonal, the purified antibodies that remain after these selection steps are able to recognize many different epitopes on the surface of the microorganism of interest, but they do not recognize the surface epitopes of other microorganisms.

The term "binding agent" refers to a molecule that can specifically and selectively bind to a second (i.e., different) molecule of interest. The interaction may be non-covalent, for example, as a result of hydrogen-bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator moiety" refers to a molecule that can be measured in a quantitative assay. For example, an indicator moiety may comprise an enzyme that may be used to convert a substrate to a product that can be measured. An indicator moiety may be an enzyme that catalyzes a reaction that generates bioluminescent emissions (e.g., luciferase). Or, an indicator moiety may be a radioisotope that can be quantified. Or, an indicator moiety may be a fluorophore. Or, other detectable molecules may be used.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasma, protozoa, yeasts, and other microscopic living organisms and uses them to replicate itself. Here, "microscopic" means that the largest dimension is one millimeter or less. Bacteriophages are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, "late gene region" refers to a region of a viral genome that is transcribed late in the viral life cycle. The late gene region typically includes the most abundantly expressed genes (e.g., structural proteins assembled into the bacteriophage particle). Late genes are synonymous with class III genes and include genes with structure and assembly functions. For example, the late genes (synonymous with class III,) are transcribed in T7, e.g., from 8 minutes after infection until lysis, class I (e.g., RNA polymerase) is early from 4-8 minutes, and class II from 6-15 minutes, so there is overlap in timing of II and III. A late promoter is one that is naturally located and active in such a late gene region.

As used herein, "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for very short periods of time may be employed in some embodiments of methods described herein, but is not necessary and is for a much shorter period of time than traditional culturing for enrichment, if it is used at all.

As used herein "recombinant" refers to genetic (i.e., nucleic acid) modifications as usually performed in a laboratory to bring together genetic material that would not otherwise be found. This term is used interchangeably with the term "modified" herein.

Samples

Each of the embodiments of the methods and systems of the invention can allow for the rapid detection and quantification of microbes in a sample. For example, methods according to the present invention can be performed, most preferably, in about two hours or less.

Microbes detected by the methods and systems of the present invention include pathogens that are of commercial, medical or veterinary concern. Such pathogens include Gram-negative bacteria, Gram-positive bacteria, mycoplasmas and viruses. Any microbe for which an infectious agent that is specific for the particular microbe has been identified can be detected by the methods of the present invention. Those skilled in the art will appreciate that there is no limit to the application of the present methods other than the availability of the necessary specific infectious agent/microbe pairs.

Bacterial cells detectable by the present invention include, but are not limited to, bacterial cells that are food or water borne pathogens. Bacterial cells detectable by the present invention include, but are not limited to, all species of *Salmonella*, all strains of *Escherichia coli*, including, but not limited to *E. coli* O157:H7, all species of *Listeria*, including, but not limited to *L. monocytogenes*, and all species of *Camplyobacter*. Bacterial cells detectable by the present invention include, but are not limited to, bacterial cells that are pathogens of medical or veterinary significance. Such pathogens include, but are not limited to, *Bacillus* spp., *Bordetella pertussis, Camplyobacter jejuni, Chlamydia pneumoniae, Clostridium perfringens, Enterobacter* spp., *Klebsiella pneumoniae, Mycoplasma pneumoniae, Salmonella typhi, Shigella sonnei, Staphylococcus aureus*, and *Streptococcus* spp.

The sample may be environmental or food or water samples and medical or veterinary samples. Samples may be liquid, solid, or semi-solid. Samples may be swabs of solid surfaces. Samples may include environmental materials, such as the water samples, or the filters from air samples or aerosol samples from cyclone collectors. Samples may be of meat, poultry, processed foods, milk, cheese, or other dairy products. Medical or veterinary samples include, but are not limited to, blood, sputum, cerebrospinal fluid, and fecal samples and different types of swabs.

Samples may be used directly in the detection methods of the present invention, without preparation, concentration, or dilution. For example, liquid samples, including but not limited to, milk and juices, may be assayed directly. Samples may be diluted or suspended in solution, which may include, but is not limited to, a buffered solution or a bacterial culture medium. A sample that is a solid or semi-solid may be suspending in a liquid by mincing, mixing or macerating the solid in the liquid. A sample should be maintained within a pH range that promotes bacteriophage attachment to the host bacterial cell. A sample should also contain the appropriate concentrations of divalent and monovalent cations, including but not limited to $Na^+$, $Mg^{2+}$, and $K^+$. Preferably a sample is maintained at a temperature that maintains the viability of any pathogen cells contained within the sample.

Preferably throughout detection assays, the sample is maintained at a temperature that maintains the viability of any pathogen cell present in the sample. During steps in which bacteriophages are attaching to bacterial cells, it is preferable to maintain the sample at a temperature that facilitates bacteriophage attachment. During steps in which bacteriophages are replicating within an infected bacterial cell or lysing such an infected cell, it is preferable to maintain the sample at a temperature that promotes bacteriophage replication and lysis of the host. Such temperatures are at least about 25 degrees Celsius (C), more preferably no greater than about 45 degrees C., most preferably about 37 degrees C. It is also preferred that the samples be subjected to gentle mixing or shaking during bacteriophage attachment, replication and cell lysis.

Assays may include various appropriate control samples. For example, control samples containing no bacteriophages or control samples containing bacteriophages without bacteria may be assayed as controls for background signal levels.

Indicator Infectious Agents

As described in more detail herein, the compositions, methods, systems and kits of the invention may comprise infectious agents for use in detection of such microorganisms. In certain embodiments, the invention may comprise a composition comprising a recombinant bacteriophage having an indicator gene inserted into a late gene region of the bacteriophage. As described in more detail below, in certain embodiments of the infectious agent, the indicator gene does not encode a fusion protein. For example, in certain embodiments, expression of the indicator gene during bacteriophage replication following infection of a host bacterium results in a soluble indicator protein product. In certain embodiments, the indicator gene may be inserted into a late gene region of the bacteriophage. In a recombinant bacteriophage the late gene region may be a class III gene region.

In some embodiments, the indicator phage is derived from T7, T4 or another phage. An indicator bacteriophage may also be derived from T7-like, T4-like, JG04, JG04-like, or any other bacteriophage having a genome with at least 99, 98, 97, 96, 95, 94, 93, 92, 91, 90, 89, 88, 87, 86, 85, 84, 83, 82, 81, 80, 79, 78, 77, 76, 75, 74, 73, 72, 71, or 70% homology to T7, T7-like, T4, T4-like, JG04, or JG04-like phages. In some embodiments, the indicator phage is derived from a natural phage isolated from the environment, such as JG04 phage, a T4-like phage isolated as described in the Examples. The genetic modifications may avoid deletions of wild-type genes and thus remain more similar to the wild-type infectious agent than many commercially available phage, e.g. T7SELECT®415. Such naturally derived bacteriophage may be more specific for bacteria that are found in the environment than bacteriophage that are commercially available and as such, genetically distinct from phage found in the environment.

Moreover, phage genes thought to be nonessential may have unrecognized function. For example, an apparently nonessential gene may have an important function in elevating burst size with subtle cutting, fitting, or trimming functions in assembly. As such, deleting genes to insert an indicator may be detrimental. Most phages can package a DNA that is a few percent larger than their natural genome. With this consideration, a smaller indicator gene may be a more appropriate choice for modifying a bacteriophage, especially one with a smaller genome. OpLuc and NANO-LUC® proteins are only about 20 kDa (approximately 500-600 bp to encode), while FLuc is about 62 kDa (approximately 1,700 bp to encode). For comparison, the genome of T7 is around 40 kbp, while the T4 genome is about 170 kbp.

In some indicator phage embodiments, the indicator gene may be inserted into an untranslated region to avoid disruption of functional genes, leaving wild-type phage genes intact, which may lead to greater fitness when infecting non-laboratory strain bacteria. Additionally, stop codons at all three reading frames may help to increase expression by reducing read-through, also known as leaky expression. This strategy may also eliminate the possibility of a fusion protein being made at low levels, which would manifest as background signal (e.g., luciferase) that cannot be separated from the phage.

An indicator gene may express a variety of biomolecules. The indicator gene is a gene that expresses a detectable product or an enzyme that produces a detectable product. For example, in one embodiment the indicator gene encodes a luciferase enzyme. Various type of luciferase may be used. In alternate embodiments, and as described in more detail herein, the luciferase is one of Oplophorus luciferase, Firefly luciferase, or an engineered luciferase.

Thus, in some embodiments, the present invention comprises a modified bacteriophage comprising a non-bacteriophage indicator gene in the late (class III) gene region. In some embodiments, the non-native indicator gene is under the control of a late promoter. Using a viral late gene promoter insures the reporter gene (luciferase) is not only expressed at high levels, like viral capsid proteins, but also does not shut down like endogenous bacterial genes or even early viral genes.

In some embodiments, the late promoter is a T4- or T7-like promoter, or another phage promoter similar to that found in the natural phage without genetic modification. The late gene region may be a class III gene region, and the bacteriophage may be derived from T7, T4, T4-like, JG04, or another natural bacteriophage having a genome with at least 90% homology to T7, T4 or T4-like phages. In preferred embodiments, the indicator gene does not encode a fusion protein.

Genetic modifications to infectious agents may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a bacteriophage genome such that it is under the control of a bacteriophage promoter. In some embodiments, the non-native indicator gene is not part of a fusion protein. That is, in some embodiments, a genetic modification may be configured such that the indicator protein product does not comprise polypeptides of the natural bacteriophage. In some embodiments, the indicator protein product is soluble. In some embodiments, the invention comprises a method for detecting a microorganism of interest comprising the step of incubating a test sample with such a modified bacteriophage.

In some embodiments, the non-native indicator gene is not contiguous with a gene encoding a structural phage protein and therefore does not yield a fusion protein. In some embodiments, expression of the indicator gene in progeny bacteriophage following infection of host bacteria results in a soluble protein product.

Unlike systems which employ a fusion of a detection moiety to the capsid protein (i.e., a fusion protein), some embodiments of the present invention express a soluble luciferase. This may greatly increase the sensitivity of the assay (down to a single bacterium), and simplifies the assay, allowing the assay to be completed in less than an hour for some embodiments, as opposed to several hours due to additional purification steps required with constructs that produce detectable fusion proteins. Further, fusion proteins may be less active than soluble proteins due, e.g., to protein folding constraints that may alter the conformation of the enzyme active site or access to the substrate.

Furthermore, fusion proteins by definition limit the number of the moieties attached to subunits of a protein in the bacteriophage. For example, using a commercially available system designed to serve as a platform for a fusion protein would result in about 415 copies of the fusion moiety, corresponding to the about 415 copies of the gene 10B capsid protein in each T7 bacteriophage particle. Without this constraint, infected bacteria can be expected to express many more copies of the detection moiety (e.g., luciferase) than can fit on the bacteriophage. Additionally, large fusion proteins, such as a capsid-luciferase fusion, may inhibit assembly of the bacteriophage particle, thus yielding fewer bacteriophage progeny. Thus a soluble, non-fusion indicator gene product may be preferable.

In some embodiments, the indicator phage encodes a detectable enzyme. The indicator may emit light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, Oplophorus luciferase is the indicator moiety. In some embodiments, NANOLUC® is the indicator moiety. Other engineered luciferases or other enzymes that generate detectable signals may also be appropriate indicator moieties.

Also, the use of a soluble detection moiety eliminates the need to isolate contaminating parental phage from the lysate of the infected sample cells. With a fusion protein system, any bacteriophage used to infect sample cells would have the detection moiety attached, and would be indistinguishable from the daughter bacteriophage also containing the detection moiety. As detection of sample bacteria relies on the detection of newly created (de novo synthesized) detection moiety, using fusion constructs requires additional steps to separate old (parental) moieties from newly created (daughter bacteriophage) moieties. This may be accomplished by washing the infected cells multiple times, prior to the completion of the bacteriophage life cycle, inactivating excess parental phage after infection by physical or chemical means, and/or chemically modifying the parental bacteriophage with a binding moiety (such as biotin), which can then be bound and separated (such as by streptavidin-coated sepharose beads). However, even with all these attempts at isolation, parental phage typically remain when a high multiplicity of infection (MOI) is used to assure infection of a low number of sample cells, creating background signal that may obscure detection of signal from infected cell progeny phage.

By contrast, with the soluble detection moiety expressed in some embodiments of the present invention, purification of the parental phage from the final lysate is unnecessary, as the parental phage will not have any detection moiety attached. Thus any detection moiety present after infection must have been created de novo, indicating the presence of an infected bacterium or bacteria. To take advantage of this benefit, the production and preparation of parental phage may include purification of the phage from any free detection moiety produced during the production of parental bacteriophage in bacterial culture. Standard bacteriophage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). The Examples herein describe the use cesium chloride isopycnic ultracentrifugation as part of the preparation of recombinant phage of the invention so as to separate parental phage particles from contaminating luciferase protein produced upon propagation of the phage in the bacteria stock. In this way, the recombinant bacteriophage of the invention is substantially free of any luciferase generated during production of the bacteria. Removal of residual luciferase present in the phage stock can substantially reduce background signal seen when the recombinant bacteriophage are incubated with a test sample.

In some embodiments of modified bacteriophage, the late promoter (class III promoter, e.g., from T7 or T4) has high affinity for RNA polymerase of the same native bacteriophage (e.g., T7 or T4, respectively) that transcribes genes for structural proteins assembled into the bacteriophage particle. These proteins are the most abundant proteins made by the phage, as each bacteriophage particle comprises dozens or hundreds of copies of these molecules. The use of a viral late promoter can ensure optimally high level of expression of the luciferase detection moiety. The use of a late viral promoter derived from, specific to, or active under the original wild-type bacteriophage the Indicator Phage is derived from (e.g., the T4 or T7 late promoter with a T4- or T7-based system) can further ensure optimal expression of the detection moiety. The use of a standard bacterial (non-viral/non-bacteriophage) promoter may in some cases be detrimental to expression, as these promoters are often down-regulated during bacteriophage infection (in order for the bacteriophage to prioritize the bacterial resources for phage protein production). Thus, in some embodiments, the phage is preferably engineered to encode and express at high level a soluble (free) indicator moiety, which does not limit expression to the number of subunits of a phage structural component.

Embodiments employing modified bacteriophage of the invention may allow rapid detection of specific bacterial strains, with total assay times as fast as 45 minutes-1.5 hours. The amount of time required may be somewhat shorter or longer depending on the strain of bacteriophage and the strain of bacteria to be detected in the assay.

The strategy of using indicator phage that produce soluble luciferase employs phage (e.g., T4 phage) engineered to express a soluble luciferase during replication instead of a capsid protein-luciferase fusion. Expression of luciferase is driven by a viral capsid promoter (e.g., the Soc promoter in T4 bacteriophage), yielding high expression. Parental phage will be free of luciferase, so any luciferase detected in the assay must come from replication of progeny phage released from the bacterial cells. Thus, there is no need to separate out the parental phage and the progeny phage.

In some embodiments, at least part of the sample comprising the bacteria to be quantified is spin filtered to remove the media and an appropriate multiplicity of biotinylated T4 phage that express luciferase are added. The parental and progeny phage in the filtrate from the infected bacteria may then be collected, e.g., by centrifugation and the level of luciferase quantified using a luminometer.

FIG. 1 depicts a schematic representation of the genomic structure of a recombinant bacteriophage of the invention, Indicator Phage T7SELECT®415-Luc. For the embodiment depicted in FIG. 1, the detection moiety is encoded by a Firefly luciferase gene 100 inserted within the late (class III) gene region 110, which is expressed late in the viral life cycle. Late genes are generally expressed at higher levels than other phage genes, as they code for structural proteins. Thus, in the embodiment of the recombinant phage depicted by FIG. 1, the indicator gene (i.e., Firefly luciferase) is inserted into the late gene region, just after gene 10B (major capsid protein), and is a construct comprising the Firefly luciferase gene 100. The construct depicted in FIG. 1 was designed to include stop codons 120 in all 3 reading frames to ensure luciferase is not incorporated into the gene 10B product. Also as depicted by FIG. 1, the construct may comprise the consensus T7 late promoter 130 to drive transcription and expression of the luciferase gene. The construct may also comprise a composite untranslated region synthesized from several T7 UTRs 140. This construct ensures soluble Firefly luciferase is produced such that expression is not limited to the number of capsid proteins inherent in the phage display system.

As noted herein, in certain embodiments, it may be preferred to utilize infectious agents that have been isolated from the environment for production of the infectious agents of the invention. In this way, infectious agents that are specific to naturally derived microorganisms may be generated.

Figure 2:
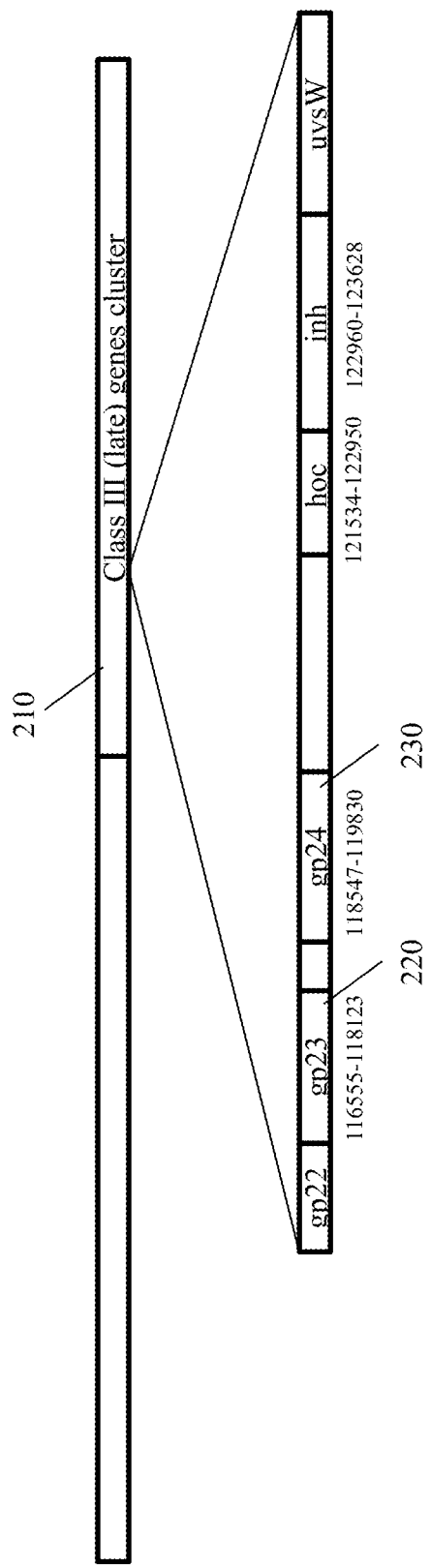
FIG. 2 shows the genome of bacteriophage JG04, a T4-like bacteriophage which was isolated from sewage treatment plant samples and shares ~98% homology with T4-like phage RB69. Capsid proteins gp23 and gp24 are within the late gene region, consisting of structural genes, which code for virion proteins. As these virion proteins are expressed at a very high level, any genes inserted into this region can be expected to have similar expression levels, as long as late gene promoters and/or other similar control elements are used.

For example, FIG. 2 shows the genome of bacteriophage JG04, a natural phage having about 98% sequence homology to a T4-like bacteriophage, RB69. Isolation of the JG04 bacteriophage from a sewage treatment plant sample is described with particularity in the Examples herein. As discussed in the Examples, the capsid proteins, gp23 (220) and gp24 (230) are within the late gene region (210), consisting of structural genes, which code for virion proteins. As these virion proteins are expressed at a very high level, any genes inserted into this region can be expected to have similar expression levels, as long as late gene promoters and/or other similar control elements are used. The bacteriophage construct depicted in FIG. 2 has the sequence as set forth in SEQ ID NO: 3.

Figure 3:
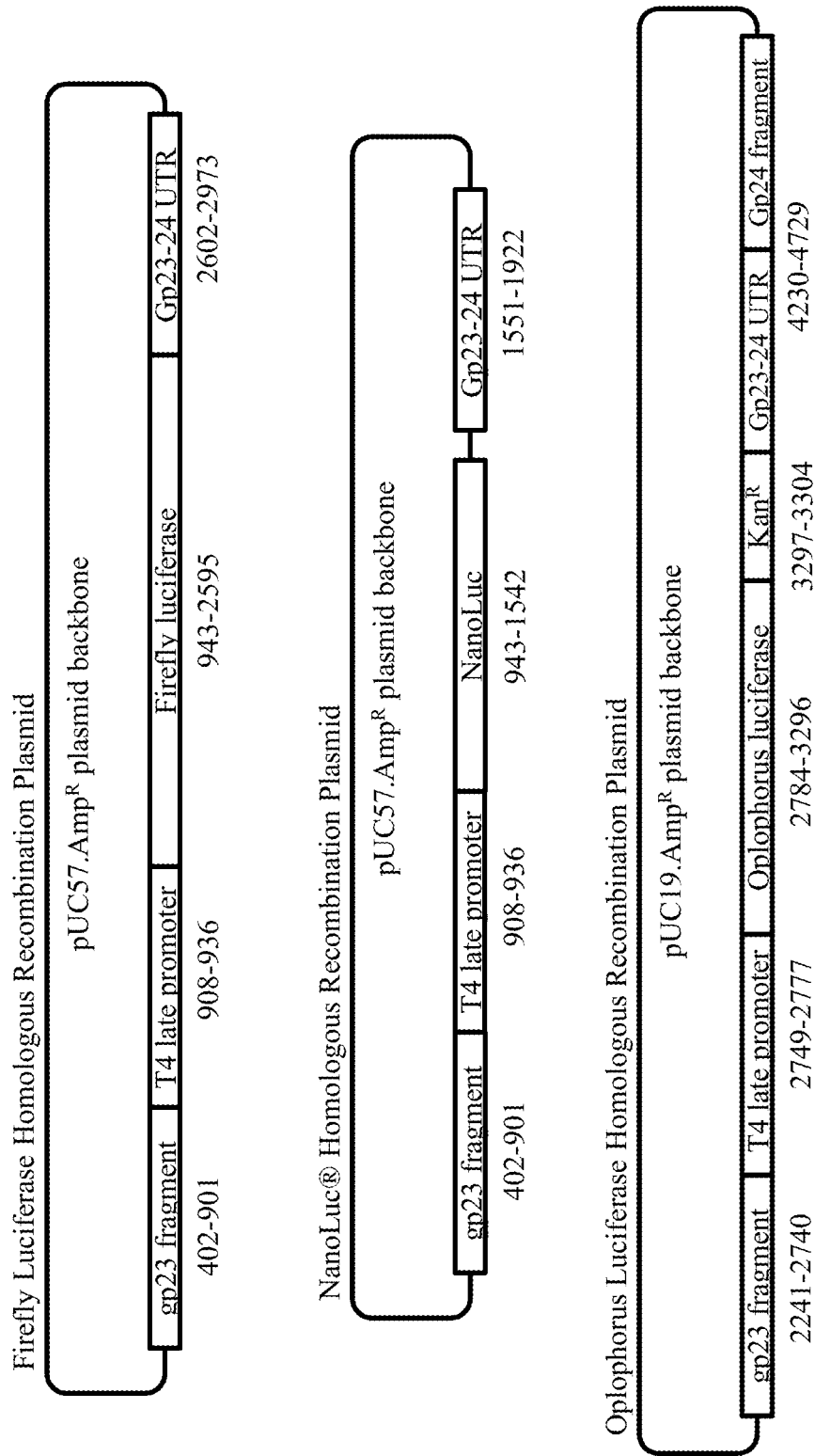
FIG. 3 shows three homologous recombination plasmid constructs carrying three different luciferase genes. Firefly luciferase, NANOLUC® luciferase, and Oplophorus luciferase genes are each inserted into a pUC57.Amp$^R$ plasmid backbone. In each construct, a fragment of the gp23 capsid protein gene is followed by a T4 late promoter, the respective luciferase gene, and a gp23-24 untranslated region. The Oplophorus construct additionally comprises a fragment of the gp24 gene downstream of the untranslated region.

The compositions of the invention may comprise various infectious agents and/or indicator genes. For example, FIG. 3 shows three homologous recombination plasmid constructs carrying three different luciferase genes. Three constructs were made and used in recombination with JG04 to generate recombinant bacteriophage of the invention. Thus, the top construct in FIG. 3 shows a recombination plasmid having Firefly luciferase construct used for homologous recombination insertion of the Firefly luciferase into JG04: homologous recombination plasmid pUC57.HR.Fluc, corresponding to SEQ ID NO. 5. The middle construct in FIG. 3 shows a recombination plasmid used for homologous recombination insertion of the NANOLUC® luciferase into JG04: homologous recombination plasmid pUC57.HR.NANOLUC® corresponding to SEQ ID NO. 6; and the lower construct in FIG. 3 shows a recombination plasmid used for homologous recombination insertion of the Oplophorus luciferase into JG04: homologous recombination plasmid pUC19.HR.OpLuc.KanR, corresponding to SEQ ID NO. 7.

In some embodiments, indicator phage according to the invention comprise JG04 genetically engineered to comprise any one of the three constructs shown in FIG. 3. That is, an indicator phage comprising the sequence of SEQ ID NO. 3, further comprising additional sequence inserted between nucleotides 116,555 and 119,830 of SEQ ID NO. 3 corresponding to nucleotides 402-2,973 of SEQ ID NO. 5 (or a portion thereof); or nucleotides 402-1,922 of SEQ ID NO. 6 (or a portion thereof), also called JG04-NANOLUC® Indicator Phage in Examples 6 and 11 herein; or nucleotides 2,241-4,729 of SEQ ID NO. 7 (or a portion thereof), also called JG04-OpLuc Indicator Phage in Examples 7-9 herein. For example, a portion thereof may comprise the luciferase portion only (i.e., nucleotides 943-2,595 of SEQ ID NO. 5; or nucleotides 943-1,542 of SEQ ID NO. 6; or nucleotides 2,784-3,296 of SEQ ID NO. 7). A portion thereof may further comprise the T4 late promoter (i.e., nucleotides 908-936 of either SEQ ID NO. 5 or NO. 6, or nucleotides 2,749-2,777 of SEQ ID NO. 7). In other embodiments, such indicator phage are comprised in systems or kits according to the invention. Methods described herein may also utilize such indicator phage.

Figure 4:
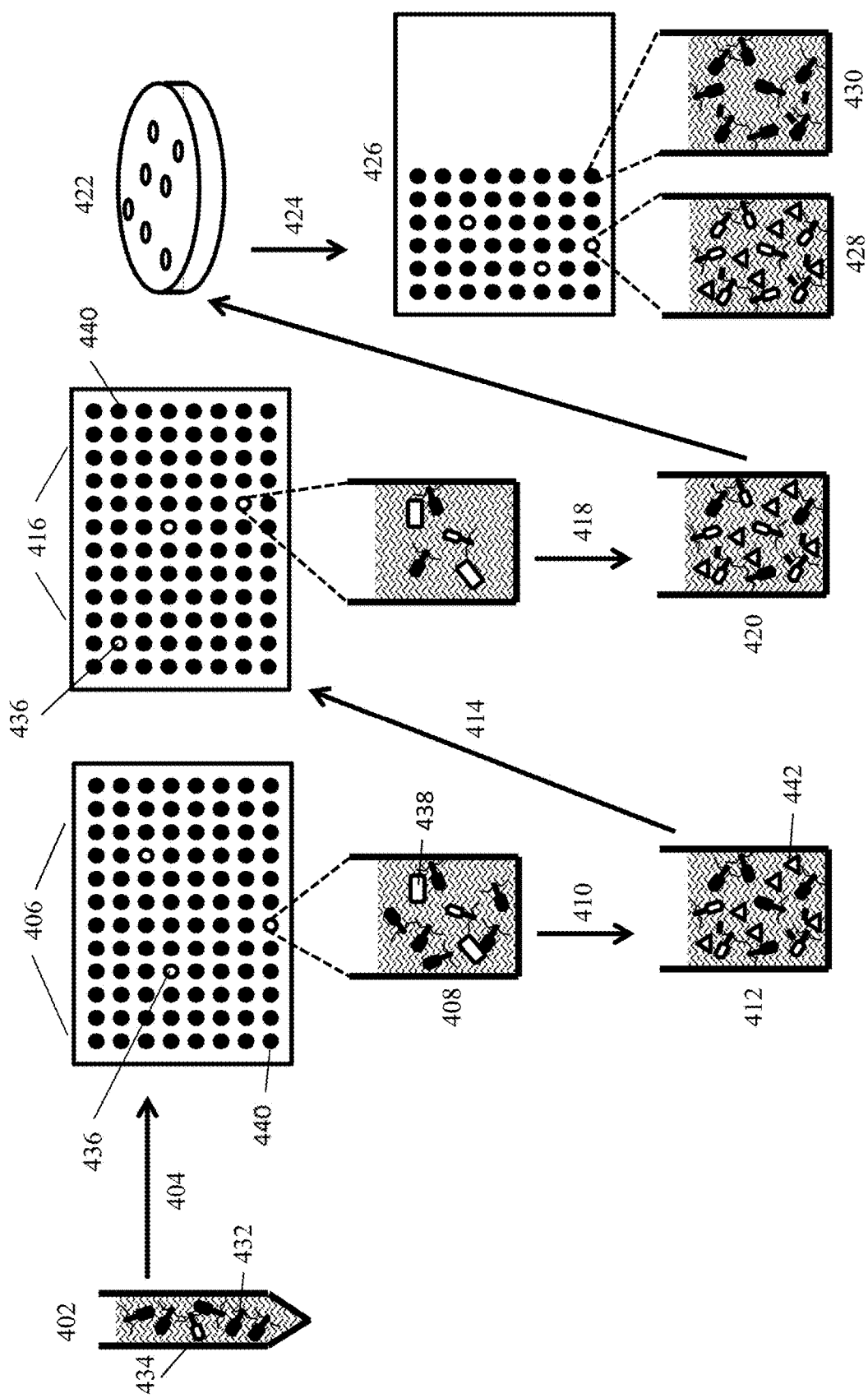
FIG. 4 depicts the isolation of recombinant phage from modifications of JG04 bacteriophage using the plasmid constructs such as those shown in FIG. 3 using a series of sequential infection and dilution steps to identify recombinant phage that express an indicator gene.

FIG. 4 depicts the isolation of recombinant phage from modifications of JG04 bacteriophage using the plasmid constructs shown in FIG. 3 and described in Example 6.

In the first step 402, bacteria transformed with homologous recombination plasmid are infected with bacteriophage, resulting in progeny phage with a mixture of parental and recombinant phage with a ratio of approximately 20,000 wild-type 432:1 recombinant phage 434. The resulting recombinant phage mix is diluted 404 into 96-well plates 406 to give an average of 3 recombinant transducing units (TU) per plate, which corresponds to about 625 infectious units (IU) of mostly wild-type phage per well. The 96-well plate is assayed for luciferase activity to identify wells 436 containing recombinant phage as compared to wells 440 containing wild-type bacteriophage. Bacteria 438 are added

408; for example, each well may contain about 50 μL of turbid *E. coli* O157:H7. This allows the phage to replicate and produce the luciferase enzyme 442. After 2 hours of incubation at 37° C. shown in 410, wells may be screened for the presence of luciferase 442. Any positive wells are likely to have been inoculated with a single recombinant phage, and at this stage the mixture may contain a ratio of approximately 600 wild-type phage:1 recombinant, an enrichment over the original 20,000:1 ratio. In one embodiment, soluble luciferase and phage were present at approximate ratio of 625 wild-type:1 recombinant. Progeny from this enriched culture 412 may be subjected to additional limiting dilution assay(s) 414 to verify the ratio and determine the actual concentration of recombinant phage transducing units. For example, about 3 recombinant TU per 96-well plate 416 may be aliquoted 414 from the first purification stock, leading to an approximate inoculation of ~20 mostly wild-type phage per well of a second dilution assay plate 420. Any positive luciferase wells are likely to have been inoculated with a single recombinant along with ~20 wild-type phage. These wells may be analyzed for presence of luciferase 442.

After addition of bacteria and incubation (e.g., 37° C. for 2 hours) 418, soluble luciferase and phage are present at approximately 20 wild-type: 1 recombinant 420. Finally, a plaque assay may be performed 422 to screen for recombinants that express luciferase 446. A small number of individual (e.g., n=48) plaques may be individually picked and screened on a third multiwell plate 426 for luciferase activity 436. In an embodiment, this approach should insure that about 3 recombinants would be in the mix of plaques being screened. One plaque may be removed from the plate to each well of a 96-well plate 424 and a luciferase assay performed 426 to determine which wells contained phage exhibiting luciferase activity 442. Wells 428 demonstrating luciferase activity represent pure recombinant phage 434, while wells without luciferase activity 430 represent pure wild-type phage 432.

Individual plaques may then be suspended in buffer or media (e.g., 100 μL TMS), and an aliquot (e.g., about 5 μL) added to a well containing a turbid *E. coli* O157:H7 culture, and assayed after incubation (e.g., about 45 minutes to 1 hour at 37° C.). Positive wells are expected to contain a pure culture of recombinant phage. Still, it may be preferred, in certain embodiments to include an additional round of plaque purification.

Thus, as exemplified by FIG. 4, recombinant phage generated by homologous recombination of the appropriate recombination plasmid with JG04 can be isolated from a mixture comprising 0.005% of total phage. Following isolation, large scale production may be performed to obtain high titer stocks appropriate for use in the *E. coli* O157:H7 detection assay. For example, as described in more detail in the Examples herein, cesium chloride isopycnic density gradient centrifugation may be used to separate phage particles from contaminating luciferase protein to reduce background.

In this way, and as described in more detail in the Examples below, recombinant bacteriophage having the luciferase gene of interest (e.g., Firefly, Oplophorus or an engineered luciferase such as NANOLUC®) inserted into a bacteriophage derived from the environment may be generated.

Methods of Using Infectious Agents for Detecting Microorganisms

As noted herein, in certain embodiments, the invention may comprise methods of using infectious particles for detecting microorganisms. The methods of the invention may be embodied in a variety of ways.

Thus, the methods of the present invention utilizes the high specificity of binding agents that recognize and bind to a particular microorganism of interest as a means to amplify a signal and thereby detect low levels of a microorganism (e.g., a single microorganism) present in a sample. For example, infectious agents (e.g., bacteriophage) specifically recognize surface receptors of particular microorganisms and thus specifically infect those microorganisms. As such, these infectious agents may be appropriate binding agents for targeting a microorganism of interest. Some embodiments of the invention utilize the specificity of binding and high-level genetic expression capacity of infectious agents for rapid and sensitive targeting to infect and facilitate detection of a microorganism of interest.

Thus, in an embodiment, the invention may comprise a method for detecting a microorganism of interest in a sample comprising the steps of: incubating the sample with an infectious agent that infects the microorganism of interest, wherein the infectious agent comprises an indicator gene such that expression of the indicator gene during bacteriophage replication following infection of microorganism of interest results in a soluble indicator protein product; and detecting the indicator protein product, wherein positive detection of the indicator protein product indicates that the microorganism of interest is present in the sample.

A variety of infectious agents may be used. In alternate embodiments, bacteriophages, phages, mycobacteriophages (such as for TB and paraTB), mycophages (such as for fungi), mycoplasma phages, and any other virus that can invade living bacteria, fungi, mycoplasma, protozoa, yeasts, and other microscopic living organisms can be employed to target a microorganism of interest. For example, in an embodiment, where the microorganism of interest is a bacterium, the infectious agent may comprise a bacteriophage. As discussed herein, such bacteriophage may replicate inside of the bacteria to generate hundreds of progeny bacteria. Detection of the indicator gene inserted into the bacteriophage can be used as a measure of the bacteria in the sample. For example, well-studied phages of *E. coli* include T1, T2, T3, T4, T5, T7, and lambda; other *E. coli* phages available in the ATCC collection, for example, include phiX174, S13, Ox6, MS2, phiV1, fd, PR772, and ZIK1. Alternatively, natural bacteriophage may be isolated from a variety of environmental sources. A source for phage isolation may be selected based on the location where a microorganism of interest is expected to be found. Thus, in some embodiments, the indicator bacteriophage comprises an indicator moiety and infection of a single *E. coli* cell may be detected in an amplified signal generated via the indicator moiety. Thus the method may comprise detecting an indicator moiety produced during phage replication, wherein detection of the indicator indicates that the bacterium of interest is present in the sample.

In an embodiment, the invention may comprise a method for detecting a bacteria of interest in a sample comprising the steps of: incubating the sample with a recombinant bacteriophage that infects the bacteria of interest, wherein the recombinant bacteriophage comprises an indicator gene inserted into a late gene region of the bacteriophage such that expression of the indicator gene during bacteriophage replication following infection of host bacteria results in a soluble indicator protein product; and detecting the indicator protein product, wherein positive detection of the indicator protein product indicates that the bacteria of interest is present in the sample. In an embodiment, and as described in detail herein, the amount of indicator moiety detected corresponds to the amount of the bacteria of interest present in the sample.

In an embodiment, the late gene region is a class III gene region. As described in more detail herein, insertion of the indicator gene into the late class III gene region may ensure that the indicator gene is expressed in high quantities upon replication in the bacterium.

As described above for the compositions of the invention, the bacteriophage is derived from T7, T4, T4-like, JG04, or another natural bacteriophage having a genome with at least 90% homology to T7, T4 or other T4-like phage.

Also, in certain embodiments, the indicator gene does not encode a fusion protein. Thus, in certain embodiments, expression of the indicator gene during bacteriophage replication following infection of host bacteria results in a soluble indicator protein product.

A variety of indicator moieties may be used. In certain embodiments, the indicator gene may encode a luciferase enzyme. For example, the luciferase may be one of Oplophorus luciferase, Firefly luciferase, or an engineered luciferase.

As described in more detail herein, the methods and systems of the invention may utilize a variety of multiplicities of infection (MOI). In certain embodiments, the MOI is higher that standard assays. Such a relatively high MOI may allow for infection of microorganisms that are present at very low amounts in the sample. For example, in certain embodiments, the bacteriophage concentration for the incubating step is greater than $1 \times 10^7$ PFU/mL.

In certain embodiments, the recombinant infectious agent may be purified so as to be free of any residual indicator protein that may be generated upon production of the infectious agent stock. Thus, in certain embodiments, and as described in more detail herein, the recombinant bacteriophage may be purified using cesium chloride isopycnic density gradient centrifugation prior to incubation with the sample. When the infectious agent is a bacteriophage, this purification may have the added benefit of removing bacteriophage that do not have DNA (i.e., empty phage).

As described further below, in certain embodiments, the method may employ a step whereby the microorganism of interest is concentrated or captured from a large volume of sample. Thus, in certain embodiments, the method may comprise a step for capturing the microorganism from the sample on a solid support before the incubating step.

In some embodiments, the method may include contacting a microorganism captured on a solid support (e.g., a magnetic bead or a filter substrate) with a plurality of the specific infectious agent (e.g., indicator bacteriophage) and allowing the bacteriophage to bind and infect the bacteria. In other embodiments, capture of the microorganism is not necessary for detection. A variety of solid supports may be used. In certain embodiments, the solid support may comprise a multi-well plate, a filter, a bead, or a lateral flow strip, a filter strip, filter disc, or filter paper, or thin films designed for culturing cells (e.g., PetriFilm by 3M). Other solid supports may also be appropriate.

The microorganism of interest may be purified from the sample by using a binding agent. For example, in certain embodiments, the capturing step further comprises binding microorganism with a capture antibody. The antibody may be used in conjunction with the solid support. For example, in certain embodiments, the capture antibody facilitates binding of the microorganism to the solid support.

The method of the invention may comprise various steps to increase sensitivity. For example, as discussed in more detail herein, the method may comprise a step for washing the captured and infected microorganism, after adding the bacteriophage but before incubating, to remove excess parental bacteriophage and/or luciferase or other reporter protein contaminating the bacteriophage preparation.

In contrast to assays known in the art, detection of the microorganism of interest may be completed without the need for culturing the sample as a way to increase the population of the microorganisms. Thus, in certain embodiments, detection of the microorganism of interest is completed in less time than a time period required for increasing the number of microorganisms by 4-fold or 10-fold using culturing for enrichment. For example, in certain embodiments the total time required for detection is less than 6.0 hours, 5.0 hours, 4.0 hours, 3.0 hours, 2.5 hours, 2.0 hours, 1.5 hours, 1.0 hour, 45 minutes, or less than 30 minutes.

Also, in contrast to assays known in the art, the method of the invention can detect individual microorganisms. Thus, in certain embodiments, the method may detect ≤10 cells of the microorganism (i.e., 1, 2, 3, 4, 5, 6, 7, 8, 9 microorganisms) present in a sample.

Thus, aspects of the present invention provide methods for detection of microorganisms in a test sample via an indicator moiety. In some embodiments, where the microorganism of interest is a bacteria, the indicator moiety may be associated with an infectious agent such as an indicator bacteriophage. The indicator moiety may react with a substrate to emit a detectable signal or may emit an intrinsic signal (e.g., fluorescent protein). In some embodiments, the detection sensitivity can reveal the presence of as few as 50, 20, 10, 9, 8, 7, 6, 5, 4, 3, or 2 cells of the microorganism of interest in a test sample. In some embodiments, even a single cell of the microorganism of interest may yield a detectable signal.

In some embodiments, the indicator moiety associated with the infectious agent may be detectable during or after replication of the infectious agent. Many different types of detectable biomolecules suitable for use as indicator moieties are known in the art, and many are commercially available. In some embodiments the indicator phage comprises an enzyme, which serves as the indicator moiety. In some embodiments, the genome of the indicator phage is modified to encode a soluble protein. In some embodiments, the indicator phage encodes a detectable enzyme. The indicator may emit light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, Oplophorus luciferase is the indicator moiety. In some embodiments, NANOLUC® is the indicator moiety. Other engineered luciferases or other enzymes that generate detectable signals may also be appropriate indicator moieties.

Detecting the indicator may include detecting emissions of light. In some embodiments, a luminometer may be used to detect the indicator (e.g., luciferase). However, other machines or devices may also be used. For example, a spectrophotometer, CCD camera, or CMOS camera may detect color changes and other light emissions.

In some embodiments, indicator phage is genetically engineered to contain the gene for an enzyme, such as a luciferase, which is only produced upon infection of bacteria that the phage specifically recognizes and infects. In some embodiments, the indicator moiety is expressed late in the viral life cycle. In some embodiments, as described herein, the indicator is a soluble protein (e.g., soluble luciferase) and is not fused with a phage structural protein that limits its copy number.

In various embodiments of the methods of the invention, the microorganism may be detected without any purification of the microorganisms from a sample. For example, in certain embodiments, a sample containing one or a few microorganisms of interest may be applied directly to an assay container such as a spin column, an microtiter well, or a filter and the assay is conducted in that assay container. Various embodiments of such assays are disclosed herein.

For example, aliquots of a test sample comprising bacteria may be applied to a spin column and after infection with a recombinant bacteriophage and an optional washing to remove any excess bacteriophage, the amount of soluble indicator detected will be proportional to the amount of bacteriophage that are produced by infected bacteria. Example 4 describes such an assay.

Or, aliquots of a test sample may be distributed directly into wells of a multi-well plate, indicator phage may be added, and after a period of time sufficient for infection, a lysis buffer may be added as well as a substrate for the indicator moiety (e.g., luciferase substrate for a luciferase indicator) and assayed for detection of the indicator signal. Examples 5-6 describe embodiments of the method performed on filter plates. Examples 7-9 herein describe assay variations called the "No concentration assay."

For example, in many embodiments, multi-well plates are used to conduct the assays. The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

Thus in some embodiments utilizing indicator phage, the invention comprises a method for detecting a microorganism of interest comprising the steps of capturing at least one sample microorganism; incubating the at least one microorganism with a plurality of indicator phage; allowing time for infection and replication to generate progeny phage and express soluble indicator moiety; and detecting the progeny phage, or preferably the indicator, wherein detection of the indicator demonstrates that the microorganism is present in the sample.

For example, in some embodiments the test sample microorganism may be captured by binding to the surface of a plate, or by filtering the sample through a bacteriological filter (e.g., 0.45 m pore size spin filter or plate filter). In an embodiment, the infectious agent (e.g., indicator phage) is added in a minimal volume to the captured sample directly on the filter. In an embodiment, the microorganism captured on the filter or plate surface is subsequently washed one or more times to remove excess unbound infectious agent. In an embodiment, media (e.g., Luria-Bertani also called LB broth herein) is added for further incubation time, to allow replication of phage and high-level expression of the gene encoding the indicator moiety. However, a surprising aspect of embodiments of the assays is that the incubation step only needs to be long enough for a single phage life cycle. The amplification power of using bacteriophage was previously thought to require more time, such that the phage would replicate for several cycles. A single replication of indicator phage is sufficient to facilitate sensitive and rapid detection according to some embodiments of the present invention.

Soluble indicator (e.g., luciferase) is released into the surrounding liquid upon lysis of the bacteria, which may then be measured and quantified. In an embodiment, the solution is then spun through the filter, and the filtrate collected for assay by addition of a substrate for the indicator enzyme (e.g., luciferase substrate). The filtrate may thus be removed from the capture solid support and analyzed in a new receptacle (e.g., in a luminometer), or the indicator signal may be measured directly on the filter.

In various embodiments, the purified parental indicator phage does not comprise the detectable indicator itself, because the parental phage may be purified before it is used for incubation with a test sample. Expression of late (Class III) genes occurs late in the viral life cycle. In some embodiments of the present invention, parental phage may be purified to exclude any existing indicator protein (e.g., luciferase). In some embodiments, expression of the indicator gene during progeny bacteriophage replication following infection of host bacteria results in a soluble indicator protein product. Thus, in many embodiments, it is not necessary to separate parental from progeny phage in the detecting step. In an embodiment, the microorganism is a bacterium and the indicator phage is a bacteriophage. In an embodiment, the indicator moiety is soluble luciferase, which is released upon lysis of the host microorganism.

Thus, in an alternate embodiment, the indicator substrate may be incubated with the portion of the sample that remains bound to a filter or bound to a plate surface. Accordingly, in some embodiments the solid support is a 96-well filter plate (or regular 96-well plate), and the substrate reaction may be detected by placing the plate directly in the luminometer.

For example, in an embodiment, the invention may comprise a method for detecting *E. coli* O157:H7 comprising the steps of: infecting cells captured on a 96-well filter plate with a plurality of parental indicator phage capable of expressing luciferase upon infection; washing excess phage away; adding LB broth and allowing time for phage to replicate and lyse the specific *E. coli* target (e.g., 30-90 minutes); and detecting the indicator luciferase by adding luciferase substrate and measuring luciferase activity directly in the 96-well plate, wherein detection of luciferase activity indicates that the *E. coli* O157:H7 is present in the sample.

In another embodiment, the invention may comprise a method for detecting *E. coli* O157:H7 comprising the steps of: infecting cells in liquid solution or suspension in a 96-well plate with a plurality of parental indicator phage capable of expressing luciferase upon infection; allowing time for phage to replicate and lyse the specific *E. coli* target (e.g., 30-90 minutes); and detecting the indicator luciferase by adding luciferase substrate and measuring luciferase activity directly in the 96-well plate, wherein detection of luciferase activity indicates that the *E. coli* O157:H7 is present in the sample. In such an embodiment no capturing step is necessary. In some embodiments, the liquid solution or suspension may be a consumable test sample, such as a vegetable wash. In some embodiments, the liquid solution or suspension may be vegetable wash fortified with concentrated LB broth or Nutrient Broth. In some embodiments, the liquid solution or suspension may be bacteria diluted in LB Broth.

In some embodiments, lysis of the microorganism may occur before, during, or after the detection step. Experiments suggest that infected unlysed cells may be detectable upon addition of luciferase substrate in some embodiments. Presumably, luciferase may exit cells and/or luciferase substrate may enter cells without complete cell lysis. Thus, for embodiments utilizing the spin filter system, where only luciferase released into the lysate (and not luciferase still inside intact bacteria) is analyzed in the luminometer, lysis is required for detection. However, for embodiments utilizing filter plates or 96-well plates with sample in solution or suspension, where the original plate full of intact and lysed cells is directly assayed in the luminometer, lysis is not necessary for detection.

In some embodiments, the reaction of indicator moiety (e.g., luciferase) with substrate may continue for 30 minutes or more, and detection at various time points may be desirable for optimizing sensitivity. For example, in embodiments using 96-well filter plates as the solid support and luciferase as the indicator, luminometer readings may be taken initially and at 10- or 15-minute intervals until the reaction is completed.

Surprisingly, high concentrations of phage utilized for infecting test samples (i.e., high MOI) have successfully achieved detection of very low numbers of target microorganism in a very short timeframe. The incubation of phage with a test sample in some embodiments need only be long enough for a single phage life cycle. In some embodiments, the bacteriophage concentration for this incubating step is greater than $7 \times 10^6$, $8 \times 10^6$, $9 \times 10^6$, $1.0 \times 10^7$, $1.1 \times 10^7$, $1.2 \times 10^7$, $1.3 \times 10^7$, $1.4 \times 10^7$, $1.5 \times 10^7$, $1.6 \times 10^7$, $1.7 \times 10^7$, $1.8 \times 10^7$, $1.9 \times 10^7$, $2.0 \times 10^7$, $3.0 \times 10^7$, $4.0 \times 10^7$, $5.0 \times 10^7$, $6.0 \times 10^7$, $7.0 \times 10^7$, $8.0 \times 10^7$, $9.0 \times 10^7$, or $1.0 \times 10^8$ PFU/mL.

Success with such high concentrations of phage is surprising because the large numbers of phage were previously associated with "lysis from without," which killed target cells and thereby prevented generation of useful signal from earlier phage assays. It is possible that the clean-up of prepared phage stock described herein helps to alleviate this problem (e.g., clean-up by cesium chloride isopycnic density gradient ultracentrifugation), because in addition to removing any contaminating luciferase associated with the phage, this clean-up may also remove ghost particles (particles that have lost DNA). The ghost particles can lyse bacterial cells via "lysis from without," killing the cells prematurely and thereby preventing generation of indicator signal. Electron microscopy demonstrates that a crude JG04 lysate (i.e., before cesium chloride clean-up) may have greater than 50% ghosts. These ghost particles may contribute to premature death of the microorganism through the action of many phage particles puncturing the cell membrane. Thus ghost particles may have contributed to previous problems where high PFU concentrations were reported to be detrimental. Moreover, a very clean phage prep allows the assay to be performed with no wash steps, which makes the No Concentration assay possible.

Spin Column Assays

Figure 5:
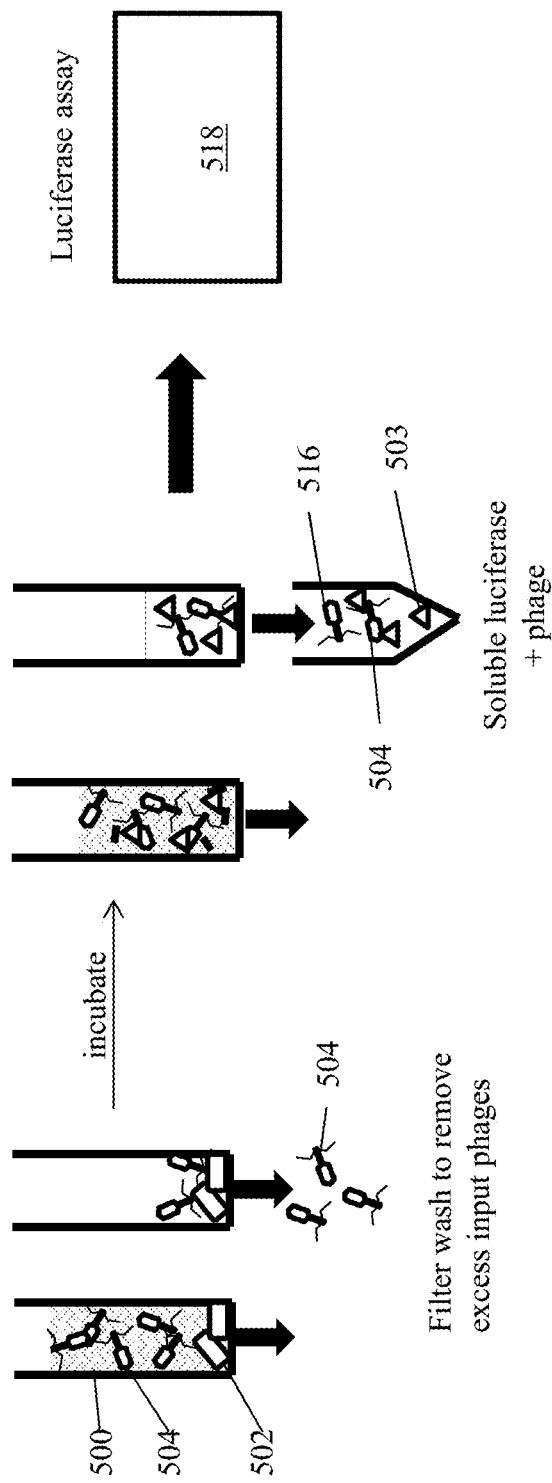
FIG. 5 depicts the use of indicator phage encoding a soluble luciferase to detect bacterial cells via detection of luciferase generated from replication of progeny phage during infection of the bacterial cells, according to an embodiment of the invention FIG. 6 demonstrates sensitivity for detection of target bacteria using indicator phage with spin columns, according to an embodiment of the invention. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG).

FIG. 5 shows a strategy of using indicator phage that produce soluble luciferase according to an embodiment of the invention. In this method, the phage (e.g., T7, T4, or JG04 phage) may be engineered to express a soluble luciferase during replication of the phage. Expression of luciferase is driven by a viral capsid promoter (e.g., the bacteriophage T7 or T4 late promoter), yielding high expression. Parental phage will be free of luciferase, so the luciferase detected in the assay must come from replication of progeny phage during infection of the bacterial cells. Thus, there is generally no need to separate out the parental phage from the progeny phage.

In these experiments, at least part of the sample 500 comprising the *E. coli* bacteria 502 to be quantified is placed in a spin column filter and centrifuged to remove the LB broth, and an appropriate multiplicity of T7 phage 504 genetically engineered to express soluble luciferase 503 are added. The infected cells may be incubated for a time sufficient for replication of progeny phage and cell lysis to occur (e.g., 30-90 minutes at 37° C.). The parental 504 and progeny phage 516 plus free luciferase 503 in the lysate may then be collected, e.g., by centrifugation, and the level of luciferase in the filtrate quantified using a luminometer 518. Alternatively, a high through-put method may be employed where bacterial samples are applied to a 96-well filter plate, and after all manipulations listed above are performed, may be directly assayed for luciferase in the original 96-well filter plate without a final centrifugation step.

Data from example experiments of embodiments of the invention are shown in FIGS. 6-9. The results demonstrate alternative embodiments of the invention utilizing indicator phage to assay sample bacteria via detection of soluble luciferase produced by the infection of bacteria with indicator phage. Indicator detection level calibrated as relative light units (RLU) is plotted against cell concentrations determined from the standard overnight colony forming unit (CFU) assay and expressed as "cells per assay," thus demonstrating similar sensitivity. Increasing luciferase signal corresponds to increasing input sample cells, demonstrating a dose-dependent response.

Figure 6:
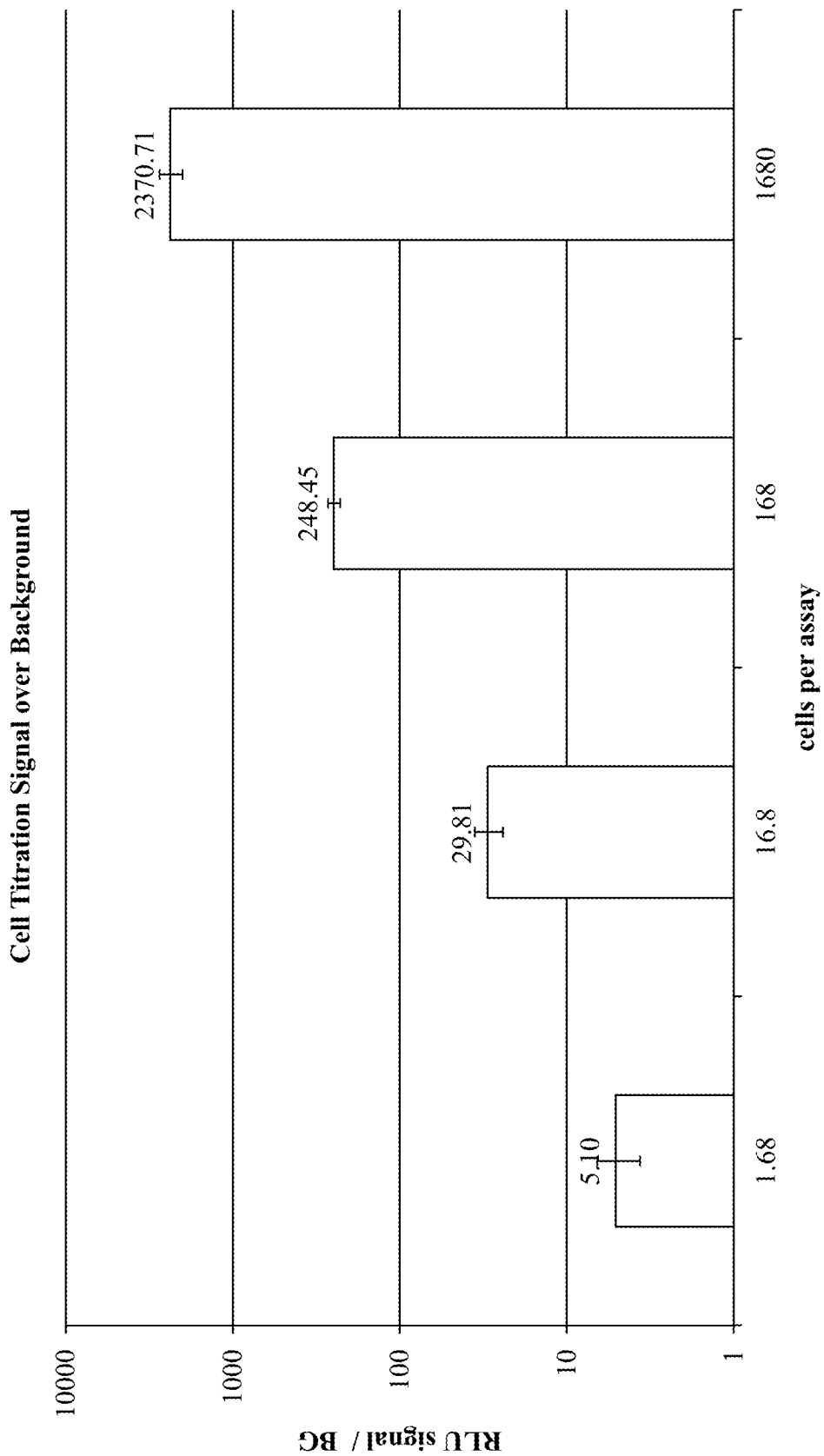

As shown in FIG. 6 the method of the invention may demonstrate high sensitivity for detection of target bacteria using indicator phage with spin column filters. In this assay, a test sample may be collected on a spin filter by centrifugation and incubated with indicator phage comprising a gene for soluble luciferase (e.g., as shown in FIG. 1). Following incubation for a time sufficient for infection (e.g., 10 minutes at room temperature), the filter may be washed and spun to remove excess input phage. Media (e.g., LB broth) may be added and incubated (e.g., for 30 minutes at 37° C.) to allow replication of progeny phage and lysis of bacteria. Filters may be spun again to remove the filtrate, which may be transferred to a luminometer plate, and a luciferase assay was performed (e.g., using a Promega® luminometer with injection of Luciferase Assay Reagent, Promega, Inc.). The cell count may be corrected according to the number of colonies in the parallel CFU assay.

As shown in FIG. 6, approximately 1,700 bacterial cells may be detected in the original sample, and further assay of serial dilutions may demonstrate detection down to an average of 1.7 cells, corresponding to actual detection of 1 or 2 cells. This shows that infection of as few as 1 to 3 *E. coli* cells can provide a measurable signal, via luciferase activity. This also shows statistical significance for the presence or absence of even a single cell over background (p value=0.018).

Figure 7:
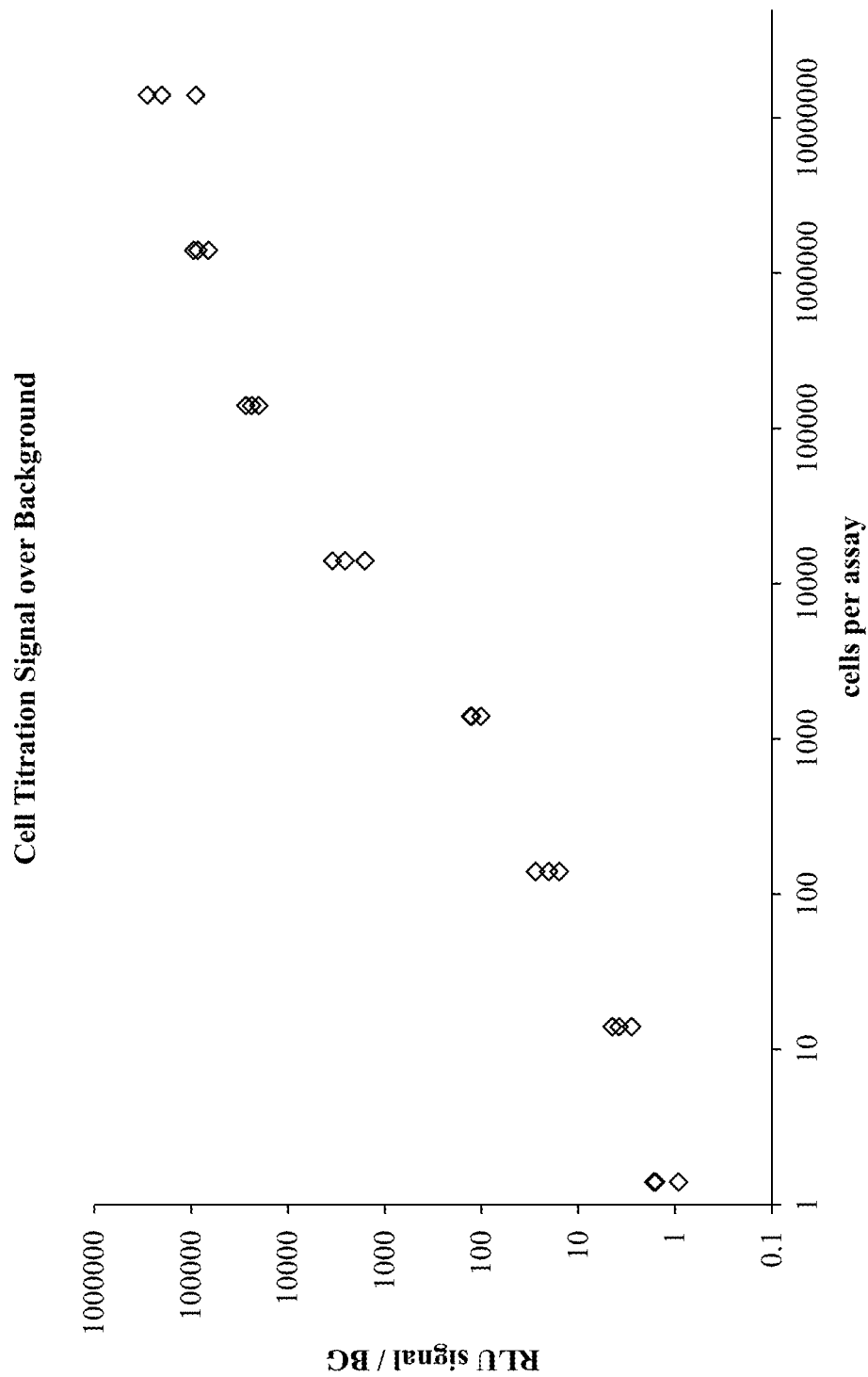
FIG. 7 demonstrates detection of target bacteria over a range of titers using indicator phage with spin columns, according to an embodiment of the invention. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG).

FIG. 7 demonstrates the very large detection range of the same method described for the assay of FIG. 5 using serial dilutions across a broader range of cell numbers. This shows detection may range from an average of 1.4 cells to 14 million cells.

Filter Plate Assays

Figure 8:
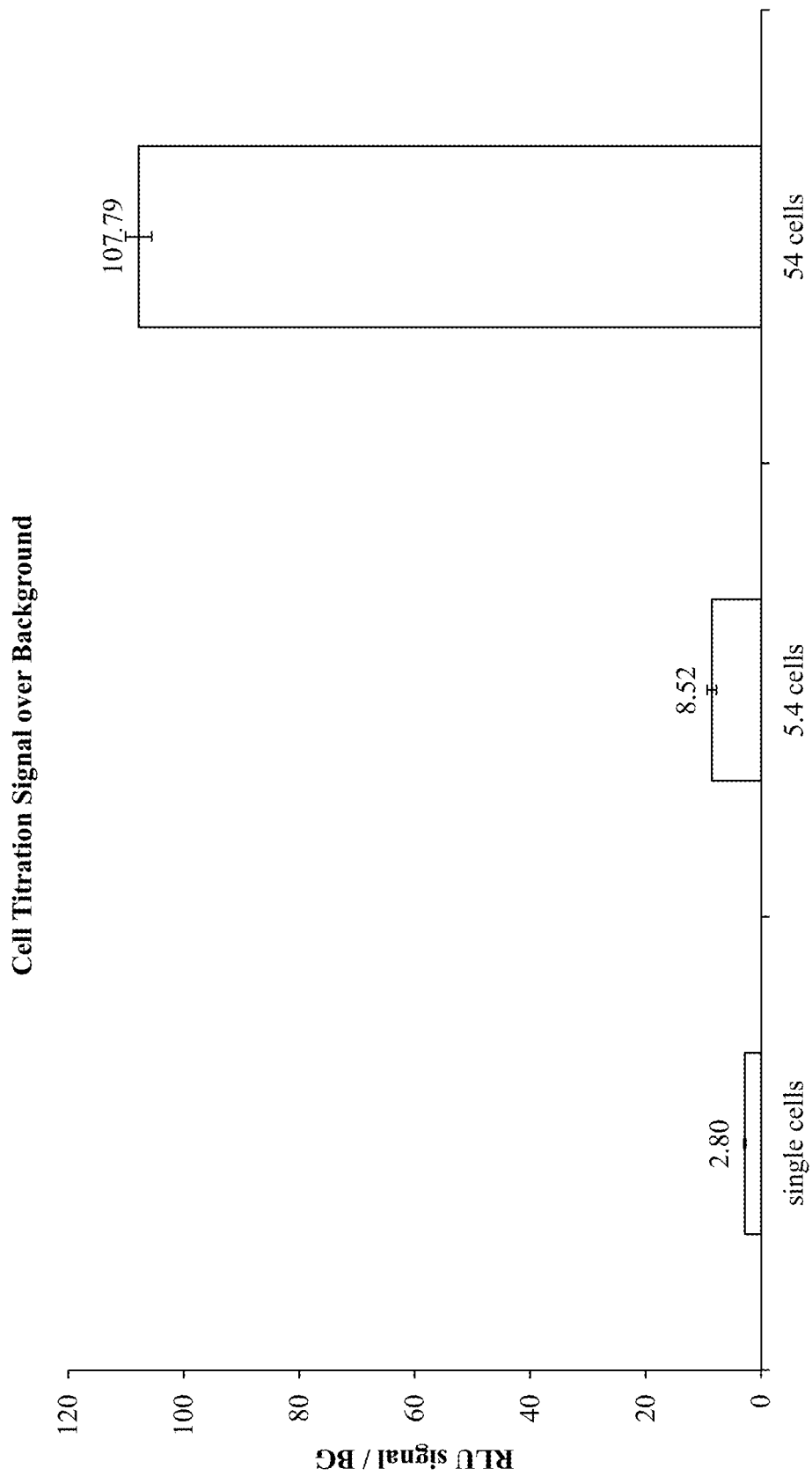
FIG. 8 demonstrates sensitivity for detection of target bacteria using indicator phage with 96-well filter plates, according to an embodiment of the invention. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG).

As noted above, in certain embodiments, the assay may be conducted directly in the well of a microtiter assay plate. For example, FIG. 8 demonstrates the use of indicator phage with a 96-well filter plate for capture and detection. The method is the same as described above for FIG. 5, except that the entire assay is performed in a 96-well filter plate, including the luciferase reaction. This embodiment reduces manipulations and materials compared to the spin filter method. The reduced manipulations and use of a 96-well filter plate is amenable to a high throughput assay situation, and may be adapted for use with a liquid handling robot according to embodiments of the invention. FIG. 8 shows that in this embodiment, a 96-well filter plate may be used to detect single E. coli cells (0.5 cells average assayed, confirming that about one-half of the wells received single cells), 5.4 and 54 cells.

Figure 9:
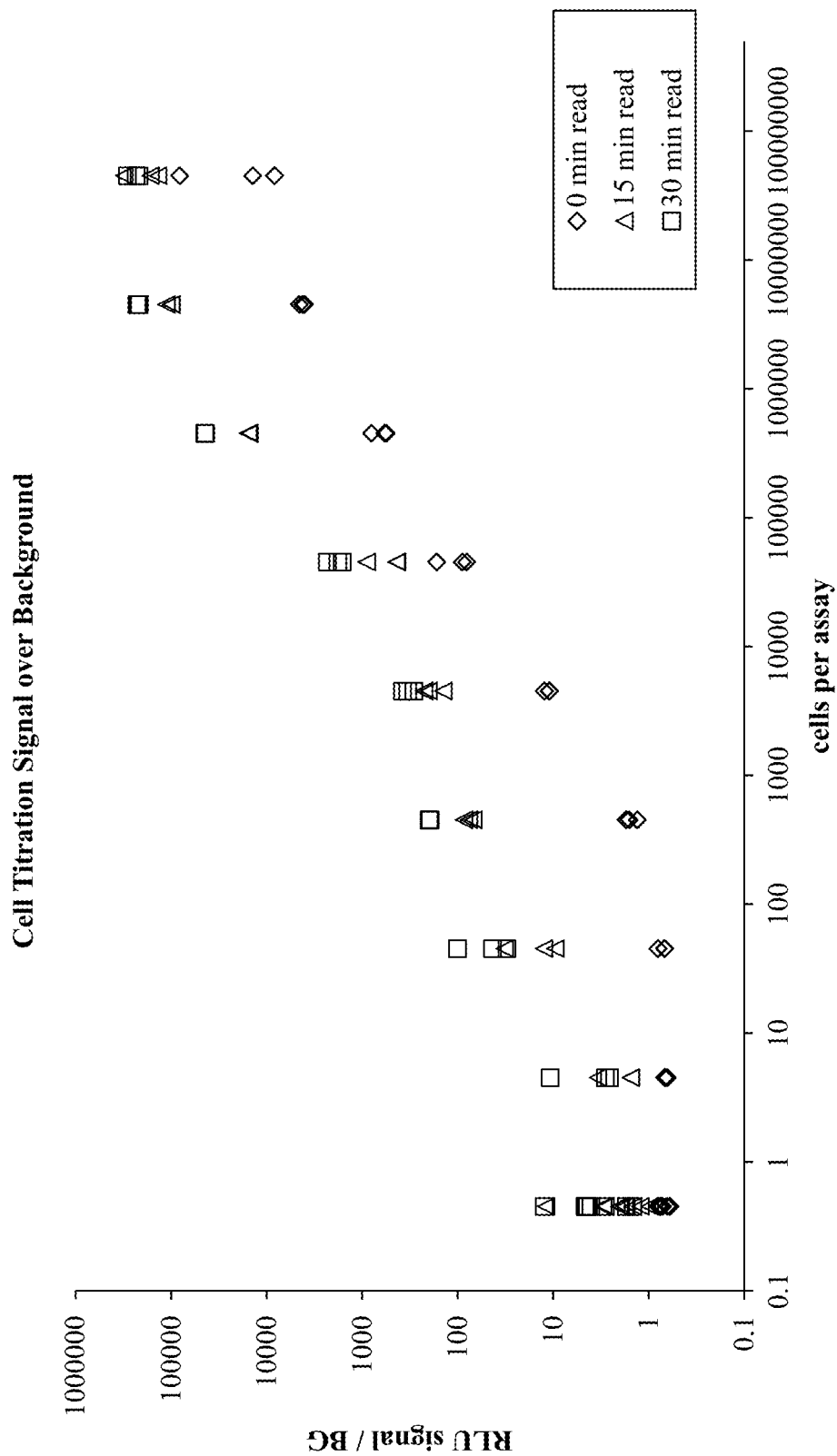
FIG. 9 demonstrates detection of target bacteria over a range of titers using indicator phage with 96-well filter plates, according to an embodiment of the invention. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG). The detection of luciferase activity may be continued for an extended period of time. Here, reading ◇ represents 0 time (i.e., a baseline control); Δ after 15 minutes (min); and □ after 30 minutes.

FIG. 9 demonstrates that in certain embodiments, a very large detection range of cell concentrations may be achieved for the same assay, using the 96-well system, from less than 1 cell per assay on average (single cells) to at least 14 million cells per assay. Multiple reads at different time points after addition of the luciferase substrate may demonstrate varied sensitivity. Sensitivity for detecting <10 cells was achieved with a 15 minute read, and sensitivity down to single cell levels may be achieved at the 30 minute read. Thus time may be saved if tens of cells or less need not be detected. Note signal increases in response to increased number of input sample cells in both experiments, again demonstrating a dose-dependent response.

Figure 10:
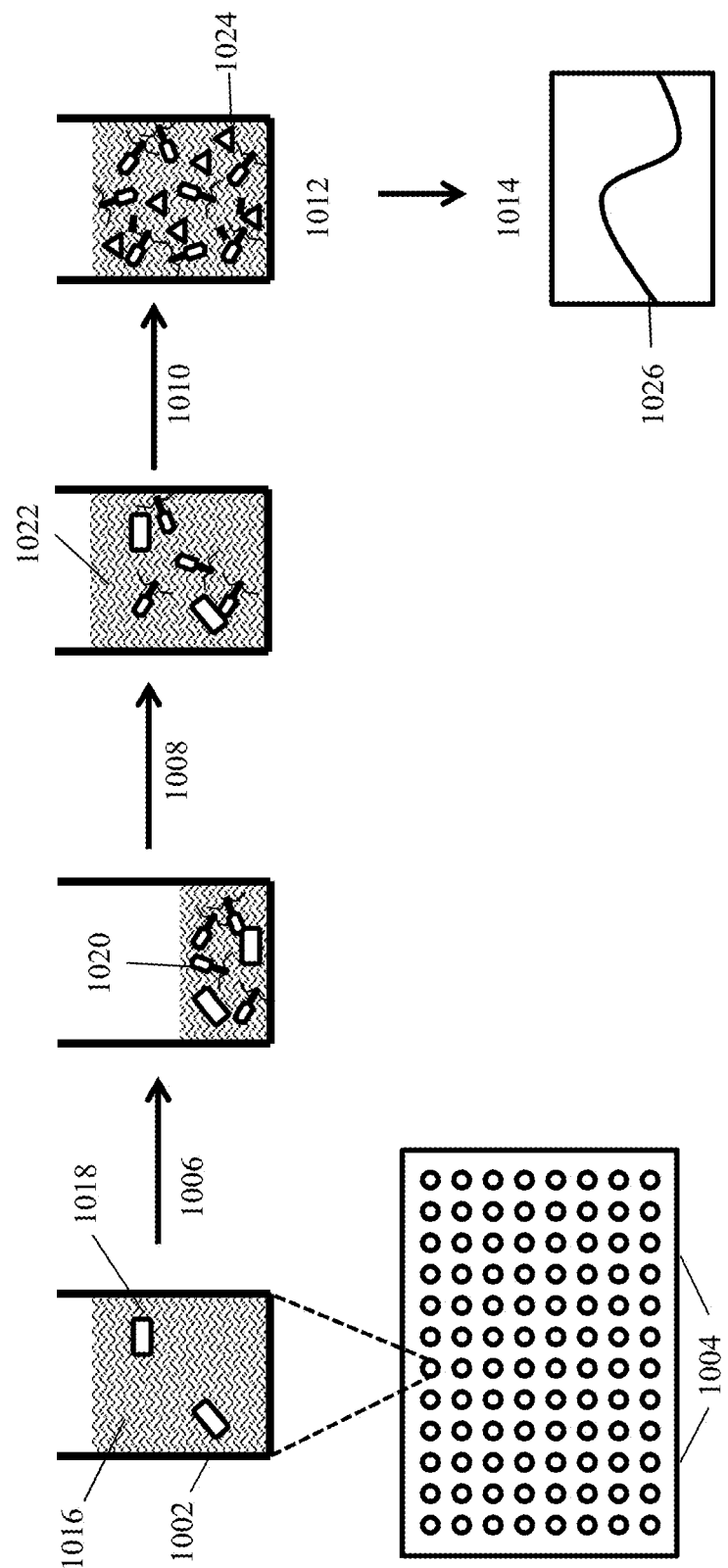
FIG. 10 depicts a filter plate assay for detecting bacteria of interest using a modified bacteriophage according to an embodiment of the invention where bacteria and recombinant phage are incubated on filter plates and after generation of progeny bacteriophage the indicator protein is detected directly without removal of the incubation medium.
Figure 11:
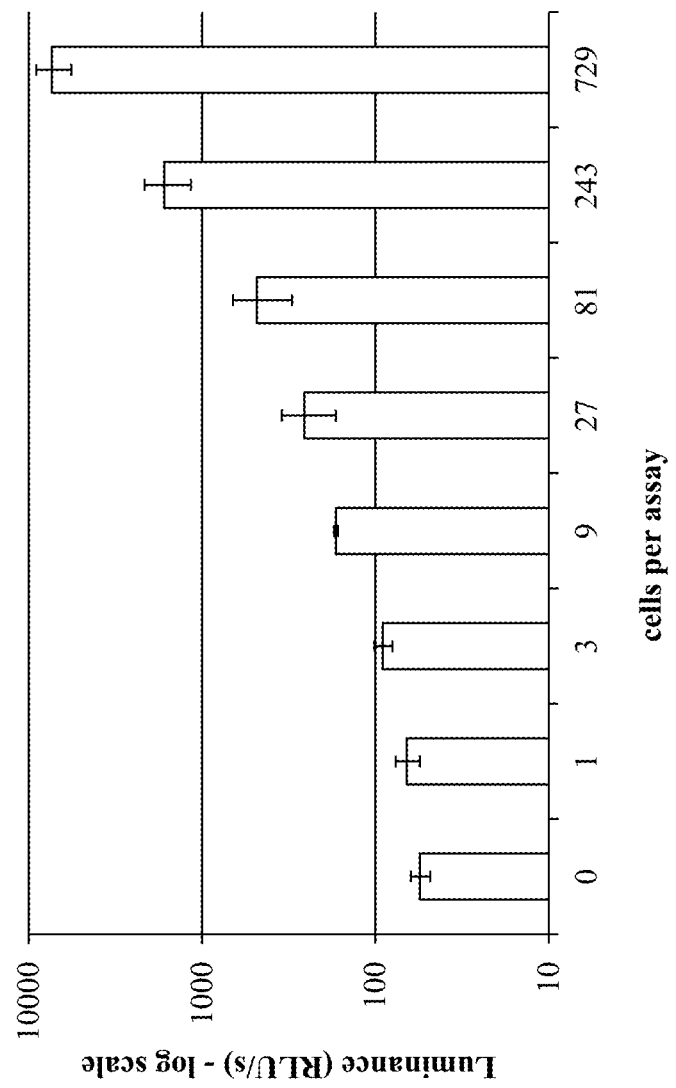
FIG. 11 shows results from a filter plate assay using JG04-NANOLUC® phage to detect E. coli O157:H7 cells in samples with known cell numbers. The approximate number of E. coli O157:H7 cells in each assay is indicated on the X-axis. The signal provided by the soluble luciferase produced upon infection of the bacteria is shown on the Y-axis as relative luminal units (RLU) over background (BG) signal (i.e., no cells) (RLU/BG).

FIG. 10 depicts a filter plate assay for detecting bacteria of interest using a modified bacteriophage according to an embodiment of the invention. An actual experiment utilizing this assay is described in Example 6. Briefly, samples 1016 that include a bacterium of interest 1018 may be added to wells 1002 of a multi-well filter plate 1004 and spun 1006 to concentrate the samples by removal of liquid from the sample. Genetically modified phage 1020 are added to wells and incubated with additional media added for enough time sufficient for adsorption 1008 followed by infection of target bacteria and advancement of the phage life cycle 1010 (e.g., ~45 minutes). Finally, luciferase substrate is added and reacts with any luciferase present 1024. The resulting emission is measured in a luminometer 1014 which detects luciferase activity 1026. FIG. 11 shows results from a filter plate assay as described in FIG. 10, using JG04-NANO-LUC® phage to detect E. coli O157:H7 cells in samples with known cell numbers. Student's t-Test showed a p value of 0.034 between 0 cells and 1 cell per assay, demonstrating statistical significance.

Figure 12:
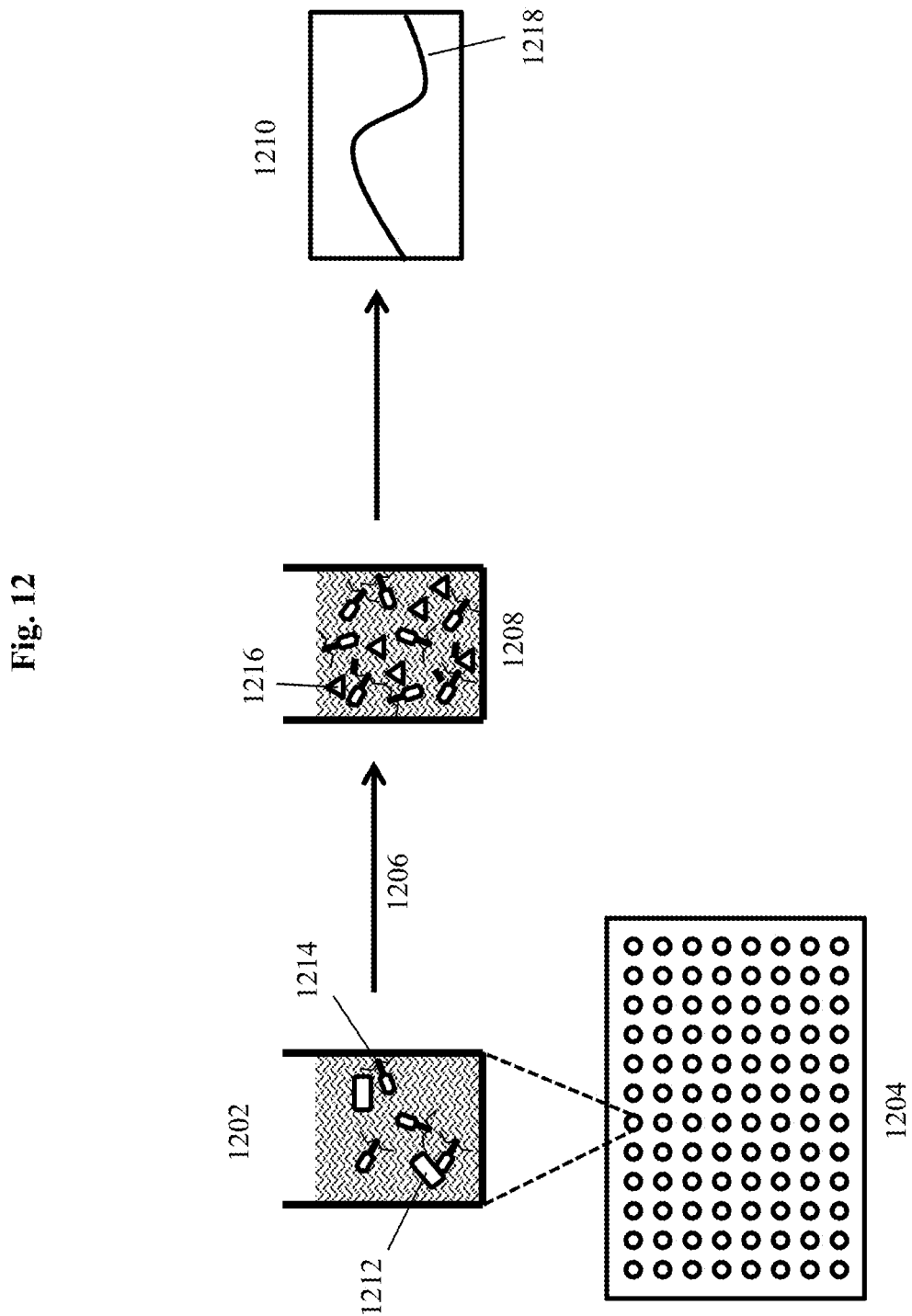
FIG. 12 depicts a "No Concentration Assay" for detecting a bacterium of interest using a modified bacteriophage according to an embodiment of the invention.

In certain embodiments, the assay may be performed without concentrating the bacterium on or near the capture surface. FIG. 12 illustrates a "No Concentration Assay" for detecting a bacterium of interest using a modified bacteriophage according to an embodiment of the invention. Aliquots of indicator phage 1214 are distributed to the individual wells 1202 of a multi-well plate 1204, and then test sample aliquots containing bacteria 1212 are added and incubated 1206 (e.g., 45 minutes at 37° C.) for a period of time sufficient for phage to replicate and generate soluble indicator 1216 (e.g., luciferase). The plate wells 1208 containing soluble indicator and phage may then be assayed 1210 to measure the indicator activity on the plate 1218 (e.g., luciferase assay). Actual experiments utilizing this method are described in Examples 7-9. In this embodiment, the test samples are not concentrated (e.g., by centrifugation) but are simply incubated directly with indicator phage for a period of time and subsequently assayed for luciferase activity.

Figure 13:
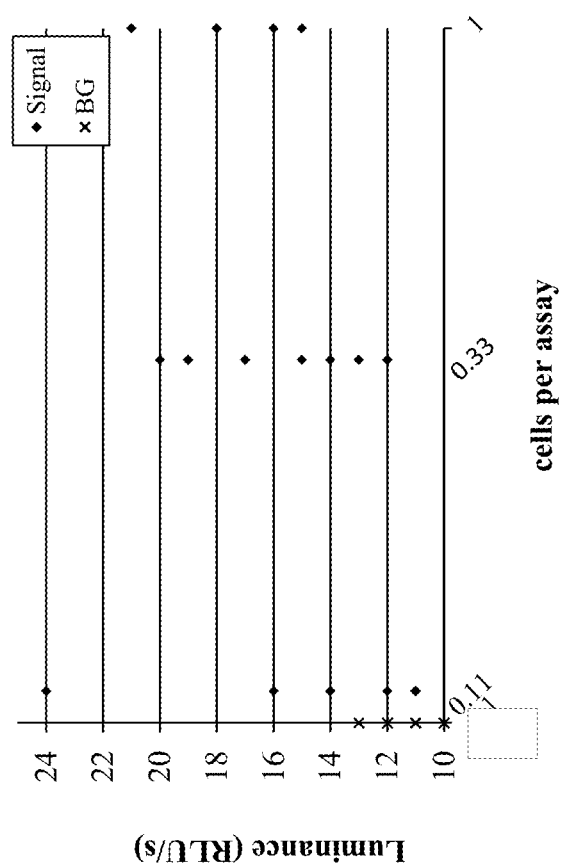
FIG. 13 shows results from a No Concentration Assay using JG04-OpLuc phage to detect E. coli O157:H7 cells in samples with known cell numbers in the low number range. The approximate number of E. coli O157:H7 cells in each assay is indicated on the X-axis. The signal provided by the soluble luciferase produced upon infection of the bacteria is shown on the Y-axis as relative luminal units (RLU) as compared to background (X) signal (i.e., no cells).

FIG. 13 shows results from a No Concentration Assay type assay as depicted in FIG. 12 using JG04-OpLuc phage to detect E. coli O157:H7 cells in samples with known cell numbers in the low number range (i.e., very diluted cell samples). This experiment, as described in Example 7, demonstrates that statistically significant differences can be seen between the signal from 0 cells and 1 cell per assay (p value=0.0024 by ANOVA test), demonstrating the ability to detect single cells. Thus the assay is surprisingly sensitive. Samples with fewer than 1 cell per well appear to show a proportional number of wells above the background signal.

Figure 14:
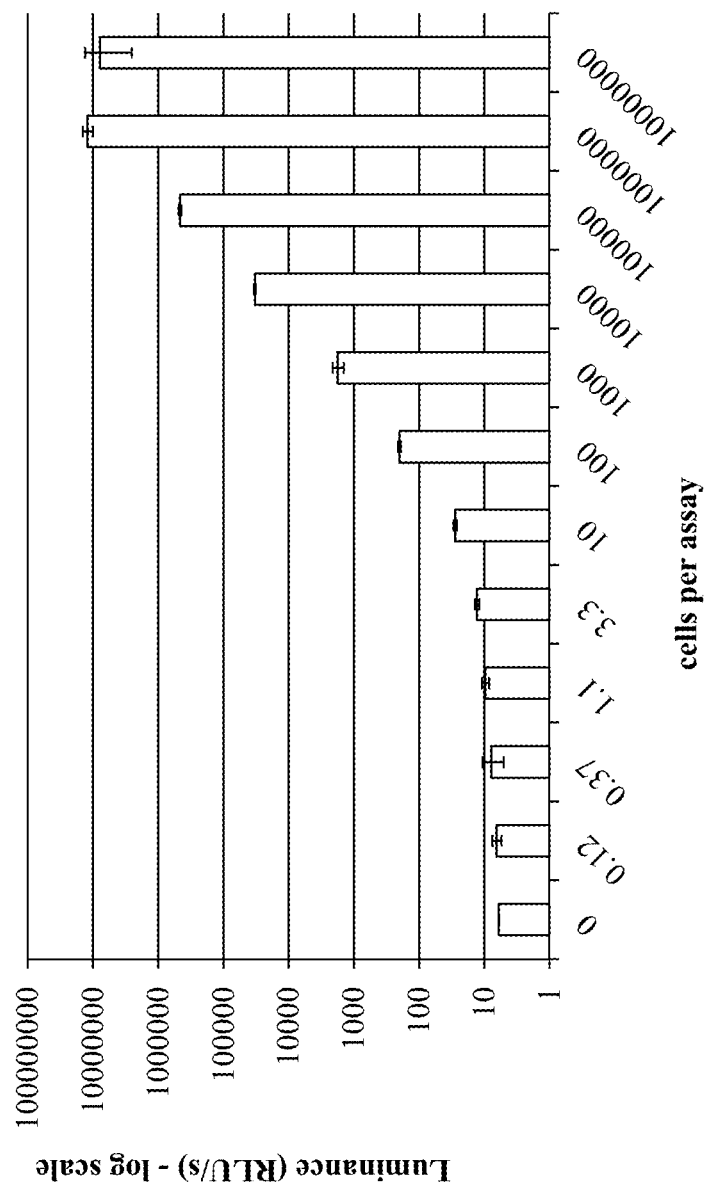
FIG. 14 shows results from a No Concentration Assay using JG04-OpLuc phage to detect E. coli O157:H7 cells in samples with known cell numbers in the low to high number range. The approximate number of E. coli O157:H7 cells in each assay is indicated on the X-axis. The signal provided by the soluble luciferase produced upon infection of the bacteria is shown on the Y-axis as relative luminal units (RLU).

FIG. 14 shows results from a No Concentration Assay using JG04-OpLuc phage to detect E. coli O157:H7 cells in samples with known cell numbers in the very low to very high number range (i.e., samples containing less than 1 cell per assay to millions of cells). This experiment, as described in Example 8, demonstrates statistically significant differences between the signal from 0 cells and 1.1 cell per assay (p value=0.000702 by Student's t-Test), demonstrating the ability to detect single cells. More bacterial cells per assay show increasing signal in a dose dependent manner, up to at least $10^6$ bacterial cells/assay, surprisingly demonstrating a very wide range of detection.

Figure 15:
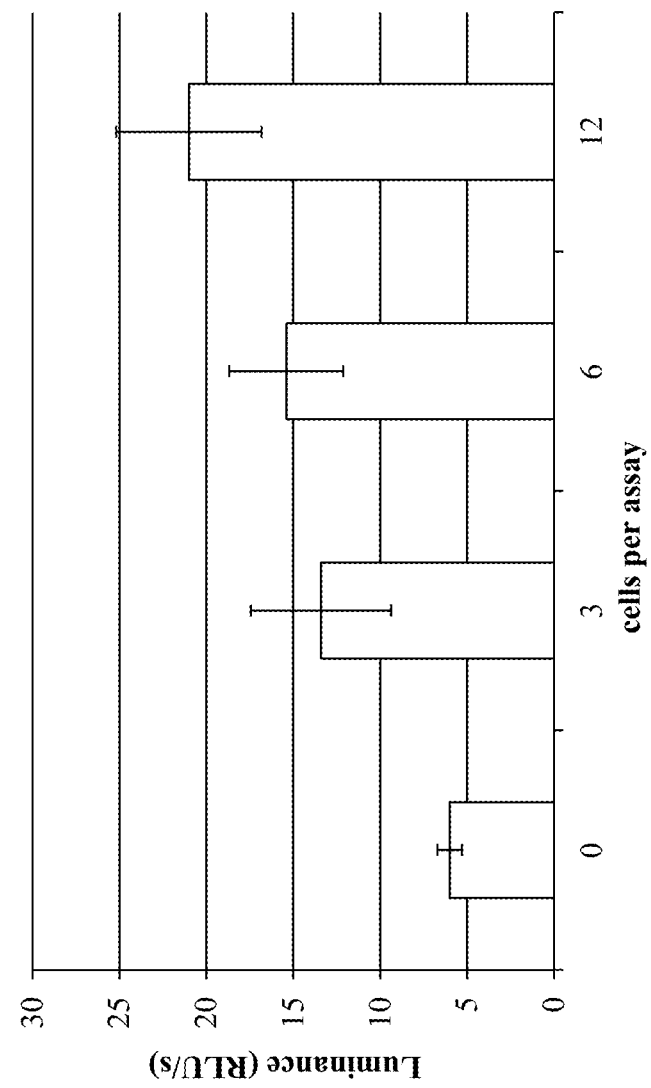
FIG. 15 shows results from a No Concentration Assay using JG04-OpLuc phage to detect E. coli O157:H7 cells in Vegetable Wash samples with known cell numbers. The approximate number of E. coli O157:H7 cells in each assay is indicated on the X-axis. The signal provided by the soluble luciferase produced upon infection of the bacteria is shown on the Y-axis as relative luminal units (RLU).

FIG. 15 shows results from a No Concentration Assay using JG04-OpLuc phage to detect E. coli O157:H7 cells in Vegetable Wash samples with known cell numbers, as described in Example 9.

To prepare the vegetable wash, vegetable leaves (e.g., spinach or lettuce) may be weighed and added to a clean plastic bag. One mL of LB (+/− 0.01-0.05% Tween®20) was added per each gram (g) of vegetable. Leaves and solution are mixed manually for a few minutes. Liquid is then extracted from the plastic bag and used as the "vegetable wash." Using this method, ~1 million bacteria were found to reside on a single spinach leaf (1-2 g)

The assay is quantitative in that the signal detected is proportional to the amount of the microorganism of interest in the sample. For example, in the experiment depicted in FIG. 15, known numbers of E. coli O157:H7 cells were added to vegetable wash samples to simulate contamination of vegetables with pathogenic bacteria. The experiment using vegetable wash samples demonstrates marked differences between the signal from 0 cells and 3 cells per assay, demonstrating the ability to detect single-digit cell numbers in vegetable wash. Using more bacterial cells per assay shows increasing signal in a dose dependent manner. The vegetable wash contains about $10^6$ non-target bacteria/mL, corresponding to at least $10^5$ non-target bacteria per sample in this assay (including the 0 cells E. coli O157:H7 control). The ability to discern as few as 3 target bacterial cells from $10^5$ non-target bacteria is surprising and again demonstrates the specificity of the assay.

Capture of the Microorganism Prior to Exposure to Infectious Agent

In some embodiments, the present invention comprises methods and systems that do not require a step for capturing microorganisms. Other embodiments allow physical isolation of bacterial cells from a sample. Methods described herein may serve as means to facilitate detection of low levels of a microorganism (e.g., a single microorganism) present in a sample. A capturing step may be based on a specific binding agent, such as an antibody that recognizes the microorganism of interest, or it may be based on selection for other features of the microorganism, such as size fractionation.

In some embodiments, a microorganism is captured based on physical features other than molecular specificity (e.g., size). In some embodiments, the present invention utilizes the physical size of the microorganism to capture it on a solid support. In some embodiments, the solid support is a filter. For example, filtering a sample through a bacteriological filter (e.g., 0.45 µm pore size spin filter) allows smaller substances to pass through while retaining intact bacteria. Alternatively, a plate filter may be used to capture a microorganism, or a variety of other filter devices may be used (e.g., 96-well filter plate).

For example, the method may include the step of collecting the microorganism on a solid support, such as for example by filtering a sample through a bacteriological filter. After size-based capture, any binding agent that specifically targets the microorganism of interest may be employed. For example, an infectious agent may be incubated with the captured microorganism, in order to specifically target and identify the microorganism of interest. Other methods of isolating the microorganisms in the sample may be used. In some embodiments, detection steps may be performed before, simultaneously with, or after such capture steps.

In some embodiments, binding agents with high specificity for a microorganism of interest may be employed as a means to facilitate specific capture of low levels of a microorganism (e.g., a single microorganism) present in a sample. In some embodiments, a large volume of liquid sample to be tested may need to be effectively concentrated before further testing.

For example, a single bacterium, which may have a volume of about one cubic micrometer, can be isolated from a one-milliliter sample having a volume of $10^{12}$ cubic micrometers. In such embodiments the capturing step may comprise contacting the sample with a plurality (an excess) of affinity-purified capture antibodies or antibody fragments.

Some embodiments utilize affinity-purified and/or reverse-purified surface-specific antibodies or antibody fragments generated against antigenic molecules found on the surface of a specific microorganism of interest. Such antibodies or antibody fragments can specifically identify a microorganism for capture or detection purposes or both. Antibodies demonstrating specific recognition of surface antigens on a wide variety of bacteria or other microorganisms are available commercially from a number of sources, such as Kirkegaard & Perry Laboratories, Inc. (KPL) or Abcam.

In some embodiments of the invention, affinity-purified and/or reverse-purified surface-specific antibodies that recognize the microbial surface antigens of a particular microorganism (e.g., *E. coli* O157:H7) do not recognize other similar microorganisms (e.g., *E. coli* B). In some embodiments, antibodies specific to, e.g., *E. coli* B or *E. coli* O157:H7 do not recognize cells of *Salmonella typhimurium* or *Staphylococcus epidermidis*. This represents another surprising discovery, as many bacteria have, e.g., surface lipopolysaccharide (Gram-negative bacteria) or lipoteichoic acid (Gram-positive bacteria) molecules that were previously believed to be highly similar, especially between closely related species.

Methods for antibody-based capture disclosed herein may be adapted to any bacterium or other microorganism of interest (e.g. pathogenic microorganisms) for which surface-specific antibodies are available which do not cross-react with other microorganisms.

For example, in some embodiments, a capturing step of the invention may use capture antibodies or antibody fragments that are specific for the microorganism to facilitate capture of the microorganism. In some embodiments, capture antibodies may be conjugated to a chemical moiety that binds with another binding agent attached to a solid support (e.g. beads or a plate surface). For example, in some embodiments, the capture antibody may be biotinylated to facilitate binding to streptavidin bound to a solid support. In some embodiments, the solid support comprises magnetic beads. In other embodiments, a solid support comprises a plate surface or the surfaces of a multi-well plate (e.g., an ELISA plate). For example, an ELISA plate may be coated with an antibody that specifically recognizes the microorganism of interest.

In certain embodiments, the microorganism may be isolated from other components of the sample through binding of the microorganism to a free capture antibody or antibody fragment that subsequently binds to a solid support. In some embodiments, the capture antibody or antibody fragment comprises a binding agent (e.g., biotin) that binds to a second agent (e.g., streptavidin) bound to a solid support.

In some embodiments, e.g., if the capture antibody is labeled with biotin, the method may further comprise contacting the sample with a plurality of magnetic streptavidin-coated beads to bind the bacterium-antibody complex, and sequestering the bead-antibody-bacterium complex with a magnet to isolate the bacteria. Or, other methods of purifying the biotin-antibody: bacterium complex may be used. With such embodiments, a bacterium in a one-milliliter sample can be concentrated to about one microliter (~1000-fold), facilitating further detection and/or quantification by methods described herein.

Thus, in some embodiments, the invention comprises a method for detecting a microorganism of interest wherein the capture step comprises specifically isolating the microorganism from other components in the sample.

Alternatively, in some embodiments the capturing step may be based on other features of the microorganism of interest, such as size. In embodiments utilizing size-based capture, the solid support may be a spin column filter. In some embodiments, the solid support comprises a 96-well filter plate. Or, the solid support for capture may be a location on an array, or a mobile support, such as a bead.

Thus, in some embodiments, a target microorganism may be captured and isolated from a large volume before detection using the methods described above. For example, the microorganism may be specifically isolated using attributes of a capture antibody or antibody fragment. In some embodiments, the capture antibody is biotinylated such that it facilitates subsequent binding of cell-antibody complexes to magnetic streptavidin beads. The biotin on the antibody can bind tightly to the streptavidin on the magnetic bead. Or the capture antibody may be conjugated to another protein or other molecule, which facilitates capture on beads or another solid support. Such embodiments may provide increased sensitivity, particularly where the initial sample volume is large. Thus, the method may comprise the steps of attaching a plurality of binding agents that can specifically bind to a surface antigen on the microorganism of interest, which thereby facilitates binding to a capture solid support.

Alternatively, another chemical moiety that binds the anti-bacterium antibody may be used to coat magnetic beads. For example, a bead coated with a secondary antibody that recognizes or binds the anti-bacterium antibody may be used. The bacteria bound to the beads may then be isolated. In an embodiment, the efficiency of capture may be quantified by plating the bacteria bound to the beads and the unbound supernatant fraction and counting the resultant colonies (CFU). In other embodiments, the signal generated by reaction with substrate (i.e., substrate reagent for the indicator moiety) is measured for detection.

In some embodiments, the specificity of antibodies is demonstrated using specific capture on a solid support. A method of the invention may comprise the step of retrieving and concentrating a microorganism (e.g., a bacterium) from a sample by the use of a substrate with a binding agent specific for the microorganism. In an embodiment, the binding agent is immobilized on a solid support (e.g. magnetic beads) or is free and subsequently immobilized on a solid support. The immobilized microorganism may then be removed from the sample (e.g., by aspiration, decanting, magnetic force, or other appropriate isolation techniques) and detected by a variety of techniques.

Figure 16:
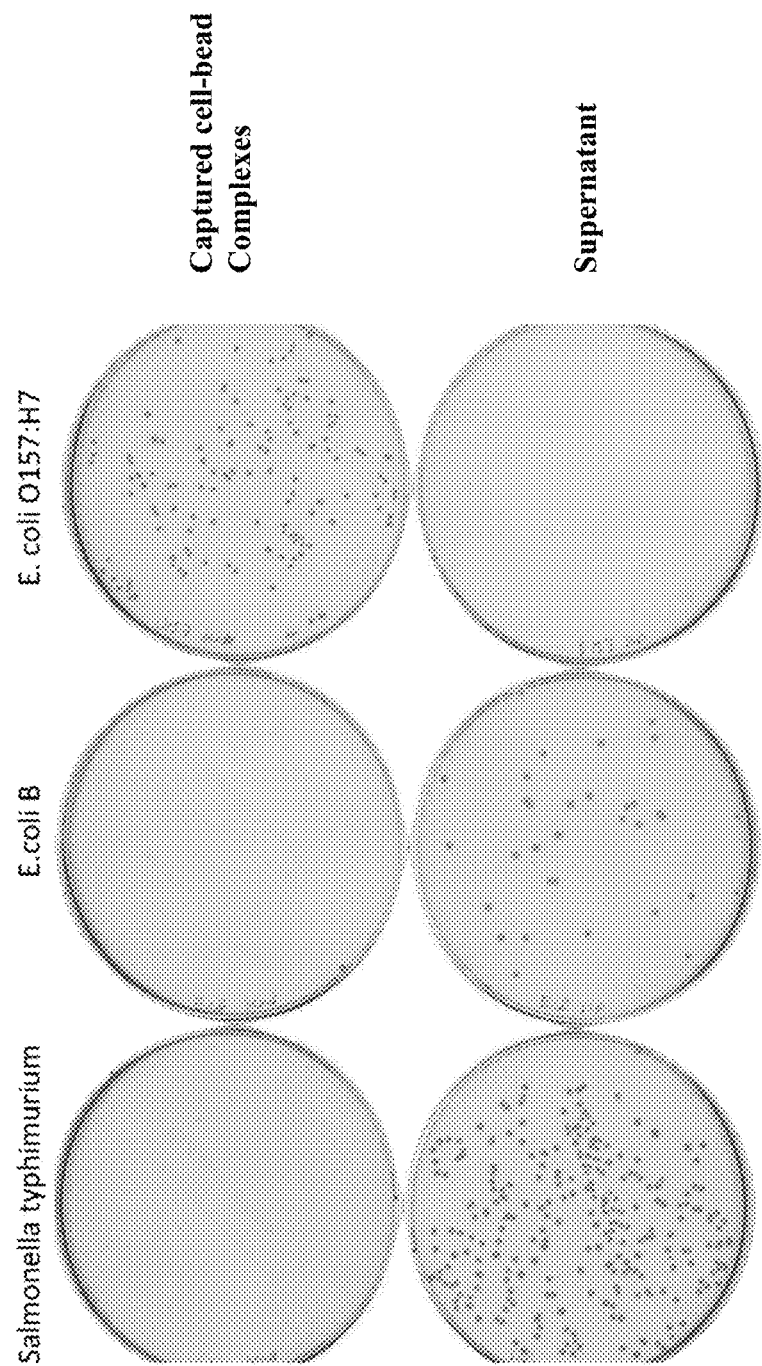
FIG. 16 demonstrates specific and quantitative capture of E. coli O157:H7 using affinity-purified, surface-specific antibodies, according to an embodiment of the invention.

FIG. 16 depicts an example embodiment of specific capture of E. coli O157:H7 but not E. coli B or S. typhimurium from samples by the use of antibodies produced against intact E. coli O157:H7. Thus, in certain embodiments magnetic beads coated with streptavidin may be used to isolate E. coli O157:H7 preincubated with free biotinylated polyclonal antibodies (KPL), affinity-purified and reverse-purified to minimize cross-reactivity with other microbial species. In certain embodiments, the E. coli O157:H7 will only be present in the captured fraction (i.e., bead fraction) when specific E. coli O157:H7 antibodies were used, and no bacteria will be recovered in the supernatant (unbound) fraction. In certain embodiments, E. coli B and S. typhimurium cells are found only in the supernatant fraction when E. coli O157:H7-specific antibodies are used, illustrating the remarkable specificity of these antibodies. In the absence of antibody, all three types of bacteria were found in the supernatant fraction.

Hybrid Immuno-Phage (HIP) Assay

In certain embodiments, the methods of the present invention combine the use of a binding agent (e.g., antibody) to purify and/or concentrate a microorganism of interest from the sample in addition to detection with an infectious agent. For example, in certain embodiments, the present invention comprises a method for detecting a microorganism of interest in a sample comprising the steps of: capturing the microorganism from the sample on a prior support using a capture antibody specific to the microorganism of interest; incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product; and detecting the indicator protein product, wherein positive detection of the indicator protein product indicates that the microorganism of interest is present in the sample.

Figure 17:
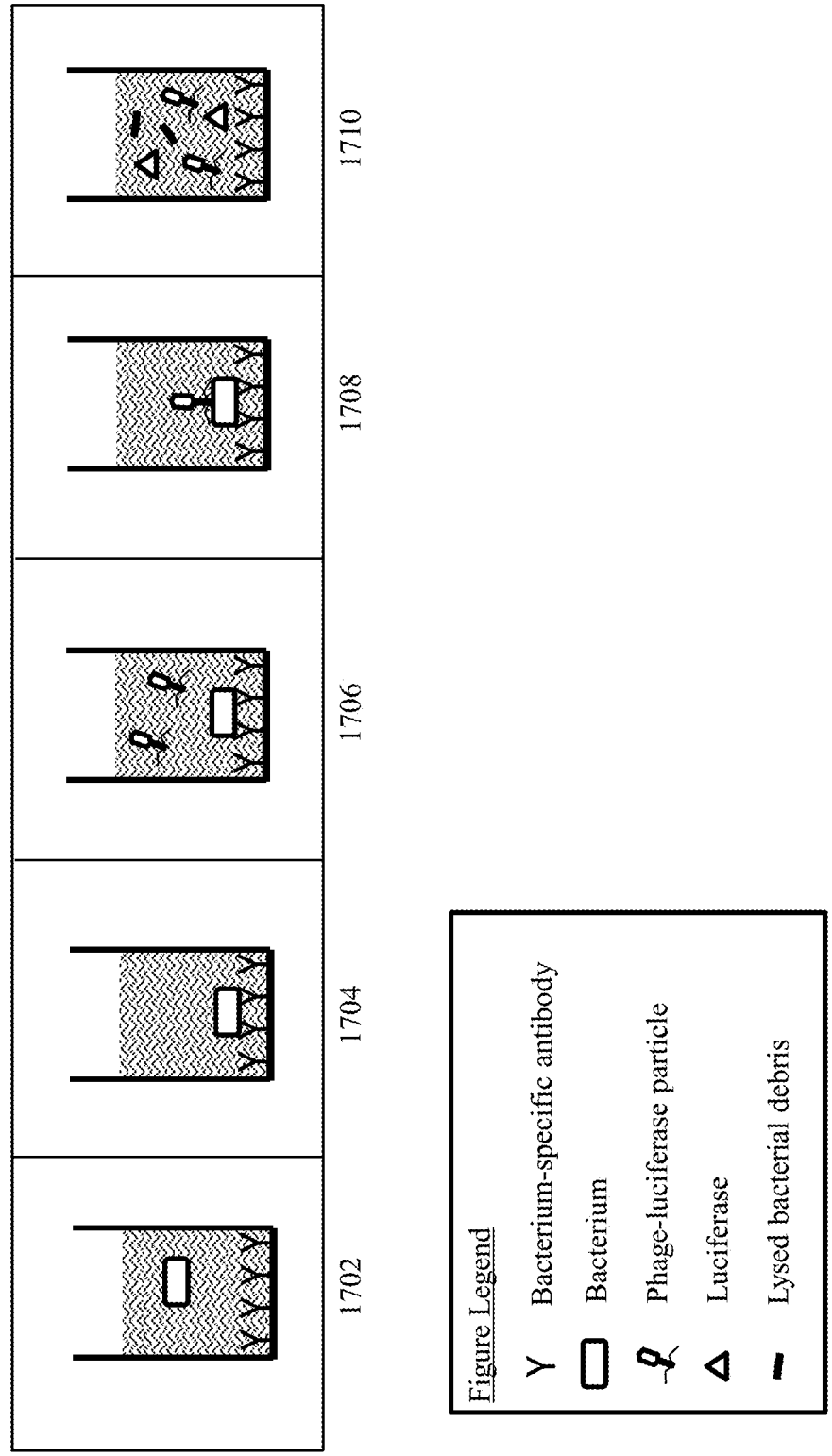
FIG. 17 depicts a Hybrid Immuno-Phage (HIP) Assay for detecting a bacterium of interest using a modified bacteriophage according to an embodiment of the invention wherein antibodies to the microorganism of interest are used to capture the microorganism on the surface of the assay well prior to incubation with a recombinant infectious agent having an indicator gene.

For example, FIG. 17 depicts a Hybrid Immuno-Phage (HIP) Assay for detecting a bacterium of interest using a modified bacteriophage according to an embodiment of the invention. The sample is first applied to the microtiter plate well coated with bacterium-specific antibodies 1702. The plate is then centrifuged to facilitate binding of the bacterium to the capture antibodies 1704. Following sufficient time to allow for complete bacteria capture, a solution containing bacterium-specific NANOLUC®-phage is added to each sample 1706. Incubation with the phage results in the binding and attachment of a single or multiple phages to the captured bacterium 1708. Finally, the sample is incubated to facilitate phage replication and luciferase expression, which leads to cell lysis and release of soluble luciferase 1710.

Figure 18:
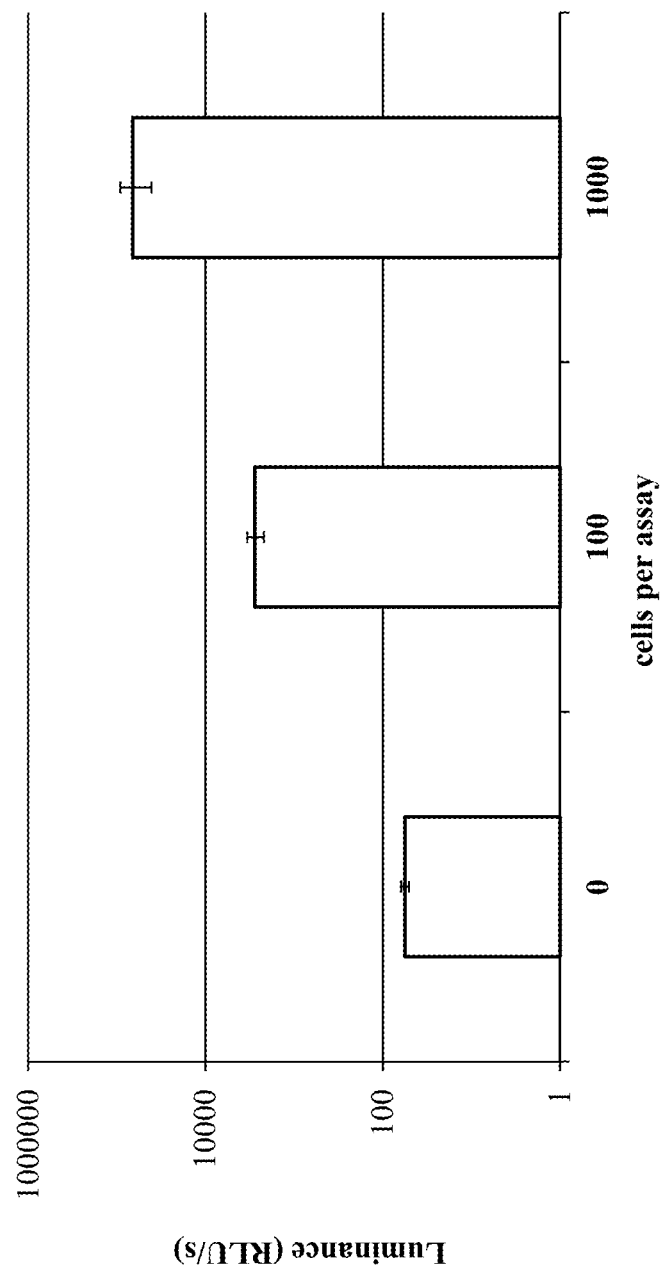
FIG. 18 shows results from a HIP assay using JG04-NANOLUC® phage to detect E. coli O157:H7 cells in samples with known cell numbers, on a logarithmic scale. The approximate number of E. coli O157:H7 cells in each assay is indicated on the X-axis. The signal provided by the soluble luciferase produced upon infection of the bacteria is shown on the Y-axis as relative luminal units (RLU).

FIG. 18 shows results from a HIP assay using JG04-NANOLUC® phage to detect E. coli O157:H7 cells in samples with known cell numbers, as described in Example 11, on a log scale. The HIP assay was able to detect 100 and 1,000 E. coli O157:H7 cells in LB media with approximately $2\times10^6$ PFU JG04-NANOLUC® phage. The average signal over a no-cell sample ranged from approximately 50-fold for the 100 cell sample to over 1,000-fold for the 1,000 cell sample.

In some embodiments, the incubating step of the methods described herein comprises a final bacteriophage concentration of greater than $7\times10^6$, $8\times10^6$, $9\times10^6$, $1.0\times10^7$, $1.1\times10^7$, $1.2\times10^7$, $1.3\times10^7$, $1.4\times10^7$, $1.5\times10^7$, $1.6\times10^7$, $1.7\times10^7$, $1.8\times10^7$, $1.9\times10^7$, $2.0\times10^7$, $3.0\times10^7$, $4.0\times10^7$, $5.0\times10^7$, $6.0\times10^7$, $7.0\times10^7$, $8.0\times10^7$, $9.0\times10^7$, or $1.0\times10^8$ PFU/mL. This high phage concentration was previously purported to be detrimental to such an assay, and thus yields surprising results. In some embodiments, the methods of the invention require less than 3 hours, less than 2.5 hours, less than 2 hours, less than 1.5 hours, or less than 1 hour for detection of a microorganism of interest. In some embodiments, the methods can detect as few as 100, 50, 20, 10, 9, 8, 7, 6, 5, 4, 3, or 2 cells of the microorganism of interest. These are shorter timeframes than were previously thought possible. In some embodiments, even a single cell of the microorganism is detectable. In additional embodiments, the invention comprises systems (e.g., computer systems, automated systems or kits) comprising components for performing the methods disclosed herein, and/or using the modified infectious agents described herein.

Systems and Kits of the Invention

In some embodiments, the invention comprises systems (e.g., automated systems or kits) comprising components for performing the methods disclosed herein. Some embodiments described herein are particularly suitable for automation or kits, given the minimal amount of reagents and materials required to perform the methods. In certain embodiments, each of the components of the a kit may comprise a self-contained unit that is deliverable from a first site to a second site.

In some embodiments, the invention comprises a systems or kits for rapid detection of a microorganism of interest in a sample. The systems or kits may in certain embodiments comprise a component for incubating the sample with an infectious agent specific for the microorganism of interest, wherein the infectious agent comprises an indicator moiety and a component for detecting the indicator moiety. In some embodiments of both the systems and the kits of the invention, the infectious agent is a recombinant bacteriophage that infects the microorganism of interest, and the recombinant bacteriophage comprises an indicator gene inserted into a late gene region of the bacteriophage as the indicator moiety such that expression of the indicator gene during bacteriophage replication following infection of host bacteria results in a soluble indicator protein product. Some systems further comprise a component for capturing the microorganism of interest on a solid support.

In certain embodiments, the systems and/or kits may further comprise a component for washing the captured microorganism sample. Additionally or alternatively, the systems and/or kits may further comprise a component for determining amount of the indicator moiety, wherein the amount of indicator moiety detected corresponds to the amount of microorganism in the sample. For example, in certain embodiments, the system or kit may comprise a luminometer or other device for measuring a luciferase enzyme activity.

In some systems and/or kits, the same component may be used for multiple steps. In some systems and/or kits, the steps are automated or controlled by the user via computer input and/or wherein a liquid-handling robot performs at least one step.

Thus in certain embodiments, the invention may comprise a system for rapid detection of a microorganism of interest in a sample, the system comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing. Some embodiments additionally comprise a component for determining amount of the microorganism of interest in the sample, wherein the amount of indicator moiety detected corresponds to the amount of microorganism in the sample. Such systems can include various embodiments and subembodiments analogous to those described above for methods of rapid detection of microorganisms. In an embodiment, the microorganism is a bacterium and the infectious agent is a bacteriophage. In a computerized system, the system may be fully automated, semi-automated, or directed by the user through a computer (or some combination thereof).

In some embodiments, the system may comprise a component for isloated the microorganism of interest from the other components in the sample.

In an embodiment, the invention comprises a system comprising components for detecting a microorganism of interest comprising: a component for isolating at least one microorganism from other components in the sample; a component for infecting the at least one microorganism with a plurality of a parental infectious agent; a component for lysing the at least one infected microorganism to release progeny infectious agents present in the microorganism; and a component for detecting the progeny infectious agents, or a constituent of the progeny infectious agents, wherein detection of the infectious agent or a constituent of the infectious agent, indicates that the microorganism is present in the sample.

The systems may comprise a variety of components for detection of progeny infectious agents. For example, in an embodiment, the progeny infectious agent (e.g., bacteriophage) may comprise an indicator moiety. In an embodiment, the indicator moiety in the progeny infectious agent (e.g., bacteriophage) may be a detectable moiety that is expressed during replication, such as a soluble luciferase protein.

In other embodiments, the invention may comprise a kit for rapid detection of a microorganism of interest in a sample, the system comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing. Some embodiments additionally comprise a component for determining amount of the microorganism of interest in the sample, wherein the amount of indicator moiety detected corresponds to the amount of microorganism in the sample. Such kits can include various embodiments and subembodiments analogous to those described above for methods of rapid detection of microorganisms. In an embodiment, the microorganism is a bacterium and the infectious agent is a bacteriophage.

In some embodiments, the kit may comprise a component for isolated the microorganism of interest from the other components in the sample.

In an embodiment, the invention comprises a kit comprising components for detecting a microorganism of interest comprising: a component for isolating at least one microorganism from other components in the sample; a component for infecting the at least one microorganism with a plurality of a parental infectious agent; a component for lysing the at least one infected microorganism to release progeny infectious agents present in the microorganism; and a component for detecting the progeny infectious agents, or a constituent of the progeny infectious agents, wherein detection of the infectious agent or a constituent of the infectious agent, indicates that the microorganism is present in the sample.

The kits may comprise a variety of components for detection of progeny infectious agents. For example, in an embodiment, the progeny infectious agent (e.g., bacteriophage) may comprise an indicator moiety. In an embodiment, the indicator moiety in the progeny infectious agent (e.g., bacteriophage) may be a detectable moiety that is expressed during replication, such as a soluble luciferase protein.

These systems and kits of the invention include various components. As used herein, the term "component" is broadly defined and includes any suitable apparatus or collections of apparatuses suitable for carrying out the recited method. The components need not be integrally connected or situated with respect to each other in any particular way. The invention includes any suitable arrangements of the components with respect to each other. For example, the components need not be in the same room. But in some embodiments, the components are connected to each other in an integral unit. In some embodiments, the same components may perform multiple functions.

Computer Systems and Computer Readable Media

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

A computer system may comprise a computer, an input device, a display unit, and/or the Internet. The computer may further comprise a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit allows the computer to connect to other databases and the Internet through an I/O interface. The communication unit allows the transfer to, as well as reception of data from, other databases. The communication unit may include a modem, an Ethernet card, or any similar device which enables the computer system to connect to databases and networks such as LAN, MAN, WAN and the Internet. The computer system thus may facilitate inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may comprise a single type of computer-readable medium such as random access memory (RAM). In other embodiments, the computing device may comprise two or more types of computer-readable medium such as random access memory (RAM), a disk drive, and cache. The computing device may be in communication with one or more external computer-readable mediums such as an external hard disk drive or an external DVD drive.

As discussed above, the embodiment comprises a processor which is configured to execute computer-executable program instructions and/or to access information stored in memory. The instructions may comprise processor-specific instructions generated by a compiler and/or an interpreter from code written in any suitable computer-programming language including, for example, C, C++, C #, Visual Basic, Java, Python, Perl, JavaScript, and ActionScript (Adobe Systems, Mountain View, Calif.). In an embodiment, the computing device comprises a single processor. In other embodiments, the device comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device comprises a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, the computing device may include a data store in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device may be in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof.

Some of the embodiments of the technology described herein can be defined according to any of the following numbered paragraphs:

(1) A recombinant bacteriophage comprising an indicator gene inserted into a late gene region of the bacteriophage, and optionally wherein the late gene region is a class III gene region, and optionally wherein transcription of the indicator gene is controlled by a bacteriophage class III or "late" promoter.

(2) The recombinant bacteriophage of paragraph 1, wherein the bacteriophage is derived from T7, T4, T4-like, JG04, or another natural bacteriophage having a genome with at least 90% homology to T7, JG04, T4, or other T4-like phage; and/or wherein the amount of indicator moiety detected corresponds to the amount of the microorganism of interest present in the sample.

(3) The bacteriophage of any of paragraphs 1-2, wherein the indicator gene does not encode a fusion protein and/or wherein the indicator gene is adjacent to a major capsid gene, and optionally wherein expression of the indicator gene during bacteriophage replication following infection of a host bacterium results in a soluble indicator protein product.

(4) The bacteriophage of any of paragraphs 1-3, wherein the indicator gene encodes a luciferase enzyme, and optionally wherein the luciferase is one of Oplophorus luciferase, Firefly luciferase, or an engineered luciferase.

(5) A method for detecting a microorganism of interest in a sample comprising the steps of: incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product; and detecting the indicator protein product, wherein positive detection of the indicator protein product indicates that the microorganism of interest is present in the sample.

(6) The method of paragraph 5, wherein the late gene region is a class III gene region, and optionally wherein transcription of the indicator gene is controlled by a bacteriophage class III promoter.

(7) The method of paragraph 5 or 6, wherein the bacteriophage is derived from T7, T4, T4-like, JG04, or another natural bacteriophage having a genome with at least 90% homology to T7, T4 or other T4-like phage, and/or wherein the amount of indicator moiety detected corresponds to the amount of the microorganism of interest present in the sample.

(8) The method of any of paragraphs 5-7, wherein the indicator gene does not encode a fusion protein and/or wherein the indicator gene is adjacent to a major capsid gene, and optionally wherein expression of the indicator gene during bacteriophage replication following infection of a host bacterium results in a soluble indicator protein product.

(9) The method of any of paragraphs 5-8, wherein the indicator gene encodes a luciferase enzyme, and optionally wherein the luciferase is one of Oplophorus luciferase, Firefly luciferase, or an engineered luciferase.

(10) The method of any of paragraphs 5-9, wherein the bacteriophage concentration for the incubating step is greater than $1 \times 10^7$ PFU/mL, and optionally wherein the recombinant bacteriophage is purified using cesium chloride isopycnic density gradient centrifugation prior to incubation with the sample.

(11) The method of any of paragraphs 5-10, further comprising a step for capturing the microorganism from the sample on a solid support before the incubating step; and optionally wherein the solid support comprises a multi-well plate or a filter; and optionally wherein the capturing step further comprises binding microorganism with a capture antibody; and optionally wherein the capture antibody facilitates binding of the microorganism to the solid support; and optionally wherein the method further comprises a step for washing the captured and infected microorganism, after adding the bacteriophage but before incubating, to remove excess bacteriophage and/or contaminating reporter protein, such as luciferase.

(12) The method of any of paragraphs 5-11, wherein detection of the microorganism of interest is completed in less time than a time period required for increasing the number of microorganisms by 4-fold or 10-fold using culturing for enrichment; and optionally wherein the method can detect ≤10 cells of the microorganism in the sample; and optionally wherein the total time required for detection is less than 2 hours.

(13) A system for rapid detection of a microorganism of interest in a sample, comprising: a component for incubating the sample with an infectious agent specific for the microorganism of interest, wherein the infectious agent comprises an indicator moiety; and a component for detecting the indicator moiety; and optionally further comprising a component for determining amount of the microorganism of interest in the sample, wherein the amount of indicator moiety detected corresponds to the amount of microorganism in the sample; and optionally further comprising a component for capturing the microorganism of interest on a solid support, and/or further comprising a component for washing the captured microorganism sample, and optionally wherein the same component may be used for multiple steps.

(14) The system of paragraph 13, wherein the infectious agent is a recombinant bacteriophage that infects the microorganism of interest, wherein the recombinant bacteriophage comprises an indicator gene inserted into a late gene region of the bacteriophage as the indicator moiety such that expression of the indicator gene during bacteriophage replication following infection of host bacteria results in a soluble indicator protein product; and optionally wherein the steps are automated or controlled by the user via computer input and/or wherein a liquid-handling robot performs at least one step; or wherein the system comprises a kit.

(15) Non-transient computer readable media for use with the method of any of paragraphs 5-12 and/or the system of any of paragraphs 13-14.

EXAMPLES

Results depicted in the following examples, except for example 11, were obtained without culturing for enrichment or without incubation of the sample to achieve replication of sample cells. Further, in the "no concentration assay," indicator phage added directly to a sample, without concentrating the cells, could infect and detect a low number of cells, even a single bacterium.

Example 1. Creation of Indicator Phage

Indicator Phage were created using the T7SELECT®415-1 phage display system from Millipore, Inc. Briefly, purified T7SELECT® DNA was purchased and digested with DNA restriction enzymes EcoRI and HindIII (New England Biolabs®), and the cut DNA was subsequently purified. The gene for wild-type Firefly luciferase (from the common Eastern firefly, Photinus pyralis) was synthesized with a bacteriophage T7 upstream region including the late T7 promoter, to ensure high levels of expression of the luciferase gene.

The synthesized luciferase gene is designated SEQ ID NO. 1. This gene was amplified by PCR to include compatible restriction enzyme recognition sites for EcoRI and HindIII to ensure the new gene could be inserted into the T7SELECT®415-1 genome, using the following primers:

TATCTGAATTCTAAGTAACTGATAATACGACTCACTATAGGGAGACCACAA
C, designated SEQ ID NO. 2, and AATGA*AAGCTTT*TACAATTTGGACTTTCCGCCCTTCTTGG,
designated SEQ ID NO. 3.

Additionally, stop codons in all 3 reading frames were added upstream of the luciferase start site, to terminate production of the bacteriophage major capsid protein, the gene 10B product. The T7SELECT®415-1 phage display system is designed to create a fusion product of the gene 10B major capsid protein and any small protein inserted downstream of it. The addition of the stop codons ensures no fusion product is made, and allows the relatively large luciferase gene to be expressed in soluble form. The PCR product was digested with EcoR1 and HindIII, purified, and ligated into the T7SELECT®415-1. The ligation product was inserted into MegaX DH10B electrocompetent cells (Invitrogen®) using a Bio-Rad MicroPulser™ electroporation system, and the culture plated on E. coli for plaques. Plaques were picked, and phage were grown in E. coli DH10B and purified via sucrose density gradient centrifugation for use as Indicator Phage, T7SELECT®415-Luc.

FIG. 1 depicts the genomic structure of an example Indicator Phage, T7SELECT®415-Luc. The detectable indicator moiety is encoded by the Firefly luciferase gene inserted within the Class III gene region, expressed late in the viral life cycle and at higher levels than other phage genes. The construct contains stop codons to ensure the luciferase is not incorporated into a native gene product, such as the capsid protein gene 10B, and is thus also not a fusion protein. Thus this construct allows progeny phage to express soluble Firefly luciferase as the indicator to be detected.

Example 2. Isolation and Purification of E. coli O157:H7 Specific Bacteriophage from the Environment Samples from the Hyperion Sewage Treatment Plant were obtained along with water samples from the neighboring Ballona wetlands. The samples were mixed with powdered Nutrient Broth (Gibco, Inc.) to 1× and inoculated with E. coli O157:H7 (ATCC 43888) from 3 mL of turbid culture. The sample was incubated for 3 hours @ 37° C. with shaking to enrich for phage that infect E. coli O157:H7, lysed with 120 μL chloroform, vortexed for 15 seconds, and a 1 mL sample was centrifuged for 2 minutes at 6800 g. The supernatants were filtered (0.45 μm filter) and plated for plaques on E. coli O157:H7. This sample was plated out in plaque assays in various dilutions to obtain well isolated plaques. Individual plaques were stabbed with disposable pipette tips and resuspended in 100 μL TMS buffer (50 mM Tris-HCl, pH 7.4, 10 mM $MgCl_2$, and 100 mM NaCl).

Aliquots of 5 μL of resuspended plaques were spot-tested in overlay agar on E. coli strains O157:H7, B, and DH10B, and on a strain of Salmonella. Phage that only cleared O157:H7 were amplified in E. coli O157:H7, the lysates clarified by centrifugation, and the particles put into TMS buffer using ZEBA® Buffer Exchange columns.

Eight closely related phage isolates were grown on E. coli O157:H7, purified, and the genomes isolated and sequenced. Three genomic types all showed 98% homology to the T4-like phage RB69. The late genes were mapped based on this homology, and phage JG04 was selected for further study. FIG. 2 shows JG04, and the genome of JG04 is designated SEQ ID NO. 4.

Example 3. Creation and Purification of Recombinant Indicator Phage

Based on sequence analysis and location of the late gene region, homologous recombination sequences were synthesized with inserts for various reporter genes, consisting of different luciferase proteins, as shown in FIG. 3. Specifically, three constructs were used: Firefly luciferase homologous recombination plasmid, pUC57.HR.Fluc, corresponding to SEQ ID NO. 5; NANOLUC® Homologous Recombination Plasmid, pUC57.HR.NANOLUC® corresponding to SEQ ID NO. 6; and Oplophorus Luciferase Homologous Recombination Plasmid, pUC19.HR.OpLuc.KanR, corresponding to SEQ ID NO. 7.

Luciferase genes were inserted with an upstream T4 late gene promoter, to ensure expression during the viral late stage. In some cases, a kanamycin resistance marker was also inserted to allow for selection of infected cells under the kanamycin antibiotic. These regions were flanked with up to 500 bp of sequence matching the capsid proteins, gp23 and gp24. These synthesized sequences were carried by the Ampicillin resistant pUC57 or pUC19 plasmid.

Plasmids containing the synthesized sequences were transformed into electroporation competent *E. coli* O157:H7 using a BIORAD® Gene Pulser® II electroporator, conferring resistance to Ampicillin. Colonies were screened for positive transformation by assaying with the appropriate luciferase substrate (D-luciferin for Firefly luciferase, coelenterazine for Oplophorus luciferase, and either coelenterazine or NANOGLO® for NANOLUC®). *E. coli* O157:H7 harboring a plasmid with iuc flanked by sequences homologous with phage JG04 were grown in Ampicillin-containing LB broth bacterial cultures were grown in Ampicillin containing LB broth to approximately $10^7$ cells/mL. Cultures were then infected with phage JG04 at an MOI of 1 and incubated for 45 minutes at 37° C. with shaking to lyse cells. Lysates contained a mixture of mostly wild-type phage with a minority of recombinant phage created by homologous recombination of the wild-type phage genome with the homologous recombination plasmid.

In order to determine the ratio of recombinant to wild-type phage, limiting dilution assays based on the TCID50 (tissue culture infectious dose 50%) were used to both determine the concentration of infectious units (IU/mL), akin to number of virus particles or plaque forming units, and to determine the number of luciferase transducing units (TU/mL). In these assays, the sample was serially diluted, with each dilution aliquoted into replicates wells with *E. coli* O157:H7 bacteria. Any wells that show luciferase activity must have been infected with at least one recombinant phage. Any wells that showed cell lysis had been infected by at least one phage. Based on the highest dilution where each of these cases occurred, the original concentrations were back-calculated. These initial phage mixtures from transformed cells typically yielded a ratio of 20,000 wild-type IU for each recombinant phage TU. Steps were then taken to isolate and amplify the recombinant phage.

As illustrated in FIG. 4, recombinant phage were isolated from a mixture comprising 0.005% of total phage. The phage mixtures were diluted into 96 well plates to give an average of 3 recombinant TU per plate, which breaks down to about 625 IU of mostly wild-type phage per well. Each well contained 50 µL of turbid *E. coli* O157:H7. After 2 hours of incubation at 37° C., wells were sampled and screened for the presence of luciferase. Any positive wells would likely have been inoculated with a single recombinant phage, and ~600 wild-type phage, which is an enrichment over the original 20,000:1 ratio. Progeny from this enriched culture was subjected to another limiting dilution assay to verify the ratio and determine the actual concentration of recombinant phage transducing units.

Again, 3 recombinant TU per 96-well plate were aliquoted from this stock, leading to an approximate inoculation of ~20 mostly wild-type phage per well. Any positive luciferase wells were likely to have been inoculated with a single recombinant along with ~20 wild-type phage. These wells were analyzed for luciferase activity, and any positive wells were subjected to the limiting dilution assay to determine the ratio of TU to IU, then to plaque assay to obtain well-isolated plaques.

At this point, the expected ratio of wild-type to recombinants was about 20:1.48 plaques were individually picked and screened for luciferase transducing ability, insuring about 3 recombinants were in the mix of plaques being screened. Each plaque was suspended in 100 µL TMS, and 5 µL was added to a well containing a turbid *E. coli* O157:H7 culture, and wells were assayed after incubation for 45 minutes to 1 hour at 37° C.

Positive wells were expected to contain a pure culture of recombinant phage, but an additional round of plaque purification was standard procedure. Large scale production was performed to obtain high titer stocks appropriate for use in the *E. coli* O157:H7 detection assay. Cesium chloride isopycnic density gradient centrifugation was used to separate phage particles from contaminating luciferase protein to reduce background.

Example 4. Bacterial Detection Via Indicator Phage Using Spin Column Filters

FIG. 5 illustrates use of indicator phage and spin column filters for bacterial detection, according to an embodiment of the invention. In an example experiment, *E. coli* DH10B was grown in Luria-Bertani broth (LB) at 37° C. with shaking. T7SELECT® 415-Luc phage were diluted to $10^8$ PFU/40 µL ($2.5 \times 10^9$ PFU/mL). Cells were counted and diluted to 3000, 300, 30 and 3 cells/mL. A CFU assay was performed in parallel with the following luciferase assay to determine the actual number of input cells per assay.

For each cell dilution, 0.1 mL was added to filters in triplicate. Filters were spun at 600 g for 1 minute. Next, 40 µL of each of the phage dilution was added to each filter, followed by incubation for 10 min at room temperature. Filters were washed twice by addition of 400 PBST (0.05% Tween®), followed by centrifugation at 600 g for 1 minute. Next 50 µL LB was added, followed by incubation for 30 minutes at 37° C. Filters were spun at 6800 g for 2 minutes. Next, 30 µL of the filtrate was transferred to a LUMI-TRAC® 200 96-well luminometer plate, and a luciferase assay was performed in a Promega® luminometer with injection of 100 µL Luciferase Assay Reagent (Promega, Inc.). Cell count was corrected according to the number of colonies in the parallel CFU assay. The signal to background ratio was obtained by dividing each well's signal by the average of signal from zero cell controls. FIG. 6 shows results demonstrating high sensitivity of the assay for detecting as few as 1 to 3 *E. coli* cells, via luciferase activity. FIG. 7 shows results demonstrating the very large detection range of the same method using serial dilutions of the starting bacterial sample. This shows detection from an average of 1.4 cells to 14 million cells.

Example 5. Bacterial Detection Via Indicator Phage Using 96-Well Filter Plates

*E. coli* DH10B was grown in LB at 37° C. with shaking. T7SELECT®415-Luc phage were diluted to $4 \times 10^7$ PFU/20 µL in LB ($2 \times 10^9$ PFU/mL). Cells were counted and diluted to 500, 50 and 5 cells/mL (0.1 mL was added to each wells, giving ~50, 5 and <1 cells shown in FIG. 5). A CFU assay was performed in parallel with the following luciferase assay to determine the actual number of input cells per assay.

For each cell dilution, 0.1 mL was added to multiple wells in a 96-well filter plate: 9 wells for 0.5 cells and 3 wells for 50 cells, 5 cells and the zero cell control. The 96-well filter plate was spun at 1200 rpm (263 rcf) for 3 minutes. Next 20 µL of the phage dilution was added to each filter and incubated for 10 minutes at room temperature, followed by 30 minutes at 37° C. The luciferase assay was performed directly in the original filter plate with 100 µL Luciferase Assay Reagent (Promega, Inc.) injection using a Promega® Luminometer, and plates were read immediately following injection and reread at 15 and 30 minutes thereafter. Cell count was corrected according to the number of colonies in the parallel CFU assay. Signal to background ratios were obtained by dividing each well's signal by the average of signal from zero cell controls.

FIG. 8 shows results demonstrating the use of the 96-well filter plate for detecting single *E. coli* cells in each well (0.5 cells on average were assayed, such that about one-half of the wells received single cells), and 5.4 and 54 cells per well.

FIG. 9 shows results demonstrating a very large cell detection range, using the 96-well filter plate system, from less than 1 cell per well on average (single cells) to at least 14 million cells per well.

Example 6. Filter Plate Assay Using JG04-NANOLUC® Indicator Phage and Low Cell Concentration

*E. coli* O157:H7 cells were grown in LB at 37° C. with 220 rpm shaking. JG04-NANOLUC® Indicator Phage were prepared to $10^6$ PFU/20 µL. Cells were counted and diluted to 7290, 2430, 810, 270, 90, 30, 10 and 0 cells/mL. Aliquots of 100 µL of each sample were deposited into wells of a PERKINELMER® Optiplate 96-well Grey Luminometer 0.45 µm filter plate in replicates.

As illustrated in FIG. 10, plates were loaded into a swinging bucket centrifuge and spun at 2400 rpm for 3 minutes. 20 µL of JG04-NANOLUC® phage dilution was added to each well, giving a final concentration of $5\times10^7$ PFU/mL. Plates were incubated for 10 minutes at room temperature, 200 µL PBST was added to each well, and plates were spun down for 3 minutes at 2400 rpm to wash away excess parental JG04-NANOLUC® phage.

Next, 50 µL LB was added to each well and plates were incubated for 45 minutes in a 37° C. incubator without shaking. Aliquots of 10 µL Promega® Renilla Luciferase Lysis Buffer were added to wells, analyte was transferred to the wells, and luciferase assay was performed with 50 µL Promega® NANOGLO® Reagent injection. Samples with cells were compared to 0 cell controls.

As seen in FIG. 11, the NANOLUC® Filter Plate results show statistically significant differences between the signal from 0 cells and 1 cell/assay (p value=0.034 by Student's t-Test), demonstrating the ability to detect single cells. More bacterial cells per assay show increasing signal in a dose dependent manner.

Example 7. No Concentration Assay with Low Cell Concentrations

In preparation for an experiment similar to the assay illustrated in schematic FIG. 12, *E. coli* O157:H7 cells were grown in LB at 37° C. with 220 rpm shaking. JG04-OpLuc Indicator Phage were prepared to $1.2\times10^7$ PFU/20 µL, and 20 µL aliquots were distributed to wells of a PERKINELMER® Optiplate 96-well Grey Luminometer plate. Cells were counted and diluted to 10, 3.3, 1.1 and 0 cells/mL. Aliquots of 100 µL of each sample were distributed into wells in replicates (12× for 0.11 and 0.33 cells/assay and 5× for 1 cell/assay), giving a final phage concentration of $10^8$ PFU/mL.

Plates were incubated for 45 minutes in a 37° C. incubator without shaking. Finally, 10 µL PROMEGA® Renilla Luciferase Lysis Buffer was added to each well, and the luciferase assay was performed with 50 µL PROMEGA® Renilla Luciferase Assay Reagent (coelenterazine) injection. Samples were compared to 0 cell controls.

As seen in FIG. 13, the No Concentration Assay with low cell concentration samples results show statistically significant differences between the signal from 0 cells and 1 cell/assay (p value=0.0024 by ANOVA test), demonstrating the ability to detect single cells. Thus the assay is surprisingly sensitive. Samples with fewer than 1 cell per well appear to show a proportional number of wells above the background signal.

Example 8. No Concentration Assay with Wide Cell Concentration Range

In a similar experiment with higher cell concentrations, *E. coli* O157:H7 cells were grown in LB at 37° C. with 220 rpm shaking. JG04-OpLuc Indicator Phage were prepared to $1.2\times10^7$ PFU/20 µL, and 20 µL aliquots were distributed to wells of a PERKINELMER® Optiplate 96-well Grey Luminometer plate. Cells were counted and diluted to $10^8$, $10^7$, $10^6$, $10^5$, $10^4$, $10^3$, $10^2$, 33, 11, 3.7, 1.2 and 0 cells/mL. Aliquots of 100 µL of each sample were distributed into wells in replicates, giving a final phage concentration of $10^8$ PFU/mL.

Plates were incubated for 45 minutes in a 37° C. incubator without shaking. 10 µL PROMEGA® Renilla Luciferase Lysis Buffer was added to each well, and luciferase assay was performed with 50 µL PROMEGA® Renilla Luciferase Assay Reagent (coelenterazine) injection. Samples were compared to 0 cell controls.

As seen in FIG. 14, the experiment for the No Concentration Assay with a very wide range of cell concentration samples shows statistically significant differences between the signal from 0 cells and 1.1 cell/assay (p value=0.000702 by Student's t-Test), demonstrating the ability to detect single cells. More bacterial cells per assay show increasing signal in a dose dependent manner, up to at least $10^6$ bacterial cells/mL, surprisingly demonstrating a very wide range of detection.

Example 9. No Concentration Assay with Vegetable Wash Samples

To prepare the vegetable wash, vegetable leaves (e.g., spinach or lettuce) were weighed and added to a clean plastic bag. One mL of LB (+/−0.01-0.05% Tween®20) was added per each gram (g) of vegetable. Leaves and solution were mixed manually for a few minutes. Liquid was then extracted from the plastic bag and used as the "vegetable wash." Using this method, ~1 million bacteria were found by CFU to reside on a single spinach leaf (1-2 g).

*E. coli* O157:H7 cells were grown in LB at 37° C. with 220 rpm shaking. JG04-OpLuc Indicator Phage were prepared to $1.2\times10^7$ PFU/20 µL, and 20 µL aliquots were distributed to wells of a PERKINELMER® Optiplate 96-well Grey Luminometer plate. Cells were counted and diluted into Vegetable Wash at 120, 60, 30, and 0 cells/mL. Aliquots of 100 µL of each sample were distributed into wells in replicates, giving a final phage concentration of $10^8$ PFU/mL.

Plates were incubated for 45 minutes in a 37° C. incubator without shaking. 10 µL PROMEGA® Renilla Luciferase Lysis Buffer was added to each well, and luciferase assay was performed with 50 µL PROMEGA® Renilla Luciferase Assay Reagent (coelenterazine) injection. Samples were compared to 0 cell controls.

As seen in FIG. 15, the experiment for the No Concentration Assay using vegetable wash samples shows marked differences between the signal from 0 cells and 3 cells/assay, demonstrating the ability to detect single-digit cell numbers in vegetable wash. Using more bacterial cells per assay shows increasing signal in a dose dependent manner. The vegetable wash contains about $10^6$ non-target bacteria/mL, corresponding to about $10^5$ non-target bacteria in this assay (including the 0 cell *E. coli* O157:H7 control). The ability to discern as few as 3 target bacterial cells from $10^5$ non-target bacteria is surprising and again demonstrates the specificity of the assay.

Example 10. Specific and Quantitative Capture of *E. coli* O157:H7 Using Antibodies and Beads FIG. 16 depicts an example experiment demonstrating that antibodies against *E. coli* O157:H7 and magnetic streptavidin-coated beads captured *E. coli* O157:H7 specifically and quantitatively from samples, but not *E. coli* B or *Salmonella typhimurium* in samples. In order to demonstrate specificity in capturing intact, viable bacterial cells from solution, polyclonal antibodies to surface epitopes of *E. coli* O157:H7 were purchased from KPL (affinity- and reverse-purified to minimize cross-reactivity).

Cultures of both *E. coli* species and *S. typhimurium* were grown in LB broth, harvested, and washed with phosphate buffer (1.1 mM $KH_2PO_4$, 5.6 mM $Na_2HPO_4$, 154 mM NaCl, pH 7.4). The washed cells were then counted and diluted to a concentration between 5-20 cells per mL.

A sample containing *E. coli* O157:H7 was combined with a solution containing BSA and biotin-conjugated antibody. Approximately 10 ng biotinylated, polyclonal anti-*E. coli* antibody (equivalent to about $4 \times 10^{10}$ antibody molecules) produced by KPL was added to each of the cell suspensions. A control experiment, where antibody was not added to the cell suspension, was also performed in parallel. The BSA concentration was ~1%, and the total biotin-antibody was 10 ng. The mixture was rotated end-over-end for 1 hour.

Following incubation with antibodies, $4 \times 10^7$ streptavidin-coated magnetic microparticles (Invitrogen®/Life Technologies) were added to the mixture and incubated a further 30 minutes. The cell-antibody-bead complexes were then collected using a magnetic stand, and the unbound fraction (supernatant) was removed. The beads were gently washed with phosphate buffer with Tween® (1.1 mM $KH_2PO_4$, 5.6 mM $Na_2HPO_4$, 154 mM NaCl, pH 7.4, 0.05% Tween®).

Both the supernatants and captured cell-bead complexes were then spread onto LB agar plates and the plates incubated overnight at 37° C. to determine CFU. Capture of *E. coli* O157:H7 with anti-O157:H7 antibodies, but not *E. coli* B or *Salmonella typhimurium*, was specific and quantitative.

Example 11. Hybrid Immuno-Phage (HIP) Assay

As illustrated in schematic FIG. 17, the Hybrid Immuno-Phage or "HIP" assay combines the benefits of bacterium-specific antibody capture with the benefits of a modified bacteriophage. The sample is first applied to the microtiter plate well coated with bacterium-specific antibodies (1702). The plate is then centrifuged to facilitate binding of the bacterium to the capture antibodies (1704). Following sufficient time to allow for complete capture of bacteria, a solution containing bacterium-specific Luc-phage is added to each sample (1706). Incubation with the phage results in the binding and attachment of a single or multiple phages to the captured bacterium (1708). Finally, the sample is incubated to facilitate phage replication and luciferase expression, which leads to cell lysis and release of soluble luciferase (1710).

In a HIP assay experiment, a white 96-well ELISA plate was coated with 300 ng monoclonal antibody (in 100 µL PBS) specific to the bacterium of interest at room temperature for 2-3 hours. Wells were washed with PBS (200 µL×3 washes), blocked with 5% BSA/PBS (300 µL) at room temperature for 1-1.5 hours, and again washed with 300 µL PBS×1. Test samples (100 µL) were applied to the wells.

The ELISA plate was centrifuged at 700×g for 30 minutes and then incubated at room temperature for 1 hour. JG04-NANOLUC® phage was added to samples (2-4×$10^6$ PFU in 10 µL LB) and incubated at room temperature for 10 minutes. Samples were washed with PBS (200 µL×2 washes). LB medium was added to samples (100 µL) and incubated at 37° C. for 1.5 hours.

NANOGLO® substrate (50 µL) was added directly to the samples, and the luminescence was measured in a luminometer. As seen in FIG. 18, the HIP assay was able to detect 100 and 1,000 *E. coli* O157:H7 cells in LB medium with approximately 2×$10^6$ PFU JG04-NANOLUC® phage. The average signal over a no-cell sample is shown on a log scale and ranged from approximately 50-fold for the 100 cell sample to over 1,000-fold for the 1,000 cell sample.

We claim:

1. A method for detecting a bacterium of interest in a sample, the method comprising the steps of:
    incubating at least one bacterium with a plurality of a bacteriophage genetically engineered to have an indicator gene inserted into a late gene region of the bacteriophage, wherein the indicator gene encodes a luciferase protein such that the luciferase protein is expressed during the replication of the bacteriophage and the luciferase protein does not form a fusion protein with a native gene product, and wherein the incubating step is performed at a temperature that is at least 37 degrees Celsius and no greater than 45 degrees Celsius; and
    detecting the luciferase protein,
    wherein detection of the luciferase protein indicates that the bacterium is present in the sample.

2. The method of claim 1, wherein expression of the luciferase protein is driven by a viral capsid promoter and the luciferase is not incorporated into the structure of the bacteriophage.

3. The method of claim 1, wherein the method is performed without culturing for enrichment of bacteria in the sample.

4. The method of claim 1, wherein the bacteriophage express a luciferase protein.

5. The method of claim 1, wherein the bacteriophage is T4 phage.

6. The method of claim 1, wherein the bacterium is *E. coli*.

7. The method of claim 1, wherein transcription of the indicator gene is driven by a constitutive bacterial promoter.

8. The method of claim 1, wherein the method further comprises isolating the bacterium from other components in the sample before contacting with the plurality of the bacteriophage.

9. The method of claim 8, wherein the isolating the bacterium comprises binding of the bacterium to a binding agent; or wherein the step of isolating the bacterium comprises contacting the bacterium with a binding agent that is bound to a solid support.

10. The method of claim 9, wherein the binding agent is an antibody specific for the bacterium.

11. The method of claim 8, wherein isolating comprises concentrating the bacterium from the sample on a bacteriological filter.

* * * * *